(12) United States Patent
Miller et al.

(10) Patent No.: US 12,240,853 B2
(45) Date of Patent: Mar. 4, 2025

(54) COMPOUNDS USEFUL IN HIV THERAPY

(71) Applicant: GlaxoSmithKline Intellectual Property (No.2) Limited, Stevenage (GB)

(72) Inventors: John F. Miller, Research Triangle Park, NC (US); Emile Johann Velthuisen, Research Triangle Park, NC (US)

(73) Assignee: GlaxoSmithKline Intellectual Property (No.2) Limited (GB)

( * ) Notice: Subject to any disclaimer, the term of this patent is extended or adjusted under 35 U.S.C. 154(b) by 74 days.

(21) Appl. No.: 16/865,678

(22) Filed: May 4, 2020

(65) Prior Publication Data

US 2023/0174534 A1   Jun. 8, 2023

Related U.S. Application Data

(60) Provisional application No. 62/814,316, filed on Mar. 6, 2019.

(51) Int. Cl.
| | | |
|---|---|---|
| C07D 473/34 | (2006.01) | |
| A61K 9/00 | (2006.01) | |
| A61K 31/70 | (2006.01) | |
| A61K 45/06 | (2006.01) | |
| A61P 31/08 | (2006.01) | |
| A61P 31/18 | (2006.01) | |
| C07D 487/04 | (2006.01) | |
| C07H 19/16 | (2006.01) | |
| C07H 19/173 | (2006.01) | |

(52) U.S. Cl.
CPC .......... *C07D 473/34* (2013.01); *A61K 9/0019* (2013.01); *A61K 31/70* (2013.01); *A61K 45/06* (2013.01); *A61P 31/18* (2018.01); *C07D 487/04* (2013.01); *C07H 19/16* (2013.01); *C07H 19/173* (2013.01)

(58) Field of Classification Search
CPC ..... C07D 487/04; C07D 473/34; A61P 31/18; A61K 31/70
See application file for complete search history.

(56) References Cited

U.S. PATENT DOCUMENTS

| | | |
|---|---|---|
| 7,339,053 B2 | 3/2008 | Kohgo et al. |
| 7,625,877 B2 | 12/2009 | Kohgo et al. |
| 8,039,614 B2 | 10/2011 | Kohgo et al. |
| 8,835,615 B2 | 9/2014 | Chang |
| 8,877,731 B2 | 11/2014 | Beigelman et al. |
| 8,927,513 B2 | 1/2015 | Manoharan et al. |
| 9,073,960 B2 | 7/2015 | Beigelman et al. |
| 9,198,972 B2 | 12/2015 | Manoharan et al. |
| 9,296,777 B2 | 3/2016 | Sofia |
| 9,346,848 B2 | 5/2016 | Beigelman et al. |
| 9,441,007 B2 | 9/2016 | Wang et al. |
| 9,566,340 B2 | 2/2017 | Manoharan et al. |
| 9,603,863 B2 | 3/2017 | Blatt et al. |
| 9,603,864 B2 | 3/2017 | Blatt et al. |
| 9,676,808 B2 | 6/2017 | Du et al. |
| 9,725,479 B2 | 8/2017 | Manoharan et al. |
| 9,770,035 B2 | 9/2017 | Narva et al. |
| 9,890,188 B2 | 2/2018 | Wang et al. |
| 10,307,439 B2 | 6/2019 | Blatt et al. |
| 10,537,589 B2 | 1/2020 | Hazuda et al. |
| 2005/0215512 A1* | 9/2005 | Kohgo .................. A61P 43/00 536/27.3 |
| 2015/0274767 A1 | 10/2015 | Girijavallabhan et al. |
| 2015/0366887 A1 | 12/2015 | Blatt et al. |
| 2015/0366888 A1 | 12/2015 | Blatt et al. |
| 2018/0055867 A1 | 3/2018 | Hazuda et al. |
| 2019/0022115 A1 | 1/2019 | Girijavallabhan et al. |
| 2019/0185508 A1 | 6/2019 | Alexandrea et al. |

FOREIGN PATENT DOCUMENTS

| | | |
|---|---|---|
| EP | 1 589 026 | 3/2008 |
| EP | 2177527 A1 | 4/2010 |
| WO | WO 00/69876 | 11/2000 |
| WO | WO 2003/035012 | 5/2003 |
| WO | WO 2020/031131 | 2/2013 |

(Continued)

OTHER PUBLICATIONS

Medication Safety An Essential Guide (Year: 2009).*
Prodrugs and Targeted Delivery: Towards Better ADME Properties (Year: 2011).*
Anderson et al, Journal of Controlled Release, vol. 19, No. 3, Mar. 1992, pp. 219-229.
Bibby David et al., International Journal of Pharmaceutics, vol. 144, No. 1, Sep. 1996, pp. 61-70.
Keykavous Parang et al., Nucleosides and Nucleotides, vol. 17, No. 6., Jun. 1998, pp. 990.
Lupia et al., Antimicrobial Agents and Chemotherapy, vol. 37, No. 4, Apr. 1993, pp. 818-824.
Masayuki Kageyama et al., Organic Letters, vol. 13, No. 19, Oct. 2011, pp. 5264-5266.

(Continued)

*Primary Examiner* — Medhanit W Bahta
*Assistant Examiner* — Manahil Mirghani Ali Abdalhameed
(74) *Attorney, Agent, or Firm* — W. Brett Stauffer

(57) ABSTRACT

The invention relates to a compound of the formula:

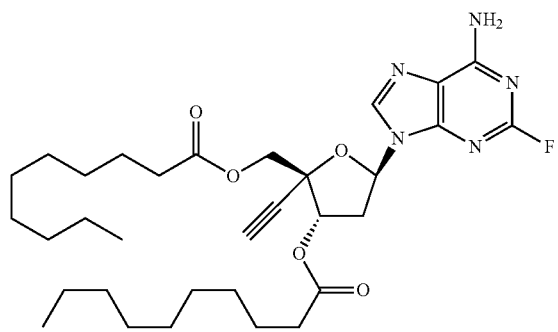

salts thereof, pharmaceutical compositions thereof, as well as methods of treating or preventing HIV in subjects.

16 Claims, 28 Drawing Sheets

(56) References Cited

FOREIGN PATENT DOCUMENTS

| WO | WO 13/096679 | | 6/2013 | | |
|---|---|---|---|---|---|
| WO | WO 13/142525 | | 9/2013 | | |
| WO | WO 2014/209979 | | 12/2014 | | |
| WO | WO 2015/054465 | | 4/2015 | | |
| WO | 2015143712 | A1 | 10/2015 | | |
| WO | WO 2015/148746 | | 10/2015 | | |
| WO | 2016/057866 | A1 | 4/2016 | | |
| WO | 2016066283 | A1 | 5/2016 | | |
| WO | WO 2016/100569 | | 6/2016 | | |
| WO | WO 2017/053216 | | 3/2017 | | |
| WO | WO-2017139519 | A1 * | 8/2017 | ......... | A61K 31/7076 |
| WO | 2017/223280 | A2 | 12/2017 | | |
| WO | 2018085307 | A1 | 5/2018 | | |
| WO | WO 2019/171285 | | 9/2019 | | |
| WO | 2019199667 | A2 | 10/2019 | | |
| WO | WO 2020/044257 | | 3/2020 | | |
| WO | 2020178798 | A1 | 9/2020 | | |

OTHER PUBLICATIONS

Parang et al., Antiviral Chemistry and Chemother International Medical Press, vol. 9., No. 4, Jan. 1998, pp. 311-323.
U.S. Appl. No. 62/639,667, filed Mar. 7, 2018.
U.S. Appl. No. 62/716,494, filed Aug. 9, 2018.
U.S. Appl. No. 62/884,191, filed Aug. 8, 2019.
U.S. Appl. No. 62/892,577, filed Aug. 28, 2019.
U.S. Appl. No. 62/993,300, filed Mar. 23, 2020.
U.S. Appl. No. 62/724,647, filed Aug. 30, 2018.
Agarwal, H.K., et al. "Emtricitabine Prodrugs with Improved Anti-HIV Activity and Cellular Uptake." Molecular Pharmaceutics; 2013; pp. 467-476; vol. 10(2).
Dabrowska-Mas, "Insights on Fatty Acids in Lipohilic Prodrug Strategy." Internationsl Research Journal of Pure and Applied Chemistry; 2017; pp. 2-5; vol. 14(4).
Irby, D., et al., "Lipid-Drug Conjugate for Enhancing Drug Delivery" Molecular Pharmaceutics; 2017; pp. 1325-1338; vol. 14(5).
Krovi, et al., "Injectable long-acting human immunodeficiency virus antiretroviral prodrugs with improved pharmacokinetic profiles." International Journal of Pharmacecutics; 2018; pp. 371-377; vol. 552(1-2).
PCT/IB2019/051799, Third Party Observations, dated Jul. 7, 2020.
"ViiV Healthcare Announces Investigational Injectable Cabotegravir is Superior to Oral Standard of Care for HIV Prevention in Women," HIV Articles, https://www.natap.org/2020/HIV/110920_01.htm (4 pages).
"ViiV Healthcare Announces Superior Efficacy of Investigational, Long-Acting Injectable Formulation of Cabotegravir Dosed Every Two Months over Daily Oral PrEP," Businesswire, https://www.businesswire.com/news/home/20200707005511/en/ViiV-Healthcare-Announces-Superior-Efficacy-Investigational-Long-Acting (3 pages).
Barrett et al., "Extended-Duration MK-8591-Eluting Implant as a Candidate for HIV Treatment and Prevention," Antimicrobial Agents and Chemotherapy 2018, vol. 62, issue 10, e01058-18 (13 pages).
Gulick et al., "Long-Acting HIV Drugs for Treatment and Prevention," Annu. Rev. Med. 2019. 70:137-150.
Remnar, "Making the Leap from Daily Oral Dosing to Long-Acting Injectables: Lessons from the Antipsychotics," Molecular Pharmaceutics, 2014, 11, pp. 1739-1749.
Senter et al., "The Role of Rat Serum Carboxylesterase in the Activation of Paclitaxel and Camptothecin Prodrugs," Cancer Research 56, 1996, pp. 1471-1474.
Banerjee et al., "Poly(ethylene glycol)-Prodrug Conjugates: Concept, Design and Applications", Journal of Drug Delivery, Hindawi Publishing Corporation, vol. 2012, 2012, pp. 1-17.
U.S. Appl. No. 62/639,667, filed Mar. 7, 2018/ GlaxoSmithKline Intellectual Property No. 2 Ltd.
U.S. Appl. No. 62/716,494, filed Aug. 9, 2018/ GlaxoSmithKline Intellectual Property No. 2 Ltd.
U.S. Appl. No. 62/724,647, filed Aug. 30, 2018/ GlaxoSmithKline Intellectual Property No. 2 Ltd.
U.S. Appl. No. 62/814,316, filed Mar. 6, 2019/ GlaxoSmithKline Intellectual Property No. 2 Ltd. and ViiV Healthcare Company.
U.S. Appl. No. 62/884,191, filed Aug. 8, 2019/ GlaxoSmithKline Intellectual Property No. 2 Ltd. and ViiV Healthcare Company.
U.S. Appl. No. 62/892,577, filed Aug. 28, 2019/ GlaxoSmithKline Intellectual Property No. 2 Ltd. and ViiV Healthcare Company.
U.S. Appl. No. 62/993,300, filed Mar. 23, 2020/ ViiV Healthcare Company.
WO 2019/171285/Sep. 12, 2019/ GlaxoSmithKline Intellectual Property No. 2 Ltd. and ViiV Healthcare Company.
WO 2020/031131/Feb. 13, 2020/ GlaxoSmithKline Intellectual Property No. 2 Ltd. and ViiV Healthcare Company.
WO 2020/044257/Mar. 5, 2020/ GlaxoSmithKline Intellectual Property No. 2 Ltd. and ViiV Healthcare Company.
PCT/IB2020/051878/Mar. 4, 2020/ GlaxoSmithKline Intellectual Property No. 2 Ltd. and ViiV Healthcare Company.

* cited by examiner

EFdA

Example 18

Mean plasma concentration-time profiles of Example 17 and EFdA after single IM injection of Example 17 at 20 mg equivalent of EFdA/kg in male Wistar Han rats (N = 3/time point)

Mean plasma concentration-time profiles of Example 18, EFdA and Met1 after single IM injection of Example 18 at 20 mg equivalent of EFdA/kg in male Wistar Han rats (N = 3/time point)

Mean plasma concentration-time profiles of Example 31, EFdA and Met1 after single IM injection of Example 31 at 20 mg equivalent of EFdA/kg in male Wistar Han rats (N = 3/time point)

Mean plasma concentration-time profiles of Example 32, EFdA, Met1 and Met2 after single IM injection of Example 32 at 20 mg equivalent of EFdA/kg in male Wistar Han rats (N = 3/time point)

Mean plasma concentration-time profiles of Example 37, EFdAA, Met1 and Met2 after single IM injection of Example 37 at 20 mg equivalent of EFdA/kg in male Wistar Han rats (N = 3/time point)

Mean plasma concentration-time profiles of Example 38, EFdA, Met1 and Met2 after single IM injection of Example 38 at 20 mg equivalent of EFdA/kg in male Wistar Han rats (N = 3/time point)

Mean plasma concentration-time profiles of Example 39, EFdA, Met1 and Met2 after single IM injection of Example 39 at 20 mg equivalent of EFdA/kg in male Wistar Han rats (N = 3/time point)

Mean plasma concentration-time profiles of Example 40 and EFdA after single IM injection of Example 40 at 20 mg equivalent of EFdA/kg in male Wistar Han rats (N = 3/time point)

Mean plasma concentration-time profiles of Example 42, EFdA, Met1 and Met2 after single IM injection of Example 42 at 20 mg/kg in male Wistar Han rats (N=3/time point)

Mean plasma concentration-time profiles of Example 45, EFdA, Met1 and Met2 after single IM injection of Example 45 at 20 mg equivalent of EFdA/kg in male Wistar Han rats (N = 3/time point)

Mean plasma concentration-time profiles of Example 61 and EfdA after single IM injection of Example 61 at 20 mg equivalent of EFdA/kg in male Wistar Han rats (N = 3/time point)

COMPOUNDS USEFUL IN HIV THERAPY

CROSS-REFERENCE TO RELATED APPLICATIONS

This application is filed as a continuation application under 35 U.S.C. § 111(a) claiming priority to International Application No. PCT/IB2020/051878 filed Mar. 4, 2020 which claims priority from U.S. Provisional Application No. 62/814,316 filed Mar. 6, 2019, the disclosure of which is incorporated by reference herein in its entirety.

FIELD OF THE INVENTION

The present invention relates to compounds, pharmaceutical compositions, and methods of use thereof in connection with individuals infected with HIV. In particular, such methods of use encompass e.g., methods for treating HIV and methods of preventing HIV.

BACKGROUND OF THE INVENTION

Human immunodeficiency virus type 1 (HIV-1) infection leads to the contraction of acquired immune deficiency disease (AIDS). The number of cases of HIV continues to rise, and currently an estimated over thirty-five million individuals worldwide suffer from HIV infection e.g., http://www.sciencedirect.com/science/article/pii/S235230181630087X?via %3Dihub Presently, long-term suppression of viral replication with antiretroviral drugs is the only option for treating HIV-1 infection. Indeed, the U.S. Food and Drug Administration has approved twenty-five drugs over six different inhibitor classes, which have been shown to greatly increase patient survival and quality of life. However, additional therapies are still believed to be required due to a number of issues including, but not limited to undesirable drug-drug interactions; drug-food interactions; non-adherence to therapy; drug resistance due to mutation of the enzyme target; and inflammation related to the immunologic damage caused by the HIV infection.

Currently, almost all HIV positive patients are treated with therapeutic regimens of antiretroviral drug combinations termed, highly active antiretroviral therapy ("HAART"). However, HAART therapies are often complex because a combination of different drugs must be administered often daily to the patient to avoid the rapid emergence of drug-resistant HIV-1 variants. Despite the positive impact of HAART on patient survival, drug resistance can still occur and the survival and quality of life are not normalized as compared to uninfected persons [Lohse Ann Intern Med 2007 146; 87-95]. Indeed, the incidence of several non-AIDS morbidities and mortalities, such as cardiovascular disease, frailty, and neurocognitive impairment, are increased in HAART-suppressed, HIV-infected subjects [Deeks Annu Rev Med 2011; 62:141-155]. This increased incidence of non-AIDS morbidity/mortality occurs in the context of, and is potentially caused by, elevated systemic inflammation related to the immunologic damage caused by HIV infection [Hunt J Infect Dis 2014][Byakagwa J Infect Dis 2014][Tenorio J Infect Dis 2014].

Modern antiretroviral therapy (ART) has the ability to effectively suppress HIV replication and improve health outcomes for HIV-infected persons, but is believed to not be capable of completely eliminating HIV viral reservoirs within the individual. HIV genomes can remain latent within mostly immune cells in the infected individual and may reactivate at any time, such that after interruption of ART, virus replication typically resumes within weeks. In a handful of individuals, the size of this viral reservoir has been significantly reduced and upon cessation of ART, the rebound of viral replication has been delayed [Henrich T J J Infect Dis 2013][Henrich T J Ann Intern Med 2014]. In one case, the viral reservoir was eliminated during treatment of leukemia and no viral rebound was observed during several years of follow-up [Hutter G N Engl J Med 2009]. These examples suggest the concept that reduction or elimination of the viral reservoir may be possible and can lead to viral remission or cure. As such, ways have been pursued to eliminate the viral reservoir, by direct molecular means, including excision of viral genomes with CRISPR/Cas9 systems, or to induce reactivation of the latent reservoir during ART so that the latent cells are eliminated. Induction of the latent reservoir typically results in either direct death of the latently infected cell or killing of the induced cell by the immune system after the virus is made visible. As this is performed during ART, viral genomes produced are believed to not result in the infection of new cells and the size of the reservoir may decay.

HAART therapies are often complex because a combination of different drugs must be administered often daily to the patient to avoid the rapid emergence of drug-resistant HIV-1 variants. Despite the positive impact of HAART on patient survival, drug resistance can still occur.

Current guidelines recommend that therapy includes three fully active drugs. See e.g. https://aidsinfo.nih.gov/guidelines. Additionally, two drug combinations may be employed as therapeutic regimens. Typically, first-line therapies combine two to three drugs targeting the viral enzymes reverse transcriptase and integrase. It is believed that sustained successful treatment of HIV-1-infected patients with antiretroviral drugs employ the continued development of new and improved drugs that are effective against HIV strains that have formed resistance to approved drugs. For example an individual on a regimen containing 3TC/FTC (lamivudine/emtricitabine) may select for the M184V mutation that reduces susceptibility to these drugs by >100 fold. See e g., https://hivdb.stanford.edu/dr-summary/resistance-notes/NRTI Another way to potentially address preventing formation of mutations is to increase patient adherence to a drug regimen. One manner that may be employed to accomplish this is by reducing the dosing frequency. For parenteral administration, it is believed to be advantageous to have drug substances with high lipophilicity in order to reduce solubility and limit the release rate within interstitial fluid. However, most nucleoside reverse transcriptase inhibitors are hydrophilic thereby potentially limiting their use as long acting parenteral agents.

There remains a need for compounds which may address the shortcomings set forth above.

SUMMARY OF THE INVENTION

In one aspect, the invention provides a compound of the formula (I):

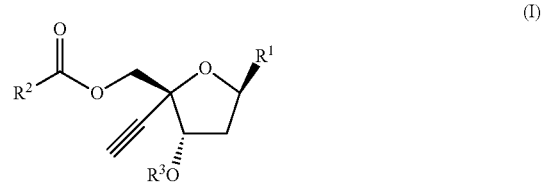

(I)

wherein:
R[1] is:

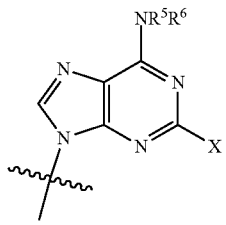

wherein:
X is selected from the group consisting of NH$_2$, F and Cl;
R[5] is selected from the group consisting of H and (C$_1$-C$_{14}$) alkyl;
R[6] is selected from the group consisting of H and —(C=O)—(C$_1$-C$_{14}$) alkyl;
R[2] is selected from the group consisting of (C$_1$-C$_{24}$) alkyl; (CH$_2$)$_{n1}$—O—(CH$_2$CH$_2$O)$_{n2}$—(C$_1$-C$_{14}$ alkyl) where n1 and n2 are integers independently selected from 1-4; —R[7]—NH—(C=O)—R[8] wherein R[7] may be (C$_1$-C$_{14}$) alkyl and R[8] may be independently selected from H and (C$_1$-C$_{14}$) alkyl; —R[9]—(C$_6$-C$_{14}$) aryl, wherein R[9] is a bond or (C$_1$-C$_6$) alkyl; —R[10]—(C$_3$-C$_{14}$) cycloalkyl, wherein R[10] is a bond or (C$_1$-C$_6$) alkyl; —(C$_1$-C$_{20}$) alkylene-(C=O)—O—R[11] wherein R[11] may be selected from H and (C$_1$-C$_{20}$)alkyl;

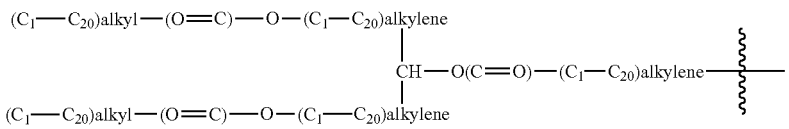

and;
R[3] is selected from the group consisting of H, —(C=O)—(C$_1$-C$_{24}$) alkyl; —(C=O)—O—(C$_1$-C$_{24}$) alkyl; and C$_3$-C$_{14}$ cycloalkyl; or
R[2] and R[3] join together to form a C$_3$ to C$_{28}$ cyclic structure; and
with the proviso that when R[2] is (C$_1$-C$_{14}$ alkyl) at least one of R[3], R[5] and R[6] is not H.

In another aspect, the invention provides pharmaceutical compositions comprising a compound of Formula (I) or a pharmaceutically acceptable salt thereof and an excipient.

In another aspect, the invention provides a method of treating an HIV infection in a subject at risk for developing an HIV infection, comprising administering to the subject a compound of Formula (I), or a pharmaceutically acceptable salt thereof.

In another aspect, the invention provides a method of preventing an HIV infection in a subject at risk for developing an HIV infection, comprising administering to the subject a compound of Formula (I), or a pharmaceutically acceptable salt thereof.

In another aspect, there is provided a compound of Formula (I) or a pharmaceutically acceptable salt thereof for use in therapy.

In another aspect, there is provided a compound of Formula (I) or a pharmaceutically acceptable salt thereof for use in treating an HIV infection.

In another aspect, there is provided a compound of Formula (I) or a pharmaceutically acceptable salt thereof for use in preventing an HIV infection.

In another aspect, there is provided the use of a compound of Formula (I) or a pharmaceutically acceptable salt thereof in the manufacture of a medicament for treating an HIV infection.

In another aspect, there is provided the use of a compound of Formula (I) or a pharmaceutically acceptable salt thereof in the manufacture of a medicament for preventing an HIV infection.

These and other aspects are encompassed by the invention as set forth herein.

DETAILED DESCRIPTION OF REPRESENTATIVE EMBODIMENTS

Figure 1A:
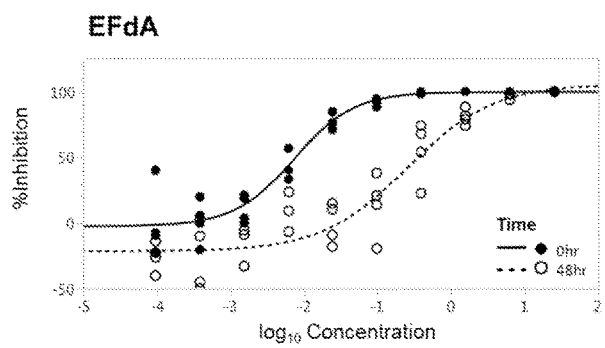
FIG. 1A illustrates an IC$_{50}$ curve shift from t=0 to t=48 h for EFdA.

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings, unless otherwise noted.

As used herein unless otherwise specified and subject to other embodiments set forth herein, "alkyl" e.g., refers to a monovalent saturated aliphatic hydrocarbyl group having e.g., from 1 to 24 carbon atoms, from 1 to 20 carbon atoms, from 1 to 14 carbon atoms or, from 1 to 6 carbon atoms. "$(C_x$-$C_y)$alkyl" refers to alkyl groups having from x to y carbon atoms. The term "alkyl" includes, by way of example, linear and branched hydrocarbyl groups such as, e.g., methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). For the purposes of the invention, alkyl may be interpreted to encompass alkylene groups defined herein.

Subject to various embodiments set forth herein, "Alkylene" or "alkylene" refers to divalent e.g., saturated aliphatic hydrocarbyl groups having from 1 to 6 carbon atoms. The alkylene groups include branched and straight chain hydrocarbyl groups. For example, "$(C_1$-$C_6)$alkylene" is meant to include methylene, ethylene, propylene, 2-methypropylene, dimethylethylene, pentylene, and so forth. As such, the term "propylene" could be exemplified by the following structure:

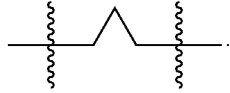 [SMILES: *CCC*]

Likewise, the term "dimethylbutylene" could be exemplified by any of the following three structures or more:

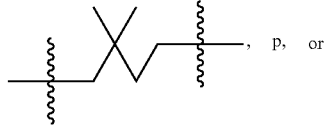, p, or

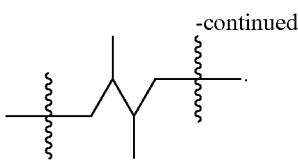

Furthermore, the term "$(C_1-C_6)$alkylene" is meant to include such branched chain hydrocarbyl groups as cyclopropylmethylene, which could be exemplified by the following structure:

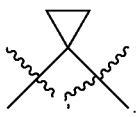

"Alkenyl" refers to a linear or branched hydrocarbyl group having, e.g., from 2 to 10 carbon atoms and in some embodiments from 2 to 6 carbon atoms or 2 to 4 carbon atoms and having at least 1 site of vinyl unsaturation ($>C=C<$). For example, $(C_x-C_y)$alkenyl refers to alkenyl groups having from x to y carbon atoms and is meant to include for example, ethenyl, propenyl, isopropylene, 1,3-butadienyl, and the like.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, $(C_2-C_6)$alkynyl is meant to include ethynyl, propynyl, and the like.

"Alkoxy" refers to the group —O-alkyl wherein alkyl is defined herein, e.g., $C_1$ to $C_6$ alkoxy. Alkoxy includes, by way of example, methoxy, ethoxy, n-propoxy, isopropoxy, n-butoxy, t-butoxy, sec-butoxy, and n-pentoxy.

""Aryl" refers to an aromatic group of from e.g., 6 to 14 carbon atoms or preferably 5 to 6 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring). As set forth herein, aryl groups may be substituted.

"AUC" refers to the area under the plot of plasma concentration of drug (not logarithm of the concentration) against time after drug administration.

"Cycloalkyl" refers to a saturated or partially saturated cyclic group of from e.g, 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8-tetrahydronaphthalene-5-yl). The term "cycloalkyl" includes cycloalkenyl groups, such as cyclohexenyl. Examples of cycloalkyl groups include, for instance, adamantyl, cyclopropyl, cyclobutyl, cyclohexyl, cyclopentyl, cyclooctyl, cyclopentenyl, and cyclohexenyl. Examples of cycloalkyl groups that include multiple bicycloalkyl ring systems are bicyclohexyl, bicyclopentyl, bicyclooctyl, and the like. Two such bicycloalkyl multiple ring structures are exemplified and named below:

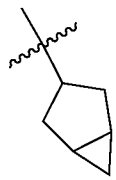

bicyclohexyl, and

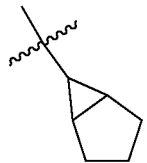

bicyclohexyl.

"$(C_u-C_v)$cycloalkyl" refers to cycloalkyl groups having u to v carbon atoms.

"$EC_{50}$" refers to the concentration of a drug that gives half-maximal response.

"$IC_{50}$" refers to the half-maximal inhibitory concentration of a drug. Sometimes, it is also converted to the $pIC_{50}$ scale ($-\log IC_{50}$), in which higher values indicate exponentially greater potency.

"Haloalkyl" refers to substitution of an alkyl group with 1 to 3 halo groups (e.g., bifluoromethyl or trifluoromethyl).

"Heteroaryl" refers to an aromatic group of from 1 to 14 carbon atoms, e.g., 6 heteroatoms selected from oxygen, nitrogen, and sulfur and includes single ring (e.g. imidazolyl) and (e.g. benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6, 7,8-tetrahydroquinolin-3-yl). In some embodiments, the nitrogen and/or the sulfur ring atom(s) of the heteroaryl group are optionally oxidized to provide for the N-oxide ($N{\rightarrow}O$), sulfinyl, or sulfonyl moieties. More specifically the term heteroaryl includes, but is not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

"Heterocycle" refers "Heterocyclic" or "heterocycle" or "heterocycloalkyl" or "heterocyclyl" refers to a saturated or partially saturated cyclic group having from 1 to 14 carbon atoms and from 1 to 6 heteroatoms selected from nitrogen, sulfur, phosphorus or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g.

1,2,3,4-tetrahydroquinoline-3-yl, 5,6,7,8-tetrahydroquinoline-6-yl, and decahydroquinolin-6-yl). In one embodiment, the nitrogen, phosphorus and/or sulfur atom(s) of the heterocyclic group are optionally oxidized to provide for the N-oxide, phosphinane oxide, sulfinyl, sulfonyl moieties. More specifically the heterocyclyl includes, but is not limited to, tetrahydropyranyl, piperidinyl, piperazinyl, 3-pyrrolidinyl, 2-pyrrolidon-1-yl, morpholinyl, and pyrrolidinyl. A prefix indicating the number of carbon atoms (e.g., $C_3$-$C_{10}$) refers to the total number of carbon atoms in the portion of the heterocyclyl group exclusive of the number of heteroatoms.

"Fused heterocyclic" or "fused heterocycle" refer to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused heterocyclic group:

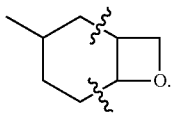

"Cyclic structure" refers to a series of carbon atoms connected to form a ring. In various embodiments, the cyclic structure may include e.g., cycloalkyl and heterocyclic groups. As noted herein, "$C_x$ to $C_y$ cyclic structure" refers to a cyclic structure wherein x and y are set forth such that the structure may contain x to y carbon atoms. Such a structure may be optionally substituted as set forth herein.

"Compound", "compounds", "chemical entity", and "chemical entities" as used herein refers to a compound encompassed by the generic formulae (I), (Ia), (II) and (IIa) disclosed herein, any subgenus of these generic formulae, and any forms of the compounds within the generic and subgeneric formulae, including the racemates, stereoisomers, and tautomers of the compound or compounds.

The term "heteroatom" means nitrogen, oxygen, or sulfur and includes any oxidized form of phosphorus, nitrogen, such as N(O) {$N^+$—$O^-$} and sulfur such as S(O) and S(O)$_2$, and the quaternized form of any basic nitrogen.

"Oxo" refers to a (=O) group.

"Polymorphism" refers to when two or more clearly different phenotypes exist in the same population of a species where the occurrence of more than one form or morph. In order to be classified as such, morphs must occupy the same habitat at the same time and belong to a panmictic population (one with random mating).

"Protein binding" refers to the binding of a drug to proteins in blood plasma, tissue membranes, red blood cells and other components of blood.

"Protein shift" refers to determining a binding shift by comparing the $EC_{50}$ values determined in the absence and presence of human serum.

"Racemates" refers to a mixture of enantiomers. In an embodiment of the invention, the compounds of Formulas I, Ia, II and IIa or pharmaceutically acceptable salts thereof, are enantiomerically enriched with one enantiomer wherein all of the chiral carbons referred to are in one configuration. In general, reference to an enantiomerically enriched compound or salt, is meant to indicate that the specified enantiomer will comprise more than 50% by weight of the total weight of all enantiomers of the compound or salt.

"Solvate" or "solvates" of a compound refer to those compounds, as defined above, which are bound to a stoichiometric or non-stoichiometric amount of a solvent. Solvates of a compound includes solvates of all forms of the compound. In certain embodiments, solvents are volatile, non-toxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The term 'atropisomer' refers to a stereoisomer resulting from an axis of asymmetry. This can result from restricted rotation about a single bond where the rotational barrier is high enough to allow differentiation of the isomeric species up to and including complete isolation of stable non-interconverting diastereomer or enantiomeric species. One skilled in the art will recognize that upon installing a nonsymmetrical $R^x$ to core, the formation of atropisomers is possible. In addition, once a second chiral center is installed in a given molecule containing an atropisomer, the two chiral elements taken together can create diastereomeric and enantiomeric stereochemical species. Depending upon the substitution about the Cx axis, interconversion between the atropisomers may or may not be possible and may depend on temperature. In some instances, the atropisomers may interconvert rapidly at room temperature and not resolve under ambient conditions. Other situations may allow for resolution and isolation but interconversion can occur over a period of seconds to hours or even days or months such that optical purity is degraded measurably over time. Yet other species may be completely restricted from interconversion under ambient and/or elevated temperatures such that resolution and isolation is possible and yields stable species. When known, the resolved atropisomers were named using the helical nomenclature. For this designation, only the two ligands of highest priority in front and behind the axis are considered. When the turn priority from the front ligand 1 to the rear ligand 1 is clockwise, the configuration is P, if counterclockwise it is M.

"As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication. "Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002. Pharmaceutically acceptable salts may be prepared in situ during the final isolation and purification of the compound, or by separately reacting the purified compound in its free acid or free base form with a suitable base or acid, respectively. Further to the above, illustrative pharmaceutically acceptable acid salts of the compounds of the present invention can be prepared from the following acids, including, without limitation formic, acetic, propionic, benzoic, succinic, glycolic, gluconic, lactic, maleic, malic, tartaric, citric, nitic, ascorbic, glucuronic, maleic, fumaric, pyruvic, aspartic, glutamic, benzoic, hydrochloric, hydrobromic, hydroiodic, isocitric, trifluoroacetic, pamoic, propionic, anthranilic, mesylic, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, p-hydroxybutyric, galactaric and galacturonic acids. Preferred pharmaceutically acceptable salts include the salts of hydrochloric acid and trifluoroacetic acid. Illustrative pharmaceutically acceptable inorganic base salts of the compounds of the present invention include metallic ions. More preferred metallic ions include, but are not limited to, appropriate alkali metal salts, alkaline earth metal salts and other physiological acceptable metal ions. Salts derived from inorganic bases include aluminum, ammonium, calcium, copper, ferric, ferrous, lithium, magnesium, manganic salts, manganous, potassium, sodium, zinc, and the like and in their usual valences. Exemplary base salts include aluminum, calcium, lithium, magnesium, potassium, sodium and zinc. Other exemplary base salts include the ammonium, calcium, magnesium, potassium, and sodium salts. Still other exemplary base salts include, for example, hydroxides, carbonates, hydrides, and alkoxides including NaOH, KOH, $Na_2CO_3$, $K_2CO_3$, NaH, and potassium-t-butoxide. Salts derived from pharmaceutically acceptable organic non-toxic bases include salts of primary, secondary, and tertiary amines, including in part, trimethylamine, diethylamine, N,N'-dibenzylethylenediamine, chloroprocaine, choline, diethanolamine, ethylenediamine, meglumine (N-methylglucamine) and procaine; substituted amines including naturally occurring substituted amines; cyclic amines; quaternary ammonium cations; and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. All of the above salts can be prepared by those skilled in the art by conventional means from the corresponding compound of the present invention. For example, the pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salt may precipitate from solution and be collected by filtration or may be recovered by evaporation of the solvent. The degree of ionisation in the salt may vary from completely ionised to almost non-ionised. Lists of suitable salts are found in *Remington's Pharmaceutical Sciences*, 17th ed., Mack Publishing Company, Easton, Pa., 1985, p. 1418, the disclosure of which is hereby incorporated by reference only with regards to the lists of suitable salts.

"Patient" or "subject" refers to mammals and includes humans and non-human mammals. Most preferably, a "patient" is construed to refer to humans.

Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Prevention or "preventing" a disease in a patient refers to the prophylactic administration of a drug to substantially diminish the likelihood or severity of a disorder or biological manifestation thereof, or to delay the onset of such disorder or biological manifestation thereof.

Where specific compounds or generic formulas are drawn that have aromatic rings, such as aryl or heteroaryl rings, then it will be understood by one of still in the art that the particular aromatic location of any double bonds are a blend of equivalent positions even if they are drawn in different locations from compound to compound or from formula to formula. For example, in the two pyridine rings (A and B) below, the double bonds are drawn in different locations, however, they are known to be the same structure and compound:

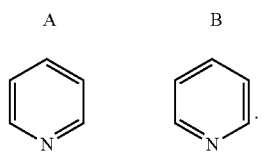

The present invention includes compounds as well as their pharmaceutically acceptable salts. Accordingly, the word "or" in the context of "a compound or a pharmaceutically acceptable salt thereof" is understood to refer to either: 1) a compound alone or a compound and a pharmaceutically acceptable salt thereof (alternative), or 2) a compound and a pharmaceutically acceptable salt thereof (in combination).

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—. In a term such as "—C($R^x$)$_2$—", it should be understood that the two $R^x$ groups can be the same, or they can be different if $R^x$ is defined as having more than one possible identity. In addition, certain substituents are drawn as —$R^xR^y$, where the "-" indicates a bond adjacent to the parent molecule and $R^y$ being the terminal portion of the functionality. Similarly, it is understood that the above definitions are not intended to include impermissible substitution patterns (e.g., methyl substituted with 5 fluoro groups). Such impermissible substitution patterns are well known to the skilled artisan.

In one aspect, there is provided a compound of the formula (I):

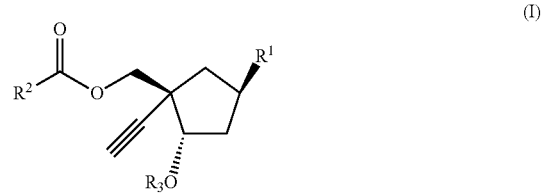

wherein:
R₁ is:

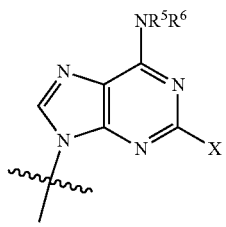

wherein:
X is selected from the group consisting of NH₂, F and Cl;
R⁵ is selected from the group consisting of H and (C₁-C₁₄) alkyl;
R⁶ is selected from the group consisting of H and —(C=O)—(C₁-C₁₄) alkyl;
R² is selected from the group consisting of (C₁-C₂₄) alkyl; (CH₂)$_{n1}$—O—(CH₂CH₂O)$_{n2}$—(C₁-C₁₄alkyl) where n1 and n2 are integers independently selected from 1-4 —R⁷—NH—(C=O)—R⁸ wherein R⁷ may be (C₁-C₁₄) alkyl and R⁸ may be independently selected from H and (C₁-C₁₄) alkyl; —R⁹—(C₆-C₁₄) aryl, wherein R⁹ is a bond or (C₁-C₆) alkyl; —R¹⁰—(C₃-C₁₄) cycloalkyl, wherein R¹⁰ is a bond or (C₁-C₆) alkyl; —(C₁-C₂₀) alkylene-(C=O)—O—R¹¹ wherein R¹¹ may be selected from H and (C₁-C₂₀)alkyl; and

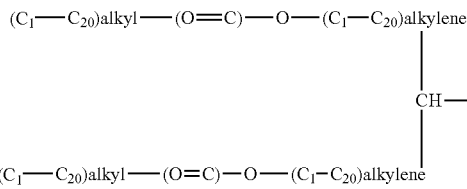

and;
R³ is selected from the group consisting of H, —(C=O)—(C₁-C₂₄) alkyl; —(C=O)—O—(C₁-C₂₄) alkyl; and C₃-C₁₄ cycloalkyl, or R² and R³ join together to form a C₃ to C₂₈ cyclic structure; and with the proviso that when R² is (C₁-C₁₄ alkyl) at least one of R³, R⁵ and R⁶ is not H.

In another aspect, the invention provides a compound of the formula (Ia):

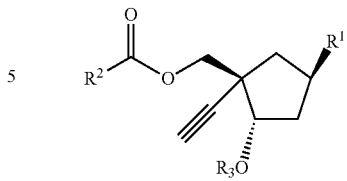

wherein:
R₁ is:

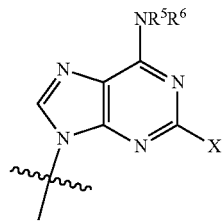

wherein:
X is selected from the group consisting of NH₂, F and Cl;
R⁵ is selected from the group consisting of H and (C₁-C₁₄) alkyl;
R⁶ is selected from the group consisting of H and —(C=O)—(C₁-C₁₄) alkyl;

R² is selected from the group consisting of (C₁-C₂₄) alkyl; C₃-C₁₄ cycloalkyl; (CH₂)$_{n1}$—O—(CH₂CH₂O)$_{n2}$—(C₁-C₁₄ alkyl) where n1 and n2 are integers independently selected from 1-4, —R⁷—NH—(C=O)—R⁸ wherein R⁷ may be (C₁-C₁₄) alkyl and R⁸ may be independently selected from H and (C₁-C₁₄) alkyl; —R⁹—(C₆-C₁₄) aryl, wherein R⁹ is a bond or (C₁-C₆) alkyl; —R¹⁰—(C₃-C₁₄) cycloalkyl, wherein R¹⁰ is a bond or (C₁-C₆) alkyl; —(C₁-C₂₀) alkylene-(C=O)—O—R¹¹ wherein R¹¹ may be selected from H and (C₁-C₂₀)alkyl; and

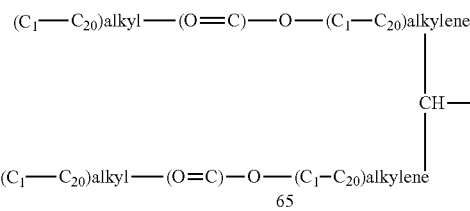

and;

R³ is selected from the group consisting of H, —(C=O)—(C₁-C₂₄) alkyl; —(C=O)—O—(C₁-C₂₄) alkyl; and C₃-C₁₄ cycloalkyl; or R² and R³ join together to form a C₃ to C₂₈ cyclic structure; and with the proviso that when R² is (C₁-C₁₈ alkyl) at least one of R³, R⁵ and R⁶ is not H.

In another aspect, there is provided a compound of the formula (II):

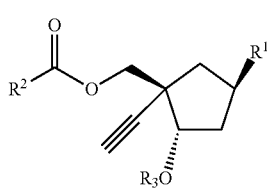

(II)

wherein:

R₁ is:

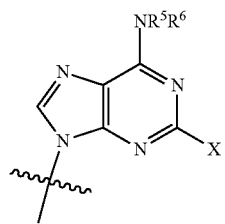

wherein

X is selected from the group consisting of NH₂, F and Cl;

R⁵ is selected from the group consisting of H and (C₁-C₁₄) alkyl;

R⁶ is selected from the group consisting of H and —(C=O)—(C₁-C₁₄) alkyl;

R² is selected from the group consisting of (C₁-C₂₄) alkyl; (CH₂)ₙ₁—O—(CH₂CH₂O)ₙ₂—(C₁-C₁₄ alkyl) where n1 and n2 are integers independently selected from 1-4 —R⁷—NH—(C=O)—R⁸ wherein R⁷ may be (C₁-C₁₄) alkyl and R⁸ may be independently selected from H and (C₁-C₁₄) alkyl; —R⁹—(C₆-C₁₄) aryl, wherein R⁹ is a bond or (C₁-C₆) alkyl; —R¹⁰—(C₃-C₁₄) cycloalkyl, wherein R¹⁰ is a bond or (C₁-C₆) alkyl; —(C₁-C₂₀) alkylene-(C=O)—O—R¹¹ wherein R¹¹ may be selected from H and (C₁-C₂₀) alkyl; and and;

R³ is selected from the group consisting of H, —(C=O)—(C₁-C₂₄) alkyl; —(C=O)—O—(C₁-C₂₄) alkyl; and C₃-C₁₄ cycloalkyl; or R² and R³ join together to form a C₃ to C₂₈ cyclic structure.

In another aspect, the invention provides a compound of the formula (IIa):

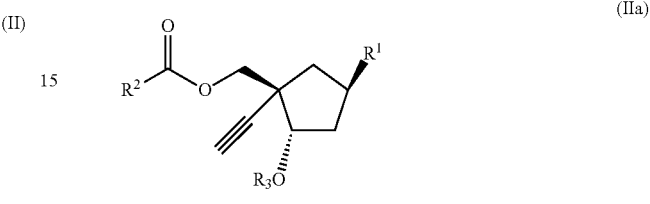

(IIa)

wherein:

R₁ is:

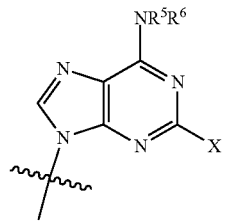

wherein:

X is selected from the group consisting of NH₂, F and Cl;

R⁵ is selected from the group consisting of H and (C₁-C₁₄) alkyl;

R⁶ is selected from the group consisting of H and —(C=O)—(C₁-C₁₄) alkyl;

R² is selected from the group consisting of (C₁-C₂₄) alkyl; C₃-C₁₄ cycloalkyl; (CH₂)ₙ₁—O—(CH₂CH₂O)ₙ₂—(C₁-C₁₄alkyl) where n1 and n2 are integers independently selected from 1-4, —R⁷—NH—(C=O)—R⁸ wherein R⁷ may be (C₁-C₁₄) alkyl and R⁸ may be independently selected from H and (C₁-C₁₄) alkyl; —R⁹—(C₆-C₁₄) aryl, wherein R⁹ is a bond or (C₁-C₆) alkyl; —R¹⁰—(C₃-C₁₄) cycloalkyl, wherein R¹⁰ is a bond or (C₁-C₆) alkyl; —(C₁-C₂₀) alkylene-(C=O)—O—R¹¹ wherein R¹¹ may be selected from H and (C₁-C₂₀) alkyl; and

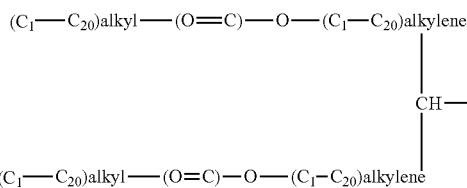

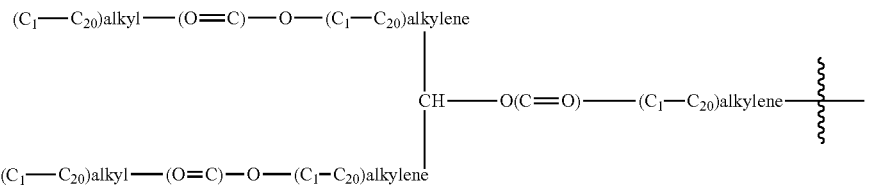

and;

R³ is selected from the group consisting of H, —(C=O)—($C_1$-$C_{24}$) alkyl; —(C=O)—O—($C_1$-$C_{24}$) alkyl; and $C_3$-$C_{14}$ cycloalkyl; or R² and R³ join together to form a $C_3$ to $C_{28}$ cyclic structure.

In one embodiment of the present invention, there is provided a compound of the formula (I), (Ia), (II) or (IIa), wherein X is F, and R⁵ and R⁶ are each H.

In one embodiment of the present invention, there is provided a compound of the formula (I), (Ia), (II) or (IIa), wherein X is F, R⁵ is H and R⁶ is —(C=O)—($C_1$-$C_{14}$) alkyl In one embodiment of the present invention, there is provided a compound of the formula (I), (Ia), (II) or (IIa), wherein R³ is H.

In one embodiment of the present invention, there is provided a compound of the formula (I), (Ia), (II) or (IIa), wherein R³ is —(C=O)—($C_1$-$C_{20}$) alkyl In one embodiment of the present invention, there is provided a compound of the formula (I), (Ia), (II) or (IIa), wherein R² is $C_6$ aryl.

In one embodiment of the present invention, there is provided a compound of the formula (I), (Ia), (II) or (IIa), wherein R² is $C_6$ cycloalkyl.

In one embodiment of the present invention, there is provided a compound of the formula (I), (Ia), (II) or (IIa), wherein R² is —($CH_2$)$_{n1}$—O—($CH_2CH_2O$)$_{n2}$—($C_1$-$C_{14}$alkyl) where n1 and n2 are integers independently selected from 1-4, more preferably n1 and n2 are independently selected from 1 and 2. In one preferred embodiment, R² is of the formula —($CH_2$)—O—($CH_2CH_2O$)$_{n2}$—($C_1$-$C_2$ alkyl) wherein n2 is 1 or 2.

In one embodiment of the present invention, there is provided a compound of the formula (I), (Ia), (II) or (IIa), wherein R¹⁰ is H.

In one embodiment of the present invention, there is provided a compound of the formula (I), (Ia), (II) or (IIa), wherein R¹⁰ is $C_1$ alkyl.

In one preferred embodiment of the present invention, R² is —($CH_2$)$_8$—(C=O)—OH. In one preferred embodiment, R² is —($CH_2$)$_{12}$—(C=O)—OH. In one preferred embodiment, R² is —($CH_2$)$_{18}$—(C=O)—OH.

In one embodiment of the present invention, there is provided a compound of the formula (I), (Ia), (II) or (IIa), wherein R² is —($CH_2$)$_3$—(C=O)—O—$C_{14}$ alkyl.

In one embodiment of the present invention, there is provided a compound of the formula (I), (Ia), (II) or (IIa), wherein R² is of the formula:

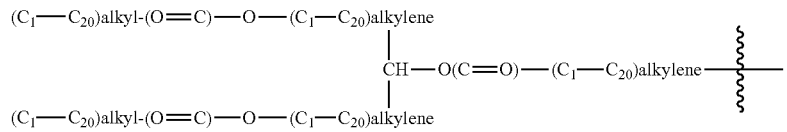

In one embodiment of the present invention, there is provided a compound of the formula (I), (Ia), (II) or (IIa), wherein R² is of the formula:

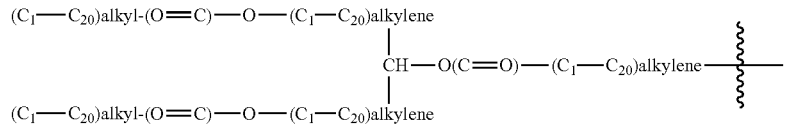

In one embodiment of the present invention, there is provided a compound of the formula (I), (Ia), (II) or (IIa), wherein R³ is H, X is F, R⁵ is H, R⁶ is H, and R² is —R⁷—NH—(C=O)—R⁸.

In one embodiment of the present invention, there is provided a compound of the formula (I), (Ia), (II) or (IIa), wherein R³ is H, X is F, R⁵ is H, R⁶ is H, and R² is —($C_1$-$C_{20}$) alkylene-(C=O)—O—R¹¹

In one embodiment of the present invention, there is provided a compound of the formula (I), (Ia), (II) or (IIa), wherein R⁹ is a bond.

In one embodiment of the present invention, there is provided a compound of the formula (I), (Ia), (II) or (IIa), wherein R⁹ is $C_1$alkyl.

In one embodiment of the present invention, there is provided a compound of the formula (I), (Ia), (II) or (IIa), wherein R² is ($C_1$-$C_{24}$) alkyl and R³ is —(C=O)—($C_1$-$C_{20}$) alkyl In one embodiment of the present invention, there is provided a compound of the formula (I), (Ia), (II) or (IIa), wherein R² is ($C_1$-$C_{24}$) alkyl, R⁵ is H and R⁶ is —(C=O)—($C_1$-$C_{14}$) alkyl.

In one embodiment of the present invention, there is provided a compound of the formula (I), (Ia), (II) or (IIa), wherein R³ is H, R⁵ is H, R⁶ is H, and R² is R⁷—NH—(C=O)—R⁸ wherein R⁷ ($C_1$-$C_4$) alkyl and R⁸ is ($C_1$-$C_{14}$) alkyl.

In one embodiment of the present invention, there is provided a compound of the formula (I), (Ia), (II) or (IIa), wherein $R^3$ is —(C=O)—($C_1$-$C_{24}$) alkyl, $R^5$ is H, $R^6$ is H, $R^2$ is —($C_1$-$C_{24}$) alkyl and X is F.

In one embodiment of the present invention, there is provided a compound of the formula (I), (Ia), (II) or (IIa), wherein $R^3$ is —(C=O)—O—($C_1$-$C_{24}$) alkyl, $R^5$ is H, $R^6$ is H, $R^2$ is —($C_1$-$C_{24}$) alkyl and X is F.

In one embodiment of the present invention, there is provided a compound wherein $R^2$ and $R^3$ join together to form a $C_3$ to $C_{28}$ cyclic structure. More preferably, in such an embodiment, $R^3$ contains —(C=O)— group attached at one end to the oxygen substituent of formula (I); in preferred embodiments, accordingly, $R^2$ and $R^3$ join together wherein $R^2$ is —$(CH_2)_p$— and $R^3$ is —(C=O)—$(CH_2)_q$— wherein p and q are selected such that a $C_3$ to $C_{28}$ cyclic structure is formed. In a most preferred embodiment, p and q are selected such that a $C_8$ to $C_{18}$ structure is formed.

The compounds of the present invention may be optionally substituted by one or more substituents. For example, in one embodiment, each of $R^2$, $R^3$, $R^5$, $R^6$, $R^7$, $R^8$, $R^9$ $R^{10}$ and $R^{11}$ may be independently and optionally substituted by one or more ($C_1$-$C_{14}$) alkyl, Cl, F, oxo, or ($C_1$-$C_6$) alkoxy. In another embodiment, each of $R^2$, $R^3$, $R^5$, $R^6$, $R^7$, $R^8$, $R^9$ $R^{10}$ and $R^{11}$ may be independently and optionally substituted by one or more ($C_1$-$C_6$) alkyl, Cl, F, oxo, or ($C_1$-$C_6$) alkoxy. Preferably, as an example, each of the ($C_6$-$C_{14}$) aryl and ($C_3$-$C_{14}$) cycloalkyl groups may be optionally substituted by one or more substituents from ($C_1$-$C_5$) alkyl, Cl, F, oxo, or ($C_1$-$C_6$) alkoxy. In various preferred embodiments, each of $R^2$, $R^3$, $R^5$, $R^6$, $R^7$, $R^8$, $R^9$ $R^{10}$ and $R^{11}$, and in particular ($C_6$-$C_{14}$) aryl (e.g., ($O_6$) aryl may be substituted by one or more —C—O—(C=O)—($C_1$-$C_6$ alkyl).

In another aspect of the present invention, the invention may encompass various individual compounds. As an example, such specific compounds may be selected from the group consisting of Table 1:

TABLE 1

| Example | Structure | Chemical Name |
|---|---|---|
| 1 | 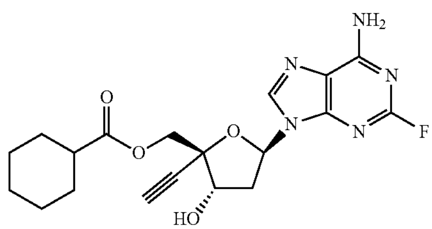 [SMILES: C#C[C@]1(COC(=O)C2CCCCC2)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl cyclohexanecarboxylate |
| 2 | 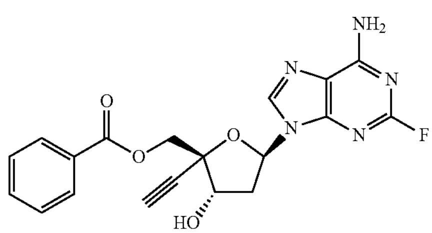 [SMILES: C#C[C@]1(COC(=O)c2ccccc2)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl) methyl benzoate |
| 3 | 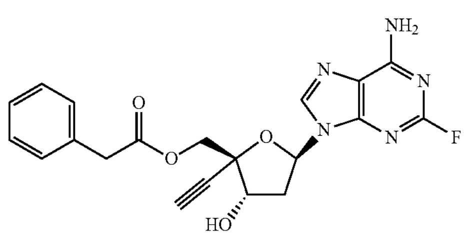 [SMILES: C#C[C@]1(COC(=O)Cc2ccccc2)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl 2-phenylacetate |
| 4 | 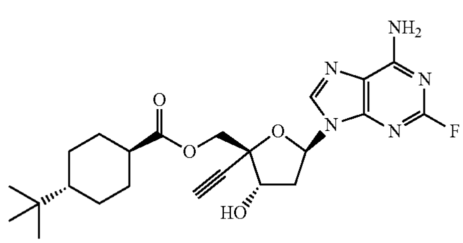 [SMILES: C#C[C@]1(COC(=O)[C@H]2CC[C@H](C(C)(C)C)CC2)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl trans-4-(tert-butyl)cyclohexane-1 carboxylate |

TABLE 1-continued

| Example | Structure | Chemical Name |
|---|---|---|
| 5 | 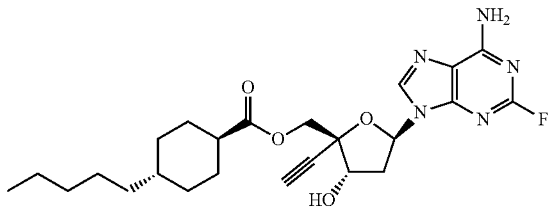 [SMILES: C#C[C@]1(COC(=O)[C@H]2CC[C@H](CCCCC)CC2)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl trans-4-pentylcyclohexane-1-carboxylate |
| 6 | 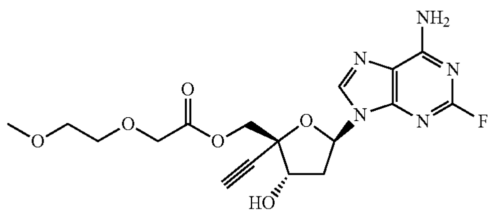 [SMILES: C#C[C@]1(COC(=O)COCCOC)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl 2-(2-methoxyethoxy)acetate |
| 7 | 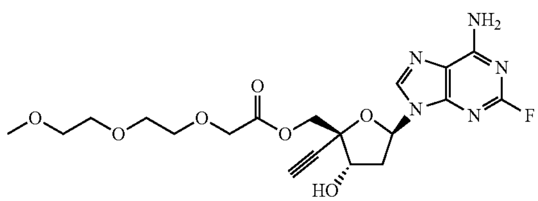 [SMILES: C#C[C@]1(COC(=O)COCCOCCOC)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl 2-(2-(2-methoxyethoxy)ethoxy)acetate |
| 8 | 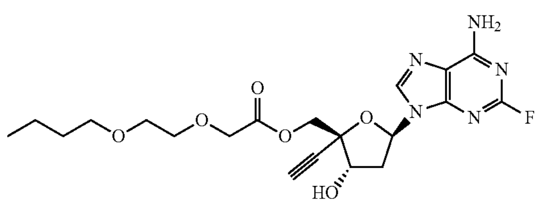 [SMILES: C#C[C@]1(COC(=O)COCCOCCCC)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl 2-(2-butoxyethoxy)acetate |
| 9 | 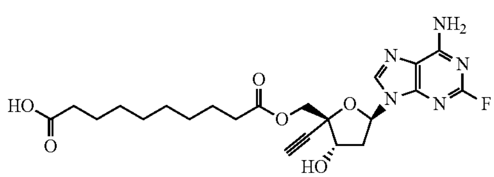 [SMILES: C#C[C@]1(COC(=O)CCCCCCCCC(=O)O)O[C@@H](n2cnc3c(N)nc(F)nc32)C[C@@H]1O] | 10-(((2R,3S,5R)-5-(6-amino-2-fluoro-9H-purin-9-yl)-2-ethynyl-3-hydroxytetrahydrofuran-2-yl)methoxy)-10-oxodecanoic acid |
| 10 | 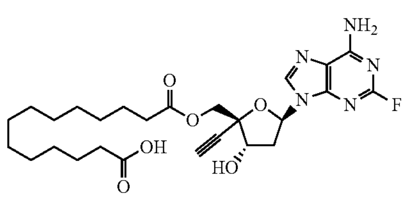 [SMILES: C#C[C@]1(COC(=O)CCCCCCCCCCCCC(=O)O)O[C@@H](n2cnc3c(N)nc(F)nc32)C[C@@H]1O] | 14-(((2R,3S,5R)-5-(6-amino-2-fluoro-9H-purin-9-yl)-2-ethynyl-3-hydroxytetrahydrofuran-2-yl)methoxy)-14-oxotetradecanoic acid |
| 11 | 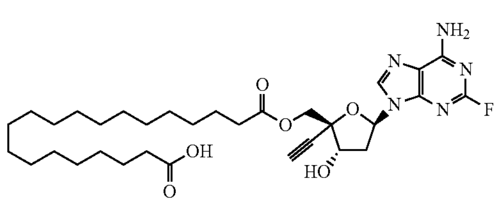 [SMILES: C#C[C@]1(COC(=O)CCCCCCCCCCCCCCCCCCC(=O)O)O[C@@H](n2cnc3c(N)nc(F)nc32)C[C@@H]1O] | 20-(((2R,3S,5R)-5-(6-amino-2-fluoro-9H-purin-9-yl)-2-ethynyl-3-hydroxytetrahydrofuran-2-yl)methoxy)-20-oxoicosanoic acid |

TABLE 1-continued

| Example | Structure | Chemical Name |
|---|---|---|
| 12 | 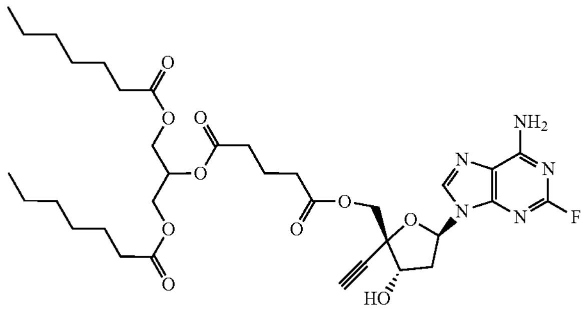 [SMILES: C#C[C@]1(COC(=O)CCCC(=O)OC(COC(=O)CCCCCC)COC(=O)CCCCCC)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl (1,3-bis(heptanoyloxy)propan-2-yl) glutarate |
| 13 | 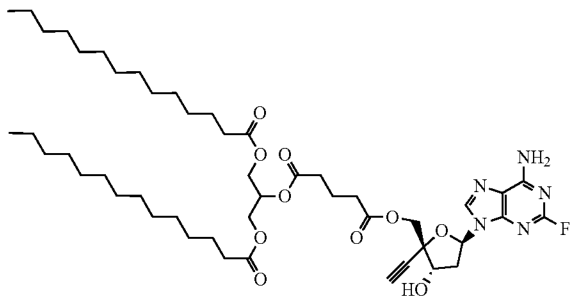 [SMILES: C#C[C@]1(COC(=O)CCCC(=O)OC(COC(=O)CCCCCCCCCCCCC)COC(=O)CCCCCCCCCCCCC)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl (1,3-bis(tetradecanoyloxy)propan-2-yl) glutarate |
| 14 | 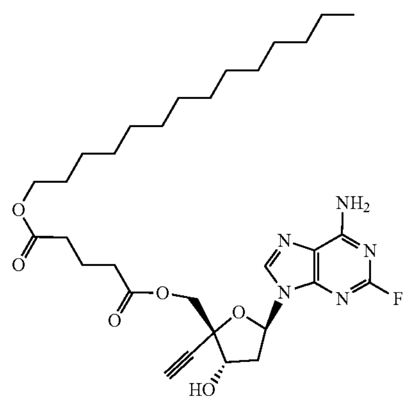 [SMILES: C#C[C@]1(COC(=O)CCCC(=O)OCCCCCCCCCCCCCC)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl tetradecyl glutarate |
| 15 | 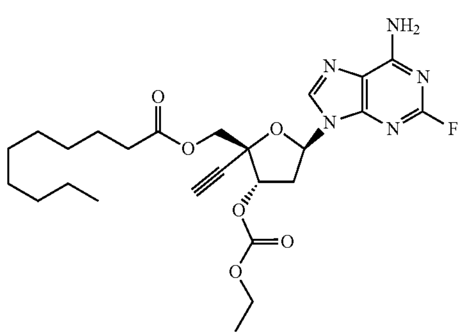 [SMILES: C#C[C@]1(COC(=O)CCCCCCCCC)O[C@@H](n2cnc3c(N)nc(F)nc32)C[C@@H]1OC(=O)OCC] | ((2R,3S,5R)-5-(6-amino-2-fluoro-9H-purin-9-yl)-3-((ethoxycarbonyl)oxy)-2-ethynyltetrahydrofuran-2-yl) methyl decanoate |

TABLE 1-continued

| Example | Structure | Chemical Name |
|---|---|---|
| 16 | 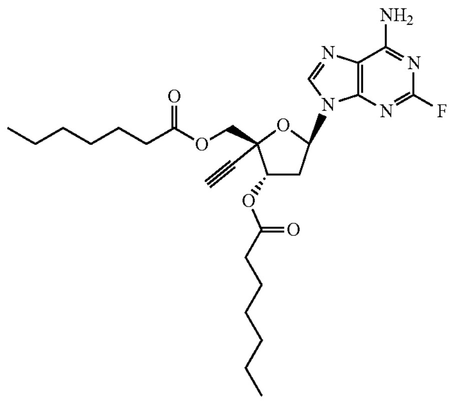 [SMILES: C#C[C@]1(COC(=O)CCCCCC)O[C@@H](n2cnc3c(N)nc(F)nc32)C[C@@H]1OC(=O)CCCCCC] | (2R,3S,5R)-5-(6-amino-2-fluoro-9H-purin-9-yl)-2-ethynyl-2-((heptanoyloxy)methyl)tetrahydrofuran-3-yl heptanoate |
| 17 | 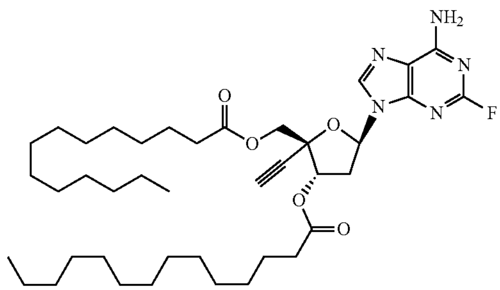 [SMILES: C#C[C@]1(COC(=O)CCCCCCCCCCCCC)O[C@@H](n2cnc3c(N)nc(F)nc32)C[C@@H]1OC(=O)CCCCCCCCCCCCC] | (2R,3S,5R)-5-(6-amino-2-fluoro-9H-purin-9-yl)-2-ethynyl-2-((tetradecanoyloxy)methyl)tetrahydrofuran-3-yl tetradecanoate |
| 18 | 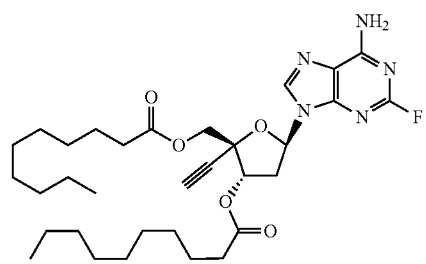 [SMILES: C#C[C@]1(COC(=O)CCCCCCCCC)O[C@@H](n2cnc3c(N)nc(F)nc32)C[C@@H]1OC(=O)CCCCCCCCC] | (2R,3S,5R)-5-(6-amino-2-fluoro-9H-purin-9-yl)-2-((decanoyloxy)methyl)-2-ethynyltetrahydrofuran-3-yl decanoate |
| 19 | 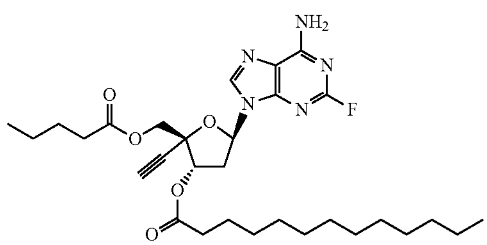 [SMILES: C#C[C@]1(COC(=O)CCCC)O[C@@H](n2cnc3c(N)nc(F)nc32)C[C@@H]1OC(=O)CCCCCCCCCCCC] | (2R,3S,5R)-5-(6-amino-2-fluoro-9H-purin-9-yl)-2-ethynyl-2-((pentanoyloxy)methyl)tetrahydrofuran-3-yl tridecanoate |
| 20 | 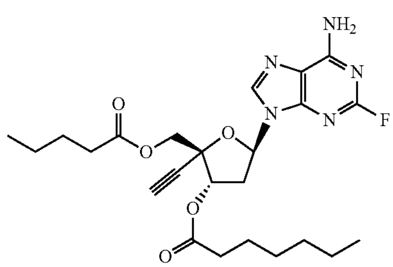 [SMILES: C#C[C@]1(COC(=O)CCCC)O[C@@H](n2cnc3c(N)nc(F)nc32)C[C@@H]1OC(=O)CCCCCC] | (2R,3S,5R)-5-(6-amino-2-fluoro-9H-purin-9-yl)-2-ethynyl-2-((pentanoyloxy)methyl)tetrahydrofuran-3-yl heptanoate |

TABLE 1-continued

| Example | Structure | Chemical Name |
|---|---|---|
| 21 | 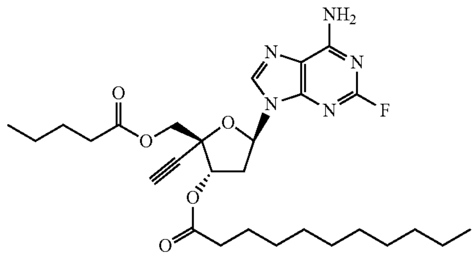 [SMILES: C#C[C@]1(COC(=O)CCCC)O[C@@H](n2cnc3c(N)nc(F)nc32)C[C@@H]1OC(=O)CCCCCCCCCC] | (2R,3S,5R)-5-(6-amino-2-fluoro-9H-purin-9-yl)-2-ethynyl-2-((pentanoyloxy)methyl)tetrahydrofuran-3-yl undecanoate |
| 22 | 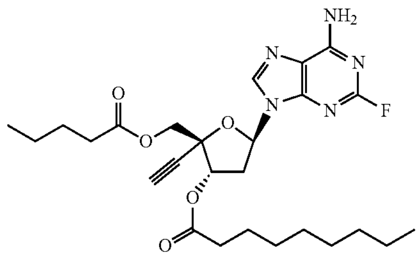 [SMILES: C#C[C@]1(COC(=O)CCCC)O[C@@H](n2cnc3c(N)nc(F)nc32)C[C@@H]1OC(=O)CCCCCCCC] | (2R,3S,5R)-5-(6-amino-2-fluoro-9H-purin-9-yl)-2-ethynyl-2-((pentanoyloxy)methyl)tetrahydrofuran-3-yl nonanoate |
| 23 | 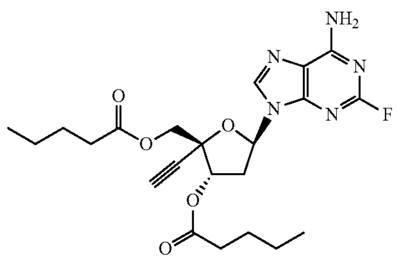 [SMILES: C#C[C@]1(COC(=O)CCCC)O[C@@H](n2cnc3c(N)nc(F)nc32)C[C@@H]1OC(=O)CCCC] | (2R,3S,5R)-5-(6-amino-2-fluoro-9H-purin-9-yl)-2-ethynyl-2-((pentanoyloxy)methyl)tetrahydrofuran-3-yl pentanoate |
| 24 | 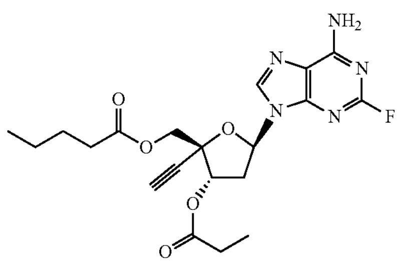 [SMILES: C#C[C@]1(COC(=O)CCCC)O[C@@H](n2cnc3c(N)nc(F)nc32)C[C@@H]1OC(=O)CC] | ((2R,3S,5R)-5-(6-amino-2-fluoro-9H-purin-9-yl)-2-ethynyl-3-(propionyloxy)tetrahydrofuran-2-yl)methyl pentanoate |
| 25 | 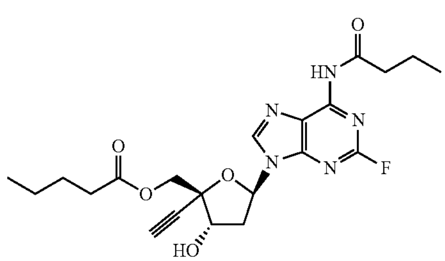 [SMILES: C#C[C@]1(COC(=O)CCCC)O[C@@H](n2cnc3c(NC(=O)CCC)nc(F)nc32)C[C@@H]1O] | ((2R,3S,5R)-5-(6-butyramido-2-fluoro-9H-purin-9-yl)-2-ethynyl-3-hydroxytetrahydrofuran-2-yl)methyl pentanoate |
| 26 | 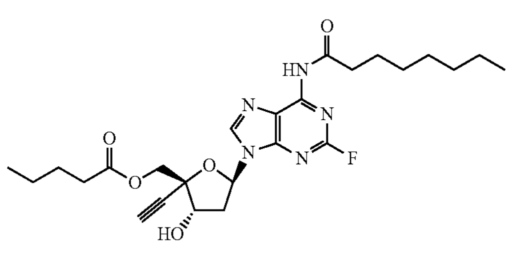 [SMILES: C#C[C@]1(COC(=O)CCCC)O[C@@H](n2cnc3c(NC(=O)CCCCCCC)nc(F)nc32)C[C@@H]1O] | ((2R,3S,5R)-2-ethynyl-5-(2-fluoro-6-octanamido-9H-purin-9-yl)-3-hydroxytetrahydrofuran-2-yl)methyl pentanoate |

TABLE 1-continued

| Example | Structure | Chemical Name |
|---|---|---|
| 27 | 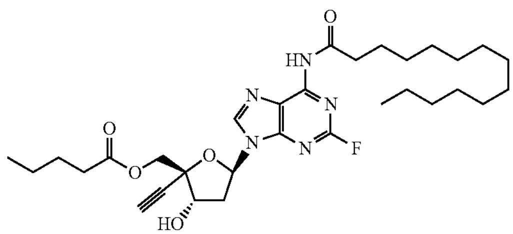 [SMILES: C#C[C@]1(COC(=O)CCCC)O[C@@H](n2cnc3c(NC(=O)CCCCCCCCCCCCC)nc(F)nc32)C[C@@H]1O] | ((2R,3S,5R)-2-ethynyl-5-(2-fluoro-6-tetradecanamido-9H-purin-9-yl)-3-hydroxytetrahydrofuran-2-yl) methyl pentanoate |
| 28 | 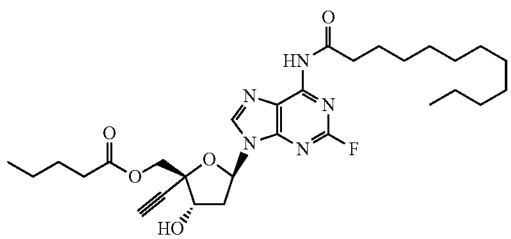 [SMILES: C#C[C@]1(COC(=O)CCCC)O[C@@H](n2cnc3c(NC(=O)CCCCCCCCCCC)nc(F)nc32)C[C@@H]1O] | ((2R,3S,5R)-5-(6-dodecanamido-2-fluoro-9H-purin-9-yl)-2-ethynyl-3-hydroxytetrahydrofuran-2-yl) methyl pentanoate |
| 29 | 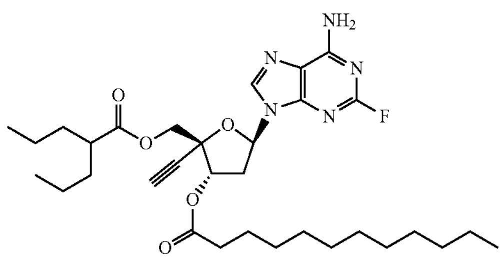 [SMILES: C#C[C@]1(COC(=O)C(CCC)CCC)O[C@@H](n2cnc3c(N)nc(F)nc32)C[C@@H]1OC(=O)CCCCCCCCCCC] | (2R,3S,5R)-5-(6-amino-2-fluoro-9H-purin-9-yl)-2-ethynyl-2-(((2-propylpentanoyl)oxy)methyl) tetrahydrofuran-3-yl dodecanoate |
| 30 | 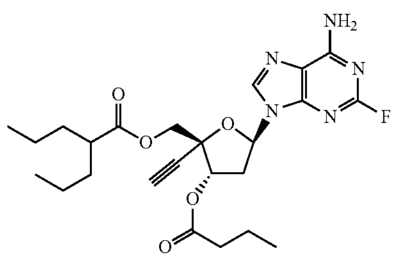 [SMILES: C#C[C@]1(COC(=O)C(CCC)CCC)O[C@@H](n2cnc3c(N)nc(F)nc32)C[C@@H]1OC(=O)CCC] | ((2R,3S,5R)-5-(6-amino-2-fluoro-9H-purin-9-yl)-3-(butyryloxy)-2-ethynyltetrahydrofuran-2-yl) methyl 2-propylpentanoate |
| 31 | 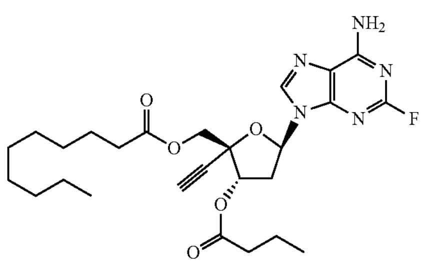 [SMILES: C#C[C@]1(COC(=O)CCCCCCCCC)O[C@@H](n2cnc3c(N)nc(F)nc32)C[C@@H]1OC(=O)CCC] | ((2R,3S,5R)-5-(6-amino-2-fluoro-9H-purin-9-yl)-3-(butyryloxy)-2-ethynyltetrahydrofuran-2-yl) methyl decanoate |
| 32 | 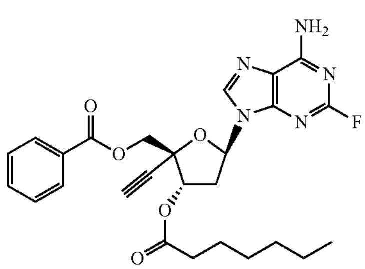 [SMILES: C#C[C@]1(COC(=O)c2ccccc2)O[C@@H](n2cnc3c(N)nc(F)nc32)C[C@@H]1OC(=O)CCCCCC] | ((2R,3S,5R)-5-(6-amino-2-fluoro-9H-purin-9-yl)-2-ethynyl-3-(heptanoyloxy)tetrahydrofuran-2-yl) methyl benzoate |

TABLE 1-continued

| Example | Structure | Chemical Name |
|---|---|---|
| 33 | 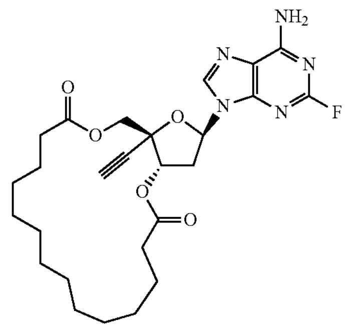 [SMILES: C#C[C@@]12COC(=O)CCCCCCCCCCCCC(=O)O[C@H]1C[C@H](n1cnc3c(N)nc(F)nc31)O2] | (2R,3aS,20aR)-2-(6-amino-2-fluoro-9H-purin-9-yl)-20a-ethynylhexadecahydro-2H-furo[3,2-b][1,5]dioxacyclononadecine-5,18-dione |
| 34 | 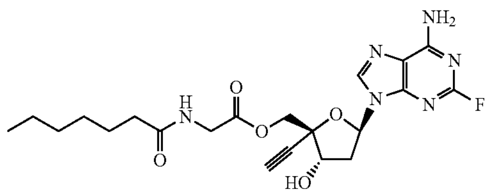 [SMILES: C#C[C@]1(COC(=O)CNC(=O)CCCCCC)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl heptanoylglycinate |
| 35 | 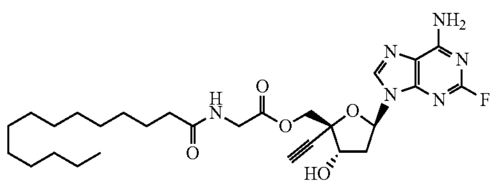 [SMILES: C#C[C@]1(COC(=O)CNC(=O)CCCCCCCCCCCCC)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl tetradecanoylglycinate |
| 36 | 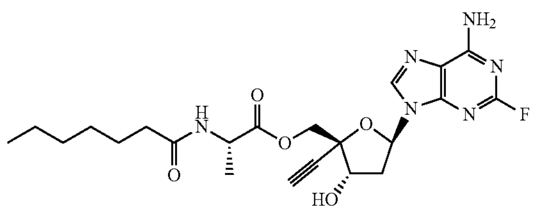 [SMILES: C#C[C@]1(COC(=O)[C@H](C)NC(=O)CCCCCC)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl heptanoyl-L-alaninate |
| 37 | 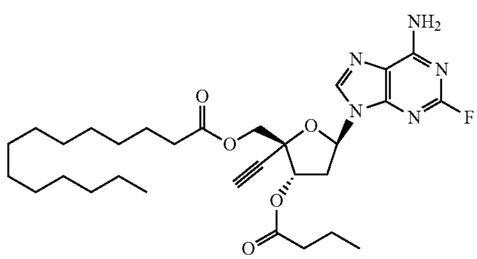 [SMILES: C#C[C@]1(COC(=O)CCCCCCCCCCCCC)O[C@@H](n2cnc3c(N)nc(F)nc32)C[C@@H]1OC(=O)CCC] | ((2R,3S,5R)-5-(6-amino-2-fluoro-9H-purin-9-yl)-3-(butyryloxy)-2-ethynyltetrahydrofuran-2-yl)methyl tetradecanoate |
| 38 | 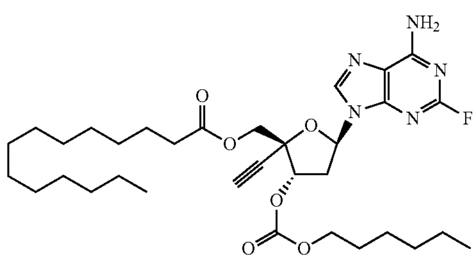 [SMILES: C#C[C@]1(COC(=O)CCCCCCCCCCCCC)O[C@@H](n2cnc3c(N)nc(F)nc32)C[C@@H]1OC(=O)OCCCCCC] | ((2R,3S,5R)-5-(6-amino-2-fluoro-9H-purin-9-yl)-2-ethynyl-3-(((hexyloxy)carbonyl)oxy)tetrahydrofuran-2-yl)methyl tetradecanoate |

TABLE 1-continued

| Example | Structure | Chemical Name |
|---|---|---|
| 39 | 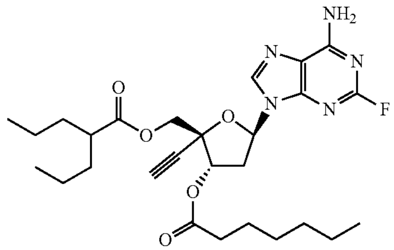 [SMILES: C#C[C@]1(COC(=O)C(CCC)CCC)O[C@@H](n2cnc3c(N)nc(F)nc32)C[C@@H]1OC(=O)CCCCCC] | (2R,3S,5R)-5-(6-amino-2-fluoro-9H-purin-9-yl)-2-ethynyl-2-(((2-propylpentanoyl)oxy)methyl) tetrahydrofuran-3-yl heptanoate |
| 40 | 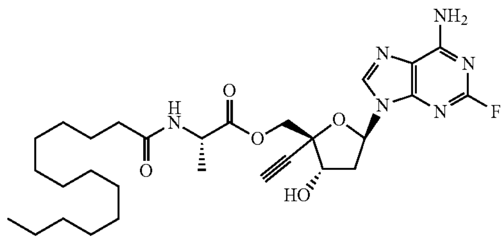 [SMILES: C#C[C@]1(COC(=O)[C@H](C)NC(=O)CCCCCCCCCCCCC)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl) methyl tetradecanoyl-L-alaninate |
| 41 | 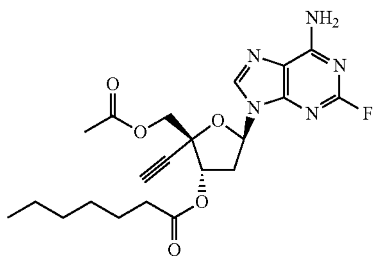 [SMILES: C#C[C@]1(COC(C)=O)O[C@@H](n2cnc3c(N)nc(F)nc32)C[C@@H]1OC(=O)CCCCCC] | (2R,3S,5R)-2-(acetoxymethyl)-5-(6-amino-2-fluoro-9H-purin-9-yl)-2-ethynyltetrahydrofuran-3-yl heptanoate |
| 42 | 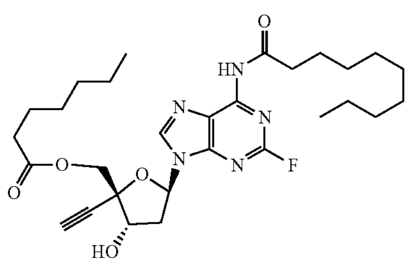 [SMILES: C#C[C@]1(COC(=O)CCCCCC)O[C@@H](n2cnc3c(NC(=O)CCCCCCCCC)nc(F)nc32)C[C@@H]1O] | ((2R,3S,5R)-5-(6-decanamido-2-fluoro-9H-purin-9-yl)-2-ethynyl-3-hydroxytetrahydrofuran-2-yl) methyl heptanoate |
| 43 | 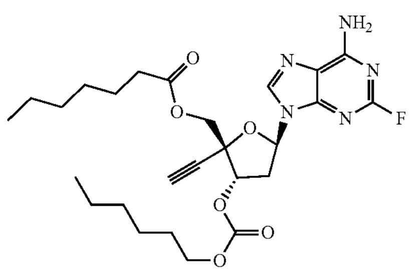 [SMILES: C#C[C@]1(COC(=O)CCCCCC)O[C@@H](n2cnc3c(N)nc(F)nc32)C[C@@H]1OC(=O)OCCCCCC] | ((2R,3S,5R)-5-(6-amino-2-fluoro-9H-purin-9-yl)-2-ethynyl-3-(((hexyloxy)carbonyl)oxy)tetrahydrofuran-2-yl)methyl heptanoate |
| 44 | 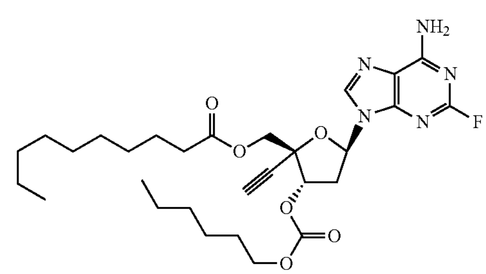 [SMILES: C#C[C@]1(COC(=O)CCCCCCCCC)O[C@@H](n2cnc3c(N)nc(F)nc32)C[C@@H]1OC(=O)OCCCCCC] | ((2R,3S,5R)-5-(6-amino-2-fluoro-9H-purin-9-yl)-2-ethynyl-3-(((hexyloxy)carbonyl)oxy)tetrahydrofuran-2-yl)methyl decanoate |

TABLE 1-continued

| Example | Structure | Chemical Name |
|---------|-----------|---------------|
| 45 | 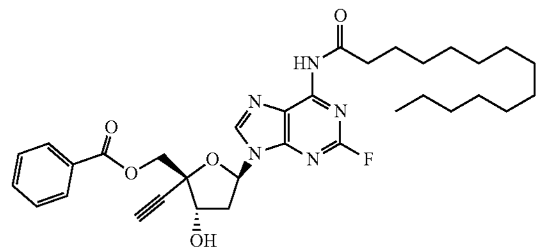 [SMILES: C#C[C@]1(COC(=O)c2ccccc2)O[C@@H](n2cnc3c(NC(=O)CCCCCCCCCCCCC)nc(F)nc32)C[C@@H]1O] | ((2R,3S,5R)-2-ethynyl-5-(2-fluoro-6-tetradecanamido-9H-purin-9-yl)-3-hydroxytetrahydrofuran-2-yl) methyl benzoate |
| 46 | 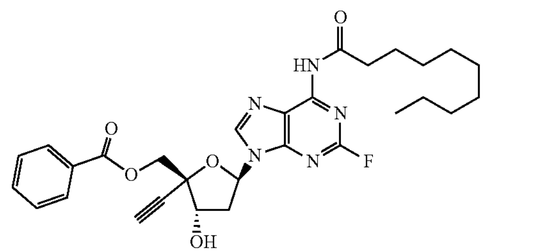 [SMILES: C#C[C@]1(COC(=O)c2ccccc2)O[C@@H](n2cnc3c(NC(=O)CCCCCCCCC)nc(F)nc32)C[C@@H]1O] | ((2R,3S,5R)-5-(6-decanamido-2-fluoro-9H-purin-9-yl)-2-ethynyl-3-hydroxytetrahydrofuran-2-yl) methyl benzoate |
| 47 | 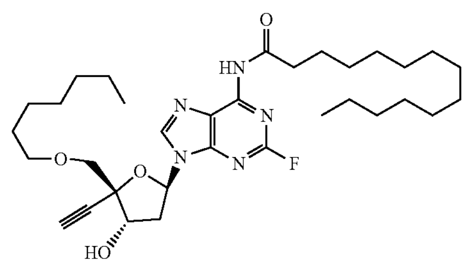 [SMILES: C#C[C@]1(COCCCCCCC)O[C@@H](n2cnc3c(NC(=O)CCCCCCCCCCCCC)nc(F)nc32)C[C@@H]1O] | ((2R,3S,5R)-2-ethynyl-5-(2-fluoro-6-tetradecanamido-9H-purin-9-yl)-3-hydroxytetrahydrofuran-2-yl) methyl heptanoate |
| 48 | 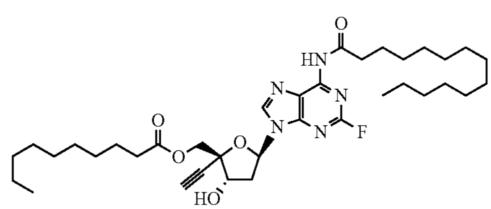 [SMILES: C#C[C@]1(COC(=O)CCCCCCCCC)O[C@@H](n2cnc3c(NC(=O)CCCCCCCCCCCCC)nc(F)nc32)C[C@@H]1O] | ((2R,3S,5R)-2-ethynyl-5-(2-fluoro-6-tetradecanamido-9H-purin-9-yl)-3-hydroxytetrahydrofuran-2-yl)methyl decanoate |
| 49 | 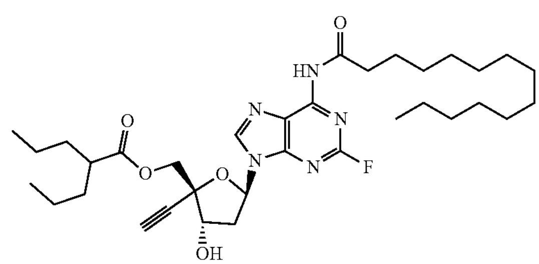 [SMILES: C#C[C@]1(COC(=O)C(CCC)CCC)O[C@@H](n2cnc3c(NC(=O)CCCCCCCCCCCCC)nc(F)nc32)C[C@@H]1O] | ((2R,3S,5R)-2-ethynyl-5-(2-fluoro-6-tetradecanamido-9H-purin-9-yl)-3-hydroxytetrahydrofuran-2-yl) methyl 2-propylpentanoate |
| 50 | 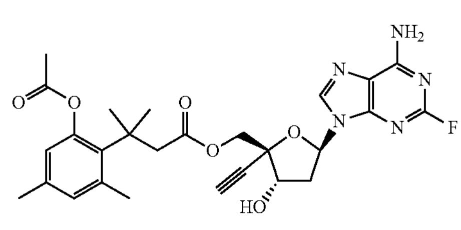 [SMILES: C#C[C@]1(COC(=O)CC(C)(C)c2c(C)cc(C)cc2OC(C)=O)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl 3-(2-acetoxy-4,6-dimethylphenyl)-3-methylbutanoate |

TABLE 1-continued

| Example | Structure | Chemical Name |
|---|---|---|
| 51 | 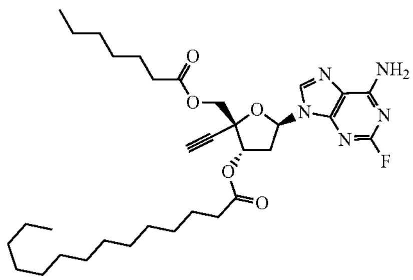 [SMILES: C#C[C@]1(COC(=O)CCCCCC)O[C@@H](n2cnc3c(N)nc(F)nc32)C[C@@H]1OC(=O)CCCCCCCCCCCCC] | (2R,3S,5R)-5-(6-amino-2-fluoro-9H-purin-9-yl)-2-ethynyl-2-((heptanoyloxy)methyl)tetrahydrofuran-3-yl tetradecanoate |
| 52 | 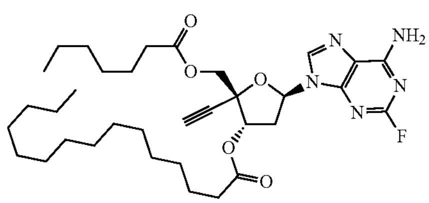 [SMILES: C#C[C@]1(COC(=O)CCCCCC)O[C@@H](n2cnc3c(N)nc(F)nc32)C[C@@H]1OC(=O)CCCCCCCCCCCCCC] | ((2R,3S,5R)-5-(6-amino-2-fluoro-9H-purin-9-yl)-2-ethynyl-3-(((tridecyloxy)carbonyl)oxy)tetrahydrofuran-2-yl)methyl heptanoate |
| 53 | 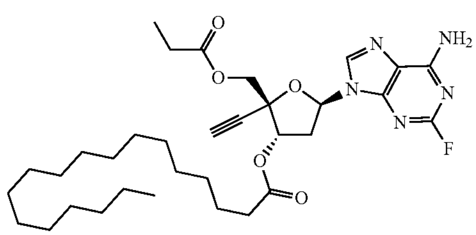 [SMILES: C#C[C@]1(COC(=O)CC)O[C@@H](n2cnc3c(N)nc(F)nc32)C[C@@H]1OC(=O)CCCCCCCCCCCCCCCCC] | (2R,3S,5R)-5-(6-amino-2-fluoro-9H-purin-9-yl)-2-ethynyl-2-((propionyloxy)methyl)tetrahydrofuran-3-yl stearate |
| 54 | 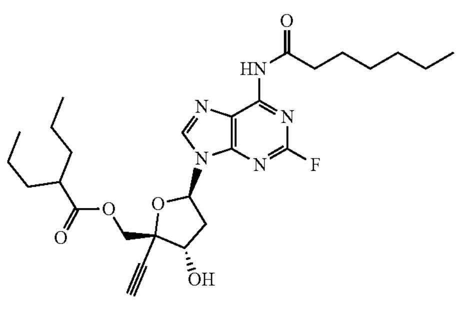 [SMILES: C#C[C@]1(COC(=O)C(CCC)CCC)O[C@@H](n2cnc3c(NC(=O)CCCCCC)nc(F)nc32)C[C@@H]1O] | ((2R,3S,5R)-2-ethynyl-5-(2-fluoro-6-heptanamido-9H-purin-9-yl)-3-hydroxytetrahydrofuran-2-yl)methyl 2-propylpentanoate |
| 55 | 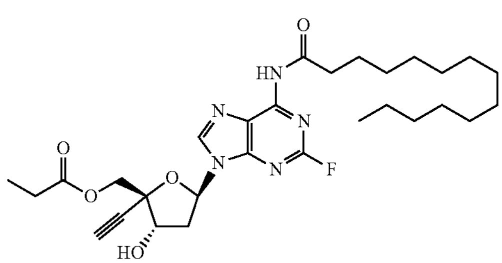 [SMILES: C#C[C@]1(COC(=O)CC)O[C@@H](n2cnc3c(NC(=O)CCCCCCCCCCCCC)nc(F)nc32)C[C@@H]1O] | ((2R,3S,5R)-2-ethynyl-5-(2-fluoro-6-tetradecanamido-9H-purin-9-yl)-3-hydroxytetrahydrofuran-2-yl)methyl propionate |
| 56 | 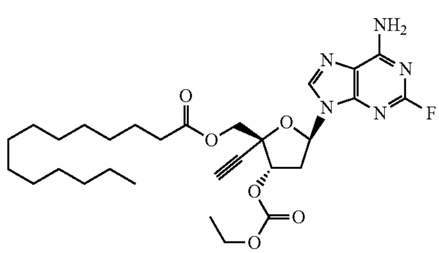 [SMILES: C#C[C@]1(COC(=O)CCCCCCCCCCCCC)O[C@@H](n2cnc3c(N)nc(F)nc32)C[C@@H]1OC(=O)OCC] | ((2R,3S,5R)-5-(6-amino-2-fluoro-9H-purin-9-yl)-3-((ethoxycarbonyl)oxy)-2-ethynyltetrahydrofuran-2-yl)methyl tetradecanoate |

TABLE 1-continued

| Example | Structure | Chemical Name |
|---|---|---|
| 57 | 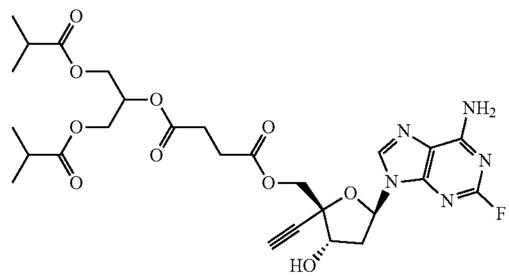 [SMILES: C#C[C@]1(COC(=O)CCC(=O)OC(COC(=O)C(C)C)COC(=O)C(C)C)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl)methyl (1,3-bis(isobutyryloxy)propan-2-yl) succinate |
| 58 | 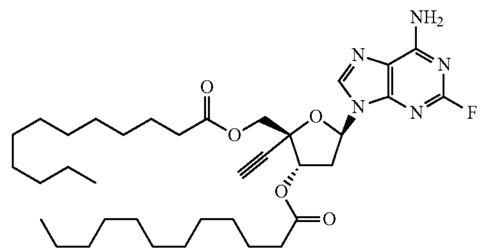 [SMILES: C#C[C@]1(COC(=O)CCCCCCCCCCC)O[C@@H](n2cnc3c(N)nc(F)nc32)C[C@@H]1OC(=O)CCCCCCCCCCC] | (2R,3S,5R)-5-(6-amino-2-fluoro-9H-purin-9-yl)-2-((dodecanoyloxy)methyl)-2-ethynyltetrahydrofuran-3-yl dodecanoate |
| 59 | 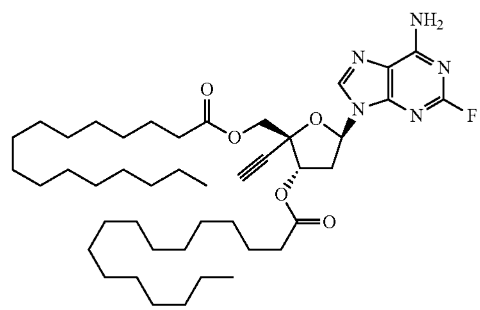 [SMILES: C#C[C@]1(COC(=O)CCCCCCCCCCCCCCC)O[C@@H](n2cnc3c(N)nc(F)nc32)C[C@@H]1OC(=O)CCCCCCCCCCCCCCC] | (2R,3S,5R)-5-(6-amino-2-fluoro-9H-purin-9-yl)-2-ethynyl-2-((palmitoyloxy)methyl)tetrahydrofuran-3-yl palmitate |
| 60 | 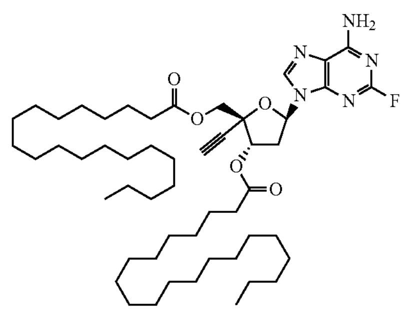 [SMILES: C#C[C@]1(COC(=O)CCCCCCCCCCCCCCCCCCC)O[C@@H](n2cnc3c(N)nc(F)nc32)C[C@@H]1OC(=O)CCCCCCCCCCCCCCCCCCC] | (2R,3S,5R)-5-(6-amino-2-fluoro-9H-purin-9-yl)-2-ethynyl-2-((icosanoyloxy)methyl)tetrahydrofuran-3-yl icosanoate |
| 61 | 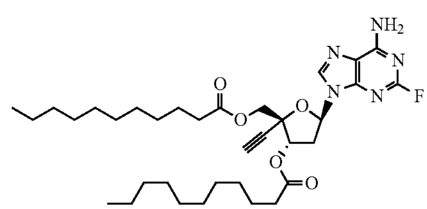 [SMILES: C#C[C@]1(COC(=O)CCCCCCCCCC)O[C@@H](n2cnc3c(N)nc(F)nc32)C[C@@H]1OC(=O)CCCCCCCCCC] | (2R,3S,5R)-5-(6-amino-2-fluoro-9H-purin-9-yl)-2-ethynyl-2-((undecanoyloxy)methyl)tetrahydrofuran-3-yl undecanoate |

TABLE 1-continued

| Example | Structure | Chemical Name |
|---|---|---|
| 62 | 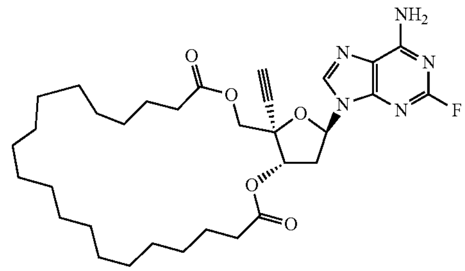 [SMILES: C#C[C@@]12COC(=O)CCCCCCCCCCCCCCCCCCC(=O)O[C@H]1C[C@H](n1cnc3c(N)nc(F)nc31)O2] | (2R,3aS,26aR)-2-(6-amino-2-fluoro-9H-purin-9-yl)-26a-ethynyldocosahydro-2H-furo[3,2-b][1,5]dioxacyclopentacosine-5,24-dione |
| 63 | 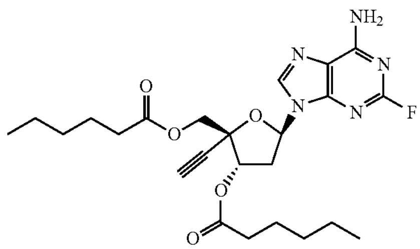 [SMILES: C#C[C@]1(COC(=O)CCCCC)O[C@@H](n2cnc3c(N)nc(F)nc32)C[C@@H]1OC(=O)CCCCC] | (2R,3S,5R)-5-(6-amino-2-fluoro-9H-purin-9-yl)-2-ethynyl-2-((hexanoyloxy)methyl)tetrahydrofuran-3-yl hexanoate |
| 64 | 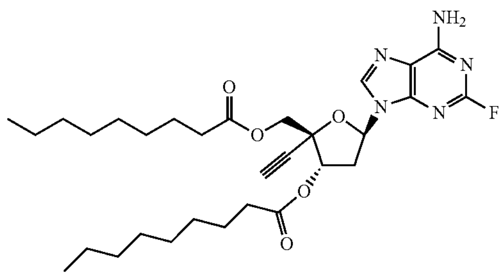 [SMILES: C#C[C@]1(COC(=O)CCCCCCCC)O[C@@H](n2cnc3c(N)nc(F)nc32)C[C@@H]1OC(=O)CCCCCCCC] | (2R,3S,5R)-5-(6-amino-2-fluoro-9H-purin-9-yl)-2-ethynyl-2-((nonanoyloxy)methyl)tetrahydrofuran-3-yl nonanoate |
| 65 | 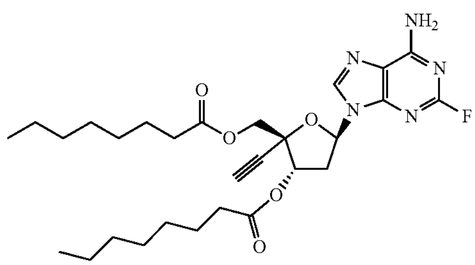 [SMILES: C#C[C@]1(COC(=O)CCCCCCC)O[C@@H](n2cnc3c(N)nc(F)nc32)C[C@@H]1OC(=O)CCCCCCC] | (2R,3S,5R)-5-(6-amino-2-fluoro-9H-purin-9-yl)-2-ethynyl-2-((octanoyloxy)methyl)tetrahydrofuran-3-yl octanoate |
| 66 | 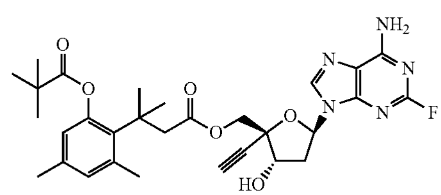 [SMILES: C#C[C@]1(COC(=O)CC(C)(C)c2c(C)cc(C)cc2OC(=O)C(C)(C)C)O[C@@H](n2cnc3c(N)nc(F)nc32)C[C@@H]1O] | ((2R,3S,5R)-5-(6-amino-2-fluoro-9H-purin-9-yl)-2-ethynyl-3-hydroxytetrahydrofuran-2-yl) methyl 3-(2,4-dimethyl-6-(pivaloyloxy)phenyl)-3-methylbutanoate |
| 67 | 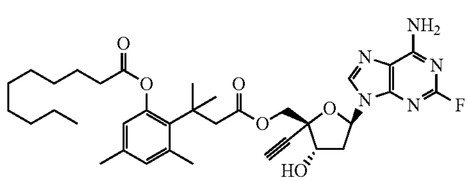 [SMILES: C#C[C@]1(COC(=O)CC(C)(C)c2c(C)cc(C)cc2OC(=O)CCCCCCCCC)O[C@@H](n2cnc3c(N)nc(F)nc32)C[C@@H]1O] | 2-(4-(((2R,3S,5R)-5-(6-amino-2-fluoro-9H-purin-9-yl)-2-ethynyl-3-hydroxytetrahydrofuran-2-yl)methoxy)-2-methyl-4-oxobutan-2-yl)-3,5-dimethylphenyl decanoate |

TABLE 1-continued

| Example | Structure | Chemical Name |
|---|---|---|
| 68 | | ((2R,3S,5R)-5-(6-amino-2-fluoro-9H-purin-9-yl)-2-ethynyl-3-hydroxytetrahydrofuran-2-yl)methyl (1,3-bis(heptanoyloxy)propan-2-yl) succinate | and pharmaceutically acceptable salts thereof.

In one embodiment, the present invention encompasses each individual compound listed in the above Table 1, or a pharmaceutically acceptable salt thereof.

In various embodiments, prodrugs of any of the compounds of formula (I), (Ia), (II) or (IIa) set forth herein are also within the scope of the present invention.

In accordance with one embodiment of the present invention, there is provided a pharmaceutical composition comprising a compound of Formulas (I), (Ia), (II) or (IIa) or a pharmaceutically acceptable salt thereof, and a pharmaceutically acceptable excipient. In a further embodiment, a compound is present in amorphous form. In a further embodiment, the compound is present in crystalline form. In various preferred embodiments, in particular, the compounds of the structure of Examples 18, 38 and 58 may be each present in crystalline form as well as amorphous form. In a further embodiment, the pharmaceutical composition is in a tablet form. In a further embodiment, the pharmaceutical composition is in parenteral form. In a further embodiment, the compound is present as a spray dried dispersion.

In accordance with one embodiment of the present invention, there is provided a method of treating an HIV infection in a subject comprising administering to the subject a compound of Formulas (I), (Ia), (II) or (IIa) or a pharmaceutically acceptable salt thereof.

In accordance with one embodiment of the present invention, there is provided a method of treating an HIV infection in a subject comprising administering to the subject a pharmaceutical composition as described herein.

In accordance with one embodiment of the present invention, there is provided a method of preventing an HIV infection in a subject at risk for developing an HIV infection, comprising administering to the subject a compound of Formulas (I), (Ia), (II) or (IIa) or a pharmaceutically acceptable salt thereof.

In accordance with one embodiment of the present invention, there is provided the use of a compound of Formula (I), (Ia), (II) or (IIa) in the manufacture of a medicament for treating an HIV infection.

In accordance with one embodiment of the present invention, there is provided the use of a compound of Formula (I), (Ia), (II) or (IIa) in the manufacture of a medicament for preventing an HIV infection.

In accordance with one embodiment of the present invention, there is provided a compound according to Formula (I), (Ia), (II) or (IIa) for use in treating an HIV infection.

In accordance with one embodiment of the present invention, there is provided a compound according to Formula (I), (Ia), (II) or (IIa) for use in preventing an HIV infection.

In accordance with one embodiment of the present invention, there is provided a method of preventing an HIV infection in a subject at risk for developing an HIV infection, comprising administering to the subject a pharmaceutical composition as described herein.

Furthermore, the compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

In another embodiment of the invention, there is provided a compound of Formula (I), (Ia), (II) or (IIa) wherein the compound or salt of the compound is used in the manufacture of a medicament for use in the treatment of an HIV infection in a human.

In another embodiment of the invention, there is provided a compound of Formula (I), (Ia), (II) or (IIa) wherein the compound or salt of the compound is used in the manufacture of a medicament for use in the prevention of an HIV infection in a human.

In one embodiment, the pharmaceutical formulation containing a compound of Formula (I), (Ia), (II) or (IIa) or a salt thereof is a formulation adapted for parenteral administration. In another embodiment, the formulation is a long-acting parenteral formulation. In a further embodiment, the formulation is a nano-particle formulation.

The compounds of the present invention and their salts, solvates, or other pharmaceutically acceptable derivatives thereof, may be employed alone or in combination with other therapeutic agents. Therefore, in other embodiments, the methods of treating and/or preventing an HIV infection in a subject may in addition to administration of a compound of Formula (I), (Ia), (II) or (IIa) further comprise administration of one or more additional pharmaceutical agents active against HIV.

In such embodiments, the one or more additional agents active against HIV is selected from the group consisting of zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, dolutegravir, cabotegravir, bictegravir, vicriviroc (Sch-C), Sch-D, TAK779, maraviroc, TAK449, didanosine, tenofovir, lopinavir, and darunavir.

As such, the compounds of the present invention of Formulas (I), (Ia), (II) or (IIa) and any other pharmaceutically active agent(s) may be administered together or separately and, when administered separately, administration may occur simultaneously or sequentially, in any order. The amounts of the compounds of Formula (I), (Ia), (II) or (IIa) of the present invention and the other pharmaceutically active agent(s) and the relative timings of administration will be selected in order to achieve the desired combined therapeutic effect. The administration in combination of a compound of the present invention of Formula (I), (Ia), (II) or (IIa) and salts, solvates, or other pharmaceutically acceptable derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The amounts of the compound(s) of Formula (I), (Ia), (II) or (IIa) or salts thereof and the other pharmaceutically active agent(s) and the relative timings of administration will be selected in order to achieve the desired combined therapeutic effect.

In addition, the compounds of the present invention of Formula (I), (Ia), (II) or (IIa) may be used in combination with one or more other agents that may be useful in the prevention or treatment of HIV. Examples of such agents include:

Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, doravirine, GSK2248761, TMC-278, TMC-125, etravirine, and similar agents;

Protease inhibitors such as saquinavir, ritonavir, indinavir, nelfinavir, amprenavir, fosamprenavir, brecanavir, darunavir, atazanavir, tipranavir, palinavir, lasinavir, and similar agents;

Entry, attachment and fusion inhibitors such as enfuvirtide (T-20), T-1249, PRO-542, PRO-140, TNX-355, BMS-806, BMS-663068 (Fostemsavir), BMS-626529 (Temsavir), 5-Helix and similar agents;

Integrase inhibitors such as raltegravir, elvitegravir, dolutegravir, bictegravir, cabotegravir and similar agents;

Maturation inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

CAPSID inhibitors such GS-6207, and similar agents.

Further examples where the compounds of the present invention may be used in combination with one or more agents useful in the prevention or treatment of HIV are found in Table 2.

TABLE 2

| FDA Approval | Brand Name | Generic Name | Manufacturer |
| --- | --- | --- | --- |
| Nucleoside Reverse Transcriptase Inhibitors (NRTIs) | | | |
| 1987 | Retrovir | zidovudine, azidothymidine, AZT, ZDV | GlaxoSmithKline |
| 1991 | Videx | didanosine, dideoxyinosine, ddI | Bristol-Myers Squibb |
| 1992 | Hivid | zalcitabine, dideoxycytidine, ddC | Roche Pharmaceuticals |
| 1994 | Zerit | stavudine, d4T | Bristol-Myers Squibb |
| 1995 | Epivir | lamivudine, 3TC | GlaxoSmithKline |
| 1997 | Combivir | lamivudine + zidovudine | GlaxoSmithKline |
| 1998 | Ziagen | abacavir sulfate, ABC | GlaxoSmithKline |
| 2000 | Trizivir | abacavir + lamivudine + zidovudine | GlaxoSmithKline |
| 2000 | Videx EC | enteric coated didanosine, ddI EC | Bristol-Myers Squibb |
| 2001 | Viread | tenofovir disoproxil fumarate, TDF | Gilead Sciences |
| 2003 | Emtriva | emtricitabine, FTC | Gilead Sciences |
| 2004 | Epzicom | abacavir + lamivudine | GlaxoSmithKline |
| 2004 | Truvada | emtricitabine + tenofovir disoproxil fumarate | Gilead Sciences |
| Non-Nucleosides Reverse Transcriptase Inhibitors (NNRTIs) | | | |
| 1996 | Viramune | nevirapine, NVP | Boehringer Ingelheim |
| 1997 | Rescriptor | delavirdine, DLV | Pfizer |
| 1998 | Sustiva | efavirenz, EFV | Bristol-Myers Squibb |
| 2008 | Intelence | Etravirine | Tibotec Therapeutics |
| 2011 | Edu rant | Rilpivirine | Tibotec Therapeutics |
| 2018 | Pifeltro | Doravirine | Merck |

TABLE 2-continued

| FDA Approval | Brand Name | Generic Name | Manufacturer |
|---|---|---|---|
| Protease Inhibitors (PIs) | | | |
| 1995 | Invirase | saquinavir mesylate, SQV | Roche Pharmaceuticals |
| 1996 | Norvir | ritonavir, RTV | Abbott Laboratories |
| 1996 | Crixivan | indinavir, IDV | Merck |
| 1997 | Viracept | nelfinavir mesylate, NFV | Pfizer |
| 1997 | Fortovase | saquinavir (no longer marketed) | Roche Pharmaceuticals |
| 1999 | Agenerase | amprenavir, APV | GlaxoSmithKline |
| 2000 | Kaletra | lopinavir+ ritonavir, LPV/RTV | Abbott Laboratories |
| 2003 | Reyataz | atazanavir sulfate, ATV | Bristol-Myers Squibb |
| 2003 | Lexiva | fosamprenavir calcium, FOS-APV | GlaxoSmithKline |
| 2005 | Aptivus | tripranavir, TPV | Boehringer Ingelheim |
| 2006 | Prezista | Darunavir | Tibotec Therapeutics |
| Fusion Inhibitors | | | |
| 2003 | Fuzeon | Enfuvirtide, T-20 | Roche Pharmaceuticals & Trimeris |
| Entry Inhibitors | | | |
| 2007 | Selzentry | Maraviroc | Pfizer |
| Integrase Inhibitors | | | |
| 2007 | Isentress | Raltegravir | Merck |
| 2013 | Tivicay | Dolutegravir | ViiV Healthcare |
| 2018 | | Bictegravir | Gilead Sciences |
| — | — | Cabotegravir | ViiV Healthcare |
| Capsid Inhibitors | | | |
| — | | GS-6207 | Gilead Sciences |

The scope of combinations of compounds of this invention with HIV agents is not limited to those mentioned above, but includes in principle any combination with any pharmaceutical composition useful for the treatment and/or prevention of HIV. As noted, in such combinations the compounds of the present invention and other HIV agents may be administered separately or in conjunction. In addition, one agent may be prior to, concurrent to, or subsequent to the administration of other agent(s).

The present invention may be used in combination with one or more agents useful as pharmacological enhancers as well as with or without additional compounds for the prevention or treatment of HIV. Examples of such pharmacological enhancers (or pharmakinetic boosters) include, but are not limited to, ritonavir, GS-9350, and SPI-452. Ritonavir is 10-hydroxy-2-methyl-5-(1-methyethyl)-1-1[2-(1-methylethyl)-4-thiazolyl]-3,6-dioxo-8,11-bis(phenylmethyl)-2,4,7,12-tetraazatridecan-13-oic acid, 5-thiazolylmethyl ester, [5S-(5S*,8R*,10R*,11R*)] and is available from Abbott Laboratories of Abbott park, Illinois, as Norvir. Ritonavir is an HIV protease inhibitor indicated with other antiretroviral agents for the treatment of HIV infection. Ritonavir also inhibits P450 mediated drug metabolism as well as the P-gycoprotein (Pgp) cell transport system, thereby resulting in increased concentrations of active compound within the organism.

GS-9350 is a compound being developed by Gilead Sciences of Foster City California as a pharmacological enhancer.

SPI-452 is a compound being developed by Sequoia Pharmaceuticals of Gaithersburg, Maryland, as a pharmacological enhancer.

In one embodiment of the present invention, a compound of Formula (I), (Ia), (II) or (IIa) is used in combination with ritonavir. In one embodiment, the combination is an oral fixed dose combination. In another embodiment, the compound of Formula (I), (Ia), (II) or (IIa) is formulated as a long acting parenteral injection and ritonavir is formulated as an oral composition. In one embodiment, a kit containing the compound of Formula (I), (Ia), (II) or (IIa) is formulated as a long acting parenteral injection and ritonavir formulated as an oral composition. In another embodiment, the compound of Formula (I), (Ia), (II) or (IIa) is formulated as a long acting parenteral injection and ritonavir is formulated as an injectable composition. In one embodiment, a kit containing the compound of Formula (I), (Ia), (II) or (IIa) is formulated as a long acting parenteral injection and ritonavir formulated as an injectable composition.

In another embodiment of the present invention, a compound of Formula (I), (Ia), (II) or (IIa) is used in combination with GS-9350. In one embodiment, the combination is an oral fixed dose combination. In another embodiment, the compound of Formula (I), (Ia), (II) or (IIa) is formulated as a long acting parenteral injection and GS-9350 is formulated as an oral composition. In one embodiment, there is provided a kit containing the compound of Formula (I), (Ia), (II) or (IIa) is formulated as a long acting parenteral injection and GS-9350 formulated as an oral composition. In another embodiment, the compound of Formula (I), (Ia), (II) or (IIa) is formulated as a long acting parenteral injection and GS-9350 is formulated as an injectable composition. In one embodiment, is a kit containing the compound of Formula (I), (Ia), (II) or (IIa) is formulated as a long acting parenteral injection and GS-9350 formulated as an injectable composition.

In one embodiment of the present invention, a compound of Formula (I), (Ia), (II) or (IIa) is used in combination with SPI-452. In one embodiment, the combination is an oral fixed dose combination. In another embodiment, the compound of Formula (I), (Ia), (II) or (IIa) is formulated as a long acting parenteral injection and SPI-452 is formulated as an oral composition. In one embodiment, there is provided a kit containing the compound of Formula (I) formulated as a long acting parenteral injection and SPI-452 formulated as an oral composition. In another embodiment, the compound of Formula (I), (Ia), (II) or (IIa) is formulated as a long acting parenteral injection and SPI-452 is formulated as an injectable composition. In one embodiment, there is provided a kit containing the compound of Formula (I), (Ia), (II) or (IIa) formulated as a long acting parenteral injection and SPI-452 formulated as an injectable composition.

In one embodiment of the present invention, a compound of Formula (I), (Ia), (II) or (IIa) is used in combination with compounds which are found in previously filed PCT/CN2011/0013021, which is herein incorporated by reference.

The above other therapeutic agents, when employed in combination with the chemical entities described herein, may be used, for example, in those amounts indicated in the Physicians' Desk Reference (PDR) or as otherwise determined by one of ordinary skill in the art.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula (I), (Ia), (II) or (IIa).

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula (I), (Ia), (II) or (IIa), wherein said virus is an HIV virus. In some embodiments, the HIV virus is the HIV-1 virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula (I), (Ia), (II) or (IIa) further comprising administration of a therapeutically effective amount of one or more agents active against an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula (I), (Ia), (II) or (IIa), further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CAPSID inhibitors, CXCR4 inhibitors; and CCR5 inhibitors.

In another embodiment of the invention, there is provided a method for preventing a viral infection in a mammal mediated at least in part by a virus in the retrovirus family of viruses which method comprises administering to a mammal, that has been diagnosed with said viral infection or is at risk of developing said viral infection, a compound of Formula (I), (Ia), (II) or (IIa).

In another embodiment of the invention, there is provided a method for preventing a viral infection in a mammal mediated at least in part by a virus in the retrovirus family of viruses which method comprises administering to a mammal, that has been diagnosed with said viral infection or is at risk of developing said viral infection, a compound of Formula (I), (Ia), (II) or (IIa), wherein said virus is an HIV virus. In some embodiments, the HIV virus is the HIV-1 virus.

In another embodiment of the invention, there is provided a method for preventing a viral infection in a mammal mediated at least in part by a virus in the retrovirus family of viruses which method comprises administering to a mammal, that has been diagnosed with said viral infection or is at risk of developing said viral infection, a compound of Formula (I), (Ia), (II) or (IIa), further comprising administration of a therapeutically effective amount of one or more agents active against an HIV virus.

In another embodiment of the invention, there is provided a method for preventing a viral infection in a mammal mediated at least in part by a virus in the retrovirus family of viruses which method comprises administering to a mammal, that has been diagnosed with said viral infection or is at risk of developing said viral infection, a compound of Formula (I), (Ia), (II) or (IIa) further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CAPSID inhibitors, CXCR4 inhibitors; and CCR5 inhibitors.

In further embodiments, the compound of the present invention of Formula (I), (Ia), (II) or (IIa) or a pharmaceutically acceptable salt thereof, is selected from the group of compounds set forth in Table 1 above.

The compounds of Table 1 were synthesized according to the Synthetic Methods, General Schemes, and the Examples described below.

In another embodiment, there is provided a pharmaceutical composition comprising a pharmaceutically acceptable diluent and a therapeutically effective amount of a compound of Formula (I), (Ia), (II) or (IIa) or a pharmaceutically acceptable salt thereof.

In certain embodiments, the compound(s) of the present invention, or a pharmaceutically acceptable salt thereof, is chosen from the compounds set forth in Table 1.

The compounds of the present invention can be supplied in the form of a pharmaceutically acceptable salt. The term "pharmaceutically acceptable salt" may refer to salts prepared from pharmaceutically acceptable inorganic and organic acids and bases. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

The compounds of Formula (I), (Ia), (II) or (IIa) of the invention may exist in both unsolvated and solvated forms. The term 'solvate' comprises the compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. $D_2O$, $d_6$-acetone, $d_6$-DMSO.

Compounds of Formula (I), (Ia), (II) or (IIa) containing one or more asymmetric carbon atoms can exist as two or more stereoisomers. Where a compound of Formula (I), (Ia), (II) or (IIa) contains an alkenyl or alkenylene group or a cycloalkyl group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the claimed compounds present invention are all stereoisomers, geometric isomers and tautomeric forms of the compounds of Formula (I), (Ia), (II) or (IIa), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC), Supercritical fluid chromatography (SFC).

Alternatively, the racemate (or a racemic precursor) may be reacted with a suitable optically active compound, for example, an alcohol, or, in the case where the compound of Formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC or SFC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of Formula (I), (Ia), (II) or (IIa) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of Formula (I), (Ia), (II) or (IIa), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labelled compounds of Formula (I), (Ia), (II) or (IIa) can generally be prepared by conventional techniques known to those skilled in the art or by processes analogous to those described herein using an appropriate isotopically-labelled reagent& in place of the non-labelled reagent previously employed.

The compounds of the present invention may be administered as prodrugs. Thus, certain derivatives of compounds of Formula (I), (Ia), (II) or (IIa), which may have little or no pharmacological activity themselves can, when administered into or onto the body, be converted into compounds of Formula (I), (Ia), (II) or (IIa) as 'prodrugs'. One example of a compound that such prodrugs may encompass is 4'-ethynyl-2-fluoro-2'-dooxyadenosine (EFdA) disclosed e.g., in U.S. Pat. No. 7,339,053. The compounds of the present invention may be administered as prodrugs. In one embodiment, the compounds of the invention are prodrugs of 4'-ethynyl-2-fluoro-2'-deoxyadenosine (EFdA) disclosed e.g., in U.S. Pat. No. 7,339,053, which is a nucleoside reverse transcriptase inhibitor of the formula:

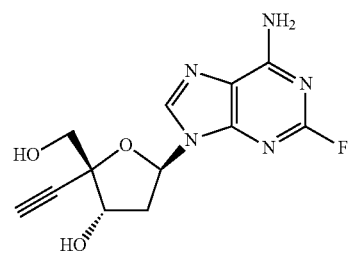 [SMILES: C#C[C@]1(CO)O[C@@H](n2cnc3c(N)nc(F)nc32)C[C@@H]1O]

4'-Ethynyl-2-fluoro-2'-deoxyadenosine (EFdA)

The prodrugs are useful in that they are capable of modulating physicochemical properties, facilitating multiple dosing paradigms and improving pharmacokinetic and/or pharmacodynamic profiles of the active parent (EFdA). For example, the prodrugs may facilitate long-acting parenteral dosing modalities, and/or improvements in antiviral persistence profiles as compared to EFdA.

Administration of the chemical entities and combinations of entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarilly, vaginally, rectally, or intraocularly. In some embodiments, oral or parenteral administration is used. Examples of dosing include, without limitation, once every seven days for oral, once every eight weeks for intramuscular, or once every six months for subcutaneous.

Pharmaceutical compositions or formulations include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see *Remington's Pharmaceutical Sciences*, Mack Publishing Company, Easton, Pennsylvania In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition may comprise from about 0.2 to 2% of the active agent in solution.

Pharmaceutical compositions of the chemical entities described herein may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

In general, the chemical entities provided will be administered in a therapeutically effective amount by any of the accepted modes of administration for agents that serve similar utilities. The actual amount of the chemical entity, i.e., the active ingredient, will depend upon numerous factors such as the severity of the disease to be treated, the age and relative health of the subject, the potency of the chemical entity used the route and form of administration, and other factors. The drug can be administered more than once a day, such as once or twice a day.

In general, the chemical entities will be administered as pharmaceutical compositions by any one of the following routes: oral, systemic (e.g., transdermal, intranasal or by suppository), or parenteral (e.g., intramuscular, intravenous or subcutaneous) administration. In certain embodiments, oral administration with a convenient daily dosage regimen that can be adjusted according to the degree of affliction may be used. Compositions can take the form of tablets, pills, capsules, semisolids, powders, sustained release formulations, solutions, suspensions, elixirs, aerosols, or any other appropriate compositions. Another manner for administering the provided chemical entities is inhalation.

The choice of formulation depends on various factors such as the mode of drug administration and bioavailability of the drug substance. For delivery via inhalation the chemical entity can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDIs typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical compositions have been developed for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, at least one chemical entity described herein in combination with at least one pharmaceutically acceptable excipient. Acceptable excipients are non-toxic, aid administration, and do not adversely affect the therapeutic benefit of the at least one chemical entity described herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, for injectable solutions, include water, saline, aqueous dextrose, and glycols.

Compressed gases may be used to disperse a chemical entity described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the chemical entity in a composition can vary within the full range employed by those skilled in the art. Typically, the composition will contain, on a weight percent (wt %) basis, from about 0.01-99.99 wt % of at least one chemical entity described herein based on the total composition, with the balance being one or more suitable pharmaceutical excipients. In certain embodiments, the at least one chemical entity described herein is present at a level of about 1-80 wt %.

In various embodiments, pharmaceutical compositions of the present invention encompass compounds of Formula (I), (Ia), (II) or (IIa), salts thereof, and combinations of the above.

Synthetic Methods

The methods of synthesis may employ readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, the methods of this invention may employ protecting groups which prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the provided chemical entities may contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this specification, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Ernka-Chemce or Sigma (St. Louis, Missouri, USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989).

Unless specified to the contrary, the reactions described herein may take place at atmospheric pressure, generally within a temperature range from −78° C. to 200° C. Further, except as employed in the Example or as otherwise specified, reaction times and conditions are intended to be approximate, e.g., taking place at about atmospheric pressure within a temperature range of about −78° C. to about 110° C. over a period of about 1 to about 24 hours; reactions left to run overnight average a period of about 16 hours.

The terms "solvent," "organic solvent," and "inert solvent" each mean a solvent inert under the conditions of the reaction being described in conjunction therewith, including, for example, benzene, toluene, acetonitrile, tetrahydrofuranyl ("THF"), dimethylformamide ("DMF"), chloroform, methylene chloride (or dichloromethane), diethyl ether, methanol, N-methylpyrrolidone ("NMP"), pyridine and the like.

Isolation and purification of the chemical entities and intermediates described herein can be affected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

EXAMPLE AND GENERAL SYNTHESIS

The following example and prophetic synthesis method serve to more fully describe the manner of making and using the above-described invention. It is understood that this in no way serve to limit the true scope of the invention, but rather is presented for illustrative purposes. Unless otherwise specified, the following abbreviations have the following meanings. If an abbreviation is not defined, it has its generally accepted meaning.

aq.=aqueous
μL=microliters
μM=micromolar
NMR=nuclear magnetic resonance
Boc=tert-butoxycarbonyl
br=broad
Cbz=benzyloxycarbonyl
d=doublet
° C.=degrees Celsius
DCM=dichloromethane
dd=doublet of doublets
DMAP=N,N-dimethylaminopyridine
DMEM=Dulbeco's Modified Eagle's Medium
DMF=N,N-dimethylformamide
DMSO=dimethylsufoxide
EDC=N-(3-Dimethylaminopropyl)-'-ethylcarbodiimide hydrochloride
EtOAc=ethyl acetate
g=gram
h or hr=hour(s)
HPLC=high performance liquid chromatography
Hz=Hertz
IU=International Units
$IC_{50}$=50% inhibitory concentration
J=coupling constant in Hz
LCMS=liquid chromatography mass spectrometry
m=multiplet
M=molar concentration
$M+H^+$=parent mass spectrum peak plus $H^+$
mg=milligram
min=minute(s)
mL=milliliter mM=millimolar
mmol=millimole
MMTr=monomethoxytrityl
MS=mass spectrum
MTBE=methyl tert-butyl ether
nM=nanomolar
PE=petroleum ether
ppm=parts per million
q.s.=sufficient amount
s=singlet
RT=room temperature
sat.=saturated
t=triplet
TBDMS=tert-butyldimethylsilyl
TBDPS=tert-butyldiphenylsilyl
TEA=triethylamine
THF=tetrahydrofuran
TMS=trimethylsilyl Additionally, various compounds of the invention may be made, in one embodiment, by way of the general synthesis routes set forth in Schemes 1-4 below:

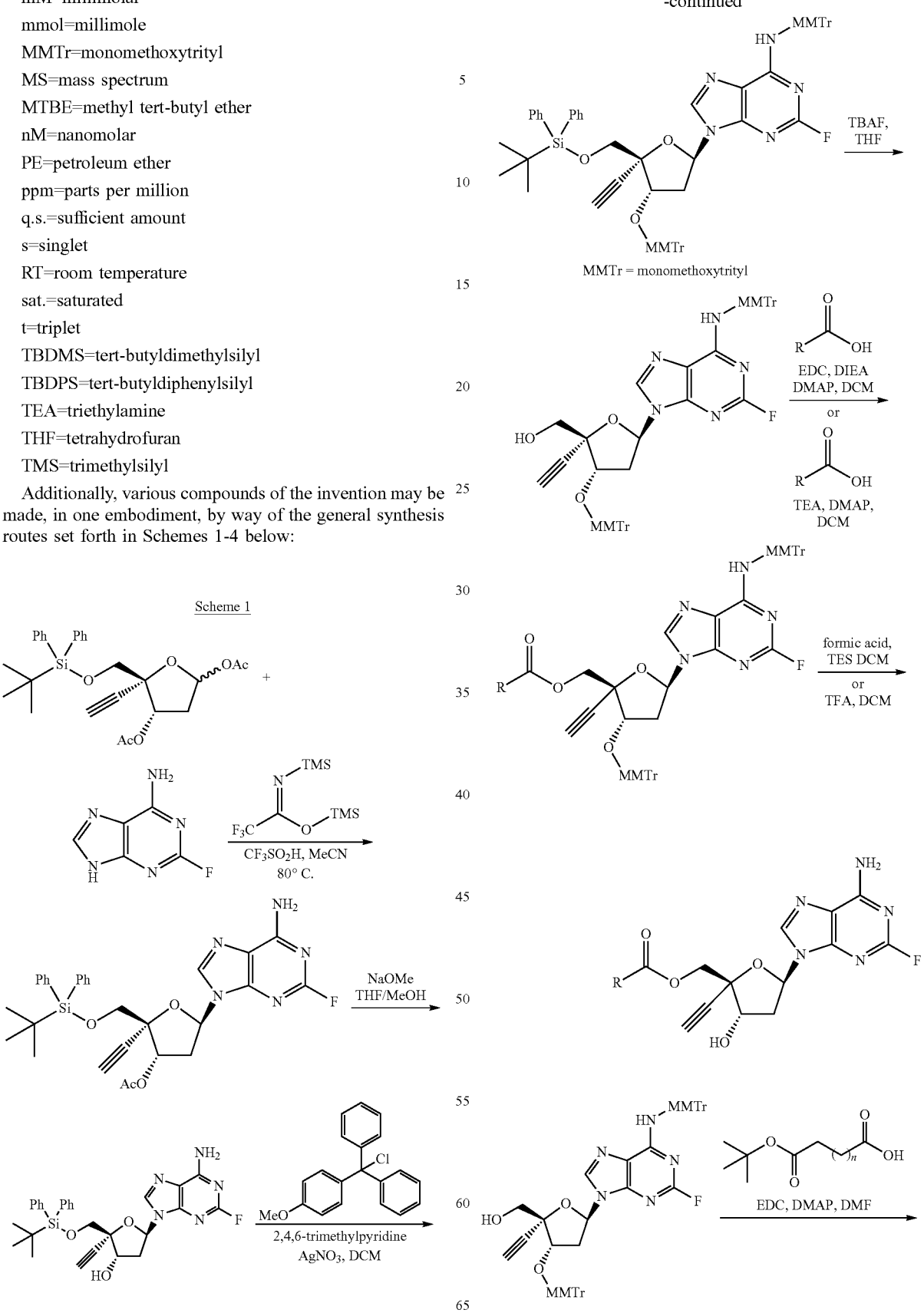

59
-continued
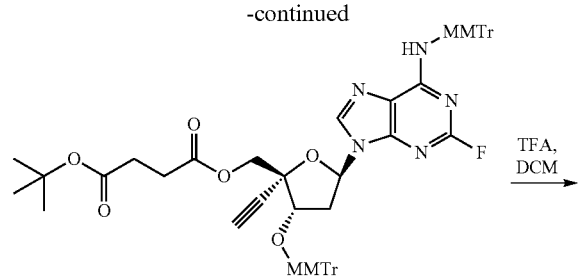
60
-continued
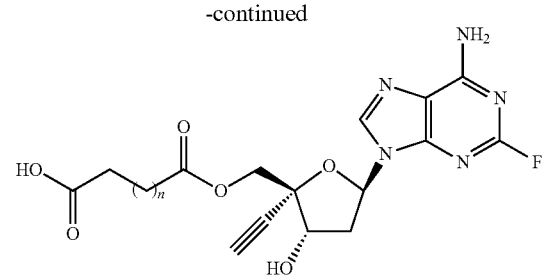
Scheme 2
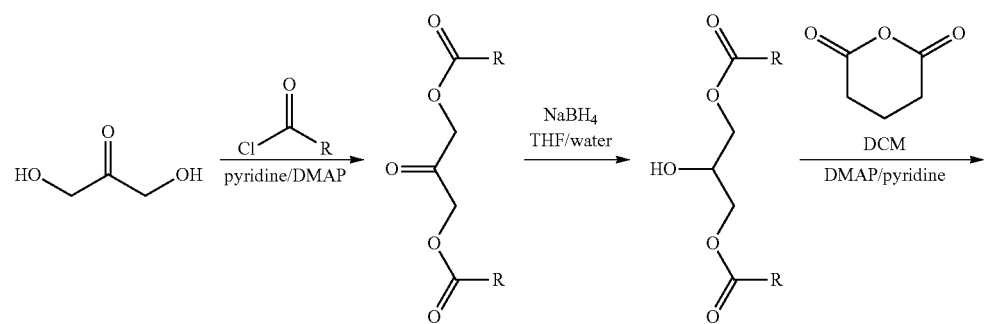
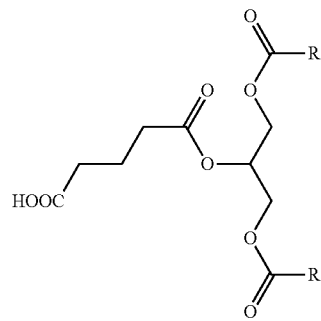
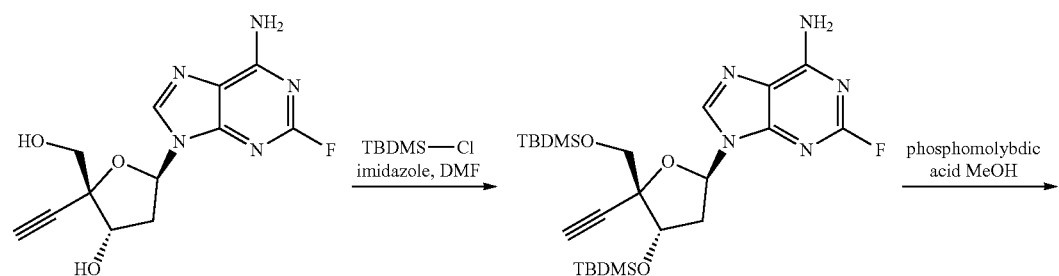

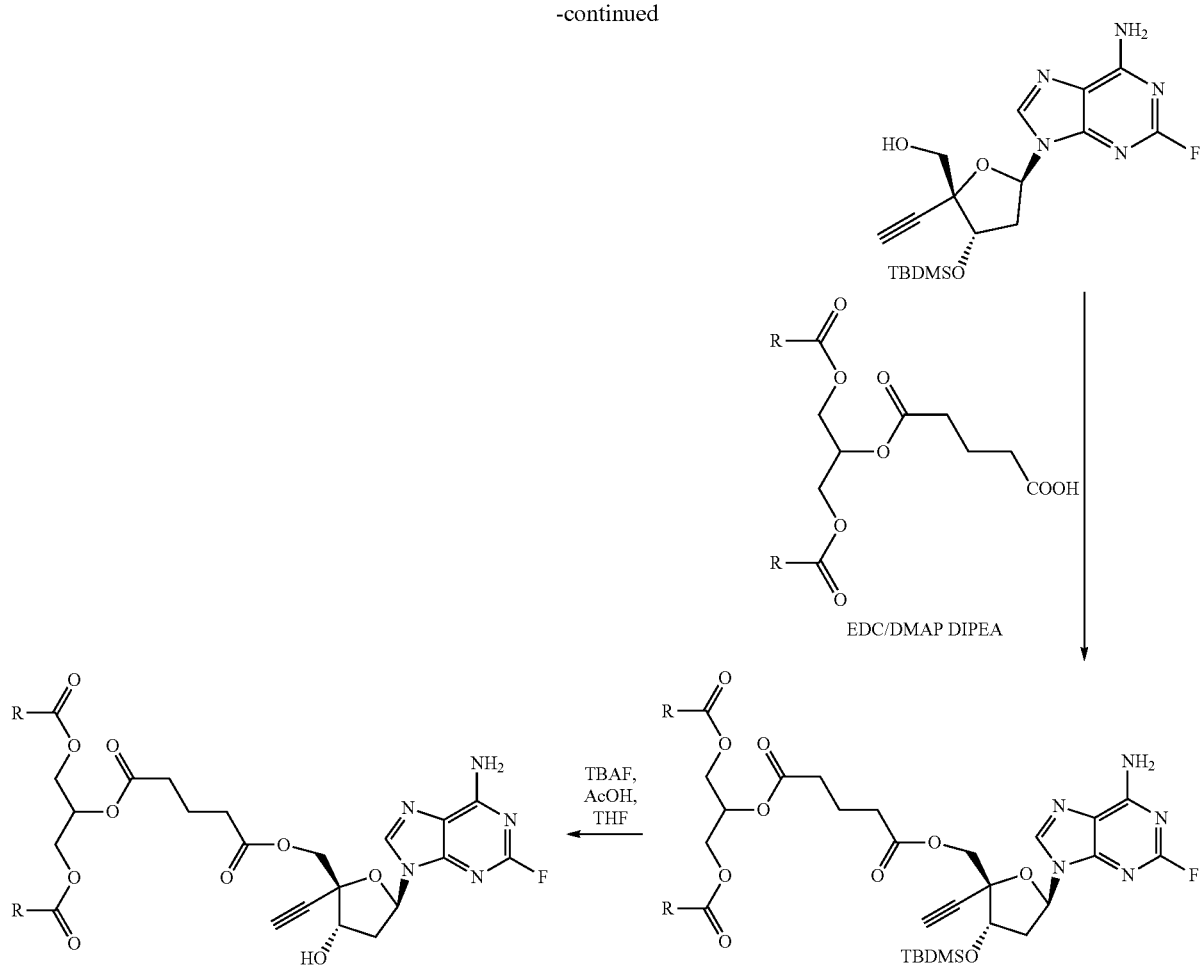
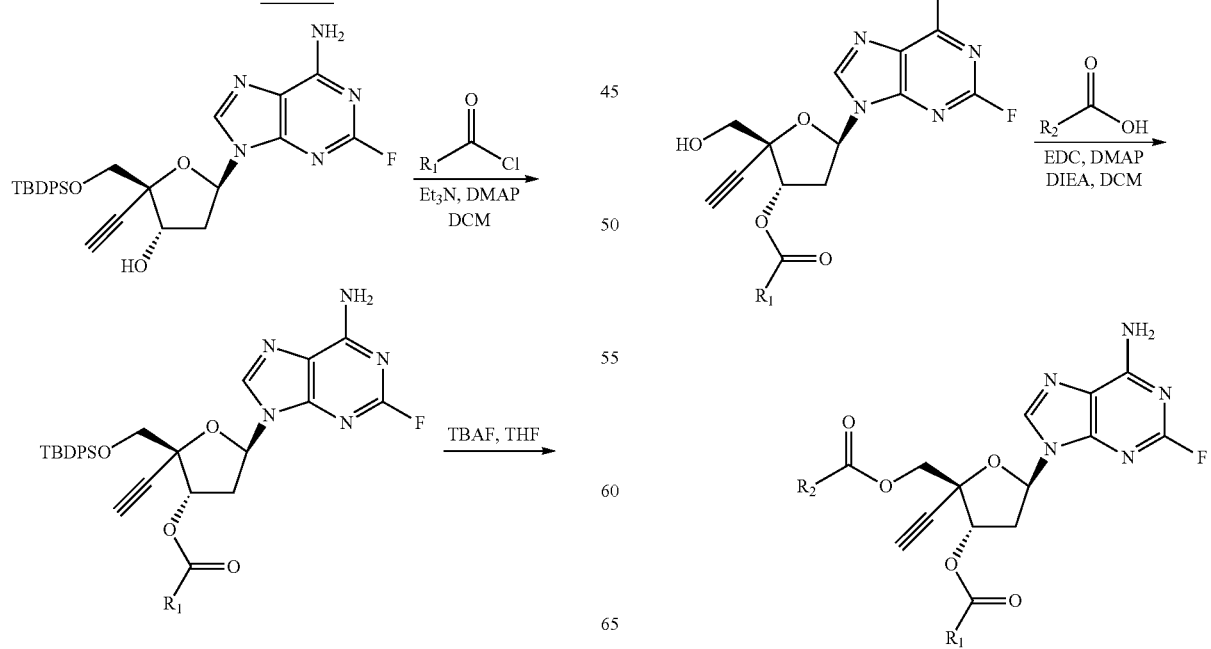
Scheme 3

63
-continued
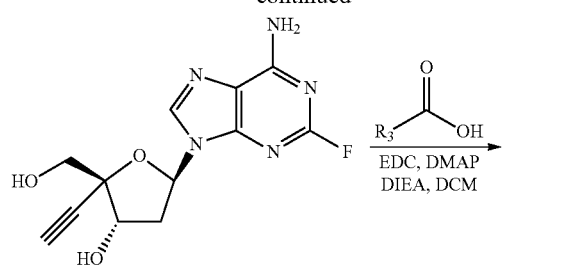
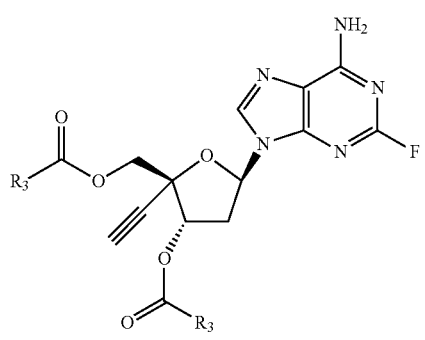
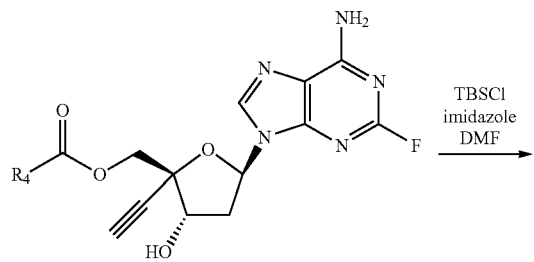
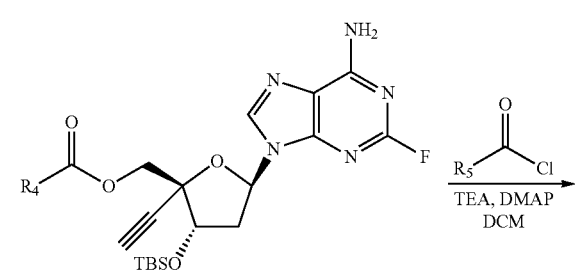
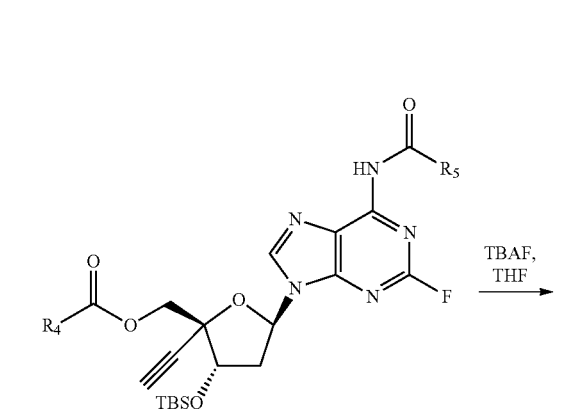
64
-continued
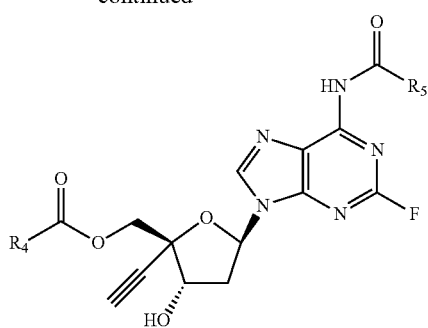
Scheme 4
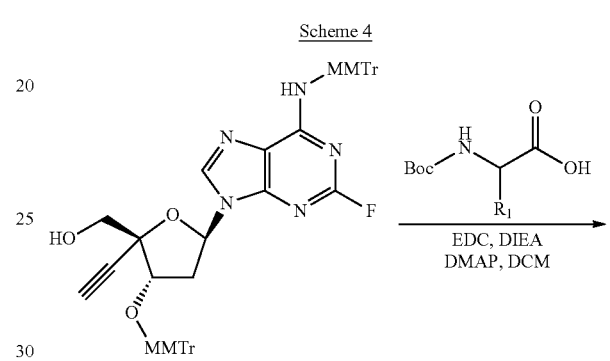
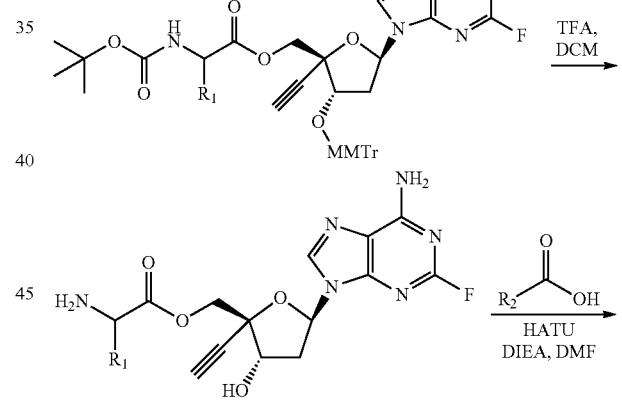
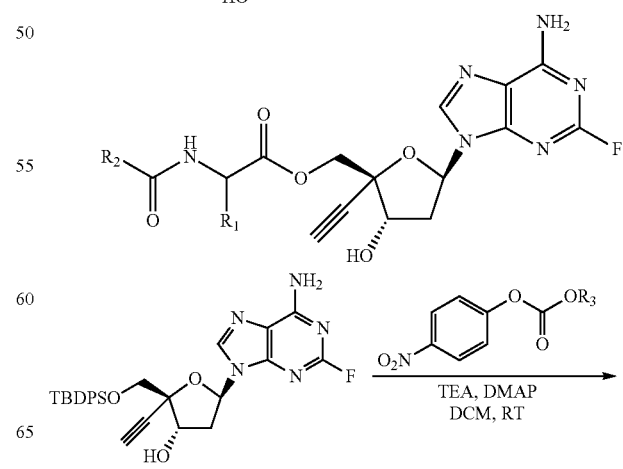

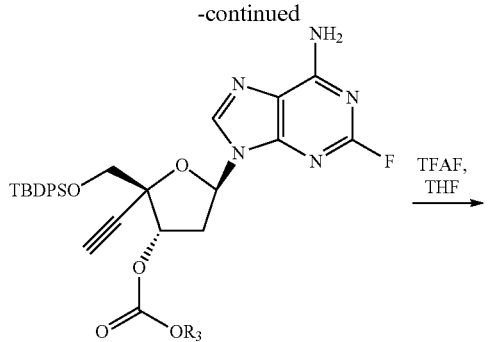

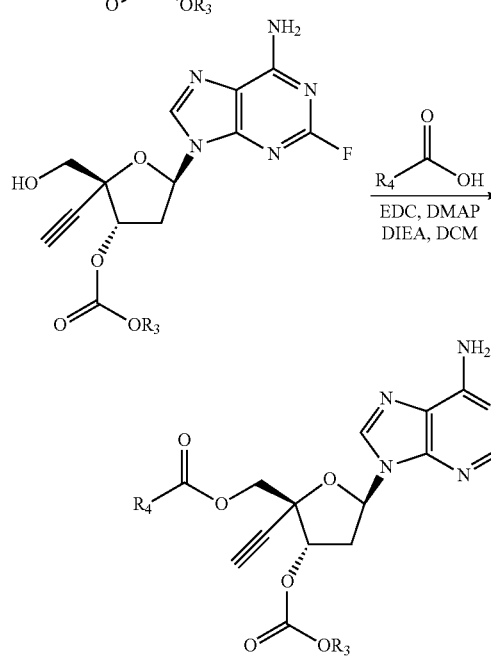

wherein n is from 0 to 20, and each of R, $R_1$, $R_2$, $R_3$, $R_4$ and $R_5$ are alkyl.

Equipment Description $^1$H NMR spectra were recorded on Varian or Bruker spectrometers. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Representative equipment and conditions for acquiring analytical low resolution LCMS are described below.
Instrumentation:
  Waters Acquity UPLC-MS system with SQ detectors
MS Conditions:
  Scan Mode: Alternating positive/negative electrospray
  Scan Range: 125-1200 amu
  Scan Time: 150 msec
  Interscan Delay: 50 msec
LC Conditions:
  The UPLC analysis was conducted on a Phenomenex Kinetex 1.7 um
  2.1×50 mm XB-C18 column at 40° C.
  0.2 uL of sample was injected using PLNO (partial loop with needle overfill) injection mode.

The gradient employed was:
  Mobile Phase A: Water+0.2% v/v Formic Acid
  Mobile Phase B: Acetonitrile+0.15% v/v Formic Acid

| Time | % A | % B | Flow Rate |
|---|---|---|---|
| 0.00 min | 95 | 5 | 1 ml/min |
| 1.1 min | 1 | 99 | 1 ml/min |
| 1.5 min | 1 | 99 | 1 ml/min |

UV detection provided by summed absorbance signal from 210 to 350 nm scanning at 40 Hz.

Example 1: ((2R,3S,5R)-5-(6-amino-2-fluoro-9H-purin-9-yl)-2-ethynyl-3-hydroxytetrahydrofuran-2-yl)methyl Cyclohexanecarboxylate

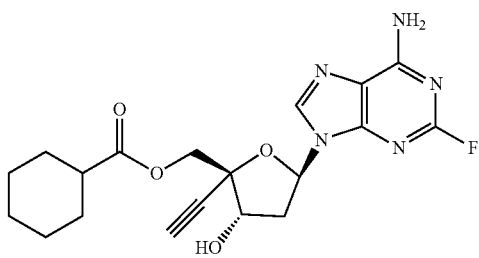 [SMILES: C#C[C@]1(COC(=O)C2CCCCC2)O[C@@H](n2cnc3c(N)nc(F)nc32)C[C@@H]1O]

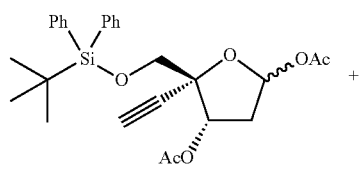

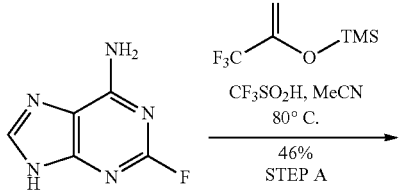

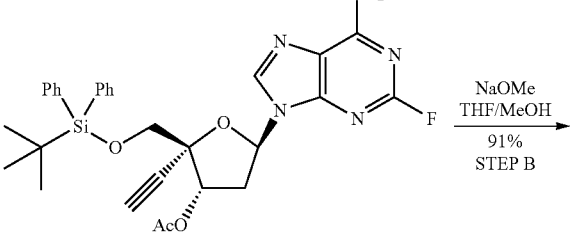

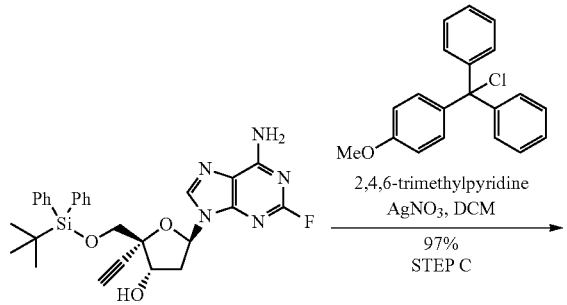

-continued

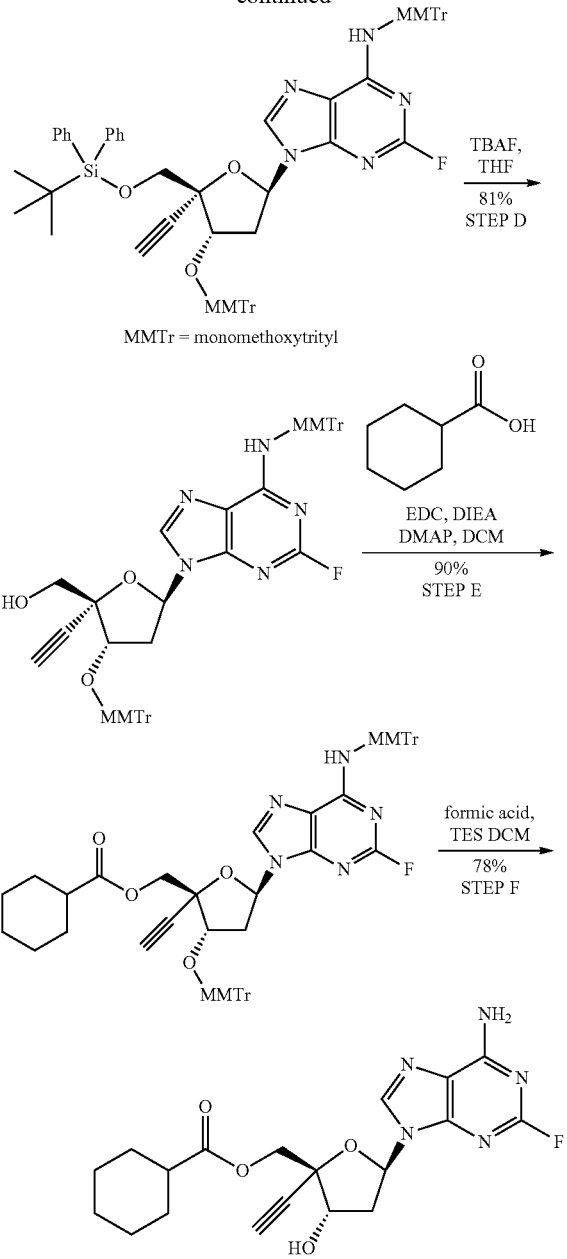

MMTr = monomethoxytrityl

Step A: (2R,3S,5R)-5-(6-amino-2-fluoro-9H-purin-9-yl)-2-(((tert-butyldiphenylsilyl)oxy)methyl)-2-ethynyltetrahydrofuran-3-yl acetate. A suspension of 2-fluoro-9H-purin-6-amine (0.545 g, 3.56 mmol) in anhydrous MeCN (10 mL) in a screw-capped glass pressure vessel under a nitrogen atmosphere was treated with trimethylsilyl 2,2,2-trifluoro-N-(trimethylsilyl)acetimidate (1.89 ml, 7.12 mmol) and heated to 80° C. with stirring in an oil bath. After 45 minutes most of the solid had dissolved. The solution was treated with (4S,5R)-5-(((tert-butyldiphenylsilyl)oxy)methyl)-5-ethynyltetrahydrofuran-2,4-diyl diacetate (1.14 g, 2.37 mmol, prepared according to Org. Lett., Vol. 13, No. 19, 2011) dissolved in MeCN (9 mL) followed by freshly prepared 0.2M trifluoromethanesulfonic acid/MeCN (2.37 ml, 0.474 mmol) (prepared by dissolving 44 μL of triflic acid in 2.5 mL of MeCN). The temperature was maintained at 80° C. After 1.5 hour at 80° C. LCMS indicated complete reaction. The solution was cooled to RT, quenched by addition of 1M aqueous HCl (3 mL). After stirring the mixture briefly, it was partitioned between saturated aqueous NaHCO$_3$ and EtOAc and the phases separated. The aqueous phase was extracted with EtOAc (2×). The combined EtOAc solutions were dried over Na$_2$SO$_4$ and concentrated at reduced pressure to give a tan solid. This material was subjected to flash chromatography (silica gel, 0-100% EtOAc/DCM) and the higher R$_f$ component isolated to afford the title compound (0.63 g, 46%) as a white solid. LCMS (ESI) m/z calcd for C$_{30}$H$_{32}$FN$_5$O$_4$Si: 573.2. Found: 574.4 (M+1)$^+$. $^1$H NMR (400 MHz, Methanol-d$_4$) δ 8.10 (s, 1H), 7.59-7.67 (m, 4H), 7.26-7.45 (m, 6H), 6.39 (t, J=6.6 Hz, 1H), 5.91 (dd, J=7.0, 5.5 Hz, 1H), 3.97 (d, J=10.9 Hz, 1H), 3.86 (d, J=10.9 Hz, 1H), 3.05-3.18 (m, 2H), 2.64-2.74 (m, 1H), 2.14 (s, 3H), 0.97-1.04 (m, 9H).

Step B: (2R,3S,5R)-5-(6-amino-2-fluoro-9H-purin-9-yl)-2-(((tert-butyldiphenylsilyl)oxy)methyl)-2-ethynyltetrahydrofuran-3-ol. To a stirred solution of (2R,3S,5R)-5-(6-amino-2-fluoro-9H-purin-9-yl)-2-(((tert-butyldiphenylsilyl)oxy)methyl)-2-ethynyltetrahydrofuran-3-yl acetate (0.62 g, 1.08 mmol) in 1:1 THF/MeOH (4 mL) was added 25% NaOMe/MeOH (3 drops). The resulting solution was stirred at RT. After 30 minutes LCMS indicated complete reaction. The solution was treated with glacial AcOH (5 drops) and concentrated to dryness at reduced pressure. The residue was partitioned between 8:2 chloroform/iPrOH and half-saturated aqueous NaHCO$_3$ and the phases separated. The aqueous phase was extracted with two additional portions of 8:2 chloroform/iPrOH. The combined organic solutions were dried over Na$_2$SO$_4$ and concentrated to dryness at reduced pressure to afford the title compound (0.52 g, 91%) as a white solid. LCMS (ESI) m/z calcd for C$_{28}$H$_{30}$FN$_5$O$_3$Si: 531.2. Found: 532.3 (M+1)$^+$. $^1$H NMR (400 MHz, Methanol-d$_4$) δ 8.17 (s, 1H), 7.53-7.66 (m, 4H), 7.22-7.45 (m, 6H), 6.32 (dd, J=7.8, 3.1 Hz, 1H), 5.01 (t, J=7.8 Hz, 1H), 3.87 (q, J=11.3 Hz, 2H), 3.05 (s, 1H), 2.90-2.99 (m, 1H), 2.63-2.72 (m, 1H), 0.94 (s, 9H).

Step C: 9-((2R,4S,5R)-5-(((tert-butyldiphenylsilyl)oxy)methyl)-5-ethynyl-4-((4-methoxyphenyl)diphenylmethoxy)tetrahydrofuran-2-yl)-2-fluoro-N-((4-methoxyphenyl)diphenylmethyl)-9H-purin-6-amine. To a stirred suspension of (2R,3S,5R)-5-(6-amino-2-fluoro-9H-purin-9-yl)-2-(((tert-butyldiphenylsilyl)oxy)methyl)-2-ethynyltetrahydrofuran-3-ol (0.510 g, 0.959 mmol) in DCM (8 mL) was added silver nitrate (0.489 g, 2.88 mmol), 2,4,6-trimethylpyridine (0.766 ml, 5.76 mmol), and (chloro(4-methoxyphenyl)methylene)dibenzene (0.889 g, 2.88 mmol). The resulting orange suspension was stirred at RT. After 2 hours LCMS indicated complete reaction. The mixture was diluted with EtOAc and filtered through celite to remove solids. The filtrate was washed with 10% aqueous citric acid (2×), saturated aqueous NaHCO$_3$ (2×), dried over Na$_2$SO$_4$ and concentrated at reduced pressure to give a pale yellow foam. This material was subjected to flash chromatography (silica gel, 0-100% EtOAc/hexanes) to afford the title compound (1.00 g, 97%) as a white foam. LCMS (ESI) m/z calcd for C$_{68}$H$_{62}$FN$_5$O$_5$Si: 1075.5. Found: 1076.7 (M+1)$^+$. $^1$H NMR (400 MHz, CDCl$_3$) δ 7.12-7.62 (m, 35H), 6.98 (s, 1H), 6.74-6.82 (m, 4H), 6.22 (t, J=6.6 Hz, 1H), 4.75 (t, J=5.9 Hz, 1H), 3.93 (d, J=11.3 Hz, 1H), 3.86 (d, J=11.3 Hz, 1H), 3.77 (s, 3H), 3.75 (s, 3H), 2.77 (s, 1H), 1.71 (t, J=6.3 Hz, 2H), 0.87 (s, 9H).

Step D: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methanol. To a stirred solution of 9-((2R,4S,5R)-5-(((tert-butyldiphenylsilyl)oxy)methyl)-5-ethynyl-4-((4-methoxyphenyl)diphenylmethoxy)tetrahydrofuran-2-yl)-2-fluoro-N-((4-methoxyphenyl)diphenylmethyl)-9H-purin-6-amine (0.99 g, 0.92 mmol) in THF (8 mL) was added 1M TBAF/THF (1.38 ml, 1.38 mmol) by dropwise addition. The resulting solution was stirred at RT. After 1 hour LCMS indicated complete reaction. The solution was treated with glacial AcOH (0.10 mL) and concentrated at reduced pressure. The residue was dissolved in MeOH/DCM and again concentrated to dryness. The residue was subjected to flash chromatography (silica gel, 0-100% EtOAc/hexanes) to afford the title compound (0.623 g, 81%) as a white solid. LCMS (ESI) m/z calcd for $C_{52}H_{44}FN_5O_5$: 837.3. Found: 838.6 (M+1)$^+$. $^1$H NMR (400 MHz, DMSO-d$_6$) δ 8.04 (s, 1H), 8.00 (s, 1H), 7.47-7.54 m, 4H), 7.12-7.38 (m, 20H), 6.79-6.88 (m, 4H), 6.04 (t, J=6.3 Hz, 1H), 5.15 (t, J=6.1 Hz, 1H), 4.47 (t, J=6.1 Hz, 1H), 3.84 (s, 1H), 3.69 (s, 3H), 3.67 (s, 3H), 3.49-3.57 (m, 1H), 3.38-3.47 (m, 1H), 1.63-1.72 (m, 1H), 1.49-1.58 (m, 1H).

Step E: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl) methyl cyclohexanecarboxylate. To a stirred solution of ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methanol (51 mg, 0.061 mmol), cyclohexanecarboxylic acid (15.60 mg, 0.122 mmol) and DMAP (7.44 mg, 0.061 mmol) in DCM (0.8 mL) was added EDC (35.0 mg, 0.183 mmol), followed by DIPEA (0.053 mL, 0.304 mmol) at ambient temperature. The mixture was allowed to stir overnight. The mixture was concentrated and then purified on silica gel (0-50% hexanes/EtOAc) to afford the title compound (53 mg, 90%) as a colorless residue. LCMS (ESI) m/z calcd for $C_{66}H_{68}FN_5O_8Si$: 1078. Found: 1079 (M+1)$^+$. LCMS (ESI) m/z calcd for $C_{59}H_{54}FN_5O_6$: 947.4. Found: 948.8 (M+1)$^+$.

Step F: ((2R,3S,5R)-5-(6-amino-2-fluoro-9H-purin-9-yl)-2-ethynyl-3-hydroxytetrahydrofuran-2-yl)methyl cyclohexanecarboxylate. To a stirred solution of ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methyl cyclohexanecarboxylate (53 mg, 0.055 mmol) in DCM (0.8 mL) was added formic acid (0.2 mL), followed by triethylsilane (0.018 mL, 0.11 mmol). The resulting orange solution was stirred for 60 minutes and was then concentrated. The residue was purified on silica gel (0-10% DCM/MeOH) to afford the title compound (17 mg, 78%) as a white solid. LCMS (ESI) m/z calcd for $C_{19}H_{22}FN_5O_4$: 403.2. Found: 404.3 (M+1)$^+$. $^1$H NMR (400 MHz, DMSO-d$_6$) 5=8.25 (s, 1H), 7.81 (br s, 2H), 6.24 (dd, J=3.8, 8.1 Hz, 1H), 5.76 (d, J=5.5 Hz, 1H), 4.75-4.69 (m, 1H), 4.41 (d, J=11.7 Hz, 1H), 4.06 (d, J=11.9 Hz, 1H), 3.61 (s, 1H), 2.88-2.80 (m, 1H), 2.54-2.42 (m, 1H, overlapping DMSO peak), 2.20-2.10 (m, 1H), 1.80-1.69 (m, 1H), 1.66-1.45 (m, 4H), 1.32-1.01 (m, 5H).

Example 2: ((2R,3S,5R)-5-(6-amino-2-fluoro-9H-purin-9-yl)-2-ethynyl-3-hydroxytetrahydrofuran-2-yl)methyl Benzoate

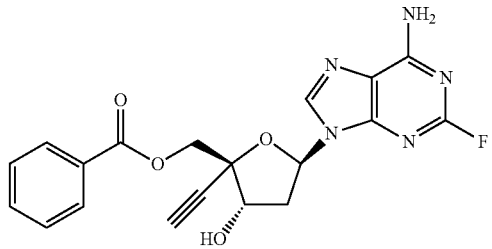 [SMILES: C#C[C@]1(COC(=O)c2ccccc2)O[C@@H](n2cnc3c(N)nc(F)nc32)C[C@@H]1O]

The title compound was prepared according to example 1, substituting benzoic acid for cyclohexanecarboxylic acid in Step E. LCMS (ESI) m/z calcd for $C_{19}H_{16}FN_5O_4$: 397.1. Found: 398.2 (M+1)$^+$. $^1$H NMR (400 MHz, DMSO-d$_6$) 5=8.27 (s, 1H), 7.91-7.86 (m, 2H), 7.81 (br s, 2H), 7.68-7.62 (m, 1H), 7.52-7.44 (m, 2H), 6.29 (dd, J=3.9, 8.2 Hz, 1H), 5.84 (d, J=5.5 Hz, 1H), 4.92-4.84 (m, 1H), 4.61 (d, J=11.9 Hz, 1H), 4.40 (d, J=11.7 Hz, 1H), 3.67 (s, 1H), 2.91-2.83 (m, 1H), 2.57-2.47 (m, 1H, overlapping DMSO peak).

Example 3: [(2R,3S,5R)-5-(6-amino-2-fluoro-9H-purin-9-yl)-2-ethynyl-3-hydroxyoxolan-2-yl]methyl 2-phenylacetate

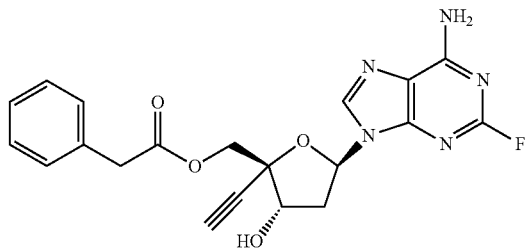 [SMILES: C#C[C@]1(COC(=O)Cc2ccccc2)O[C@@H](n2cnc3c(N)nc(F)nc32)C[C@@H]1O]

The title compound was prepared according to example 1, substituting 2-phenylacetic acid for cyclohexanecarboxylic acid in Step E. LCMS (ESI) m/z calcd for $C_{20}H_{18}FN_5O_4$: 411.1. Found: 412.6 (M+1)$^+$. $^1$H NMR (400 MHz, DMSO-d$_6$) 5=8.27 (s, 1H), 7.83 (br s, 2H), 7.29-7.20 (m, 3H), 7.19-7.13 (m, 2H), 6.26 (dd, J=4.1, 8.1 Hz, 1H), 5.77 (d, J=5.5 Hz, 1H), 4.76-4.68 (m, 1H), 4.44 (d, J=11.7 Hz, 1H), 4.15 (d, J=11.7 Hz, 1H), 3.71-3.48 (m, 3H), 2.83-2.74 (m, 1H), 2.56-2.43 (m, 1H, overlapping DMSO peak).

Example 4: ((2R,3S,5R)-5-(6-amino-2-fluoro-9H-purin-9-yl)-2-ethynyl-3-hydroxytetrahydrofuran-2-yl)methyl 2-phenylacetate

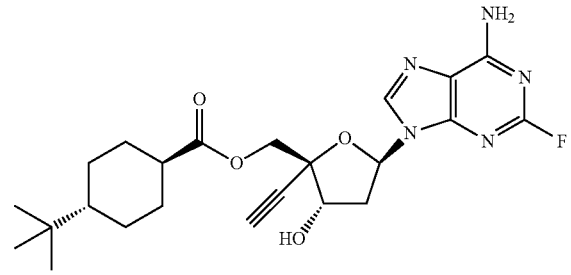 [SMILES: C#C[C@]1(COC(=O)[C@H]2CC[C@H](C(C)(C)C)CC2)O[C@@H](n2cnc3c(N)nc(F)nc32)C[C@@H]1O]

The title compound was prepared according to example 1, substituting trans-4-(tert-butyl)cyclohexanecarboxylic acid for cyclohexanecarboxylic acid in Step E. LCMS (ESI) m/z calcd for $C_{23}H_{30}FN_5O_4$: 459.2. Found: 460.3 (M+1)$^+$. $^1$H NMR (400 MHz, DMSO-$d_6$) δ=8.25 (s, 1H), 7.80 (br s, 2H), 6.23 (dd, J=3.9, 8.0 Hz, 1H), 5.75 (d, J=5.5 Hz, 1H), 4.76-4.69 (m, 1H), 4.42 (d, J=11.7 Hz, 1H), 4.05 (d, J=11.7 Hz, 1H), 3.61 (s, 1H), 2.88-2.80 (m, 1H), 2.54-2.42 (m, 1H, overlapping DMSO peak), 2.10-1.96 (m, 1H), 1.91-1.80 (m, 1H), 1.75-1.59 (m, 3H), 1.26-1.03 (m, 2H), 0.98-0.84 (m, 3H), 0.81 (s, 9H).

Example 5: ((2R,3S,5R)-5-(6-amino-2-fluoro-9H-purin-9-yl)-2-ethynyl-3-hydroxytetrahydrofuran-2-yl)methyl trans-4-pentylcyclohexane-1-carboxylate

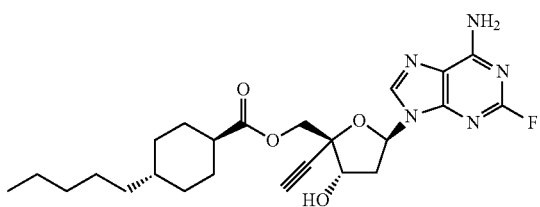 [SMILES: C#C[C@]1(COC(=O)[C@H]2CC[C@H](CCCCC)CC2)O[C@@H](n2cnc3c(N)nc(F)nc32)C[C@@H]1O]

The title compound was prepared according to example 1, substituting trans-4-pentylcyclohexanecarboxylic acid for cyclohexanecarboxylic acid in Step E. LCMS (ESI) m/z calcd for $C_{24}H_{33}FN_5O_4$: 473.2. Found: 474.4 (M+1)$^+$. $^1$H NMR (400 MHz, DMSO-$d_6$) δ=8.25 (s, 1H), 7.81 (br s, 2H), 6.23 (dd, J=3.9, 8.0 Hz, 1H), 5.75 (d, J=5.5 Hz, 1H), 4.76-4.68 (m, 1H), 4.42 (d, J=11.9 Hz, 1H), 4.05 (d, J=11.7 Hz, 1H), 3.61 (s, 1H), 2.87-2.79 (m, 1H), 2.54-2.42 (m, 1H, overlapping DMSO peak), 2.11-2.02 (m, 1H), 1.85-1.75 (m, 1H), 1.73-1.57 (m, 3H), 1.35-1.04 (m, 11H), 0.92-0.74 (m, 5H).

Example 6: ((2R,3S,5R)-5-(6-amino-2-fluoro-9H-purin-9-yl)-2-ethynyl-3-hydroxytetrahydrofuran-2-yl)methyl 2-(2-methoxyethoxy)acetate

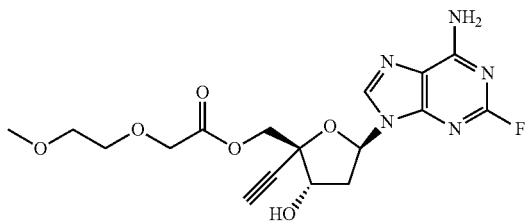 [SMILES: C#C[C@]1(COC(=O)COCCOC)O[C@@H](n2cnc3c(N)nc(F)nc32)C[C@@H]1O]

The title compound was prepared according to example 1, substituting 2-(2-methoxyethoxy)acetic acid for cyclohexanecarboxylic acid in Step E. LCMS (ESI) m/z calcd for $C_{17}H_{20}FN_5O_6$: 409.1. Found: 410.3 (M+1)$^+$. $^1$H NMR (400 MHz, DMSO-$d_6$) δ=8.27 (s, 1H), 7.83 (br s, 2H), 6.25 (dd, J=4.3, 7.9 Hz, 1H), 5.78 (d, J=5.5 Hz, 1H), 4.72-4.65 (m, 1H), 4.48 (d, J=11.7 Hz, 1H), 4.18 (d, J=11.7 Hz, 1H), 4.12 (d, J=16.7 Hz, 1H), 3.99 (d, J=16.7 Hz, 1H), 3.64 (s, 1H), 3.54-3.48 (m, 2H), 3.44-3.38 (m, 2H), 3.21 (s, 3H), 2.82-2.74 (m, 1H), 2.54-2.43 (m, 1H, overlapping DMSO peak).

Example 7: ((2R,3S,5R)-5-(6-amino-2-fluoro-9H-purin-9-yl)-2-ethynyl-3-hydroxytetrahydrofuran-2-yl)methyl 2-(2-(2-methoxyethoxy)ethoxy)acetate

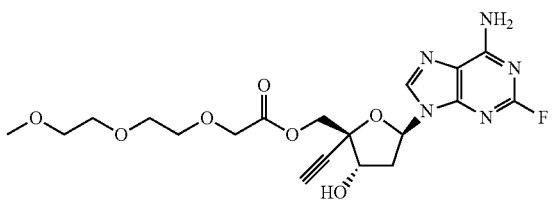 [SMILES: C#C[C@]1(COC(=O)COCCOCCOC)O[C@@H](n2cnc3c(N)nc(F)nc32)C[C@@H]1O]

The title compound was prepared according to example 1, substituting 2-(2-(2-methoxyethoxy)ethoxy)acetic acid for cyclohexanecarboxylic acid in Step E. LCMS (ESI) m/z calcd for $C_{19}H_{24}FN_5O_7$: 453.2. Found: 454.7 (M+1)$^+$. $^1$H NMR (400 MHz, DMSO-$d_6$) δ=8.27 (s, 1H), 7.82 (br s, 2H), 6.25 (dd, J=4.1, 7.9 Hz, 1H), 5.78 (d, J=5.5 Hz, 1H), 4.71-4.64 (m, 1H), 4.48 (d, J=11.7 Hz, 1H), 4.18 (d, J=11.7 Hz, 1H), 4.12 (d, J=16.9 Hz, 1H), 4.00 (d, J=16.7 Hz, 1H), 3.63 (s, 1H), 3.54-3.45 (m, 6H), 3.43-3.36 (m, 2H), 3.21 (s, 3H), 2.81-2.73 (m, 1H), 2.53-2.43 (m, 1H, overlapping DMSO peak).

Example 8: ((2R,3S,5R)-5-(6-amino-2-fluoro-9H-purin-9-yl)-2-ethynyl-3-hydroxytetrahydrofuran-2-yl)methyl 2-(2-butoxyethoxy)acetate

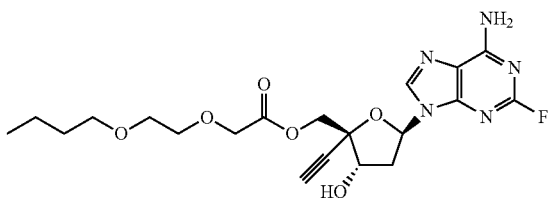 [SMILES: C#C[C@]1(COC(=O)COCCOCCCC)O[C@@H](n2cnc3c(N)nc(F)nc32)C[C@@H]1O]

The title compound was prepared according to example 1, substituting 2-(2-butoxyethoxy)acetic acid for cyclohexanecarboxylic acid in Step E. LCMS (ESI) m/z calcd for $C_{20}H_{26}FN_5O_6$: 451.2. Found: 452.3 (M+1)$^+$. $^1$H NMR (400 MHz, DMSO-$d_6$) δ=8.28 (s, 1H), 7.84 (br s, 2H), 6.26 (dd, J=4.2, 7.7 Hz, 1H), 5.79 (d, J=5.5 Hz, 1H), 4.72-4.65 (m, 1H), 4.49 (d, J=11.7 Hz, 1H), 4.19 (d, J=11.7 Hz, 1H), 4.14 (d, J=16.7 Hz, 1H), 4.02 (d, J=16.7 Hz, 1H), 3.64 (s, 1H), 3.55-3.49 (m, 2H), 3.48-3.43 (m, 2H), 3.37-3.32 (m, 2H), 2.82-2.74 (m, 1H), 2.54-2.44 (m, 1H, overlapping DMSO peak), 1.49-1.37 (m, 2H), 1.35-1.20 (m, 2H), 0.90-0.80 (m, 3H).

Example 9: 10-(((2R,3S,5R)-5-(6-amino-2-fluoro-9H-purin-9-yl)-2-ethynyl-3-hydroxytetrahydrofuran-2-yl)methoxy)-10-oxodecanoic Acid

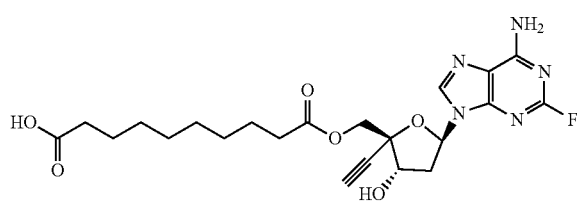 [SMILES: C#C[C@]1(COC(=O)CCCCCCCCC(=O)O)O[C@@H](n2cnc3c(N)nc(F)nc32)C[C@@H]1O]

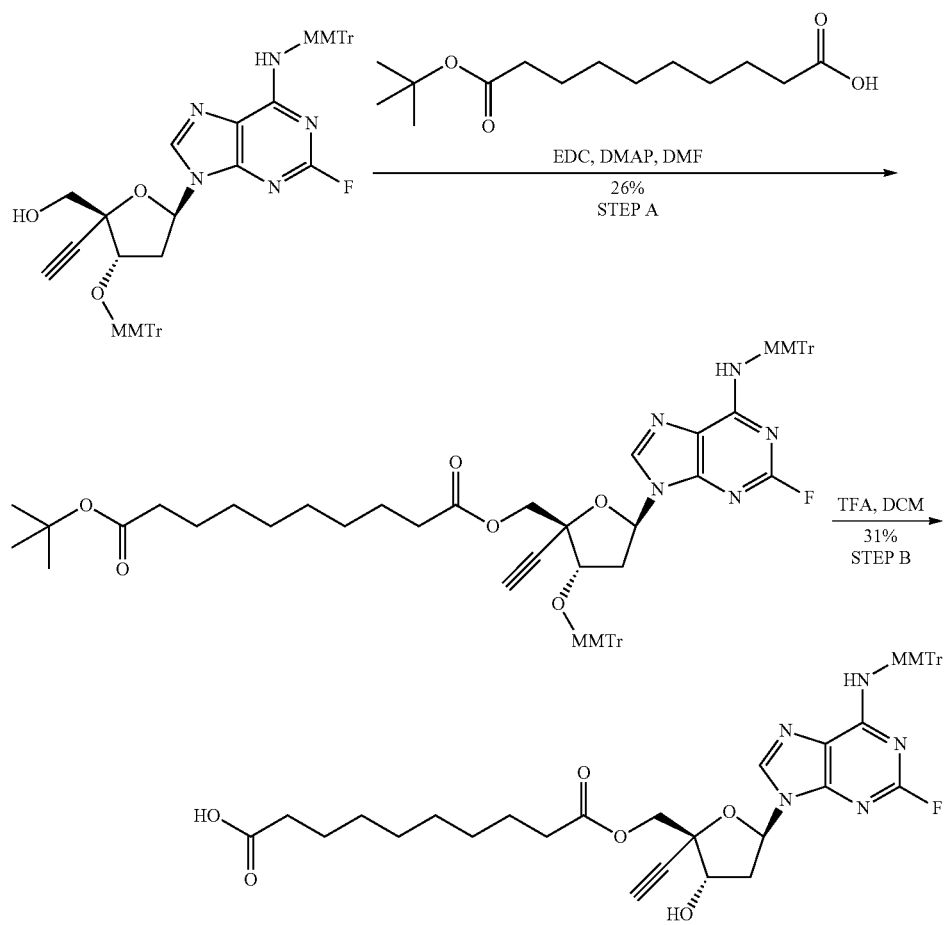

Step A: 1-(((2R,3S,5R)-5-(6-amino-2-fluoro-9H-purin-9-yl)-2-ethynyl-3-hydroxytetrahydrofuran-2-yl)methyl) 10-(tert-buty) decanedioate. 10-(tert-butoxy)-10-oxodecanoic acid (96 mg, 0.37 mmol) was dissolved in DMF (1 mL), EDC (286 mg, 1.50 mmol) and DMAP (182 mg, 1.489 mmol) were added, the resulting mixture was stirred for 2 h at RT. Then, ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methanol (260 mg, 0.310 mmol) was added, and the resulting mixture was stirred for 1 h at RT. The reaction mixture was added mixed water (10 mL) and extracted with EtOAc (3×5 mL). The combined organic phases were washed with brine (10 mL), dried over $Na_2SO_4$, and concentrated under vacuum. The residue was purified by preparative TLC (MeOH:DCM=1:20) to afford the title compound (89 mg, 26%) as a white solid. LCMS (ESI) m/z calcd for $C_{26}H_{36}FN_5O_6$: 533. Found: 534 (M+1)$^+$.

Step B: 10-(((2R,3S,5R)-5-(6-amino-2-fluoro-9H-purin-9-yl)-2-ethynyl-3-hydroxytetrahydrofuran-2-yl)methoxy)-10-oxodecanoic acid. 1-(tert-butyl) 10-(((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methyl) decanedioate (115 mg, 0.107 mmol) was dissolved in DCM (3 mL). TFA (0.158 mL, 2.13 mmol) was added, and the resulting mixture was stirred at RT. After 1 h the solution was concentrated to dryness at reduced pressure and the residue purified by RP-HPLC (C18, MeCN/water with 0.1% formic acid) to afford the title compound (15.6 mg, 31%) as a white solid. LCMS (ESI) m/z calcd for $C_{22}H_{28}FN_5O_6$: 477. Found: 478 (M+1)$^+$. $^1$H NMR (400 MHz, DMSO-d$_6$) δ 10.90 (s, 1H), 8.27 (s, 1H), 7.86 (d, J=6.0 Hz, 2H), 6.23 (dd, J=8.0, 4.4 Hz, 1H), 4.71 (t, J=5.2 Hz, 1H), 4.42 (d, J=11.6 Hz, 1H), 4.08 (d, J=11.6 Hz, 1H), 3.63 (s, 1H), 2.80-2.77 (m, 1H), 2.47 (dd, J=8.4, 3.0 Hz, 1H), 2.20-2.14 (m, 4H), 1.48-1.39 (m, 4H), 1.18 (d, J=9.4 Hz, 8H).

Example 10: 14-(((2R,3S,5R)-5-(6-amino-2-fluoro-9H-purin-9-yl)-2-ethynyl-3-hydroxytetrahydrofuran-2-yl)methoxy)-14-oxotetradecanoic Acid

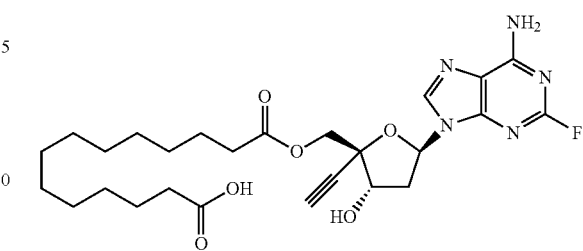

The title compound was prepared according to example 9, substituting 14-(tert-butoxy)-14-oxotetradecanoic acid for 10-(tert-butoxy)-10-oxodecanoic acid in step A. LCMS (ESI) m/z calcd for $C_{26}H_{36}FN_5O_6$: 533. Found: 534 (M+1)$^+$.
$^1$H NMR (400 MHz, Methanol-d$_4$) δ 8.15 (s, 1H), 6.30 (dd, J=3.6, 8.0 Hz, 1H), 4.87 (s, 1H), 4.47 (d, J=12.0 Hz, 1H), 4.25 (d, J=12.0 Hz, 1H), 3.17 (s, 1H), 2.91-2.88 (m, 1H), 2.70-2.64 (m, 1H), 2.29-2.18 (m, 4H), 1.63-1.55 (m, 2H), 1.51-1.43 (m, 2H), 1.26 (m, 16H).

Example 11: 20-(((2R,3S,5R)-5-(6-amino-2-fluoro-9H-purin-9-yl)-2-ethynyl-3-hydroxytetrahydrofuran-2-yl)methoxy)-20-oxoicosanoic Acid

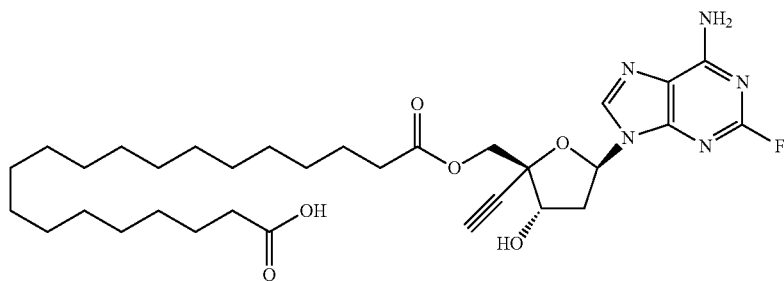 [SMILES: C#C[C@]1(COC(=O)CCCCCCCCCCCCCCCCCCC(=O)O)O[C@@H](n2cnc3c(N)nc(F)nc32)C[C@@H]1O]

The title compound was prepared according to example 9, substituting 20-(tert-butoxy)-20-oxoicosanoic acid for 10-(tert-butoxy)-10-oxodecanoic acid in step A. LCMS (ESI) m/z calcd for $C_{32}H_{48}FN_5O_6$: 617. Found: 618 (M+1)$^+$. $^1$H NMR (400 MHz, Methanol-d$_4$) δ 8.15 (s, 1H), 6.30 (dd, J=3.6, 8.0 Hz, 1H), 4.87 (s, 1H), 4.47 (d, J=12.0 Hz, 1H), 4.25 (d, J=12.0 Hz, 1H), 3.17 (s, 1H), 2.93-2.88 (m, 1H), 2.70-2.62 (m, 1H), 2.29-2.15 (m, 4H), 1.63-1.55 (m, 2H), 1.52-1.44 (m, 2H), 1.28 (m, 28H).

Example 12: ((2R,3S,5R)-5-(6-amino-2-fluoro-9H-purin-9-yl)-2-ethynyl-3-hydroxytetrahydrofuran-2-yl)methyl (1,3-bis(heptanoyloxy)propan-2-yl) glutarate

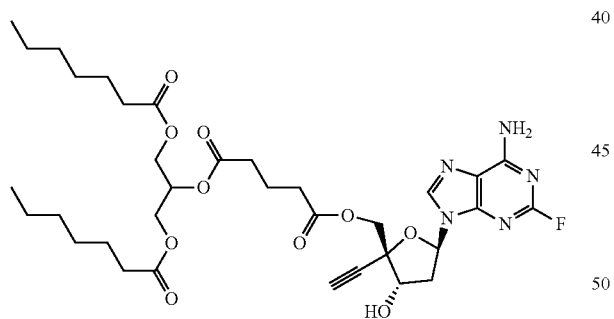

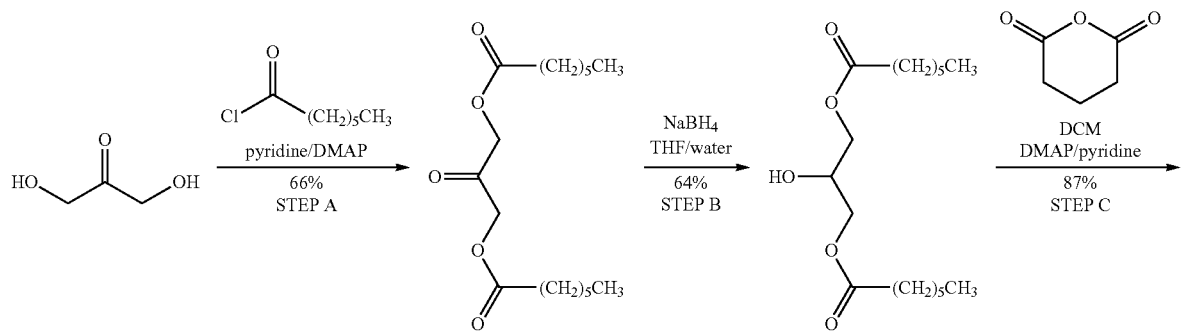

-continued

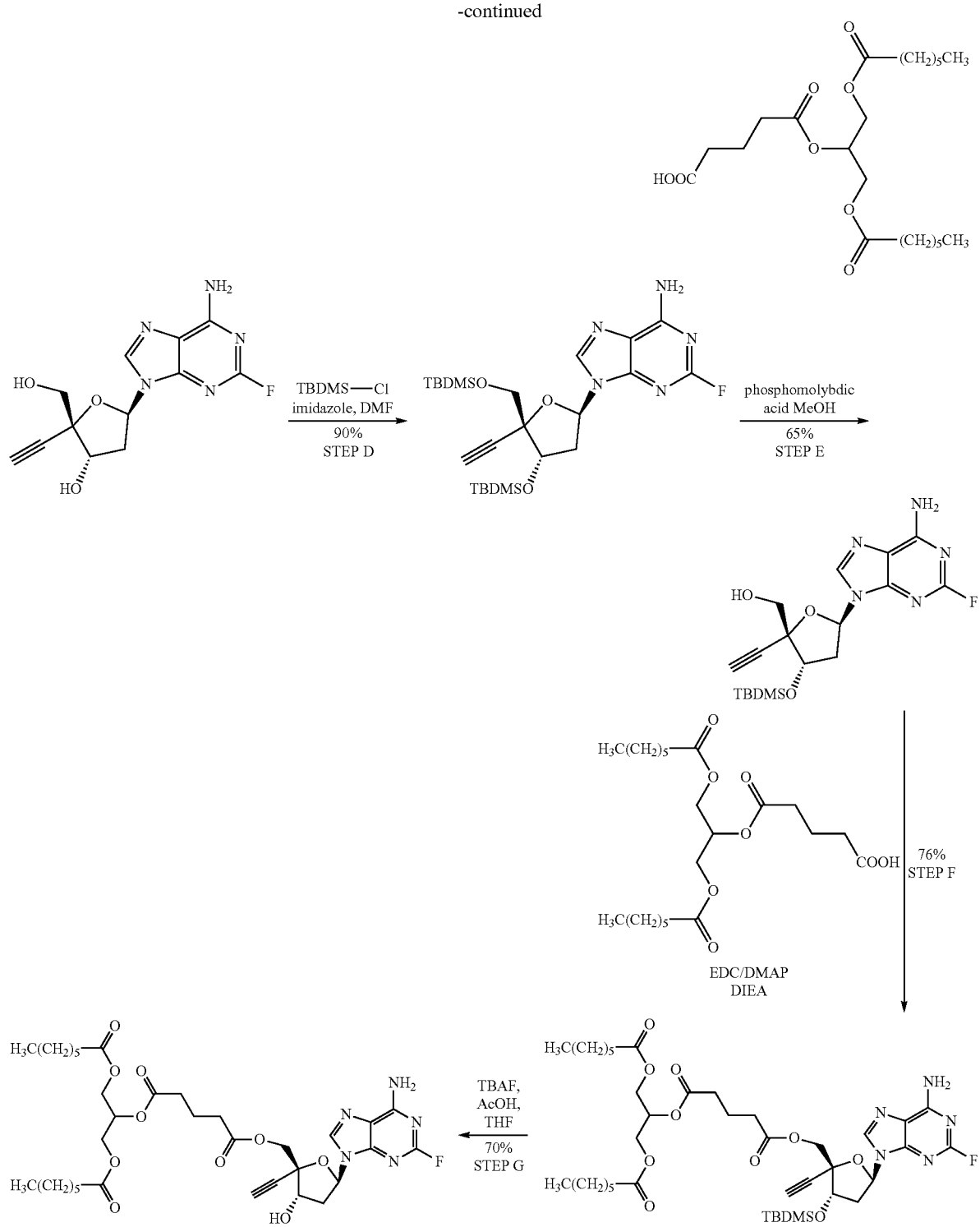

Step A: 2-oxopropane-1,3-diyl diheptanoate. To a suspension of 1,3-dihydroxypropan-2-one (500 mg, 5.55 mmol) in DCM (20 mL) was added pyridine (0.940 mL, 11.6 mmol) and heptanoyl chloride (1.76 mL, 11.4 mmol) and the mixture was stirred at ambient temperature for 18 h. The mixture was diluted with DCM and washed with water. The organic phase was washed with brine, dried ($Na_2SO_4$), concentrated and purified on silica gel (EtOAc/hexanes 0-20%) to provide 2-oxopropane-1,3-diyl diheptanoate (1.17 g, 66%) as an off-white solid. LCMS (ESI) m/z calcd for $C_{17}H_{32}O_5$: 316. Found: 315 (M−1)$^+$. $^1$H NMR (400 MHz, Chloroform-d): δ 4.77 (s, 4H), 2.45 (t, J=7.5 Hz, 4H), 1.61-1.77 (m, 4H), 1.23-1.43 (m, 12H), 0.85-0.99 (m, 6H).

Step B: 2-hydroxypropane-1,3-diyl diheptanoate. To a solution of 2-oxopropane-1,3-diyl diheptanoate (500 mg, 1.59 mmol) in THF (10 mL) was added water (0.5 mL and the mixture was cooled to 0° C. then NaBH$_4$ (36.1 mg, 0.954 mmol) was added and stirring under nitrogen atmosphere continued for 1 h and then 1 h at ambient temperature. Saturated NH$_4$Cl/water was added and the mixture was extracted with EtOAc. The organic phase was dried (Na$_2$SO$_4$), concentrated and purified on silica gel (EtOAc/hexanes 0-100%) to provide 2-hydroxypropane-1,3-diyl diheptanoate (487 mg, 64%) as a clear oil. $^1$H NMR (400 MHz, Chloroform-d): δ 4.03-4.29 (m, 5H), 2.42-2.51 (m, 1H), 2.37 (t, J=7.5 Hz, 4H), 1.61-1.74 (m, 4H), 1.24-1.44 (m, 12H), 0.86-0.98 (m, 6H).

Step C: 5-((1,3-bis(heptanoyloxy)propan-2-yl)oxy)-5-oxopentanoic acid. To a solution of 2-hydroxypropane-1,3-diyl diheptanoate (160 mg, 0.506 mmol) in DCM (1 mL)/tetrahydrofuran (1 mL)/pyridine (1 mL) was added DMAP (6.18 mg, 0.051 mmol) followed by dihydro-2H-pyran-2,6(3H)-dione (115 mg, 1.01 mmol) and the mixture was heated to 60° C. for 6.5 h. The mixture was diluted with EtOAc and washed with 1 M HCl/water. The organic phase was dried (Na$_2$SO$_4$), concentrated and purified on silica gel (MeOH/dichloromethane 0-5%) to provide 5-((1,3-bis(heptanoyloxy)propan-2-yl)oxy)-5-oxopentanoic acid (190 mg, 87%) as a clear oil. LCMS (ESI) m/z calcd for C$_{22}$H$_{33}$O$_3$: 430. Found: 431 (M−1)$^+$. $^1$H NMR (400 MHz, Chloroform-d): δ 5.21-5.35 (m, 1H), 4.28-4.42 (m, 2H), 4.09-4.25 (m, 2H), 2.40-2.53 (m, 4H), 2.27-2.38 (m, 4H), 1.99 (t, J=7.3 Hz, 2H), 1.51-1.73 (m, 4H), 1.25-1.43 (m, 12H), 0.85-0.98 (m, 6H).

Step D: 9-((2R,4S,5R)-4-((tert-butyldimethylsilyl)oxy)-5-(((tert-butyldimethylsilyl)oxy)methyl)-5-ethynyltetrahydrofuran-2-yl)-2-fluoro-9H-purin-6-amine. To a suspension of (2R,3S)-5-(6-amino-2-fluoro-9H-purin-9-yl)-2-ethynyl-2-(hydroxymethyl)tetrahydrofuran-3-ol (268 mg, 0.914 mmol) (Org. Lett., Vol. 13, No. 19, 2011, 5264-5299), in DMF (2 mL) was added imidazole (311 mg, 4.57 mmol) and TBDMS-Cl (344 mg, 2.285 mmol) and the mixture was stirred at ambient temperature for 1 h and then at 50° C. for 1 h. LCMS showed mono-silyl product only so more imidazole (311 mg, 4.57 mmol) and TBDMS-Cl (344 mg, 2.285 mmol) was added and the mixture was stirred at 50° C. under nitrogen atmosphere for 1 h. Water was added and the mixture was stirred at ambient temperature for 18 h. The mixture was filtered and the sticky solid residue was dissolved in DCM, dried (Na$_2$SO$_4$), concentrated and purified on silica gel (EtOAc/hexanes 20-100%) to provide 9-((4S,5R)-4-((tert-butyldimethylsilyl)oxy)-5-(((tert-butyldimethylsilyl)oxy) methyl)-5-ethynyltetrahydrofuran-2-yl)-2-fluoro-9H-purin-6-amine (430 mg, 90%) as an off-white solid. LCMS (ESI) m/z calcd for C$_{24}$H$_{40}$FN$_5$O$_3$Si$_2$: 521. Found: 522 (M+1)$^+$. $^1$H NMR (400 MHz, Chloroform-d): δ 8.01-8.10 (m, 1H), 6.38 (dd, J=7.2, 4.3 Hz, 1H), 5.80 (br s, 2H), 4.84 (t, J=7.0 Hz, 1H), 3.98 (d, J=11.2 Hz, 1H), 3.82 (d, J=11.2 Hz, 1H), 2.59-2.79 (m, 2H), 2.56 (s, 1H), 0.96 (s, 9H), 0.91 (s, 9H), 0.16 (s, 3H), 0.15 (s, 3H), 0.10 (s, 3H), 0.06 (s, 3H).

Step E: ((2R,3S,5R)-5-(6-amino-2-fluoro-9H-purin-9-yl)-3-((tert-butyldimethylsilyl)oxy)-2-ethynyltetrahydrofuran-2-yl)methanol. To a solution of 9-((4S,5R)-4-((tert-butyldimethylsilyl)oxy)-5-(((tert-butyldimethylsilyl)oxy)methyl)-5-ethynyltetrahydrofuran-2-yl)-2-fluoro-9H-purin-6-amine (32 mg, 0.061 mmol) in MeOH (0.7 mL) was added phosphomolybdic acid hydrate (56.0 mg, 6.13 μmol) and the mixture was stored at −5° C. for 18 h. The mixture was filtered and the yellowish solid washed with MeOH and DCM. The filtrate was concentrated and purified on silica gel (EtOAc/hexanes 20-100%) to provide ((2R,3S)-5-(6-amino-2-fluoro-9H-purin-9-yl)-3-((tert-butyldimethylsilyl) oxy)-2-ethynyltetrahydrofuran-2-yl)methanol (16.4 mg, 65%) as an off-white solid. LCMS (ESI) m/z calcd for C$_{18}$H$_{26}$FN$_5$O$_3$Si: 407. Found: 408 (M+1)$^+$. $^1$H NMR (400 MHz, DMSO-d$_6$): δ 7.74-8.04 (m, 2H), 6.26 (dd, J=6.9, 5.7 Hz, 1H), 5.30 (dd, J=6.7, 5.5 Hz, 1H), 4.77 (t, J=6.2 Hz, 1H), 3.62-3.73 (m, 1H), 3.47-3.57 (m, 2H), 2.84 (dt, J=12.5, 6.4 Hz, 1H), 2.50-2.52 (m, 1H), 2.35-2.45 (m, 1H), 0.89-0.97 (m, 9H), 0.14 (d, J=3.3 Hz, 6H).

Step F: ((2R,3S,5R)-5-(6-amino-2-fluoro-9H-purin-9-yl)-3-((tert-butyldimethylsilyl)oxy)-2-ethynyltetrahydrofuran-2-yl)methyl (1,3-bis(heptanoyloxy)propan-2-yl) glutarate. To a suspension of ((2R,3S,5R)-5-(6-amino-2-fluoro-9H-purin-9-yl)-3-((tert-butyldimethylsilyl) oxy)-2-ethynyltetrahydrofuran-2-yl)methanol (11.7 mg, 0.029 mmol) in DCM (1.5 mL) was added 5-((1,3-bis(heptanoyloxy)propan-2-yl)oxy)-5-oxopentanoic acid (25 mg, 0.057 mmol) followed by DMAP (3.5 mg, 0.029 mmol), EDC (16.5 mg, 0.0860 mmol) and DIEA (0.025 mL, 0.144 mmol) and the cloudy mixture was stirred at ambient temperature for 3.5 h. The mixture was diluted with DCM and washed with water. The organic phase was dried (Na$_2$SO$_4$), concentrated and purified on silica gel (EtOAc/hexanes 0-40-100%) to provide ((2R,3S, 5R)-5-(6-amino-2-fluoro-9H-purin-9-yl)-3-((tert-butyldimethylsilyl)oxy)-2-ethynyltetrahydrofuran-2-yl)methyl (1,3-bis(heptanoyloxy)propan-2-yl) glutarate (17.8 mg, 76%). LCMS (ESI) m/z calcd for C$_{40}$H$_{62}$FN$_5$O$_{10}$Si: 819. Found: 820 (M+1)$^+$. $^1$H NMR (400 MHz, Chloroform-d): δ 7.86 (s, 1H), 6.23-6.30 (m, 1H), 5.87-6.03 (m, 2H), 5.28 (ddd, J=5.7, 4.4, 1.3 Hz, 1H), 4.97 (t, J=7.51 Hz, 1H), 4.50 (d, J=12.2 Hz, 1H), 4.33 (dt, J=11.9, 4.4 Hz, 2H), 4.26 (d, J=11.9 Hz, 1H), 4.18 (ddd, J=11.9, 5.90, 1.6 Hz, 2H), 2.85-2.97 (m, 1H), 2.63 (s, 2H), 2.28-2.44 (m, 8H), 1.84-1.98 (m, 2H), 1.57-1.68 (m, 4H), 1.25-1.39 (m, 12H), 0.94-0.99 (m, 9H), 0.86-0.93 (m, 6H), 0.17 (s, 3H), 0.16 (s, 3H).

Step G: ((2R,3S,5R)-5-(6-amino-2-fluoro-9H-purin-9-yl)-2-ethynyl-3-hydroxytetrahydrofuran-2-yl)methyl (1,3-bis(heptanoyloxy)propan-2-yl) glutarate. To a solution of ((2R,3S,5R)-5-(6-amino-2-fluoro-9H-purin-9-yl)-3-((tert-butyldimethylsilyl)oxy)-2-ethynyltetrahydrofuran-2-yl) methyl (1,3-bis(heptanoyloxy)propan-2-yl) glutarate (17 mg, 0.021 mmol) in tetrahydrofuran (0.7 mL) at 0° C. was added ~50 uL of a solution prepared by adding acetic acid (58 uL, 1 mmol) to 1M TBAF/THF (1 mL, 1 mmol). The mixture was stored at 0° C. for 18 h then stirred 2 h at ambient temperature. The mixture was concentrated and purified on silica gel (EtOAc/hexanes 0-100%) to provide ((2R,3S,5R)-5-(6-amino-2-fluoro-9H-purin-9-yl)-2-ethynyl-3-hydroxytetrahydrofuran-2-yl)methyl (1,3-bis(heptanoyloxy)propan-2-yl) glutarate (10.3 mg, 70% yield) as a sticky solid. LCMS (ESI) m/z calcd for C$_{34}$H$_{48}$FN$_5$O$_{10}$: 705. Found: 706 (M+1)$^+$. $^1$H NMR (400 MHz, Chloroform-d): δ 7.84-7.94 (m, 1H), 6.32 (dd, J=7.5, 4.4 Hz, 1H), 5.85 (br s, 2H), 5.21-5.36 (m, 1H), 4.85 (q, J=7.07 Hz, 1H), 4.47 (s, 2H), 4.35 (ddd, J=11.9, 4.4, 2.0 Hz, 2H), 4.18 (ddd, J=11.9, 5.7, 3.3 Hz, 2H), 2.94-3.12 (m, 1H), 2.81 (s, 1H), 2.68 (dd, J=7.4, 6.2 Hz, 2H), 2.39-2.54 (m, 4H), 2.34 (t, J=7.51 Hz, 4H), 1.87-2.08 (m, 2H), 1.50-1.67 (m, 4H), 1.23-1.42 (m, 12H), 0.83-0.96 (m, 6H).

Example 13: ((2R,3S,5R)-5-(6-amino-2-fluoro-9H-purin-9-yl)-2-ethynyl-3-hydroxytetrahydrofuran-2-yl)methyl 1,3-bis(tetradecanoyloxy)propan-2-yl) glutarate

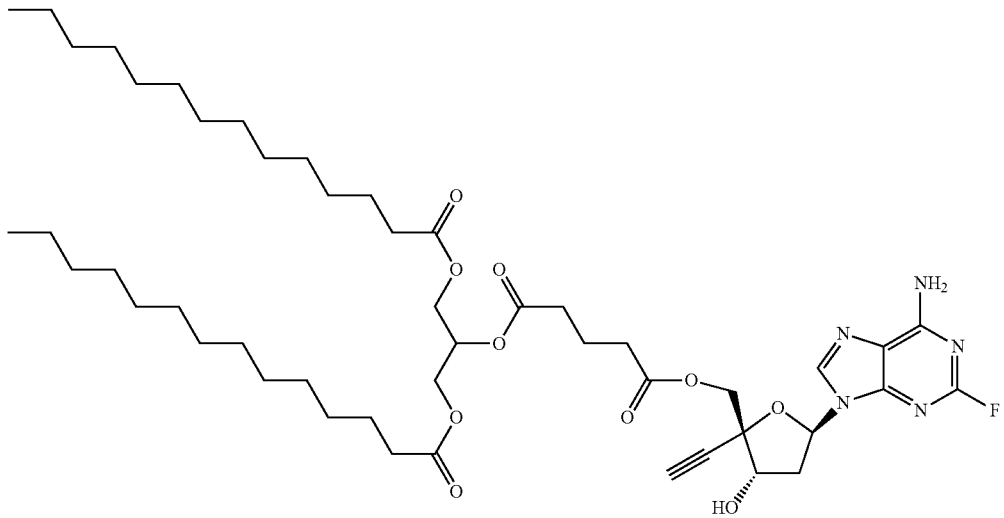 [SMILES: C#C[C@]1(COC(=O)CCCC(=O)OC(COC(=O)CCCCCCCCCCCCC)COC(=O)CCCCCCCCCCCCC)O[C@@H](n2cnc3c(N)nc(F)nc32)C[C@@H]1O]

The title compound was prepared according to example 12, substituting tetradecanoyl chloride for heptanoyl chloride in step A. LCMS (ESI) m/z calcd for $C_{48}H_{76}FN_5O_{10}$: 902. Found: 903 (M+1)$^+$. $^1$H NMR (400 MHz, Chloroform-d): δ 7.89 (s, 1H), 6.32 (dd, J=7.5, 4.4 Hz, 1H), 5.95 (d, J=1.0 Hz, 2H), 5.19-5.38 (m, 1H), 4.84 (br s, 1H), 4.47 (s, 2H), 4.34 (ddd, J=11.9, 4.5, 2.3 Hz, 2H), 4.18 (ddd, J=11.9, 5.7, 3.3 Hz, 2H), 2.92-3.10 (m, 1H), 2.81 (s, 1H), 2.68 (d, J=13.6 Hz, 2H), 2.38-2.56 (m, 4H), 2.34 (t, J=7.5 Hz, 4H), 1.88-2.08 (m, 2H), 1.59-1.64 (m, 4H), 1.19-1.40 (m, 40H), 0.83-0.97 (m, 6H).

Example 14: ((2R,3S,5R)-5-(6-amino-2-fluoro-9H-purin-9-yl)-2-ethynyl-3-hydroxytetrahydrofuran-2-yl)methyl Tetradecyl Glutarate

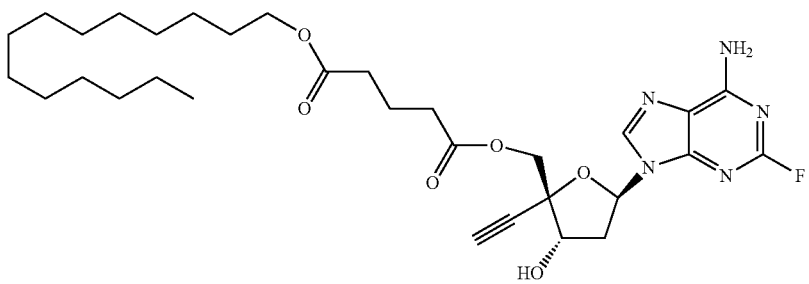 [SMILES: C#C[C@]1(COC(=O)CCCC(=O)OCCCCCCCCCCCCCC)O[C@@H](n2cnc3c(N)nc(F)nc32)C[C@@H]1O]

The title compound was obtained as a by-product from example 13, step G. LCMS (ESI) m/z calcd for $C_{31}H_{46}FN_5O_6$: 603. Found: 604 (M+1)$^+$. $^1$H NMR (400 MHz, Methanol-d$_4$): δ 8.16 (s, 1H), 6.33 (dd, J=7.9, 3.8 Hz, 1H), 4.87 (t, J=7.9 Hz, 1H), 4.50 (d, J=11.9 Hz, 1H), 4.31 (d, J=11.7 Hz, 1H), 4.06 (t, J=6.7 Hz, 2H), 3.17 (s, 1H), 2.92 (ddd, J=13.6, 7.3, 3.7 Hz, 1H), 2.68 (dt, J=13.7, 8.2 Hz, 1H), 2.23-2.47 (m, 4H), 1.84 (td, J=7.3, 1.3 Hz, 2H), 1.52-1.67 (m, 2H), 1.30 (s, 22H), 0.82-1.00 (m, 3H).

Example 15: ((2R,3S,5R)-5-(6-amino-2-fluoro-9H-purin-9-yl)-3-((ethoxycarbonyl)oxy)-2-ethynyltetrahydrofuran-2-yl)methyl Decanoate

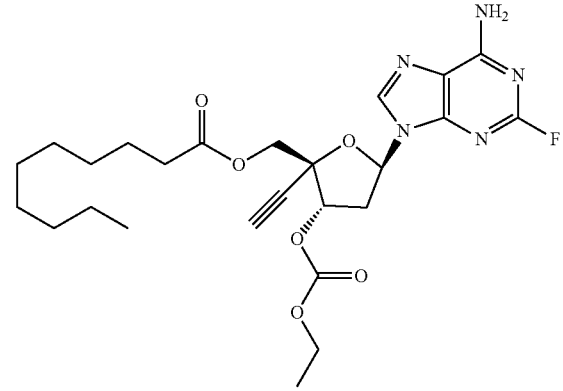 [SMILES: C#C[C@]1(COC(=O)CCCCCCCCC)O[C@@H](n2cnc3c(N)nc(F)nc32)C[C@@H]1OC(=O)OCC]

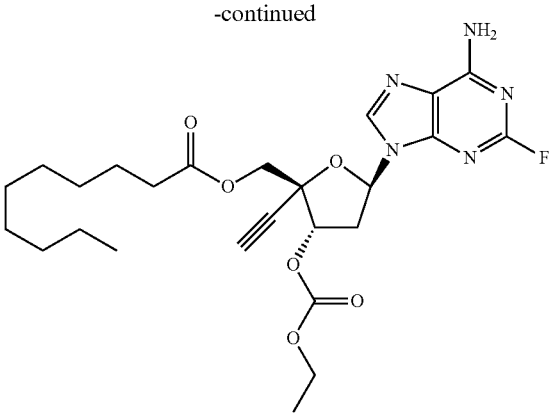

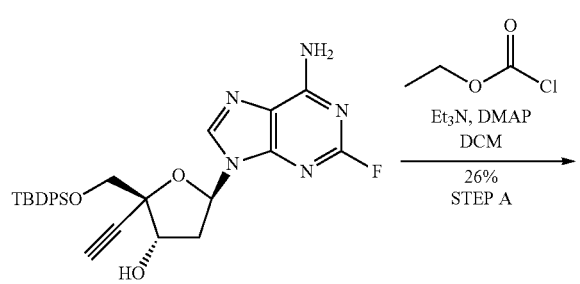

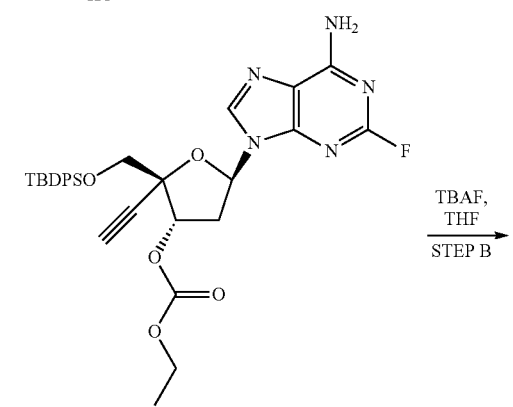

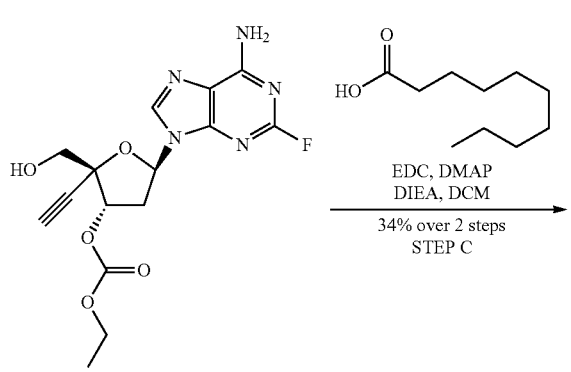

Step A: (2R,3S,5R)-5-(6-amino-2-fluoro-9H-purin-9-yl)-2-(((tert-butyldiphenylsilyl)oxy)methyl)-2-ethynyltetrahydrofuran-3-yl ethyl carbonate. To a stirred solution of (2R,3S,5R)-5-(6-amino-2-fluoro-9H-purin-9-yl)-2-(((tert-butyldiphenylsilyl)oxy)methyl)-2-ethynyltetrahydrofuran-3-ol (51 mg, 0.096 mmol), triethylamine (0.067 mL, 0.480 mmol) and DMAP (11.72 mg, 0.096 mmol) in DCM (0.8 mL) at 0° C. was added ethyl carbonochloridate (0.018 mL, 0.192 mmol) in DCM (82 uL). The mixture was stirred at 0° C. for 5 minutes, then stirred at ambient temperature for 2 hours. LCMS of the reaction mixture indicated a mixture of tri-, di- and monosubstituted compounds. The mixture was diluted with EtOAc, washed with sat'd NaHCO$_3$ mixed with brine, followed by brine only and finally dried (Na$_2$SO$_4$), filtered and concentrated. The residue was purified on silica gel (0-50% DCM/EtOAc) to afford the title compound (15 mg, 26%) as a colorless residue. LCMS (ESI) m/z calcd for C$_{31}$H$_{34}$FN$_5$O$_5$Si: 603.2. Found: 604.4 (M+1)$^+$.

Step B: (2R,3S,5R)-5-(6-amino-2-fluoro-9H-purin-9-yl)-2-ethynyl-2-(hydroxymethyl)tetrahydrofuran-3-yl ethyl carbonate. To a stirred solution of (2R,3S,5R)-5-(6-amino-2-fluoro-9H-purin-9-yl)-2-(((tert-butyldiphenylsilyl)oxy)methyl)-2-ethynyltetrahydrofuran-3-yl ethyl carbonate (15 mg, 0.025 mmol) in THF (0.5 mL) at ambient temperature was added TBAF, 1M solution in THF (0.033 mL, 0.033 mmol) and the mixture was allowed to stir for 15 minutes. AcOH (5 drops) was added, stirred for several minutes and the mixture was then concentrated. The residue was diluted with EtOAc, washed with sat'd NaHCO$_3$, then brine, dried over Na$_2$SO$_4$, filtered and concentrated to a colorless residue which was used crude in the next step. LCMS (ESI) m/z calcd for C$_{15}$H$_{16}$FN$_5$O$_5$: 365.1. Found: 366.2 (M+1)$^+$.

Step C: ((2R,3S,5R)-5-(6-amino-2-fluoro-9H-purin-9-yl)-3-((ethoxycarbonyl)oxy)-2-ethynyltetrahydrofuran-2-yl)methyl decanoate. To a solution of the crude product from the previous step, decanoic acid (8.61 mg, 0.050 mmol) and DMAP (3.05 mg, 0.025 mmol) in DCM (0.5 mL) at ambient temperature was added EDC (14.38 mg, 0.075 mmol), followed by DIPEA (0.022 mL, 0.125 mmol) and the mixture was allowed to stir overnight. The mixture was concentrated and then purified by RP-HPLC purification (C18, 10-100% MeCN/water with 0.1% FA) to afford the title compound (4.5 mg, 34% over 2 steps) as a white solid. LCMS (ESI) m/z calcd for C$_{25}$H$_{34}$FN$_5$O$_6$: 519.3. Found: 520.3 (M+1)$^+$. $^1$H NMR (400 MHz, DMSO-d$_6$) δ 8.32 (s, 1H), 8.07-7.76 (m, 2H), 6.37-6.31 (m, 1H), 5.57 (dd, J=5.3, 6.8 Hz, 1H), 4.42 (d, J=11.7 Hz, 1H), 4.28-4.13 (m, 3H), 3.83 (s, 1H), 3.24-3.15 (m, 1H), 2.73-2.61 (m, 1H), 2.35-2.14 (m, 2H), 1.50-1.38 (m, 2H), 1.31-1.11 (m, 15H), 0.84 (t, J=6.8 Hz, 3H).

Example 16: (2R,3S,5R)-5-(6-amino-2-fluoro-9H-purin-9-yl)-2-ethynyl-2-((heptanoyloxy)methyl)tetrahydrofuran-3-yl Heptanoate

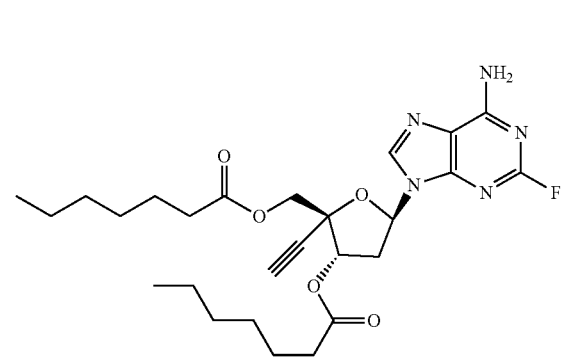 [SMILES: C#C[C@]1(COC(=O)CCCCCC)O[C@@H](n2cnc3c(N)nc(F)nc32)C[C@@H]1OC(=O)CCCCCC]

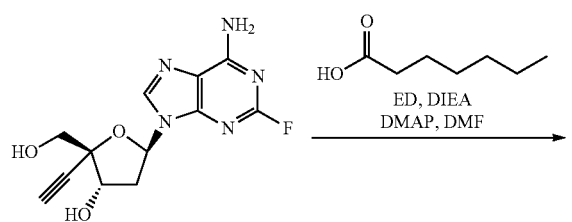

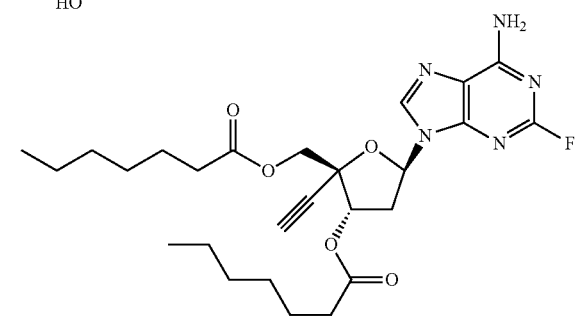

To a stirred solution of (2R,3S,5R)-5-(6-amino-2-fluoro-9H-purin-9-yl)-2-ethynyl-2-(hydroxymethyl)tetrahydrofuran-3-ol (54 mg, 0.184 mmol) (Org. Lett., Vol. 13, No. 19, 2011, 5264-5299), heptanoic acid (0.104 mL, 0.737 mmol) and DMAP (45.0 mg, 0.368 mmol) in DMF (1.6 mL) at ambient temperature was added EDC (176 mg, 0.921 mmol) followed by DIPEA (0.322 mL, 1.841 mmol) and the mixture was allowed to stir overnight. Water was added and the mixture was extracted with EtOAc. The combined extracts were washed with water, then brine, dried over Na$_2$SO$_4$, filtered and concentrated. The residue was purified on silica gel (0-10% DCM/MeOH) to afford the title compound (80 mg, 84%) as a white solid. LCMS (ESI) m/z calcd for C$_{26}$H$_{36}$FN$_5$O$_5$: 517.3. Found: 518.4 (M+1)$^+$. $^1$H NMR (400 MHz, DMSO-d$_6$) δ 8.33 (s, 1H), 8.05-7.75 (m, 2H), 6.37-6.31 (m, 1H), 5.73-5.67 (m, 1H), 4.40 (d, J=11.7 Hz, 1H), 4.22 (d, J=11.7 Hz, 1H), 3.79 (s, 1H), 3.19-3.10 (m, 1H), 2.66-2.56 (m, 1H), 2.43-2.15 (m, 4H), 1.63-1.53 (m, 2H), 1.49-1.38 (m, 2H), 1.36-1.10 (m, 12H), 0.91-0.79 (m, 6H).

Example 17: (2R,3S,5R)-5-(6-amino-2-fluoro-9H-purin-9-yl)-2-ethynyl-2-((tetradecanoyloxy)methyl)tetrahydrofuran-3-yl Tetradecanoate

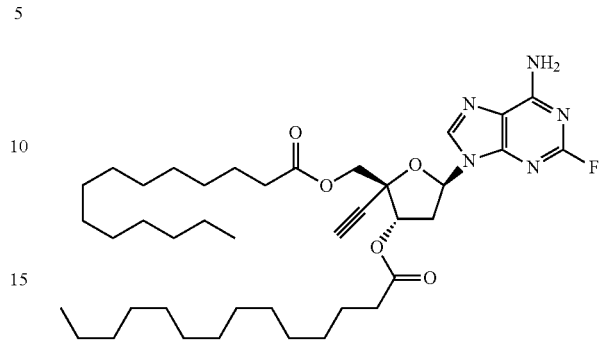

The title compound was prepared according to example 16, substituting tetradecanoic acid for heptanoic acid. LCMS (ESI) m/z calcd for C$_{40}$H$_{64}$FN$_5$O$_5$: 713.5. Found: 714.5 (M+1)$^+$. $^1$H NMR (400 MHz, Chloroform-d) δ 7.96 (s, 1H), 6.39 (t, J=6.4 Hz, 1H), 6.16 (br s, 2H), 5.61-5.66 (m, 1H), 4.48 (d, J=12.1 Hz, 1H), 4.38 (J=12.1 Hz, 1H), 2.98 (dt, J=13.8, 6.6 Hz, 1H), 2.64-2.74 (m, 2H), 2.27-2.46 (m, 4H), 1.55-1.69 (m, 4H), 1.20-1.32 (m, 40H), 0.86 (t, J=6.64 Hz, 6H).

Example 18: (2R,3S,5R)-5-(6-amino-2-fluoro-9H-purin-9-yl)-2-((decanoyloxy)methyl)-2-ethynyltetrahydrofuran-3-yl Decanoate

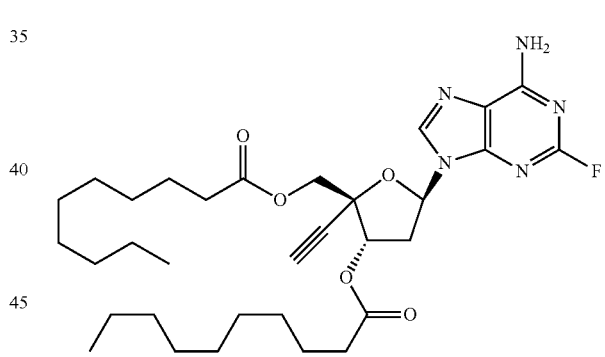

Synthesis A
The title compound was prepared according to example 16, substituting decanoic acid for heptanoic acid. LCMS (ESI) m/z calcd for C$_{32}$H$_{48}$FN$_5$O$_5$: 601.4. Found: 602.7 (M+1)$^+$. $^1$H NMR (400 MHz, Chloroform-d) δ 7.96 (s, 1H), 6.39 (t, J=6.4 Hz, 1H), 6.14-6.33 (m, 2H), 5.64 (dd, J=7.4, 5.5 Hz, 1H), 4.48 (d, J=12.1 Hz, 1H), 4.38 (d, J=12.1 Hz, 1H), 2.98 (dt, J=13.5, 6.9 Hz, 1H), 2.62-2.74 (m, 2H), 2.27-2.42 (m, 4H), 1.55-1.69 (m, 4H), 1.17-1.35 (m, 24H), 0.80-0.90 (m, 6H).

Synthesis B: Large scale preparation: To a solution of (2R,3S,5R)-5-(6-amino-2-fluoro-9H-purin-9-yl)-2-ethynyl-2-(hydroxymethyl)tetrahydrofuran-3-ol (4.75 g, 16.2 mmol), TEA (9.03 mL, 64.8 mmol) and DMAP (0.396 g, 3.24 mmol) in DCM (100 mL) was added decanoyl chloride (6.80 g, 35.6 mmol) dropwise. The resulting mixture was stirred for 2 hours at room temperature. LCMS indicated completion of reaction. The reaction was quenched with water (100 ml) and extracted with DCM (100 ml×2). The combined organic phases were dried over anhydrous Na₂SO₄ and concentrated under reduced pressure. The reaction was repeated for four times and the combined residues were purified by flash chromatography (silica gel, 660 g, pet. ether—0-80% EtOAc) to give the desired product (purity: 95%) as a white solid. The solid was triturated with EtOAc (300 ml), stirred for 0.5 h, filtered through a Buchner funnel, rinsed with EtOAc, and dried under sun lamp for 6 h (T=50° C.). This solid was stored in a cool dry place overnight to give crystalline (2R,3S,5R)-5-(6-amino-2-fluoro-9H-purin-9-yl)-2-((decanoyloxy)methyl)-2-ethynyltetrahydrofuran-3-yl decanoate (34 g, 99.43%, yield: 87%) as a white solid. LCMS (ESI) m/z calcd for $C_{32}H_{48}FN_5O_5$: 601. Found: 602 (M+1)⁺. ¹H NMR (400 MHz, Chloroform-d) δ 7.93 (s, 1H), 6.40 (t, J=6.4 Hz, 1H), 6.13 (br s, 2H), 5.65 (dd, J=6.8, 5.6 Hz, 1H), 4.49 (d, J=12.0 Hz, 1H), 4.39 (d, J=12.0 Hz, 1H), 3.02-3.00 (m, 1H), 2.78-2.67 (m, 1H), 2.66 (s, 1H), 2.43-2.30 (m, 4H), 1.67-1.58 (m, 4H), 1.40-1.17 (m, 24H), 0.89-0.86 (m, 6H).

Example 19: (2R,3S,5R)-5-(6-amino-2-fluoro-9H-purin-9-yl)-2-ethynyl-2-((pentanoyloxy)methyl)tetrahydrofuran-3-yl Tridecanoate

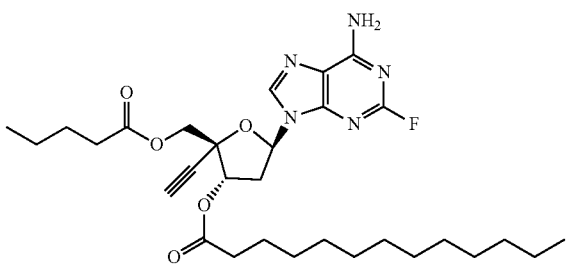 [SMILES: C#C[C@]1(COC(=O)CCCC)O[C@@H](n2cnc3c(N)nc(F)nc32)C[C@@H]1OC(=O)CCCCCCCCCCCC]

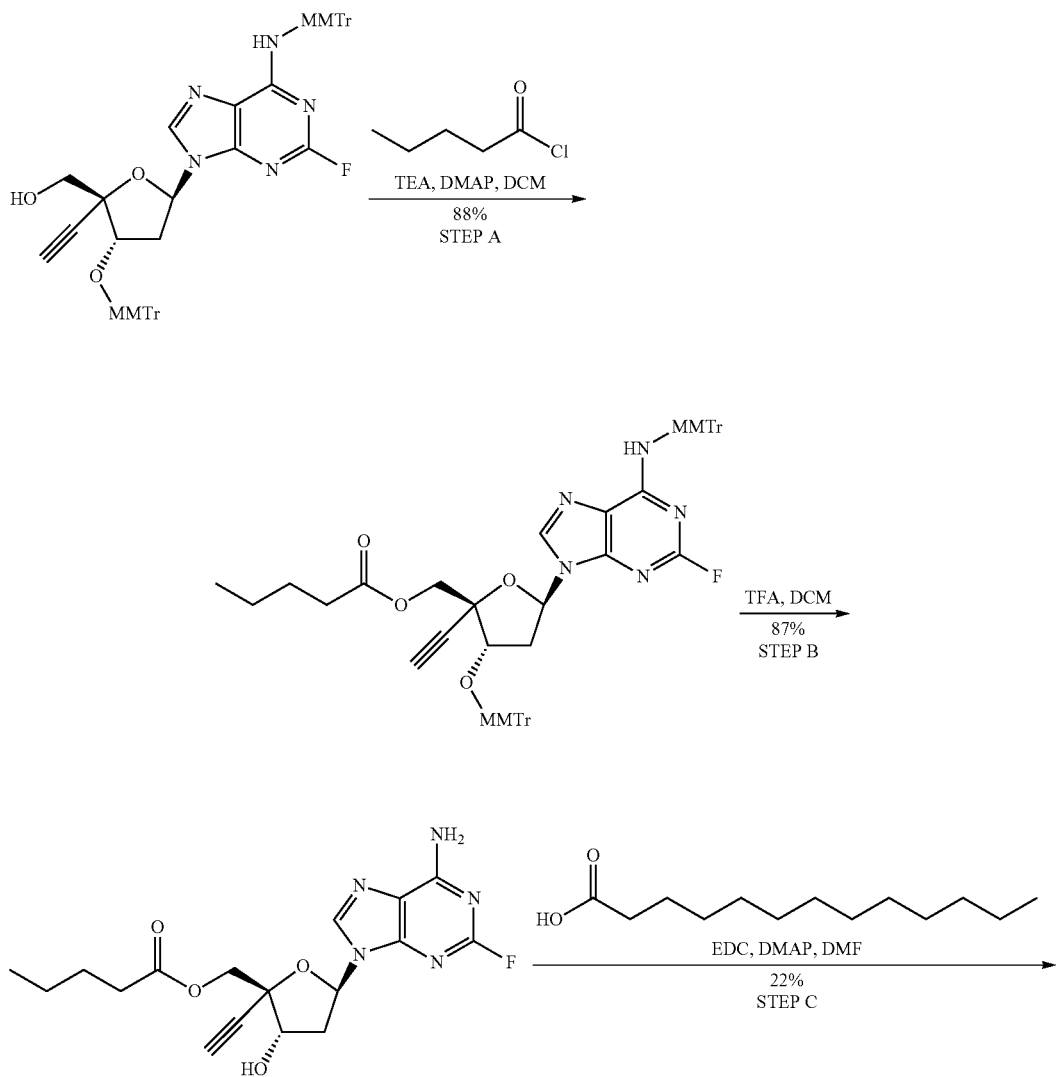

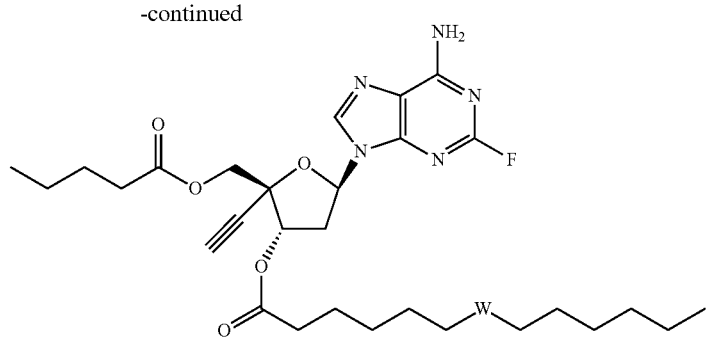

Step A: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methyl pentanoate. To a stirred solution of ((2R,3S,5R)-2-ethynyl-5-(2-fluoro-6-(((4-methoxy-phenyl)diphenylmethyl)amino)-9H-purin-9-yl)-3-((4-methoxyphenyl)diphenylmethoxy) tetrahydrofuran-2-yl) methanol (1.50 g, 1.79 mmol) and DMAP (0.109 g, 0.895 mmol) in DCM (15 mL) at 0° C. was added TEA (0.749 mL, 5.37 mmol) followed by a solution of pentanoyl chloride (0.234 mL, 1.97 mmol) in DCM (1 mL). The resulting solution was stirred at 0° C. for 10 minutes and at RT for 30 minutes. LCMS indicated complete reaction. The reaction mixture was quenched with water, extracted with EtOAc (3×20 mL), the organic phase was combined, washed with brine, dried over $Na_2SO_4$ and concentrated under vacuum. The residue was subjected to preparative—TLC (MeOH: DCM=1:20) to give the desired product (1.5 g, 88%) as a white solid. LCMS (ESI) m/z calcd for $C_{57}H_{52}FN_5O_6$: 921. Found: 922 (M+1)$^+$. $^1$H NMR (400 MHz, DMSO-d$_6$) δ 8.12-7.91 (m, 2H), 7.51 (d, J=7.6 Hz, 4H), 7.42-7.11 (m, 20H), 6.84 (d, J=8 Hz, 4H), 6.13 (s, 1H), 4.68 (s, 1H), 4.06-3.95 (m, 2H), 3.85-3.77 (m, 1H), 3.74-3.54 (m, 6H), 2.10-1.99 (m, 2H), 1.95-1.87 (m, 2H), 1.24-1.18 (m, 2H), 1.10-1.01 (m, 2H), 0.78-0.67 (m, 3H).

Step B: ((2R,3S,5R)-5-(6-amino-2-fluoro-9H-purin-9-yl)-2-ethynyl-3-hydroxytetrahydrofuran-2-yl)methyl pentanoate. ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl) methyl pentanoate (1.46 g, 1.58 mmol) was dissolved in DCM (14 mL) and TFA (3 mL), the resulting mixture was stirred for 1 h at RT. LCMS indicated complete reaction. The reaction mixture was diluted with MeOH (14 mL) and concentrated under vacuum. The residue was subjected to reverse phase HPLC purification (C18, 20-60% ACN/water with 0.1% FA) to give the desired product as a white solid (525 mg, 87%). LCMS (ESI) m/z calcd for $C_{17}H_{20}FN_5O_4$: 377. Found: 378 (M+1)$^+$. $^1$H NMR (400 MHz, DMSO-d$_6$) δ 8.28 (s, 1H), 7.87 (br, 2H), 6.24 (dd, J=8.0, 3.9 Hz, 1H), 5.80 (d, J=5.4 Hz, 1H), 4.74-4.69 (m, 1H), 4.43 (d, J=11.6 Hz, 1H), 4.09 (d, J=12.0 Hz, 1H), 3.64 (s, 1H), 2.83-2.78 (m, 1H), 2.49-2.44 (m, 1H), 2.27-2.08 (m, 2H), 1.45-1.33 (m, 2H), 1.24-1.14 (m, 2H), 0.80 (t, J=7.3 Hz, 3H).

Step C: (2R,3S,5R)-5-(6-amino-2-fluoro-9H-purin-9-yl)-2-ethynyl-2-((pentanoyloxy)methyl)tetrahydrofuran-3-yl tridecanoate. Tridecanoic acid (68.2 mg, 0.318 mmol) was dissolved in DMF (1 mL), DMAP (155 mg, 1.27 mmol) and EDC (244 mg, 1.27 mmol) were added. The resulting mixture was stirred for 2 h at RT. Then, ((2R,3S,5R)-5-(6-amino-2-fluoro-9H-purin-9-yl)-2-ethynyl-3-hydroxytetrahydrofuran-2-yl)methyl pentanoate (100 mg, 0.265 mmol) was added. The resulting mixture was stirred for overnight at RT. LCMS indicated complete reaction. The reaction mixture was quenched with water and extracted with EtOAc (3×). The organic phases were combined, washed with brine, dried over $Na_2SO_4$ and concentrated under vacuum. The residue was subjected to preparative TLC (MeOH:DCM=1:20) to give the desired product as a white solid (34 mg, 22%). LCMS (ESI) m/z calcd for $C_{30}H_{44}FN_5O_5$: 573. Found: 574 (M+1)$^+$. $^1$H NMR (400 MHz, DMSO-d$_6$) δ 8.33 (s, 1H), 7.89 (br, 2H), 6.34 (t, J=6.7 Hz, 1H), 5.70 (t, J=12.4 Hz, 1H), 4.40 (d, J=11.6 Hz, 1H), 4.21 (d, J=11.6 Hz, 1H), 3.79 (s, 1H), 3.18-3.11 (m, 1H), 2.64-2.57 (m, 1H), 2.43-2.34 (m, 2H), 2.32-2.18 (m, 2H), 1.59-1.54 (m, 2H), 1.47-1.39 (m, 2H), 1.37-1.17 (m, 20H), 0.87-0.79 (m, 6H).

Example 20: (2R,3S,5R)-5-(6-amino-2-fluoro-9H-purin-9-yl)-2-ethynyl-2-((pentanoyloxy)methyl)tetrahydrofuran-3-yl Heptanoate

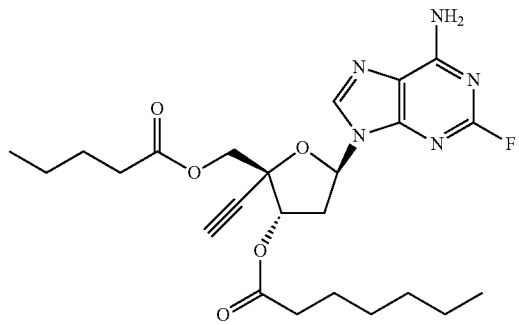 [SMILES: C#C[C@]1(COC(=O)CCCC)O[C@@H](n2cnc3c(N)nc(F)nc32)C[C@@H]1OC(=O)CCCCCC]

The title compound was prepared according to example 19, substituting heptanoic acid for tridecanoic acid in step C. LCMS (ESI) m/z calcd for $C_{24}H_{32}FN_5O_5$: 489. Found: 490 (M+1)$^+$. $^1$H NMR (400 MHz, Methanol-d$_4$) δ 8.18 (s, 1H), 6.38 (dd, J=7.2, 5.5 Hz, 1H), 5.82 (dd, J=7.3, 6.1 Hz, 1H), 4.45 (d, J=11.8 Hz, 1H), 4.33 (d, J=11.7 Hz, 1H), 3.26 (s, 1H), 3.22-3.15 (m, 1H), 2.75-2.69 (m, 1H), 2.43 (t, J=7.4 Hz, 2H), 2.32-2.24 (m, 2H), 1.71-1.63 (m, 2H), 1.52-1.43 (m, 2H), 1.36-1.26 (m, 8H), 0.92-0.86 (m, 6H).

Example 21: (2R,3S,5R)-5-(6-amino-2-fluoro-9H-purin-9-yl)-2-ethynyl-2-((pentanoyloxy)methyl)tetrahydrofuran-3-yl Undecanoate

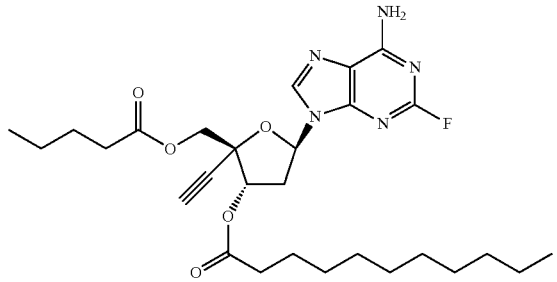 [SMILES: C#C[C@]1(COC(=O)CCCC)O[C@@H](n2cnc3c(N)nc(F)nc32)C[C@@H]1OC(=O)CCCCCCCCCC]

The title compound was prepared according to example 19, substituting undecanoic acid for tridecanoic acid in step C. LCMS (ESI) m/z calcd for $C_{28}H_{40}FN_5O_5$: 545. Found: 546 (M+1)⁺. ¹H NMR (400 MHz, Methanol-$d_4$) δ 8.18 (s, 1H), 6.38 (dd, J=7.2, 5.5 Hz, 1H), 5.82 (dd, J=7.4, 6.1 Hz, 1H), 4.45 (d, J=11.6 Hz, 1H), 4.33 (d, J=11.6 Hz, 1H), 3.25 (s, 1H), 3.22-3.15 (m, 1H), 2.75-2.68 (m, 1H), 2.43 (t, J=7.4 Hz, 2H), 2.32-2.24 (m, 2H), 1.71-1.64 (m, 2H), 1.53-1.49 (m, 2H), 1.39-1.24 (m, 16H), 0.91-0.86 (m, 6H).

Example 22: (2R,3S,5R)-5-(6-amino-2-fluoro-9H-purin-9-yl)-2-ethynyl-2-((pentanoyloxy)methyl)tetrahydrofuran-3-yl Nonanoate

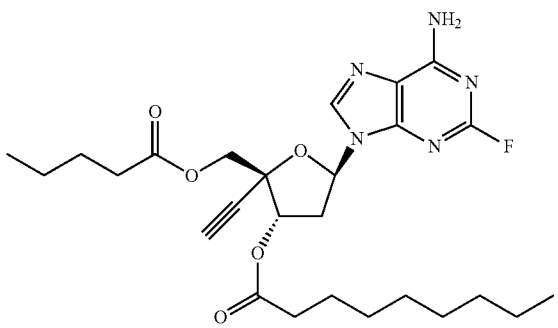 [SMILES: C#C[C@]1(COC(=O)CCCC)O[C@@H](n2cnc3c(N)nc(F)nc32)C[C@@H]1OC(=O)CCCCCCCC]

The title compound was prepared according to example 19, substituting nonanoic acid for tridecanoic acid in step C. LCMS (ESI) m/z calcd for $C_{26}H_{36}FN_5O_5$: 517. Found: 518 (M+1)⁺. ¹H NMR (400 MHz, Methanol-$d_4$) δ 8.18 (s, 1H), 6.38 (dd, J=7.2, 5.5 Hz, 1H), 5.82 (dd, J=7.4, 6.1 Hz, 1H), 4.45 (d, J=11.8 Hz, 1H), 4.33 (d, J=11.8 Hz, 1H), 3.25 (s, 1H), 3.22-3.15 (m, 1H), 2.75-2.68 (m, 1H), 2.43 (t, J=7.4 Hz, 2H), 2.33-2.22 (m, 2H), 1.71-1.64 (m, 2H), 1.55-1.47 (m, 2H), 1.39-1.26 (m, 12H), 0.92-0.85 (m, 6H).

Example 23: (2R,3S,5R)-5-(6-amino-2-fluoro-9H-purin-9-yl)-2-ethynyl-2-((pentanoyloxy)methyl)tetrahydrofuran-3-yl Pentanoate

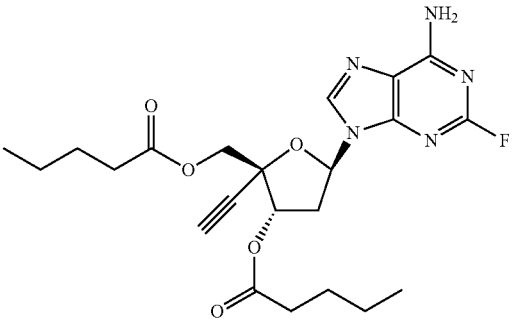 [SMILES: C#C[C@]1(COC(=O)CCCC)O[C@@H](n2cnc3c(N)nc(F)nc32)C[C@@H]1OC(=O)CCCC]

The title compound was prepared according to example 19, substituting pentanoic acid for tridecanoic acid in step C. LCMS (ESI) m/z calcd for $C_{22}H_{28}FN_5O_5$: 461. Found: 462 (M+1)⁺. ¹H NMR (400 MHz, Methanol-$d_4$) δ 8.18 (s, 1H), 6.38 (dd, J=7.2, 5.6 Hz, 1H), 5.82 (dd, J=7.3, 6.0 Hz, 1H), 4.45 (d, J=11.7 Hz, 1H), 4.33 (d, J=11.7 Hz, 1H), 3.26 (s, 1H), 3.22-3.16 (m, 1H), 2.75-2.68 (m, 1H), 2.44 (t, J=7.4 Hz, 2H), 2.33-2.21 (m, 2H), 1.69-1.62 (m, 2H), 1.56-1.47 (m, 2H), 1.45-1.36 (m, 2H), 1.33-1.24 (m, 2H), 0.95 (t, J=7.3 Hz, 3H), 0.87 (t, J=7.3 Hz, 3H).

Example 24: ((2R,3S,5R)-5-(6-amino-2-fluoro-9H-purin-9-yl)-2-ethynyl-3-(propionyloxy)tetrahydrofuran-2-yl)methyl Pentanoate

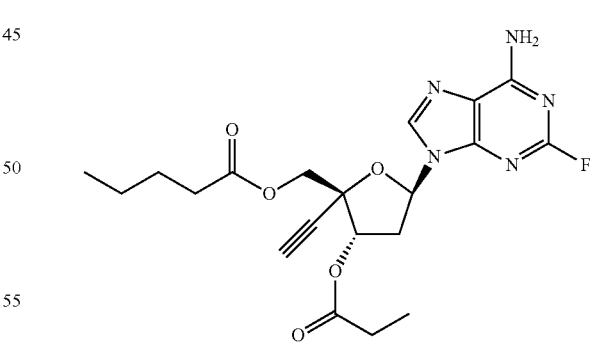

The title compound was prepared according to example 19, substituting propanoic acid for tridecanoic acid in step C. LCMS (ESI) m/z calcd for $C_{20}H_{24}FN_5O_5$: 433. Found: 456 (M+23)⁺. ¹H NMR (400 MHz, Methanol-$d_4$) δ 8.18 (s, 1H), 6.39 (dd, J=7.1, 5.8 Hz, 1H), 5.81 (dd, J=7.3, 5.8 Hz, 1H), 4.45 (d, J=11.7 Hz, 1H), 4.33 (d, J=11.8 Hz, 1H), 3.26 (s, 1H), 3.23-3.16 (m, 1H), 2.75-2.68 (m, 1H), 2.46 (dd, J=15.2, 7.6 Hz, 2H), 2.36-2.20 (m, 2H), 1.56-1.45 (m, 2H), 1.34-1.24 (m, 2H), 1.18 (t, J=7.6 Hz, 3H), 0.87 (t, J=7.3 Hz, 3H).

Example 25: ((2R,3S,5R)-5-(6-butyramido-2-fluoro-9H-purin-9-yl)-2-ethynyl-3-hydroxytetrahydrofuran-2-yl)methyl Pentanoate

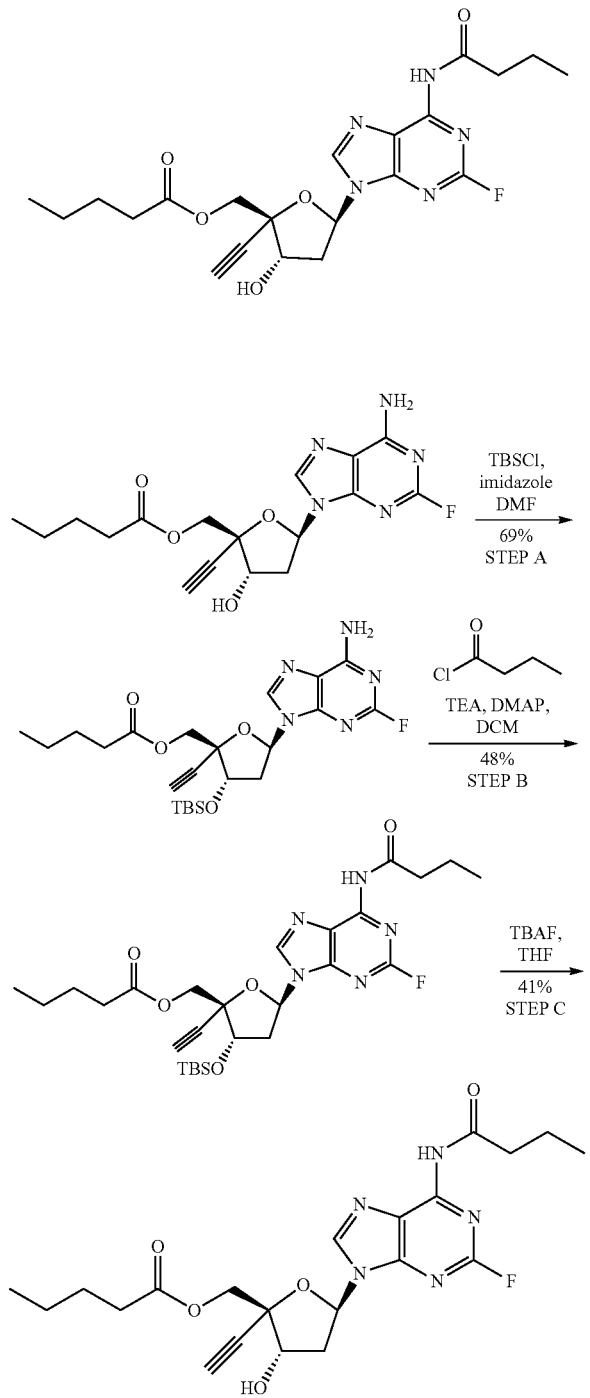

Step A: ((2R,3S,5R)-5-(6-amino-2-fluoro-9H-purin-9-yl)-3-((tert-butyldimethylsilyl)oxy)-2-ethynyltetrahydrofuran-2-yl)methyl pentanoate. ((2R,3S,5R)-5-(6-amino-2-fluoro-9H-purin-9-yl)-2-ethynyl-3-hydroxytetrahydrofuran-2-yl)methyl pentanoate (1.00 g, 2.65 mmol) was dissolved in DMF (20 mL), imidazole (0.541 g, 7.95 mmol) and tert-butylchlorodimethylsilane (1.20 g, 7.95 mmol) was added at 0° C. The resulting mixture was stirred for 16 h at RT. LCMS indicated complete reaction. The reaction was diluted with water and extracted with EA (3×). The organic phases were combined, washed with saturated brine, dried over $Na_2SO_4$ and concentrated under vacuum. The residue was subjected to flash chromatography (silica gel, 40 g, EtOAc/PE=1:3) to give the desired product (1.0 g, 69%) as a white solid. LCMS (ESI) m/z calcd for $C_{23}H_{34}FN_5O_4Si$: 491. Found: 492 (M+1)$^+$. $^1$H NMR (300 MHz, DMSO-d$_6$) δ 8.28 (s, 1H), 7.91 (br, 2H), 6.30-6.26 (m, 1H), 4.99 (t, J=7.1 Hz, 1H), 4.35 (d, J=11.8 Hz, 1H), 4.10 (d, J=11.8 Hz, 1H), 3.66 (s, 1H), 3.01-2.91 (m, 1H), 2.49-2.40 (m, 1H), 2.22-2.09 (m, 2H), 1.40-1.38 (m, 2H), 1.24-1.16 (m, 2H), 0.92 (s, 9H), 0.80 (t, J=7.3 Hz, 3H), 0.15 (s, 6H).

Step B: ((2R,3S,5R)-3-((tert-butyldimethylsilyl)oxy)-5-(6-butyramido-2-fluoro-9H-purin-9-yl)-2-ethynyltetrahydrofuran-2-yl)methyl pentanoate. ((2R,3S,5R)-5-(6-amino-2-fluoro-9H-purin-9-yl)-3-((tert-butyldimethylsilyl)oxy)-2-ethynyltetrahydrofuran-2-yl)methyl pentanoate (200 mg, 0.407 mmol) and DMAP (25.0 mg, 0.203 mmol) were dissolved in DCM (5 mL). TEA (0.227 mL, 1.63 mmol) was added at 0° C. Then a solution of butanoyl chloride (97.0 mg, 0.814 mmol) in DCM (2 mL) was added dropwise. Then the resulting mixture was stirred for 16 h at RT. LCMS indicated complete reaction. The reaction was quenched with water, and extracted with EA (3×). The organic phases were combined, washed with saturated brine, dried over $Na_2SO_4$ and concentrated under vacuum. The residue was subjected to preparative TLC (100% EtOAc) to give the desired product (110 mg, 48%) as yellow oil. LCMS (ESI) m/z calcd for $C_{27}H_{40}FN_5O_5Si$: 561. Found: 562 (M+1)$^+$. $^1$H NMR (400 MHz, Chloroform-d) δ 8.65 (s, 1H), 8.10 (s, 1H), 6.39-6.28 (m, 1H), 4.95-4.85 (m, 1H), 4.46 (d, J=11.8 Hz, 1H), 4.28 (d, J=12.0 Hz, 1H), 3.51 (s, 1H), 2.99-2.81 (m, 3H), 2.77-2.69 (m, 1H), 2.33-2.25 (m, 2H), 1.86-1.80 (m, 2H), 1.61-1.56 (m, 2H), 1.37-1.30 (m, 2H), 1.07 (t, J=7.2 Hz, 3H), 0.96 (s, 9H), 0.90 (t, J=7.3 Hz, 3H), 0.16 (d, J=4.4 Hz, 6H).

Step C: ((2R,3S,5R)-5-(6-butyramido-2-fluoro-9H-purin-9-yl)-2-ethynyl-3-hydroxytetrahydrofuran-2-yl)methyl pentanoate. ((2R,3S,5R)-3-((tert-butyldimethylsilyl)oxy)-5-(6-butyramido-2-fluoro-9H-purin-9-yl)-2-ethynyltetrahydrofuran-2-yl)methyl pentanoate (110 mg, 0.19 mmol) was dissolved in THF (10 mL), TBAF (0.38 mL, 1M in THF, 0.38 mmol) was added, the resulting mixture was stirred for 1 h at RT. LCMS indicated complete reaction. The reaction mixture was concentrated under vacuum. Water was added, the mixture was extracted with EtOAc (3×). The organic phases were combined, washed with brine, dried over $Na_2SO_4$ and concentrated under vacuum. The residue was subjected to preparative TLC (MeOH:DCM=1:10) followed by reverse phase HPLC purification (C18, MeCN/water with 0.1% formic acid)) to give the desired product (25 mg, 41%). LCMS (ESI) m/z calcd for $C_{21}H_{26}FN_5O_5$: 447. Found: 448 (M+1)$^+$. $^1$H NMR (300 MHz, DMSO-d$_6$) δ 11.04 (s, 1H), 8.61 (s, 1H), 6.35 (q, J=3.9 Hz, 1H), 5.85 (d, J=5.4 Hz, 1H), 4.75-4.71 (m, 1H), 4.43 (d, J=11.7 Hz, 1H), 4.11 (d, J=11.7 Hz, 1H), 3.68 (s, 1H), 2.91-2.83 (m, 1H), 2.58-2.51 (m, 3H), 2.28-2.07 (m, 2H), 1.62 (h, J=7.2 Hz, 2H), 1.48-1.26 (m, 2H), 1.17 (h, J=7.2 Hz, 2H), 0.93 (t, J=7.2 Hz, 3H), 0.78 (t, J=7.2 Hz, 3H).

Example 26: ((2R,3S,5R)-2-ethynyl-5-(2-fluoro-6-octanamido-9H-purin-9-yl)-3-hydroxytetrahydrofuran-2-yl)methyl Pentanoate

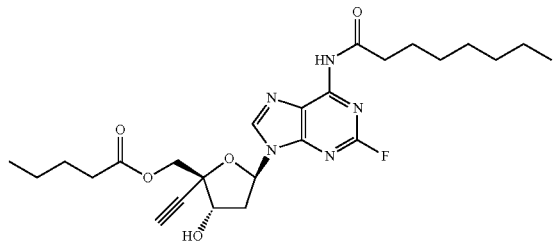 [SMILES: C#C[C@]1(COC(=O)CCCC)O[C@@H](n2cnc3c(NC(=O)CCCCCCC)nc(F)nc32)C[C@@H]1O]

The title compound was prepared according to example 25, substituting octanoyl chloride for butanoyl chloride in step B. LCMS (ESI) m/z calcd for $C_{25}H_{34}FN_5O_5$: 503. Found: 504 (M+1)⁺. ¹HNMR (400 MHz, DMSO-d6) δ 11.04 (s, 1H), 8.60 (s, 1H), 6.36-6.33 (m, 1H), 5.85 (d, J=5.2 Hz, 1H), 4.75-4.71 (m, 1H), 4.42 (d, J=11.6 Hz, 1H), 4.10 (d, J=11.6 Hz, 1H), 3.68 (s, 1H), 2.89-2.83 (m, 1H), 2.55-2.49 (m, 3H), 2.21-2.18 (m, 1H), 2.15-2.11 (m, 1H), 1.62-1.52 (m, 2H), 1.40-1.20 (m, 10H), 1.20-1.15 (m, 2H), 0.90-0.81 (m, 3H), 0.77 (t, J=7.2 Hz, 3H).

Example 27: ((2R,3S,5R)-2-ethynyl-5-(2-fluoro-6-tetradecanamido-9H-purin-9-yl)-3-hydroxytetrahydrofuran-2-yl)methyl Pentanoate

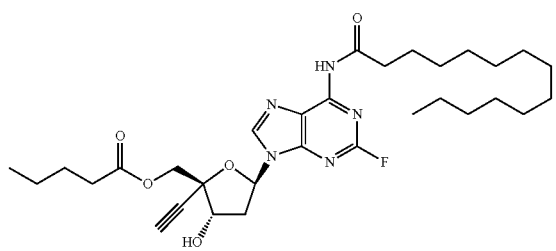 [SMILES: C#C[C@]1(COC(=O)CCCC)O[C@@H](n2cnc3c(NC(=O)CCCCCCCCCCCCC)nc(F)nc32)C[C@@H]1O]

The title compound was prepared according to example 25, substituting tetradecanoyl chloride for butanoyl chloride in step B. LCMS (ESI) m/z calcd for $C_{31}H_{46}FN_5O_5$: 587. Found: 588 (M+1)⁺. ¹H NMR (400 MHz, Methanol-d₄) δ 8.39 (s, 1H), 6.39 (dd, J=8.4, 3.6 Hz, 1H), 4.91-4.88 (m, 1H), 4.46 (d, J=11.6 Hz, 1H), 4.24 (d, J=12.0 Hz, 1H), 3.19 (s, 1H), 2.99-2.92 (m, 1H), 2.72-2.64 (m, 3H), 2.25-2.16 (m, 2H), 1.79-1.69 (m, 2H), 1.52-1.19 (m, 24H), 0.89-0.82 (m, 6H).

Example 28: ((2R,3S,5R)-5-(6-dodecanamido-2-fluoro-9H-purin-9-yl)-2-ethynyl-3-hydroxytetrahydrofuran-2-yl)methyl Pentanoate

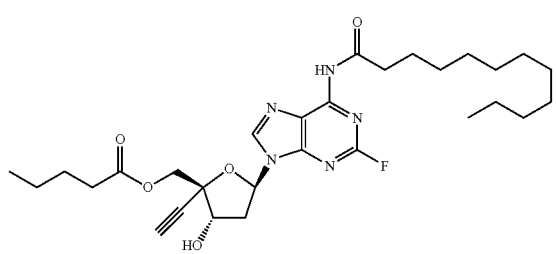 [SMILES: C#C[C@]1(COC(=O)CCCC)O[C@@H](n2cnc3c(NC(=O)CCCCCCCCCCC)nc(F)nc32)C[C@@H]1O]

The title compound was prepared according to example 25, substituting dodecanoyl chloride for butanoyl chloride in step B. LCMS (ESI) m/z calcd for $C_{29}H_{42}FN_5O_5$: 559. Found: 560 (M+1)⁺. ¹H NMR (400 MHz, DMSO-d₆) δ 11.04 (s, 1H), 8.60 (s, 1H), 6.35 (dd, J=8.0, 3.6 Hz, 1H), 5.85 (d, J=5.6 Hz, 1H), 4.75-4.71 (m, 1H), 4.43 (d, J=11.6 Hz, 1H), 4.11 (d, J=12.0 Hz, 1H), 3.68 (s, 1H), 2.86-2.82 (m, 1H), 2.57-2.49 (m, 3H), 2.21-2.11 (m, 2H), 1.58-1.57 (m, 2H), 1.37-1.13 (m, 20H), 0.85 (t, J=6.8 Hz, 3H), 0.78 (t, J=7.2 Hz, 3H).

Example 29: (2R,3S,5R)-5-(6-amino-2-fluoro-9H-purin-9-yl)-2-ethynyl-2-(((2-propylpentanoyl)oxy)methyl)tetrahydrofuran-3-yl Dodecanoate

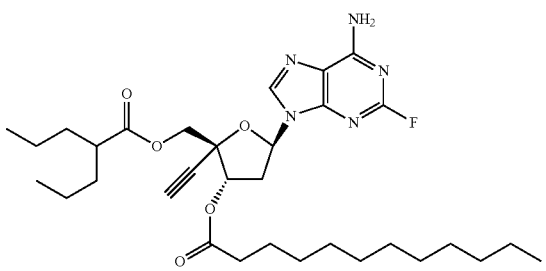 [SMILES: C#C[C@]1(COC(=O)C(CCC)CCC)O[C@@H](n2cnc3c(N)nc(F)nc32)C[C@@H]1OC(=O)CCCCCCCCCCC]

The title compound was prepared according to example 19, substituting 2-propylpentanoyl chloride for pentanoyl chloride in step A and dodecanoic acid for tridecanoic acid in step C. LCMS (ESI) m/z calcd for $C_{32}H_{48}FN_5O_5$: 601. Found: 602 (M+1)⁺. ¹H NMR (400 MHz, Chloroform-d) δ 8.05 (s, 1H), 6.42 (t, J=6.4 Hz, 1H), 5.99 (br, 2H), 5.63-5.60 (dd, J=7.1, 5.3 Hz, 1H), 4.47-4.39 (m, 2H), 3.00-2.95 (m, 1H), 2.77-2.72 (m, 1H), 2.66 (s, 1H), 2.43-2.39 (m, 3H), 1.67-1.65 (m, 2H), 1.57-1.54 (m, 2H), 1.42-1.41 (m, 2H), 1.26 (s, 20H), 0.88 (m, 9H).

Example 30: ((2R,3S,5R)-5-(6-amino-2-fluoro-9H-purin-9-yl)-3-(butyryloxy)-2-ethynyltetrahydrofuran-2-yl)methyl 2-propylpentanoate

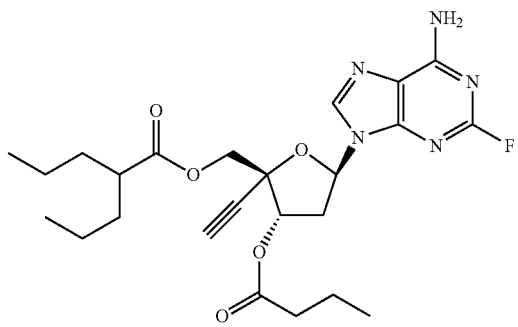 [SMILES: C#C[C@]1(COC(=O)C(CCC)CCC)O[C@@H](n2cnc3c(N)nc(F)nc32)C[C@@H]1OC(=O)CCC]

The title compound was prepared according to example 19, substituting 2-propylpentanoyl chloride for pentanoyl chloride in step A and butanoic acid for tridecanoic acid in step C. LCMS (ESI) m/z calcd for $C_{24}H_{32}FN_5O_5$: 489. Found: 490 (M+1)⁺. ¹H NMR (300 MHz, Methanol-d₄) δ 8.18 (s, 1H), 6.42-6.38 (m, 1H), 5.86-5.81 (m, 1H), 4.37-4.32 (m, 2H), 3.28-3.22 (m, 2H), 2.76-2.72 (m, 1H), 2.44-

2.42 (m, 2H), 2.31-2.29 (m, 1H), 1.75-1.67 (m, 2H), 1.51-1.45 (m, 2H), 1.39-1.14 (m, 6H), 1.00 (t, J=7.4 Hz, 3H), 0.83 (m, 6H).

Example 31: ((2R,3S,5R)-5-(6-amino-2-fluoro-9H-purin-9-yl)-3-(butyryloxy)-2-ethynyltetrahydrofuran-2-yl)methyl Decanoate

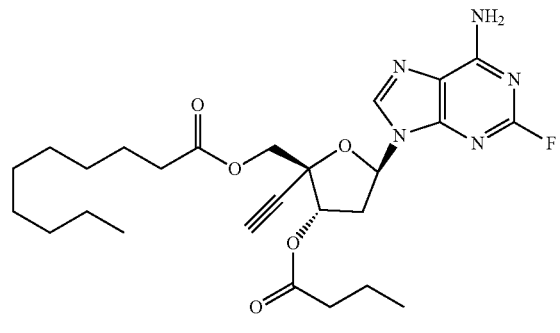 [SMILES: C#C[C@]1(COC(=O)CCCCCCCCC)O[C@@H](n2cnc3c(N)nc(F)nc32)C[C@@H]1OC(=O)CCC]

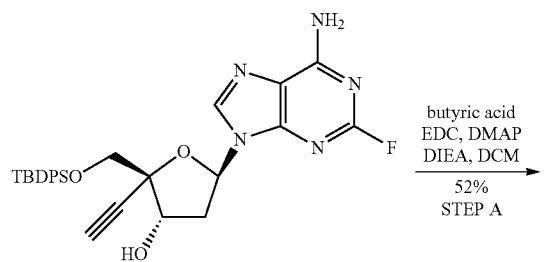

butyric acid
EDC, DMAP
DIEA, DCM
52%
STEP A

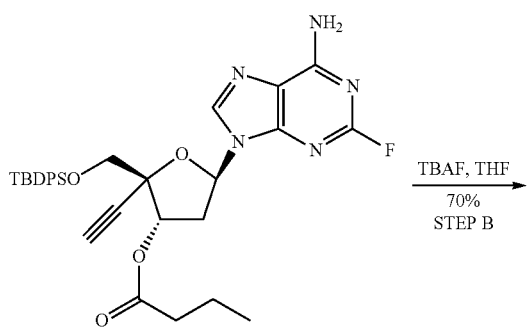

TBAF, THF
70%
STEP B

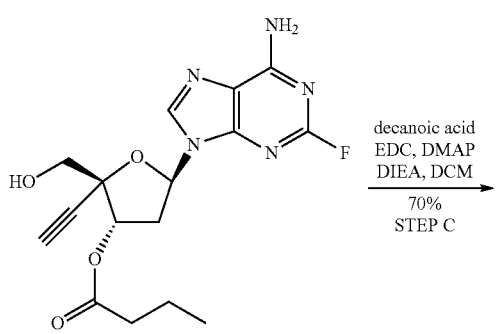

decanoic acid
EDC, DMAP
DIEA, DCM
70%
STEP C

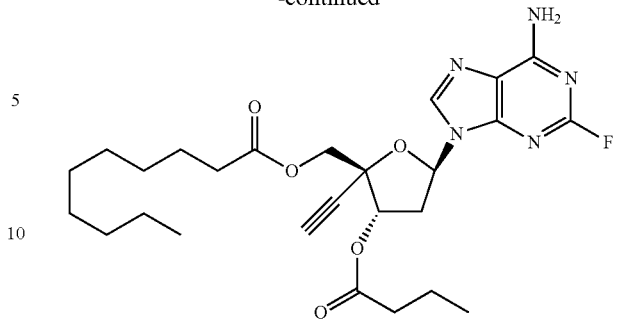

Step A: (2R,3S,5R)-5-(6-amino-2-fluoro-9H-purin-9-yl)-2-(((tert-butyldiphenylsilyl)oxy)methyl)-2-ethynyltetrahydrofuran-3-yl butyrate. A suspension of (2R,3S,5R)-5-(6-amino-2-fluoro-9H-purin-9-yl)-2-(((tert-butyldiphenylsilyl)oxy)methyl)-2-ethynyltetrahydrofuran-3-ol (800 mg, 1.505 mmol) in DCM (15 mL) was treated with butyric acid (0.275 mL, 3.01 mmol), DMAP (184 mg, 1.51 mmol), EDC (865 mg, 4.51 mmol), DIEA (1.314 mL, 7.52 mmol), and stirred at RT for 1.5 h. The reaction was concentrated and purified by flash chromatography (silica gel, 0-100% EtOAc/DCM) to give the title compound (466 mg, 52%) as white solid. LCMS (ESI) m/z calcd for $C_{32}H_{36}FN_5O_4Si$: 601.3. Found: 602.3 (M+1)$^+$. $^1$H NMR (400 MHz, Chloroform-d) δ 7.96 (s, 1H), 7.71-7.63 (m, 4H), 7.48-7.33 (m, 6H), 6.49 (dd, J=6.4, 7.2 Hz, 1H), 5.83 (dd, J=4.2, 6.8 Hz, 1H), 5.74 (br s, 2H), 4.09-4.01 (m, 1H), 4.00-3.92 (m, 1H), 2.87 (td, J=7.1, 13.9 Hz, 1H), 2.67 (ddd, J=4.1, 6.2, 13.8 Hz, 1H), 2.56 (s, 1H), 2.44-2.36 (m, 2H), 1.79-1.68 (m, 2H), 1.10 (s, 9H), 1.00 (t, J=7.4 Hz, 3H).

Step B: (2R,3S,5R)-5-(6-amino-2-fluoro-9H-purin-9-yl)-2-ethynyl-2-(hydroxymethyl)tetrahydrofuran-3-yl butyrate. An ice cold solution of (2R,3S,5R)-5-(6-amino-2-fluoro-9H-purin-9-yl)-2-(((tert-butyldiphenylsilyl)oxy)methyl)-2-ethynyltetrahydrofuran-3-yl butyrate (665 mg, 1.105 mmol) in THF (22 mL) was treated with TBAF (1M in THF) (1.66 mL, 1.66 mmol) and stirred at 0° C. for 2 h. The reaction was quenched with AcOH (~1 mL), diluted with water, and extracted with EtOAc. The combined organics were washed with brine 4×, dried over $Na_2SO_4$, filtered, and concentrated. Purification by flash chromatography [silica gel, 0-100% (3:1 EtOAc:EtOH)/hexanes] afforded the title compound (297 mg, 70%) as white solid. LCMS (ESI) m/z calcd for $C_{16}H_{18}FN_5O_4$: 363.1. Found: 364.1 (M+1)$^+$. $^1$H NMR (400 MHz, DMSO-d$_6$) δ 8.33 (s, 1H), 7.87 (br s, 2H), 6.32 (dd, J=6.2, 7.9 Hz, 1H), 5.60 (dd, J=3.2, 6.6 Hz, 1H), 5.54 (dd, J=5.5, 6.9 Hz, 1H), 3.75-3.56 (m, 3H), 3.00 (ddd, J=6.8, 7.7, 14.1 Hz, 1H), 2.57-2.52 (m, 1H), 2.43-2.33 (m, 2H), 1.62 (sxt, J=7.3 Hz, 2H), 0.94 (t, J=7.4 Hz, 3H).

Step C ((2R,3S,5R)-5-(6-amino-2-fluoro-9H-purin-9-yl)-3-(butyryloxy)-2-ethynyltetrahydrofuran-2-yl)methyl decanoate. A suspension of (2R,3S,5R)-5-(6-amino-2-fluoro-9H-purin-9-yl)-2-ethynyl-2-(hydroxymethyl)tetrahydrofuran-3-yl butyrate (248 mg, 0.683 mmol) in DCM (6.8 mL) was treated with decanoic acid (141 mg, 0.819 mmol), DMAP (83 mg, 0.683 mmol), EDC (236 mg, 1.229 mmol), DIEA (0.596 mL, 3.41 mmol), and stirred at RT for 3.5 h. The reaction was diluted with water and extracted with DCM. The DCM solution was washed with sat. $NaHCO_3$, brine, dried over $Na_2SO_4$, filtered, and concentrated. Purification by flash chromatography (silica gel, 0-100% EtOAc/DCM) afforded the title compound (261 mg, 70%) as white solid. LCMS (ESI) m/z calcd for $C_{26}H_{36}FN_5O_5$: 517.3.

Found: 518.8 (M+1)⁺. ¹H NMR (400 MHz, DMSO-d₆) δ 8.31 (s, 1H), 7.84 (br s, 2H), 6.34 (t, J=6.8 Hz, 1H), 5.69 (dd, J=5.2, 6.9 Hz, 1H), 4.40 (d, J=11.7 Hz, 1H), 4.23 (d, J=11.7 Hz, 1H), 3.76 (s, 1H), 3.15 (td, J=6.9, 13.8 Hz, 1H), 2.61 (ddd, J=5.2, 6.9, 14.1 Hz, 1H), 2.38 (dt, J=2.9, 7.3 Hz, 2H), 2.34-2.15 (m, 2H), 1.62 (sxt, J=7.3 Hz, 2H), 1.53-1.38 (m, 2H), 1.31-1.12 (m, 12H), 0.93 (t, J=7.4 Hz, 3H), 0.89-0.80 (m, 3H).

Example 32: ((2R,3S,5R)-5-(6-amino-2-fluoro-9H-purin-9-yl)-2-ethynyl-3-(heptanoyloxy)tetrahydrofuran-2-yl)methyl Benzoate

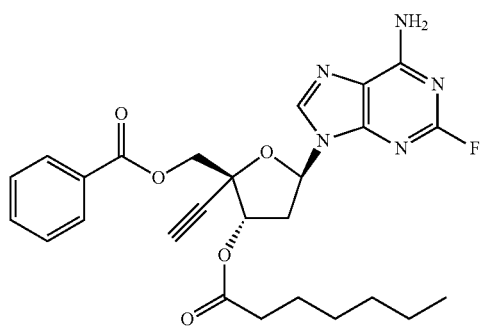 [SMILES: C#C[C@]1(COC(=O)c2ccccc2)O[C@@H](n2cnc3c(N)nc(F)nc32)C[C@@H]1OC(=O)CCCCCC]

The title compound was prepared according to example 31, substituting benzoic acid for butyric acid in step A and heptanoic acid for decanoic acid in step C. LCMS (ESI) m/z calcd for C₂₆H₂₈FN₅O₅: 509.2. Found: 510.5 (M+1)⁺. ¹H NMR (400 MHz, Chloroform-d) δ 8.06-7.99 (m, 2H), 7.85 (s, 1H), 7.61-7.54 (m, 1H), 7.49-7.41 (m, 2H), 6.42 (t, J=6.6 Hz, 1H), 5.84 (dd, J=5.5, 7.2 Hz, 1H), 5.77 (br s, 2H), 4.80 (d, J=11.9 Hz, 1H), 4.62 (d, J=11.9 Hz, 1H), 3.11 (ddd, J=6.4, 7.4, 13.8 Hz, 1H), 2.81-2.67 (m, 2H), 2.44 (t, J=7.5 Hz, 2H), 1.76-1.64 (m, 2H), 1.44-1.28 (m, 6H), 0.96-0.87 (m, 3H).

Example 33: (2R,3aS,20aR)-2-(6-amino-2-fluoro-9H-purin-9-yl)-20a-ethynylhexadecahydro-2H-furo[3,2-b][1,5]dioxacyclononadecine-5,18-dione

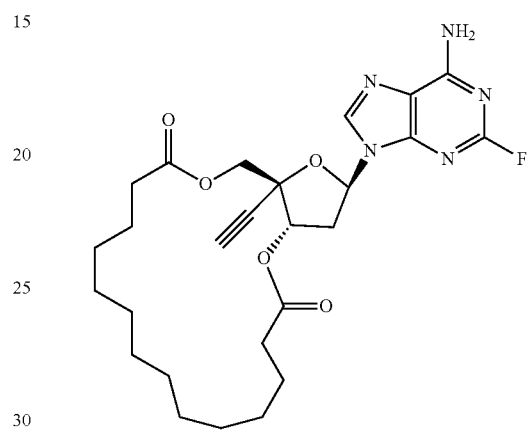

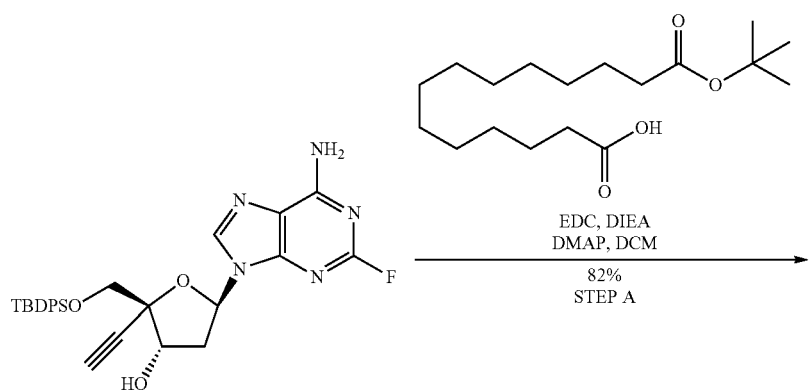

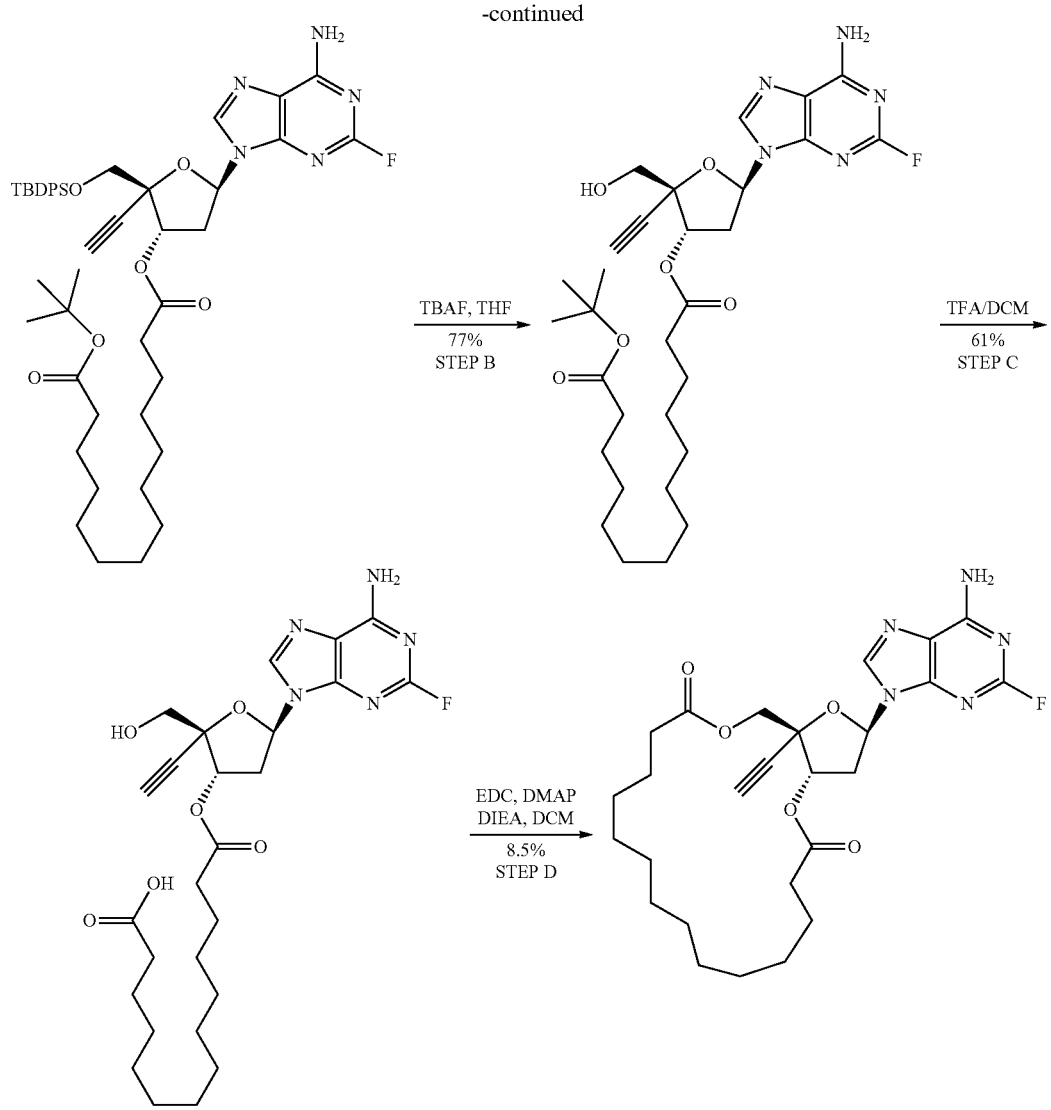

Step A: 1-((2R,3S,5R)-5-(6-amino-2-fluoro-9H-purin-9-yl)-2-(((tert-butyldiphenylsilyl)oxy)methyl)-2-ethynyltetrahydrofuran-3-yl) 14-tert-butyl tetradecanedioate. To a stirred solution of (2R,3S,5R)-5-(6-amino-2-fluoro-9H-purin-9-yl)-2-(((tert-butyldiphenylsilyl)oxy)methyl)-2-ethynyltetrahydrofuran-3-ol (146 mg, 0.275 mmol), 14-(tert-butoxy)-14-oxotetradecanoic acid (130 mg, 0.412 mmol) and DMAP (33.5 mg, 0.275 mmol) in DCM (1.5 mL) at ambient temperature was added EDC (158 mg, 0.824 mmol), followed by DIPEA (0.240 mL, 1.373 mmol) and the mixture was allowed to stir overnight. The mixture was concentrated and then purified on silica gel (0-50% DCM/EtOAc) to afford the title compound (187 mg, 82%) as a colorless residue. LCMS (ESI) m/z calcd for $C_{46}H_{62}FN_5O_6Si$: 827.5. Found: 828.7 (M+1)$^+$. $^1$H NMR (400 MHz, Chloroform-d) δ 7.96 (s, 1H), 7.70-7.63 (m, 4H), 7.47-7.35 (m, 6H), 6.49 (dd, J=6.2, 7.2 Hz, 1H), 5.90-5.74 (m, 3H), 4.05 (d, J=11.2 Hz, 1H), 3.96 (d, J=11.2 Hz, 1H), 2.90-2.81 (m, 1H), 2.70-2.63 (m, 1H), 2.56 (s, 1H), 2.41 (t, J=7.5 Hz, 2H), 2.21 (t, J=7.5 Hz, 2H), 1.75-1.52 (m, 4H), 1.45 (s, 9H), 1.40-1.22 (m, 16H), 1.10 (s, 9H).

Step B: 1-((2R,3S,5R)-5-(6-amino-2-fluoro-9H-purin-9-yl)-2-ethynyl-2-(hydroxymethyl)tetrahydrofuran-3-yl) 14-tert-butyl tetradecanedioate. To a solution of 1-((2R,3S,5R)-5-(6-amino-2-fluoro-9H-purin-9-yl)-2-(((tert-butyldiphenylsilyl)oxy)methyl)-2-ethynyltetrahydrofuran-3-yl) 14-(tert-butyl) tetradecanedioate (185 mg, 0.223 mmol) in THF (2.0 mL) was added TBAF, 1M solution in THF (0.335 mL, 0.335 mmol) and the mixture was allowed to stir at ambient temperature for 60 minutes. AcOH (335 uL) was added and the mixture was concentrated. The residue was purified on silica gel (0-10% DCM/MeOH) to afford the title compound (101 mg, 77%) as a white solid. LCMS (ESI) m/z calcd for $C_{30}H_{44}FN_5O_6$: 589.3. Found: 590.6 (M+1)$^+$. $^1$H NMR (400 MHz, Chloroform-d) δ 7.84 (s, 1H), 6.34 (dd, J=5.5, 9.3 Hz, 1H), 5.97-5.72 (m, 3H), 5.41 (dd, J=3.3, 11.4 Hz, 1H), 4.07-4.01 (m, 1H), 3.98-3.90 (m, 1H), 3.21 (ddd, J=6.3, 9.3, 13.7 Hz, 1H), 2.62 (s, 1H), 2.50-2.38 (m, 3H), 2.21 (t, J=7.5 Hz, 2H), 1.74-1.65 (m, 2H), 1.63-1.52 (m, 2H), 1.45 (s, 9H), 1.41-1.23 (m, 16H).

Step C: 14-(((2R,3S,5R)-5-(6-amino-2-fluoro-9H-purin-9-yl)-2-ethynyl-2-(hydroxymethyl)tetrahydrofuran-3-yl)oxy)-14-oxotetradecanoic acid. To a solution of 1-((2R,3S,5R)-5-(6-amino-2-fluoro-9H-purin-9-yl)-2-ethynyl-2-(hydroxymethyl)tetrahydrofuran-3-yl) 14-(tert-butyl)

tetradecanedioate (101 mg, 0.171 mmol) in DCM (3.0 mL) at ambient temperature was added TFA (50 μl, 0.649 mmol) and the mixture was stirred for 25 minutes. LCMS indicated mostly starting material remained. Additional TFA (50 uL) was added and the mixture was stirred for six hours. The mixture was concentrated and then purified on silica gel (0-10% DCM/MeOH) to afford the title compound (56 mg, 61%) as a white solid. LCMS (ESI) m/z calcd for $C_{26}H_{36}FN_5O_6$: 533.3. Found: 534.5 (M+1)$^+$. $^1$H NMR (400 MHz, DMSO-$d_6$) δ 12.03-11.75 (m, 1H), 8.33 (s, 1H), 7.97-7.74 (m, 2H), 6.31 (dd, J=6.4, 7.9 Hz, 1H), 5.67-5.41 (m, 2H), 3.79-3.55 (m, 3H), 3.04-2.94 (m, 1H), 2.57-2.46 (m, 1H, overlapping DMSO peak), 2.41-2.34 (m, 2H), 2.17 (t, J=7.4 Hz, 2H), 1.65-1.40 (m, 4H), 1.37-1.10 (m, 16H).

Step D: (2R,3aS,20aR)-2-(6-amino-2-fluoro-9H-purin-9-yl)-20a-ethynylhexadecahydro-2H-furo[(3,2-b](1,5/dioxa-cyclononadecine-5,18-dione. To a solution of 14-(((2R,3S, 5R)-5-(6-amino-2-fluoro-9H-purin-9-yl)-2-ethynyl-2-(hydroxymethyl)tetrahydrofuran-3-yl)oxy)-14-oxotetradecanoic acid (56 mg, 0.105 mmol) in DCM (6.5 mL) at ambient temperature was sequentially added DMAP (12.82 mg, 0.105 mmol), DIPEA (0.092 mL, 0.525 mmol) and EDC (60.4 mg, 0.315 mmol) and the mixture was allowed to stir for 3 days. The mixture was concentrated in the presence of Celite. Silica gel chromatography (0-50% DCM/EtOAc) afforded the title compound (4.6 mg, 8.5%) as a colorless residue. LCMS (ESI) m/z calcd for $C_{26}H_{34}FN_5O_5$: 515.3. Found: 516.8 (M+1)$^+$. $^1$H NMR (400 MHz, Chloroform-d) δ 7.92 (s, 1H), 6.39 (dd, J=5.5, 6.9 Hz, 1H), 5.87 (br s, 2H), 5.76-5.71 (m, 1H), 4.48 (d, J=11.9 Hz, 1H), 4.40 (d, J=11.7 Hz, 1H), 3.15-3.06 (m, 1H), 2.79-2.70 (m, 1H), 2.66 (s, 1H), 2.48-2.35 (m, 4H), 1.79-1.61 (m, 4H), 1.48-1.18 (m, 16H).

Example 34: ((2R,3S,5R)-5-(6-amino-2-fluoro-9H-purin-9-yl)-2-ethynyl-3-hydroxytetrahydrofuran-2-yl)methyl Heptanoylglycinate

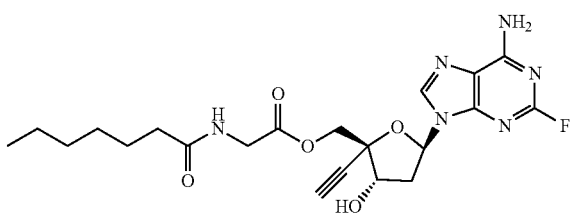 [SMILES: C#C[C@]1(COC(=O)CNC(=O)CCCCCC)O[C@@H](n2cnc3c(N)nc(F)nc32)C[C@@H]1O]

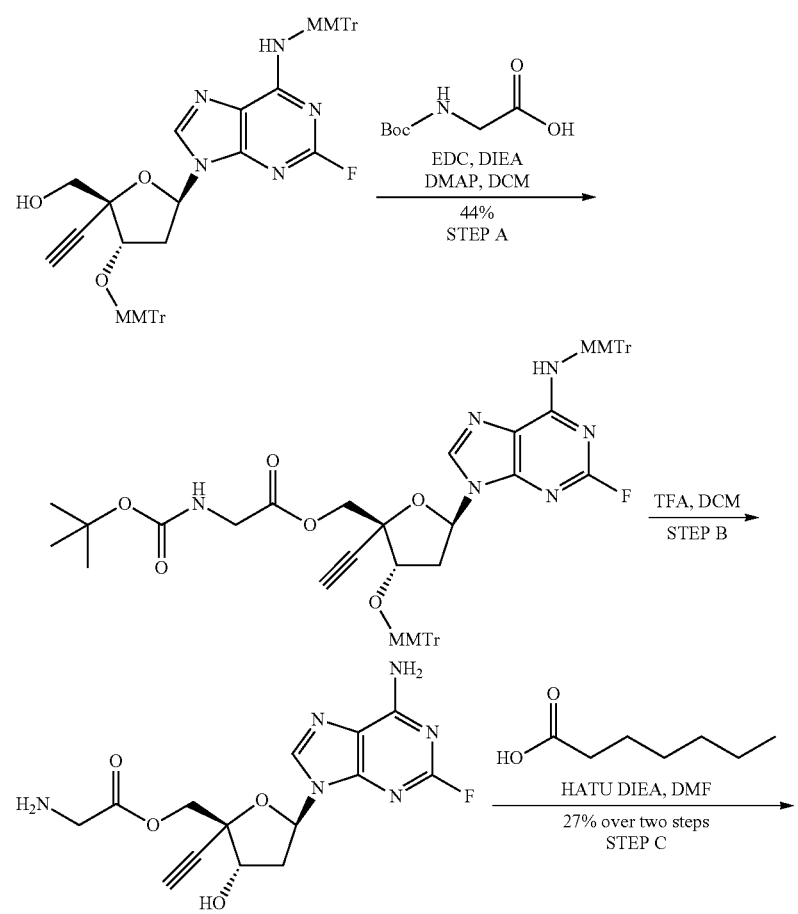

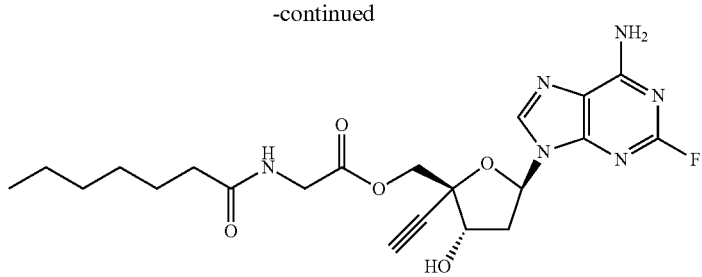

Step A: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methyl 2-(tert-butoxycarbonyl)amino)acetate. To a stirred solution of ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl) methanol (31 mg, 0.037 mmol), (tert-butoxycarbonyl) glycine (12.96 mg, 0.074 mmol) and DMAP (4.52 mg, 0.037 mmol) in DCM (0.6 mL) at ambient temperature was added EDC (21.28 mg, 0.111 mmol), followed by DIPEA (0.032 mL, 0.185 mmol). The mixture was allowed to stir for 24 hours. Additional (tert-butoxycarbonyl)glycine (12.96 mg, 0.074 mmol), DMAP (4.52 mg, 0.037 mmol), EDC (21.28 mg, 0.111 mmol) and DIPEA (0.032 mL, 0.185 mmol) were added and the mixture was stirred overnight. The mixture was concentrated and then purified on silica gel (0-50% DCM/EtOAc) to afford the title compound (16 mg, 44%) as a colorless residue. LCMS (ESI) m/z calcd for $C_{59}H_{55}FN_6O_8$: 995.1. Found: 996.3 (M+1)$^+$.

Step B: ((2R,3S,5R)-5-(6-amino-2-fluoro-9H-purin-9-yl)-2-ethynyl-3-hydroxytetrahydrofuran-2-yl)methyl 2-aminoacetate. To a solution of ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy) tetrahydrofuran-2-yl)methyl 2-((tert-butoxycarbonyl) amino)acetate (16 mg, 0.016 mmol) in DCM (0.8 mL) was added TFA (0.2 ml). The resulting orange solution was stirred overnight, then concentrated and used in the next step without further purification. LCMS (ESI) m/z calcd for $C_{14}H_{15}FN_6O_4$: 350.1. Found: 351.7 (M+1)$^+$.

Step C: ((2R,3S,5R)-5-(6-amino-2-fluoro-9H-purin-9-yl)-2-ethynyl-3-hydroxytetrahydrofuran-2-yl)methyl heptanoylulycinate. To a solution of the crude amine product from the previous step in DMF (0.6 mL) was added heptanoic acid (6.81 μl, 0.048 mmol), DIPEA (0.014 mL, 0.080 mmol) and finally HATU (12.17 mg, 0.032 mmol). The mixture was stirred for 20 minutes then purified directly by RP-HPLC (C18, 10-100% MeCN/water with 0.1% FA) to afford the title compound (4.6 mg, 27% over two steps) as a white residue. LCMS (ESI) m/z calcd for $C_{21}H_{27}FN_6O_5$: 462.2. Found: 463.8 (M+1)$^+$. $^1$H NMR (400 MHz, Methanol-d$_4$) δ 8.18 (s, 1H), 6.32 (dd, J=3.9, 7.7 Hz, 1H), 4.85-4.77 (m, 1H, overlapping water signal), 4.50 (d, J=11.7 Hz, 1H), 4.37 (d, J=11.9 Hz, 1H), 3.96 (d, J=17.6 Hz, 1H), 3.84 d, J=17.6 Hz, 1H), 3.16 (s, 1H), 2.90-2.83 (m, 1H), 2.69-2.61 (m, 1H), 2.26-2.16 (m, 2H), 1.66-1.51 (m, 2H), 1.39-1.20 (m, 6H), 0.94-0.84 (m, 3H).

Example 35: ((2R,3S,5R)-5-(6-amino-2-fluoro-9H-purin-9-yl)-2-ethynyl-3-hydroxytetrahydrofuran-2-yl)methyl Tetradecanoylglycinate

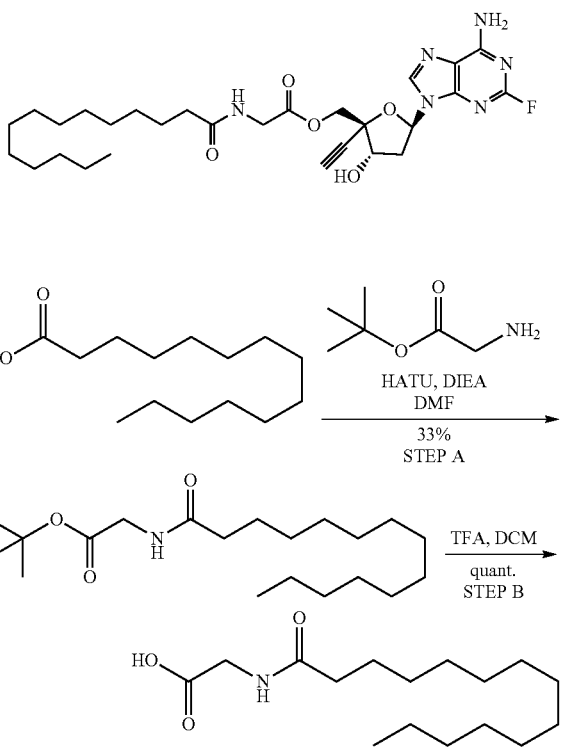

Step A: tert-butyl 2-tetradecanamidoacetate. To a solution of tetradecanoic acid (200 mg, 0.876 mmol), tert-butyl glycinate, hydrochloride (176 mg, 1.051 mmol) and DIPEA (0.459 mL, 2.63 mmol) in DMF (5 mL) was added HATU (533 mg, 1.401 mmol) and the mixture was allowed to stir at ambient temperature for 3 hours. Water was added and the mixture was extracted with EtOAc. The extracts were washed with 1N HCl, then sat'd NaHCO$_3$ at which point an emulsion formed. Brine was added and the mixture was filtered over Celite and the layers were separated. The organic phase was further washed with water, then brine, dried over Na$_2$SO$_4$, filtered and concentrated to afford the title compound (98 mg, 33%) as a white solid. $^1$H NMR (400 MHz, DMSO-d$_6$) δ=8.10-8.03 (m, 1H), 3.66 (d, J=6.0 Hz, 2H), 2.08 (t, J=7.4 Hz, 2H), 1.53-1.43 (m, 2H), 1.39 (s, 9H), 1.23 (s, 20H), 0.89-0.81 (m, 3H).

Step B: 2-tetradecanamidoacetic acid. A solution of tert-butyl tetradecanoylglycinate (98 mg, 0.287 mmol) in DCM (0.8 mL) was treated with TFA (0.2 mL, 2.60 mmol) and the mixture was stirred at ambient temperature for 2 hours. Additional TFA (0.2 mL, 2.60 mmol) was added and stirring at ambient temperature was continued overnight. The mixture was concentrated to give a sticky brown solid which was used without further purification. $^1$H NMR (400 MHz, DMSO-$d_6$) δ 12.40 (br. s, 1H), 8.08-8.02 (m, 1H), 3.72 (d, J=6.0 Hz, 2H), 2.10 (t, J=7.4 Hz, 2H), 1.56-1.42 (m, 2H), 1.34-1.15 (m, 20H), 0.91-0.80 (m, 3H).

Steps C and D: ((2R,3S,5R)-5-(6-amino-2-fluoro-9H-purin-9-yl)-2-ethynyl-3-hydroxytetrahydrofuran-2-yl)methyl tetradecanoylglycinate. The title compound was prepared from ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methanol and 2-tetradecanamidoacetic acid according to example 1, steps E and F. LCMS (ESI) m/z calcd for $C_{26}H_{41}FN_6O_5$: 560.3. Found: 561.5 (M+1)$^+$. $^1$H NMR (400 MHz, Methanol-$d_4$) δ 8.18 (s, 1H), 6.33 (dd, J=3.9, 7.7 Hz, 1H), 4.87-4.74 (m, 1H, overlapping H$_2$O peak), 4.50 (d, J=11.9 Hz, 1H), 4.38 (d, J=11.7 Hz, 1H), 3.97 (d, J=17.6 Hz, 1H), 3.84 (d, J=17.6 Hz, 1H), 3.16 (s, 1H), 2.91-2.83 (m, 1H), 2.70-2.61 (m, 1H), 2.27-2.15 (m, 2H), 1.65-1.52 (m, 2H), 1.28 (s, 20H), 0.93-0.85 (m, 3H).

Example 36: ((2R,3S,5R)-5-(6-amino-2-fluoro-9H-purin-9-yl)-2-ethynyl-3-hydroxytetrahydrofuran-2-yl)methyl heptanoyl-L-alaninate

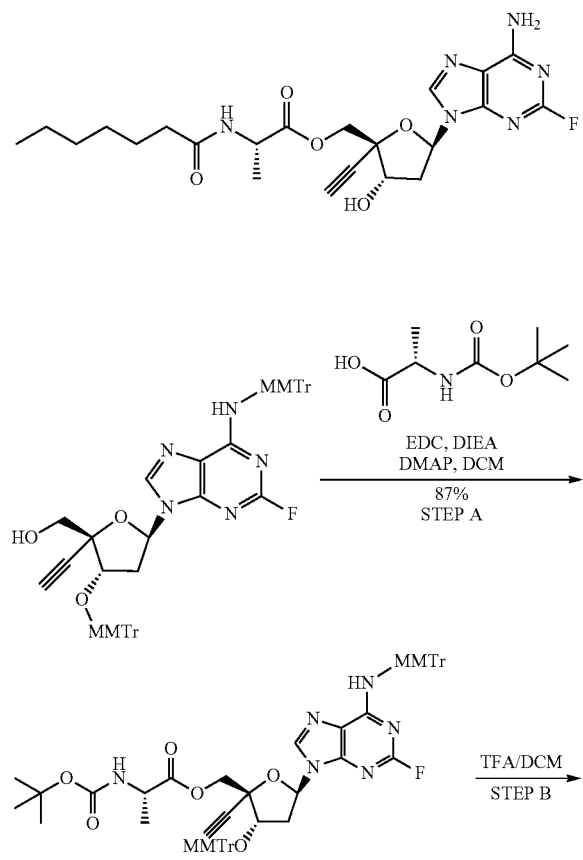

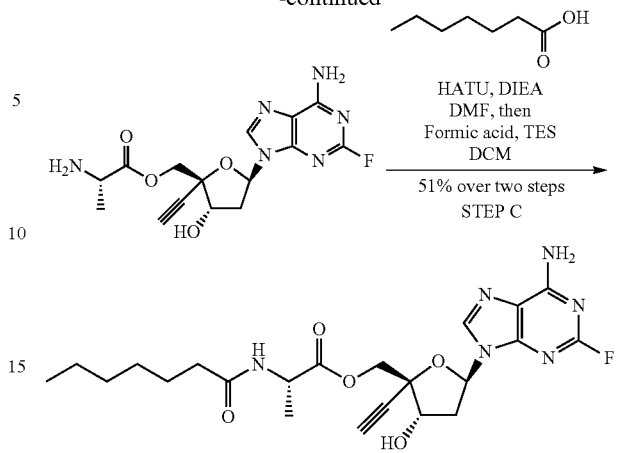

Step A: (S)-((2R,3S,5R)-2-ethynyl-5-(2-fluoro-6-(((4-methoxyphenyl)diphenylmethyl)-amino)-9H-purin-9-yl)-3-((4-methoxyphenyl)diphenylmethoxy)tetrahydrofuran-2-yl)methyl 2-((tert-butoxycarbonyl)amino)propanoate. To a stirred solution of ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methanol (39 mg, 0.047 mmol), (tert-butoxycarbonyl)-L-alanine (17.61 mg, 0.093 mmol) and DMAP (5.69 mg, 0.047 mmol) in DCM (0.5 mL) at ambient temperature was added EDC (26.8 mg, 0.140 mmol), followed by DIPEA (0.041 mL, 0.233 mmol). The mixture was allowed to stir at ambient temperature overnight. The mixture was concentrated and then purified on silica gel (0-50% hexanes/EtOAc) to afford the title compound (41 mg, 87%) as a colorless residue (41 mg). LCMS (ESI) m/z calcd for $C_{60}H_{57}FN_6O_8$: 1008.4. Found: 1009.6 (M+1)$^+$.

Step B: (S)-((2R,3S,5R)-5-(6-amino-2-fluoro-9H-purin-9-yl)-2-ethynyl-3-hydroxytetra-hydrofuran-2-yl)methyl 2-aminopropanoate. To a solution of (S)-((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methyl 2-((tert-butoxycarbonyl)-amino)propanoate (41 mg, 0.041 mmol) in DCM (0.8 mL) was added TFA (0.2 mL). The resulting orange solution was stirred for two hours, then concentrated and used in the next step without further purification. LCMS (ESI) m/z calcd for $C_{15}H_{17}FN_6O_4$: 364.1. Found: 365.1 (M+1)$^+$.

Step C: ((2R,3S,5R)-5-(6-amino-2-fluoro-9H-purin-9-yl)-2-ethynyl-3-hydroxytetra-hydrofuran-2-yl)methyl heptanoyl-L-alaninate. To a mixture of the crude product from the previous step in DMF (0.500 mL) was added heptanoic acid (6.06 mg, 0.047 mmol), DIPEA (0.024 mL, 0.140 mmol) and finally HATU (28.3 mg, 0.074 mmol) at ambient temperature and the mixture was allowed to stir for 30 minutes. Sat'd NaHCO$_3$ was added and the mixture was extracted with EtOAc. The combined extracts were washed with water, then brine, dried over Na$_2$SO$_4$, filtered and concentrated to a pale brown. The residue was dissolved in DCM (0.8 mL), treated with formic acid (0.2 mL), followed by triethylsilane (0.015 mL, 0.093 mmol) and the mixture was stirred at ambient temperature for 30 minutes. The mixture was concentrated and then purified on silica gel (0-10% DCM/MeOH) to afford the title compound (10.2 mg, 51% over two steps) as a colorless residue. LCMS (ESI) m/z calcd for $C_{22}H_{29}FN_6O_6$: 476.2. Found: 477.2 (M+1)$^+$.

¹H NMR (400 MHz, DMSO-d₆) δ 8.26 (s, 1H), 8.14-8.09 (m, 1H), 7.80 (br s, 2H), 6.25 (dd, J=5.0, 7.6 Hz, 1H), 5.77-5.74 (m, 1H), 4.68-4.52 (m, 1H), 4.32 (d, J=11.4 Hz, 1H), 4.24-4.15 (m, 2H), 3.59 (s, 1H), 2.84-2.75 (m, 1H), 2.53-2.40 (m, 1H, overlapping DMSO peak), 2.09-2.02 (m, 2H), 1.52-1.35 (m, 2H), 1.31-1.09 (m, 9H), 0.89-0.74 (m, 3H).

Example 37: ((2R,3S,5R)-5-(6-amino-2-fluoro-9H-purin-9-yl)-3-(butyryloxy)-2-ethynyltetrahydrofuran-2-yl)methyl Tetradecanoate The title compound was prepared according to example 31, substituting tetradecanoic acid for decanoic acid in step C. LCMS (ESI) m/z calcd for C₃₀H₄₄FN₅O₅: 573. Found: 574 (M+1)⁺. ¹H NMR (400 MHz, Chloroform-d) δ 7.95 (s, 1H), 6.42 (t, J=6.4 Hz, 1H), 5.80 (br s, 2H), 5.68 (dd, J=6.9, 5.5 Hz, 1H), 4.51 (d, J=11.9 Hz, 1H), 4.41 (d, J=11.9 Hz, 1H), 3.03 (ddd, J=13.8, 7.5, 6.2 Hz, 1H), 2.67-2.76 (m, 2H), 2.32-2.47 (m, 4H), 1.57-1.81 (m, 4H), 1.24-1.34 (m, 20H), 1.02 (t, J=7.39 Hz, 3H), 0.87-0.94 (m, 3H).

Example 38: ((2R,3S,5R)-5-(6-amino-2-fluoro-9H-purin-9-yl)-2-ethynyl-3-(((hexyloxy)carbonyl)oxy)tetrahydrofuran-2-yl)methyl Tetradecanoate

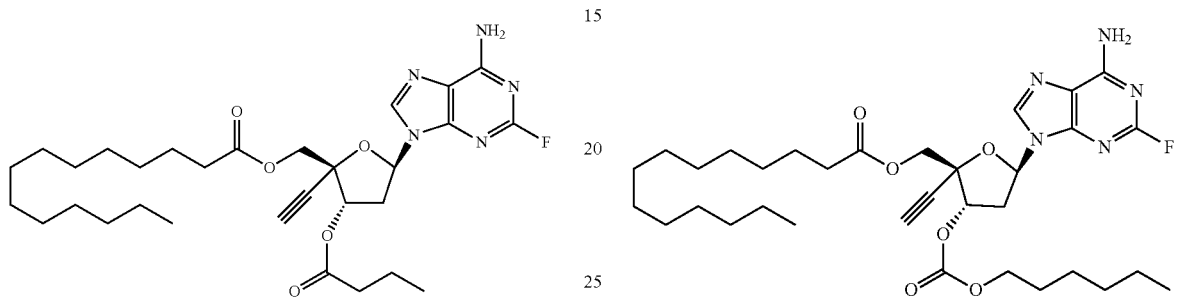

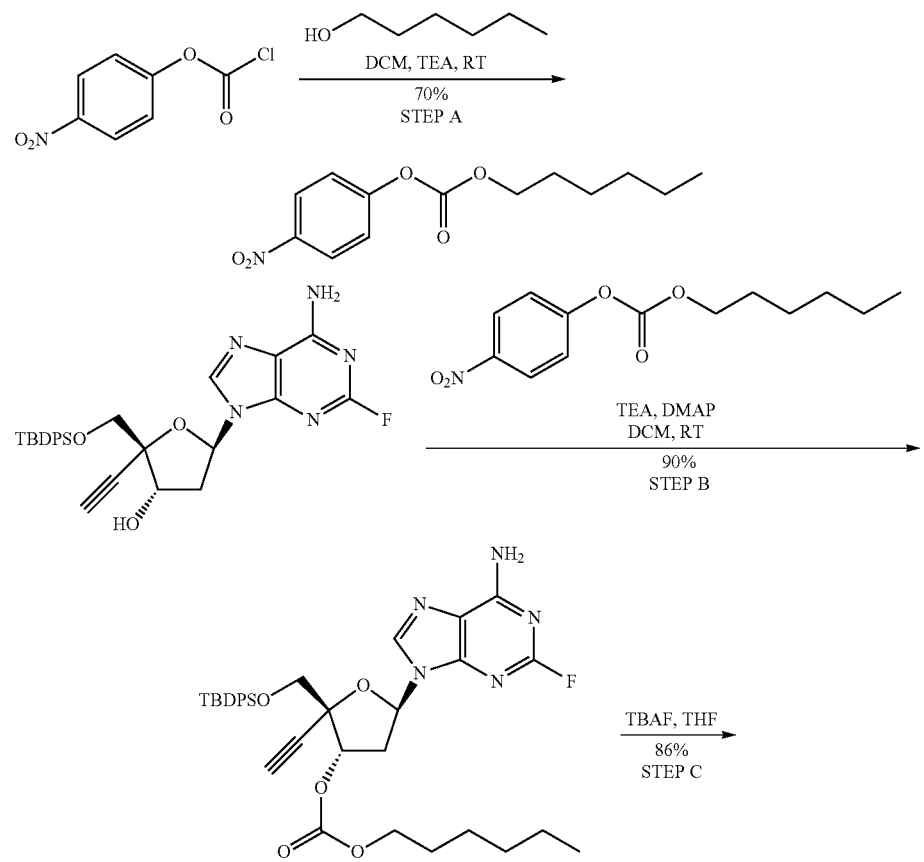

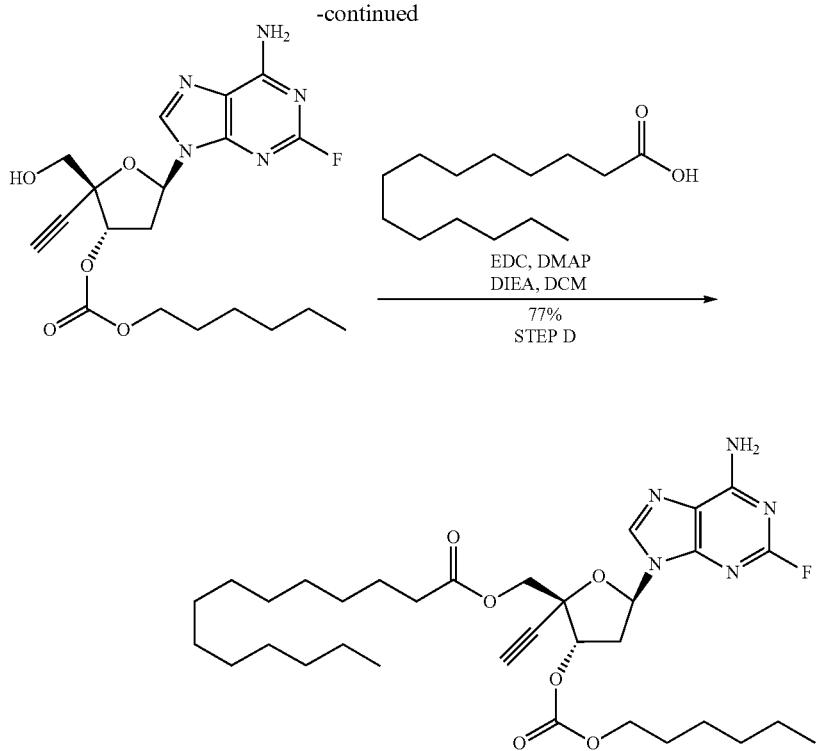

Step A: hexyl (4-nitrophenyl) carbonate. A mixture of 4-nitrophenyl carbonochloridate (2.00 g, 9.92 mmol) and hexan-1-ol (1.24 ml, 9.92 mmol) in DCM (20 mL) was treated with TEA (2.08 ml, 14.9 mmol) and the mixture was stirred at RT for 1 h. The reaction was concentrated and used in the next step without further purification.

Step B: (2R,3S,5R)-5-(6-amino-2-fluoro-9H-purin-9-yl)-2-(((tert-butyldiphenylsilyl)oxy)methyl)-2-ethynyltetrahydrofuran-3-yl hexyl carbonate. A mixture of (2R,3S,5R)-5-(6-amino-2-fluoro-4,5-dihydro-9H-purin-9-yl)-2-(((tert-butyldiphenylsilyl)oxy)methyl)-2-ethynyltetrahydrofuran-3-ol (300 mg, 0.562 mmol) and DMAP (68.7 mg, 0.562 mmol) in DCM (6.0 mL) was treated with TEA (0.235 mL, 1.69 mmol) followed by hexyl (4-nitrophenyl) carbonate (300 mg, 1.12 mmol) and the mixture was stirred at RT for 2 days. Concentrated and purified by flash chromatography (silica gel, 0-10% MeOH/DCM) to give the desired product as a white foam. (332 mg, 90%). LCMS (ESI) m/z calcd for $C_{35}H_{42}FN_5O_5Si$: 659. Found: 660 (M+1)$^+$. $^1$H NMR (400 MHz, Chloroform-d) δ 8.00 (s, 1H), 7.64-7.73 (m, 4H), 7.35-7.47 (m, 6H), 6.62 (s, 2H), 6.51 (t, J=6.7 Hz, 1H), 5.75 (dd, J=6.8, 4.4 Hz, 1H), 4.18-4.29 (m, 2H), 4.12 (d, J=11.2 Hz, 1H), 4.02 (d, J=11.0 Hz, 1H), 2.98 (dt, J=13.9, 7.0 Hz, 1H), 2.81 (ddd, J=13.8, 6.4, 4.4 Hz, 1H), 2.64 (s, 1H), 1.68-1.79 (m, 2H), 1.26-1.46 (m, 6H), 1.06-1.16 (m, 9H), 0.87-0.99 (m, 3H).

Step C: (2R,3S,5R)-5-(6-amino-2-fluoro-9H-purin-9-yl)-2-ethynyl-2-(hydroxymethyl)tetra-hydrofuran-3-yl hexyl carbonate. To a solution of (2R,3S,5R)-5-(6-amino-2-fluoro-9H-purin-9-yl)-2-(((tert-butyldiphenylsilyl) oxy)methyl)-2-ethynyltetrahydrofuran-3-yl hexyl carbonate (332 mg, 0.503 mmol) in THF (8.0 mL) was added TBAF (1M, THF) (0.843 mL, 0.843 mmol) and the mixture was stirred at RT for 1 h. The mixture was concentrated and the residue purified by flash chromatography (silica gel, 0-10% MeOH/DCM) to give the desired product as a white solid. (203 mg, 96%). LCMS (ESI) m/z calcd for $C_{19}H_{24}FN_5O_5$: 421. Found: 422 (M+1)$^+$. $^1$H NMR (400 MHz, Chloroform-d) δ 7.82 (s, 1H), 6.37 (dd, J=9.4, 5.4 Hz, 1H), 6.02 (br s, 2H), 5.66 (dd, J=6.2, 1.2 Hz, 1H), 4.18-4.29 (m, 2H), 4.07 (d, J=12.4 Hz, 1H), 3.97 (br d, J=12.6 Hz, 1H), 3.25 (ddd, J=13.9, 9.5, 6.2 Hz, 1H), 2.66 (s, 1H), 2.57 (ddd, J=14.0, 5.6, 1.4 Hz, 1H), 1.66-1.85 (m, 3H), 1.27-1.47 (m, 6H), 0.88-0.97 (m, 3H).

Step D: ((2R,3S,5R)-5-(6-amino-2-fluoro-9H-purin-9-yl)-2-ethynyl-3-(((hexyloxy)carbonyl)-oxy)tetrahydrofuran-2-yl)methyl tetradecanoate. To a stirred solution of (2R,3S)-5-(6-amino-2-fluoro-9H-purin-9-yl)-2-ethynyl-2-(hydroxymethyl)tetrahydrofuran-3-yl hexyl carbonate (50.0 mg, 0.119 mmol), EDC (45.5 mg, 0.237 mmol) and DMAP (14.5 mg, 0.119 mmol) in DCM (3.0 mL) was added tetradecanoic acid (32.5 mg, 0.142 mmol) followed by DIEA (0.083 mL, 0.48 mmol) and the mixture was stirred at RT for 16 h. The reaction mixture was concentrated and purified by flash chromatography (silica gel, 0-10% MeOH/DCM) to afford the product as a white solid. (58 mg, 77% yield). LCMS (ESI) m/z calcd for $C_{33}H_{50}FN_5O_6$: 631. Found: 632 (M+1)$^+$. $^1$H NMR (400 MHz, Chloroform-d) δ 7.91 (s, 1H), 6.50 (s, 2H), 6.39 (t, J=6.4 Hz, 1H), 5.60 (dd, J=7.0, 5.6 Hz, 1H), 4.55 (d, J=11.9 Hz, 1H), 4.41 (d, J=11.9 Hz, 1H), 4.21 (m, 2H), 3.14 (dt, J=13.4, 7.0 Hz, 1H), 2.80 (ddd, J=13.9, 6.7, 5.6 Hz, 1H), 2.71 (s, 1H), 2.28-2.42 (m, 2H), 1.55-1.76 (m, 4H), 1.28-1.44 (m, 10H), 1.25 (br s, 16H), 0.83-0.96 (m, 6H).

Example 39: (2R,3S,5R)-5-(6-amino-2-fluoro-9H-purin-9-yl)-2-ethynyl-2-(((2-propylpentanoyl)oxy)methyl)tetrahydrofuran-3-yl Heptanoate

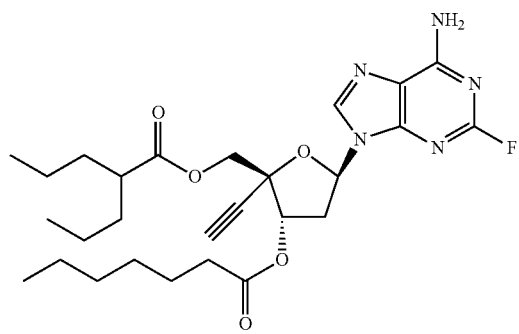 [SMILES: C#C[C@]1(COC(=O)C(CCC)CCC)O[C@@H](n2cnc3c(N)nc(F)nc32)C[C@@H]1OC(=O)CCCCCC]

The title compound was prepared according to example 19, substituting 2-propylpentanoyl chloride for pentanoyl chloride in step A and heptanoic acid for tridecanoic acid in step C. LCMS (ESI) m/z calcd for $C_{27}H_{33}FN_5O_5$: 531. Found: 532 (M+1)$^+$. $^1$H NMR (400 MHz, Chloroform-d) δ 7.96 (s, 1H), 6.43 (t, J=6.4 Hz, 1H), 5.84 (br s, 2H), 5.65 (dd, J=7.0, 5.4 Hz, 1H), 4.41-4.49 (m, 2H), 3.01 (ddd, J=13.7, 7.2, 6.3 Hz, 1H), 2.66-2.77 (m, 2H), 2.39-2.48 (m, 3H), 1.55-1.78 (m, 4H), 1.26-1.50 (m, 12H), 0.86-0.94 (m, 9H).

Example 40: ((2R,3S,5R)-5-(6-amino-2-fluoro-9H-purin-9-yl)-2-ethynyl-3-hydroxytetrahydrofuran-2-yl)methyl tetradecanoyl-L-alaninate

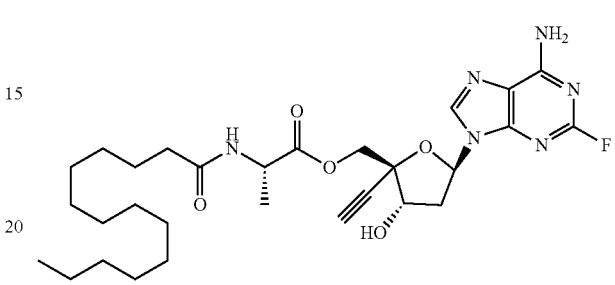

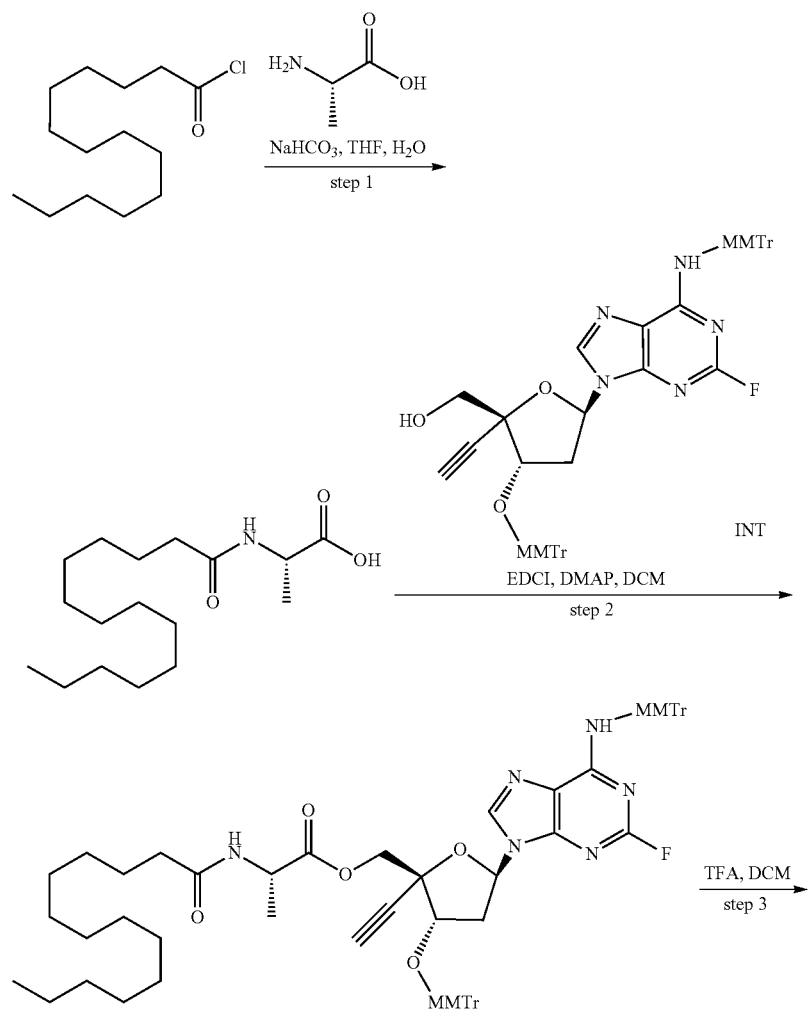

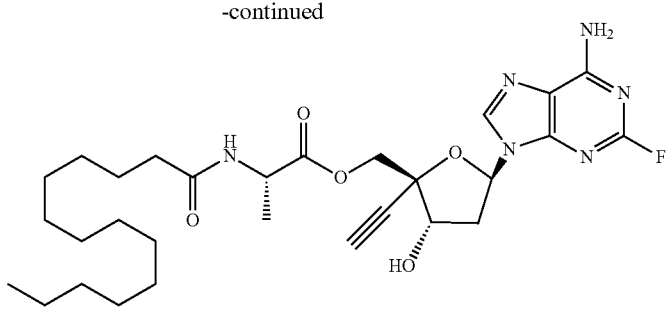

Step 1: tetradecanoyl-L-alanine. To a solution of L-alanine (10.6 g, 17.96 mmol), sodium bicarbonate (3.02 g, 35.9 mmol) in THF (40.0 mL)/Water (40 mL) at 20° C. was added tetradecanoyl chloride (2.216 g, 8.98 mmol) dropwise over 15 min. The reaction mixture was stirred at r.t. for 5 h. LCMS indicated completion of reaction. The reaction mixture was diluted with water (30 ml), and extracted with EtOAc (50 ml*2). The aqueous phase was acidified with 1 M hydrochloric acid. The resulting solid was filtered through a Buchner funnel, rinsed with water (40 mL), and collected to give the crude tetradecanoyl-L-alanine as a white solid (800 mg, 27%). LCMS (ESI) m/z calcd for $C_{17}H_{33}NO_3$:299. Found: 300 (M+H)+. 1HNMR (400 MHz, DMSO-$d_6$) δ8.02-7.91 (m, 1H), 4.16-4.05 (m, 1H), 2.05 (t, J=7.2 Hz, 2H), 1.48-1.41 (m, 2H), 1.26-1.17 (m, 23H), 0.83 (t, J=6.8 Hz, 3H).

Step 2: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl) methyl-tetradecanoyl-L-alaninate. Tetradecanoyl-L-alanine (1 g, 3.34 mmol) was dissolved in DCM (30 mL) and added EDC (3.20 g, 16.70 mmol) and DMAP (2.040 g, 16.70 mmol). The resulting mixture was stirred for 40 min at room temperature. Then, ((2R,3S,5R)-2-ethynyl-5-(2-fluoro-6-(((4-methoxyphen-yl)diphenylmethyl)amino)-9H-purin-9-yl)-3-((4-methoxyphenyl)diphenylmeth-oxy)tetrahydrofuran-2-yl)methanol (1.399 g, 1.670 mmol) was added and the resulting mixture was stirred overnight at room temperature. LCMS indicated completion of reaction. The reaction mixture was concentrated to dryness under vacuum to afford the crude product. The crude product was pre-absorbed on silica and purified on a silica column (120 g) using a 0%-60% pet. ether-EtOAc solvent gradient over 60 mins, Flow rate: 70 mL/min. The appropriate fractions were identified by UV absorbance (254 nm), combined and evaporated under vacuum to give the title product as a white solid (800 mg, 19%). LCMS (ESI) m/z calcd for $C_{69}H_{75}FN_6O_7$:1119, Found: 1120 (M+H)+. 1HNMR (400 MHz, CDCl$_3$) δ7.55-7.49 (m, 4H), 7.42-7.37 (m, 2H), 7.33-7.18 (m, 18H), 6.80 (t, J=12 Hz, 4H) 5.90 (dd, J=24.4, 7.6 Hz, 1H), 4.47-4.28 (m, 2H), 4.15-4.06 (m, 4H), 3.78 (s, 3H), 3.74 (d, J=8.0 Hz, 1H), 2.82 (d, J=8.0 Hz, 1H), 2.05 (s, 4H), 1.29-1.24 (m, 22H), 1.19-1.13 (m, 2H), 1.11-1.05 (m, 2H), 0.85 (t, J=6.4 Hz, 3H).

Step 3: ((2R,3S,5R)-5-(6-amino-2-fluoro-9H-purin-9-yl)-2-ethynyl-3-hydroxytetrahydro-furan-2-yl)methyl tetradecanoyl-L-alaninate. To a stirred solution of ((2R,3S,5R)-2-ethynyl-5-(2-fluoro-6-(((4-methoxyphenyl)diphenylmethyl) amino)-9H-purin-9-yl)-3-((4-methoxyphenyl)di-phenylmethoxy)tetrahydrofuran-2-yl)methyl tetradecanoyl-L-alaninate (800 mg, 0.715 mmol) in DCM (3 mL) at 15° C. was added TFA (300 μL, 3.89 mmol) dropwise. The reaction mixture was stirred at 15° C. for 1 h. LCMS indicated completion of reaction. The reaction mixture was diluted with NaHCO$_3$ (30 ml), and extracted with DCM (15 ml*2). The combined organic phases were washed with brine (15 ml). The organic layers were dried over anhydrous sodium sulphate and concentrated under reduced pressure to afford crude product as a white solid. The sample was pre-absorbed on silica and purified on a silica column (80 g) using a 0%-10% DCM-MeOH solvent gradient over 30 mins, Flow rate: 45 mL/min. The appropriate fractions were identified by UV absorbance (254 nm), combined and evaporated in vacuo to give ((2R,3S,5R)-5-(6-amino-2-fluoro-9H-purin-9-yl)-2-ethynyl-3-hydroxytetrahydro-furan-2-yl)methyl tetradecanoyl-L-alaninate (189 mg, 46%) as a white solid. LCMS (ESI) m/z calcd for $C_{29}H_{43}FN_6O_5$:574. Found: 575 (M+H)+. 1HNMR (400 MHz, CDCl$_3$) δ 7.95 (s, 1H), 6.32 (dd, J=7.2, 4.8 Hz, 1H), 6.05-6.07 (m, 3H), 4.75 (t, J=6.4 Hz, 1H), 4.61 (d, J=11.6 Hz, 1H), 4.52 (t, J=6.8 Hz, 1H), 4.42 (d, J=11.6, 1H), 3.31 (s, 1H), 2.98-3.02 (m, 1H), 2.79 (s, 1H), 2.63-2.70 (m, 1H), 2.21 (t, J=7.6 Hz, 2H), 1.58-1.63 (m, 2H), 1.40 (d, J=7.2 Hz, 3H) 1.24-1.31 (m, 20H), 0.83-0.89 (m, 3H).

Example 41: (2R,3S,5R)-2-(acetoxymethyl)-5-(6-amino-2-fluoro-9H-purin-9-yl)-2-ethynyltetrahydrofuran-3-yl Heptanoate

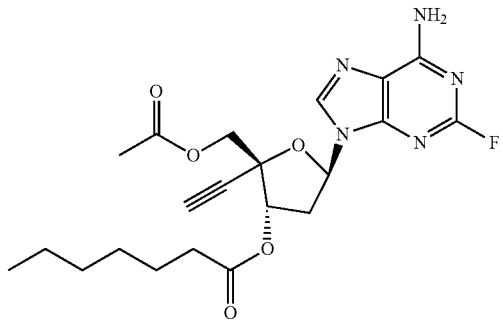 [SMILES: C#C[C@]1(COC(C)=O)O[C@@H](n2cnc3c(N)nc(F)nc32)C[C@@H]1OC(=O)CCCCCC]

The title compound was isolated as a by product from example 32 preparation. This product was formed due to the presence of acetic acid in the starting material. 1HNMR (400 MHz, CHLOROFORM-d) δ ppm 7.92 (s, 1H), 6.39 (t, J=6.4 Hz, 1H), 5.77 (br s, 2H), 5.69 (dd, J=5.5, 7.2 Hz, 1H), 4.52 (d, J=12.2 Hz, 1H), 4.38 (d, J=12.2 Hz, 1H), 3.04 (ddd, J=6.1, 7.4, 13.7 Hz, 1H), 2.76-2.63 (m, 2H), 2.42 (t, J=7.5 Hz, 2H), 2.12 (s, 3H), 1.75-1.63 (m, 2H), 1.41-1.28 (m, 6H), 0.95-0.87 (m, 3H). LCMS (m/z) ES+=448.2 (M+1), ES−=446.4 (M−1).

Example 42: ((2R,3S,5R)-5-(6-decanamido-2-fluoro-9H-purin-9-yl)-2-ethynyl-3-hydroxytetrahydrofuran-2-yl)methyl Heptanoate
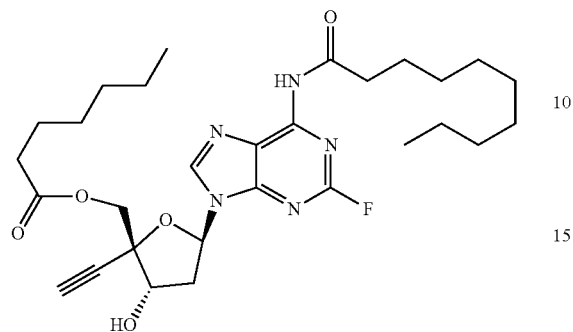
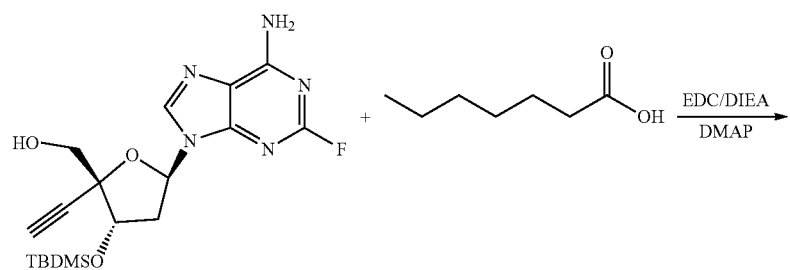
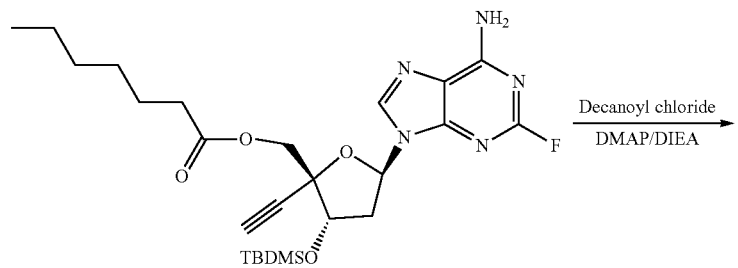
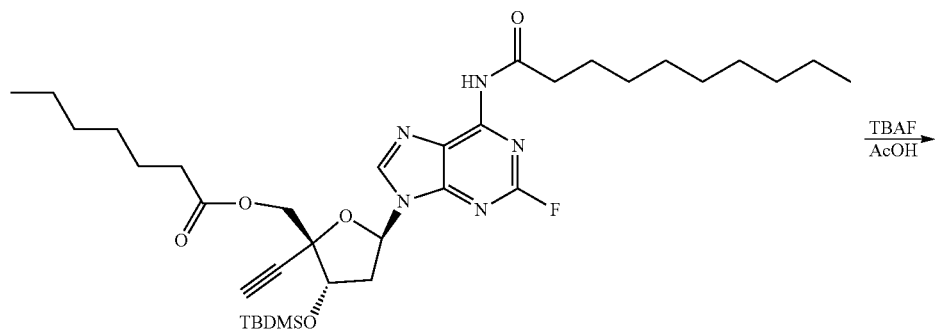

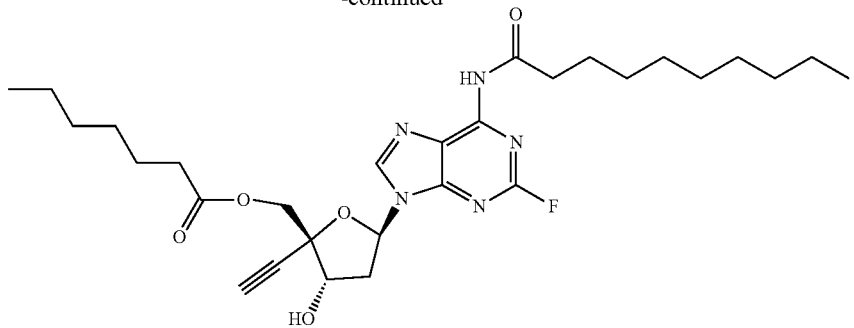

Step 1: ((2R,3S,5R)-5-(6-amino-2-fluoro-9H-purin-9-yl)-3-((tert-butyldimethylsilyl)oxy)-2-ethynyltetrahydrofuran-2-yl)methyl heptanoate. To a suspension of ((2R,3S,5R)-5-(6-amino-2-fluoro-9H-purin-9-yl)-3-((tert-butyldimethylsilyl)oxy)-2-ethynyltetrahydrofuran-2-yl)methanol (390 mg, 0.861 mmol) in DCM (25 mL) was added heptanoic acid (0.271 mL, 1.913 mmol) followed by DMAP (117 mg, 0.958 mmol), EDC (550 mg, 2.87 mmol) and DIEA (0.835 mL, 4.78 mmol) and the mixture was stirred at ambient temperature for 1.5 h. The mixture was diluted with dichloromethane and washed with water. The organic phases were dried (Na2SO4), concentrated and purified on silica gel (Biotage Isolera 1, 24 g, Gold column, EtOAc/hexanes 0-25% then 50-100%, bis-silyl impurity eluted at 25%, product eluted at 50-100%) to provide ((2R,3S,5R)-5-(6-amino-2-fluoro-9H-purin-9-yl)-3-((tert-butyldimethylsilyl)oxy)-2-ethynyltetrahydrofuran-2-yl)methyl heptanoate (360 mg, 0.686 mmol, 80% yield) as an off-white solid. $^1$HNMR (400 MHz, CHLOROFORM-d) b ppm 7.87 (s, 1H), 6.27 (dd, J=7.75, 3.70 Hz, 1H), 5.82 (br s, 2H), 4.96 (t, J=7.39 Hz, 1H), 4.48 (d, J=11.92 Hz, 1H), 4.26 (d, J=11.92 Hz, 1H), 2.84-2.98 (m, 1H), 2.58-2.72 (m, 2H), 2.28 (td, J=7.57, 3.46 Hz, 2H), 1.50-1.61 (m, 2H), 1.19-1.42 (m, 6H), 0.93-1.03 (m, 9H), 0.81-0.92 (m, 3H), 0.17 (d, J=4.29 Hz, 6H). LCMS (M+1)=520.7.

Step 2: ((2R,3S,5R)-3-((tert-butyldimethylsilyl)oxy)-5-(6-decanamido-2-fluoro-9H-purin-9-yl)-2-ethynyltetrahydrofuran-2-yl)methyl heptanoate. To a solution of ((2R,3S,5R)-5-(6-amino-2-fluoro-9H-purin-9-yl)-3-((tert-butyldimethylsilyl)oxy)-2-ethynyltetrahydrofuran-2-yl)methyl heptanoate (280 mg, 0.539 mmol) in DCM (7 mL) was added DIEA (0.565 mL, 3.23 mmol) and DMAP (65.8 mg, 0.539 mmol). The mixture was cooled to 0° C. and decanoyl chloride (0.335 mL, 1.616 mmol) was added dropwise. Stirring at 0° C. continued for 30 min [LCMS showed only s.m.] and then at ambient temperature for 1.5 h. The mixture was diluted with dichloromethane and washed with saturated NaHCO$_3$/water and the organic phases were dried (Na2SO4), concentrated, and purified on silica gel (Biotage Isolera 1, 24 g column, EtOAc/hexanes 0-10-30-100%, 50-1-1 eluted at 30%, 50-2 at 30-35%, recovered s.m. eluted at 70%) to provide ((2R,3S,5R)-3-((tert-butyldimethylsilyl)oxy)-5-(6-decanamido-2-fluoro-9H-purin-9-yl)-2-ethynyltetrahydrofuran-2-yl)methyl heptanoate (143.5 mg, 0.213 mmol, 39.5% yield) as a yellowish oil and recovered starting material. LCMS (M+1)=675.

Step 3: ((2R,3S,5R)-5-(6-decanamido-2-fluoro-9H-purin-9-yl)-2-ethynyl-3-hydroxy-tetrahydrofuran-2-yl)methyl heptanoate. To a solution of ((2R,3S,5R)-3-((tert-butyl-dimethylsilyl)oxy)-5-(6-decanamido-2-fluoro-9H-purin-9-yl)-2-ethynyltetrahydrofuran-2-yl)methyl heptanoate (138 mg, 0.205 mmol) in THF (2.5 mL) was added a solution of TBAF (0.410 mL, 0.410 mmol) (1 M/THF) containing acetic acid (0.023 mL, 0.410 mmol) and the mixture was stirred at ambient temperature for 5 h. The mixture was diluted with dichloromethane and washed with water. The organic phases were dried (Na2SO4), concentrated and purified on silica gel (Biotage Isolera 1, 4 g column, EtOAc/hexanes 0-50-100%, product eluted at 50-100%, two peaks) to provide a clear glass. An off-white solid was obtained by slow evaporation of a MeOH/water solution. $^1$HNMR (400 MHz, CHLOROFORM-d) δ ppm 8.43-8.58 (m, 1H), 8.05 (s, 1H), 6.38 (dd, J=7.39, 4.77 Hz, 1H), 4.78 (q, J=6.76 Hz, 1H), 4.47 (d, J=1.91 Hz, 2H), 2.90-3.09 (m, 3H), 2.82 (s, 1H), 2.71 (dt, J=13.71, 7.33 Hz, 1H), 2.45 (d, J=6.44 Hz, 1H), 2.36 (td, J=7.57, 2.50 Hz, 2H), 1.72-1.88 (m, 2H), 1.54-1.69 (m, 2H), 1.21-1.51 (m, 18H), 0.81-0.99 (m, 6H). LCMS (M−1)=558.4.

Example 43: ((2R,3S,5R)-5-(6-amino-2-fluoro-9H-purin-9-yl)-2-ethynyl-3-(((hexyloxy)carbonyl)oxy)tetrahydrofuran-2-yl)methyl Heptanoate

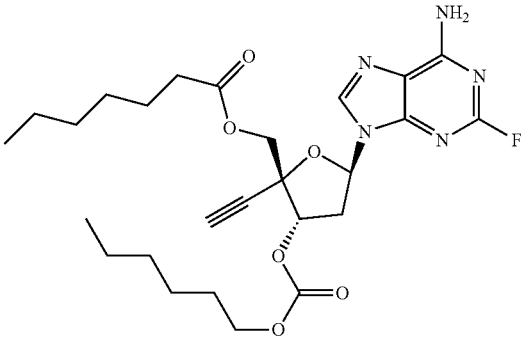 [SMILES: C#C[C@]1(COC(=O)CCCCCC)O[C@@H](n2cnc3c(N)nc(F)nc32)C[C@@H]1OC(=O)OCCCCCC]

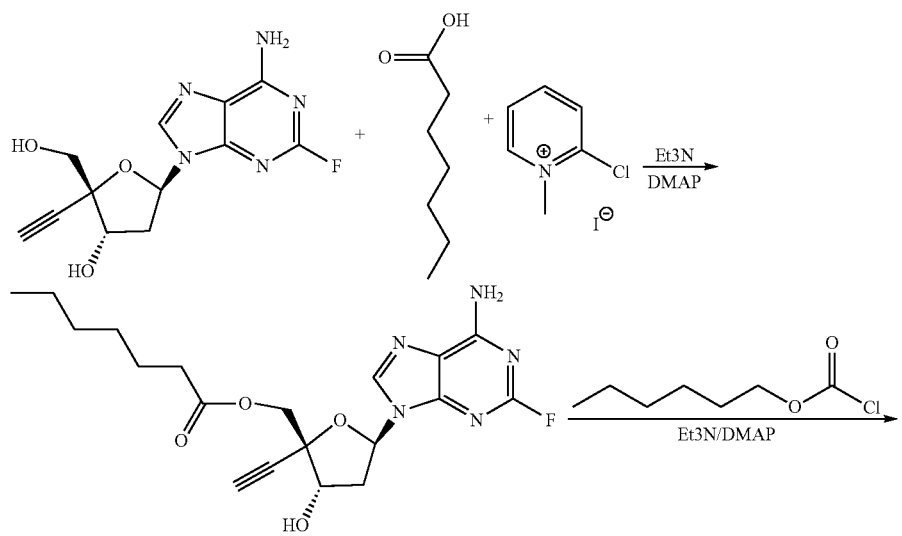

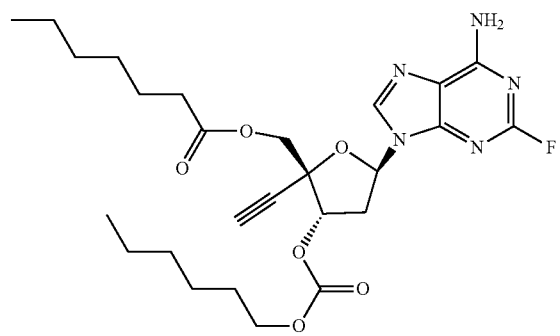

Step 1: ((2R,3S)-5-(6-amino-2-fluoro-9H-purin-9-yl)-2-ethynyl-3-hydroxytetrahydrofuran-2-yl)methyl heptanoate. To a solution of (2R,3S)-5-(6-amino-2-fluoro-9H-purin-9-yl)-2-ethynyl-2-(hydroxymethyl)tetrahydrofuran-3-ol (500 mg, 1.705 mmol) in acetonitrile (70 mL) {used sonicator to dissolve} was added heptanoic acid (0.254 mL, 1.790 mmol) and 2-chloro-1-methylpyridin-1-ium iodide (566 mg, 2.216 mmol) and the mixture was stirred at ambient temperature for 15 min. The mixture was cooled to −15° C. Ice/EtOH) and triethylamine (0.713 mL, 5.11 mmol) was added followed by N,N-dimethylpyridin-4-amine (20.83 mg, 0.170 mmol). After 2 h 45 min (final temperature −5° C.), 0.5 M HCl/water (100 mL) was added and the mixture was extracted with dichloromethane. The organic phases were washed with NaHCO₃/water, dried (Na2SO4), concentrated and purified on silica gel (Biotage Isolera 1, 80 g Gold column, MeOH/dichloromethane 3% isocratic) to provide ((2R,3S)-5-(6-amino-2-fluoro-9H-purin-9-yl)-2-ethynyl-3-hydroxytetrahydrofuran-2-yl)methyl heptanoate (330 mg, 0.814 mmol, 47.7% yield) (N70935-59-1, fractions 52-73) as an off-white solid. $^1$HNMR (400 MHz, DMSO-d6) δ ppm 8.26 (s, 1H), 7.81 (br s, 2H), 6.25 (dd, J=8.11, 4.05 Hz, 1H), 5.76 (d, J=5.25 Hz, 1H), 4.63-4.79 (m, 1H), 4.42 (d, J=11.68 Hz, 1H), 4.10 (d, J=11.68 Hz, 1H), 3.61 (s, 1H), 2.80 (ddd, J=13.35, 7.27, 3.93 Hz, 1H), 2.5-2.4 (m, 1H), 2.05-2.31 (m, 2H), 1.34-1.55 (m, 2H), 1.08-1.29 (m, 6H), 0.83 (t, J=7.03 Hz, 3H). LCMS (M+1)=406.2.

Step 2: ((2R,3S,5R)-5-(6-amino-2-fluoro-9H-purin-9-yl)-2-ethynyl-3-(((hexyloxy)carbon y) ox)tetrahydrofuran-2-yl) methyl heptanoate. To a solution of ((2R,3S,5R)-5-(6-amino-2-fluoro-9H-purin-9-yl)-2-ethynyl-3-hydroxytetrahydrofuran-2-yl)methyl heptanoate (320 mg, 0.789 mmol) in DCM (40 mL) was added Et3N (0.440 mL, 3.16 mmol) and the mixture was cooled to 0° C. then hexyl carbonochloridate (0.258 mL, 1.579 mmol) was added dropwise. After 1 h at 0° C. the mixture was stirred at ambient temperature for 1 h. DMAP (9.64 mg, 0.079 mmol) was added and after 3.5 h at ambient temperature the mixture was diluted with dichloromethane and washed with saturated NaHCO₃/water. The organic phase was dried (Na2SO4), concentrated and purified on silica gel (Biotage Isolera 1, 24 g column, EtOAc/hexanes 0-50-100%) to provide ((2R,3S,5R)-5-(6-amino-2-fluoro-9H-purin-9-yl)-2-ethynyl-3-(((hexyloxy)carbonyl)oxy)tetrahydro-furan-2-yl)methyl heptanoate (132 mg, 0.247 mmol, 31.3% yield) as a white solid (after concentration from MeCN). $^1$HNMR (400 MHz, CHLOROFORM-d) δ ppm 7.78-8.02 (m, 1H), 6.39 (t, J=6.44 Hz, 1H), 5.76 (br s, 2H), 5.61 (dd, J=7.27, 5.60 Hz, 1H), 4.56 (d, J=12.16 Hz, 1H), 4.42 (d, J=12.16 Hz, 1H), 4.22 (td, J=6.74, 2.98 Hz, 2H), 3.09-3.23 (m, 1H), 2.76-2.88 (m, 1H), 2.71 (s, 1H), 2.37 (td, J=7.57, 4.41 Hz, 2H), 1.68-1.80 (m, 2H), 1.60-1.68 (m, 2H), 1.21-1.48 (m, 12H), 0.91 (dt, J=12.28, 6.97 Hz, 6H). LCMS (M+1)=534.6.

Example 44: ((2R,3S,5R)-5-(6-amino-2-fluoro-9H-purin-9-yl)-2-ethynyl-3-(((hexyloxy)carbonyl)oxy)tetrahydrofuran-2-yl)methyl Decanoate

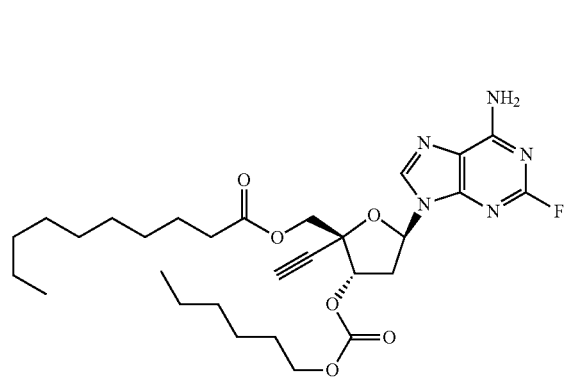 [SMILES: C#C[C@]1(COC(=O)CCCCCCCCC)O[C@@H](n2cnc3c(N)nc(F)nc32)C[C@@H]1OC(=O)OCCCCCC]

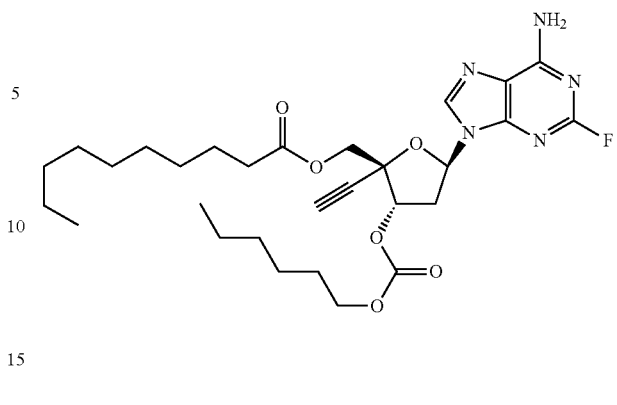

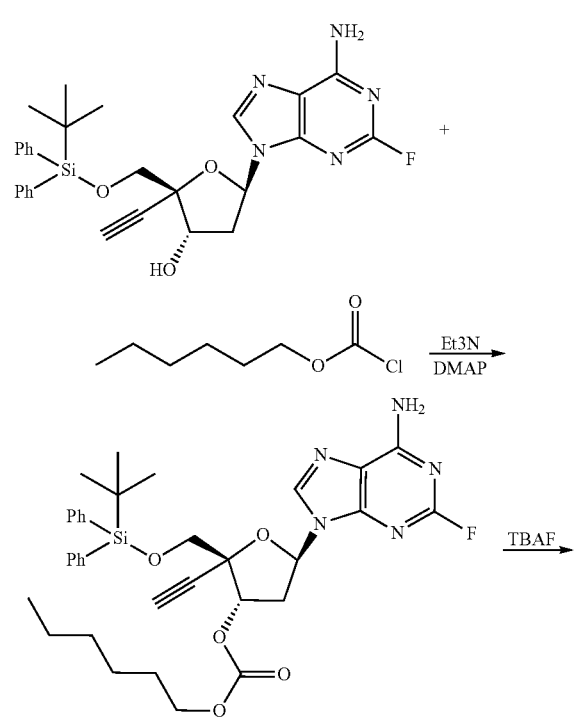

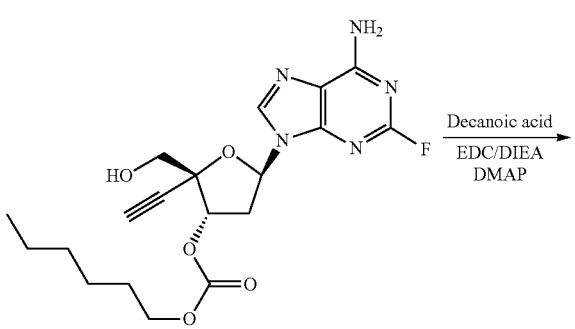

Step 1: (2R,3S,5R)-5-(6-amino-2-fluoro-9H-purin-9-yl)-2-(((tert-butyldiphenylsilyl)oxy) methyl)-2-ethynyltetrahydrofuran-3-yl hexyl carbonate. To a stirred solution of (2R,3S,5R)-5-(6-amino-2-fluoro-9H-purin-9-yl)-2-(((tert-butyldiphenylsilyl)oxy)methyl)-2-ethynyltetrahydrofuran-3-ol (500 mg, 0.940 mmol), DMAP (115 mg, 0.940 mmol) and triethylamine (0.393 mL, 2.82 mmol) at 0° C. was slowly added a solution of hexyl carbonochloridate (0.169 mL, 1.034 mmol) in DCM (1.33 mL) and the mixture was stirred at 0° C. for ~2 hours. Sat'd NaHCO₃ was added and the mixture was extracted with EtOAc. The extracts were washed with brine, dried over Na2SO4, filtered and concentrated. The residue was purified on silica gel (40 g gold column, 0-70% hexanes/EtOAc) to afford title compound as white residue (293 mg, 47%). LCMS (M+1)=660.4.

Step 2: (2R,3S,5R)-5-(6-amino-2-fluoro-9H-purin-9-yl)-2-ethynyl-2-(hydroxymethyl)tetra-hydrofuran-3-yl hexyl carbonate. To a solution of (2R,3S,5R)-5-(6-amino-2-fluoro-9H-purin-9-yl)-2-(((tert-butyldiphenylsilyl)oxy)methyl)-2-ethynyltetrahydrofuran-3-yl hexyl carbonate (347 mg, 0.526 mmol) in THF (5.0 mL) at ambient temperature was added TBAF (0.789 mL, 0.789 mmol) and the mixture was stirred for 30 minutes. The mixture was concentrated and then purified on silica gel (0-10% DCM/MeOH) to afford title compound as white solid (179 mg, 81%). LCMS (M+1)=422.2.

Step 3: ((2R,3S,5R)-5-(6-amino-2-fluoro-9H-purin-9-yl)-2-ethynyl-3-(((hexyloxy)carbon y) ox)tetrahydrofuran-2-yl) methyl decanoate. To a mixture of (2R,3S,5R)-5-(6-amino-2-fluoro-9H-purin-9-yl)-2-ethynyl-2-(hydroxymethyl)tetrahydrofuran-3-yl hexyl carbonate (179 mg, 0.425 mmol), decanoic acid (80 mg, 0.467 mmol), DMAP (51.9 mg, 0.425 mmol) and DIEA (0.371 mL, 2.124 mmol) was added EDC (163 mg, 0.849 mmol) at ambient temperature and the mixture was allowed to stir overnight. The mixture was concentrated and then purified on silica gel (0-10% DCM/MeOH) to afford title compound as white solid (173 mg, 71%). ¹HNMR (400 MHz, DMSO-d6) δ=8.31 (s, 1H), 7.85 (br s, 2H), 6.38-6.32 (m, 1H), 5.59 (dd, J=5.4, 7.0 Hz, 1H), 4.43 (d, J=11.7 Hz, 1H), 4.25 (d, J=11.7 Hz, 1H), 4.19-4.11 (m, 2H), 3.79 (s, 1H), 3.25-3.13 (m, 1H), 2.77-2.61 (m, 1H), 2.38-2.12 (m, 2H), 1.71-1.57 (m, 2H), 1.51-1.41 (m, 2H), 1.39-1.13 (m, 18H), 0.92-0.81 (m, 6H); LCMS (M+1)=576.4.

Example 45: ((2R,3S,5R)-2-ethynyl-5-(2-fluoro-6-tetradecanamido-9H-purin-9-yl)-3-hydroxytetrahydrofuran-2-yl)methyl Benzoate Step 1: ((2R,3S,5R)-5-(6-amino-2-fluoro-9H-purin-9-yl)-3-((tert-butyldimethylsilyl)oxy)-2-ethynyltetrahydrofuran-2-yl)methyl benzoate. A suspension of ((2R,3S,5R)-5-(6-amino-2-fluoro-9H-purin-9-yl)-3-((tert-butyldimethylsilyl)oxy)-2-ethynyltetrahydrofuran-2-yl)methanol (920 mg, 2.258 mmol) in DCM (22 mL) was treated with benzoic acid (331 mg, 2.71 mmol), DMAP (276 mg, 2.258 mmol), EDC (779 mg, 4.06 mmol), DIEA (1.971 mL, 11.29 mmol), and stirred at rt for 18 hours. The reaction was diluted with water, extracted with DCM, washed with sat. NaHCO$_3$, brine, dried over Na2SO4, filtered, and concentrated. Purification with column chromatography (0-100% EtOAc/DCM) afforded ((2R,3S,5R)-5-(6-amino-2-fluoro-9H-purin-9-yl)-3-((tert-butyldimethylsilyl)oxy)-2-ethynyltetrahydrofuran-2-yl)methyl benzoate (984.4 mg, 1.924 mmol, 85% yield) as white solid. $^1$HNMR (400 MHz, CHLOROFORM-d) δ ppm 7.97-7.90 (m, 2H), 7.81 (s, 1H), 7.58-7.51 (m, 1H), 7.45-7.34 (m, 2H), 6.25 (dd, J=3.5, 8.0

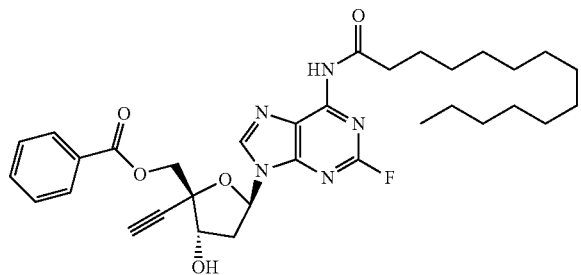 [SMILES: C#C[C@]1(COC(=O)c2ccccc2)O[C@@H](n2cnc3c(NC(=O)CCCCCCCCCCCCC)nc(F)nc32)C[C@@H]1O]

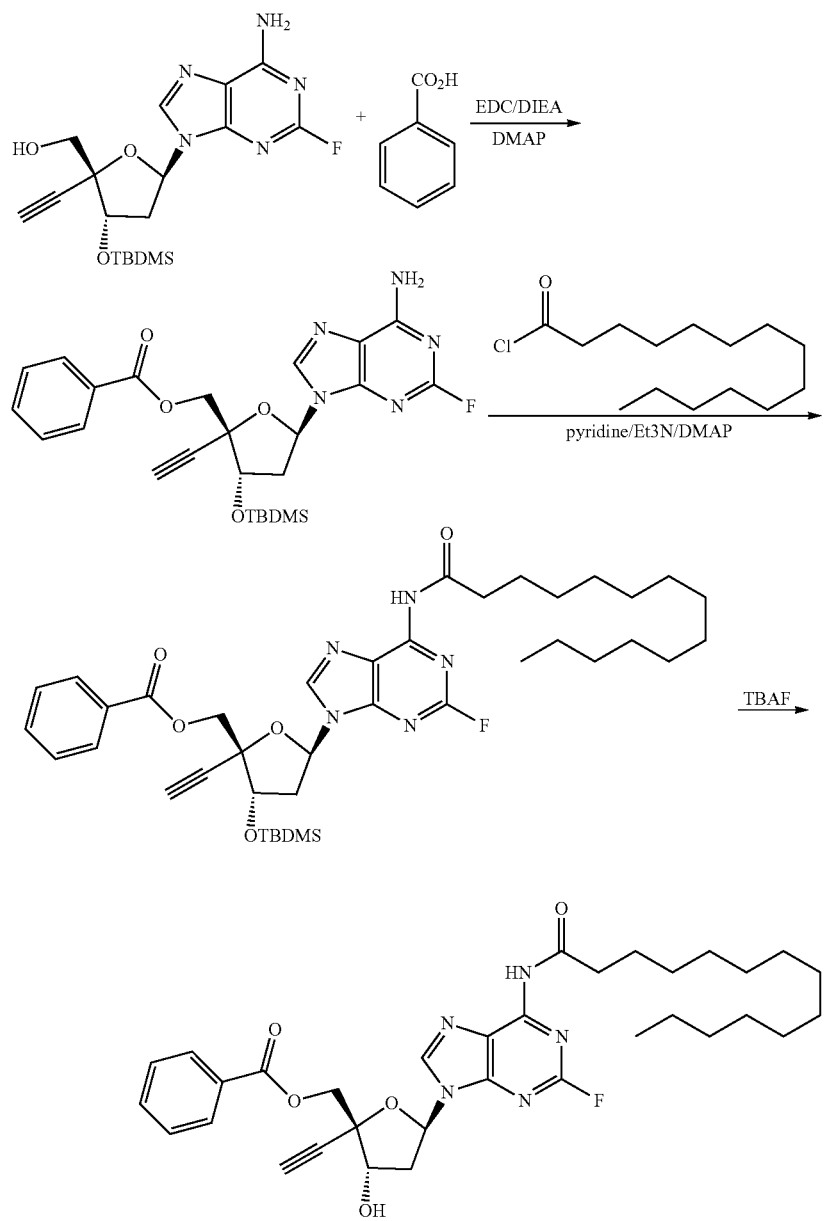

Hz, 1H), 5.66 (br s, 2H), 5.19 (dd, J=7.0, 8.2 Hz, 1H), 4.74 (d, J=12.2 Hz, 1H), 4.44 (d, J=12.2 Hz, 1H), 3.03 (ddd, J=3.3, 7.1, 13.2 Hz, 1H), 2.74-2.62 (m, 2H), 0.96 (s, 9H), 0.18 (s, 6H); LCMS (m/z) ES+=512.2 (M+1), ES−=510.4 (M−1).

Step 2: ((2R,3S,5R)-3-((tert-butyldimethylsilyl)oxy)-2-ethynyl-5-(2-fluoro-6-tetradecanamido-9H-purin-9-yl)tetrahydrofuran-2-yl)methyl benzoate. A solution of ((2R,3S,5R)-5-(6-amino-2-fluoro-9H-purin-9-yl)-3-((tert-butyldimethylsilyl)oxy)-2-ethynyltetrahydrofuran-2-yl) methyl benzoate (475 mg, 0.928 mmol) in DCM (9.2 mL) was treated with Et3N (0.388 mL, 2.79 mmol), pyridine (0.225 mL, 2.79 mmol), tetradecanoyl chloride (0.379 mL, 1.393 mmol), DMAP (11.34 mg, 0.093 mmol), and then stirred at rt for 18 hours. The reaction was diluted with water, extracted with DCM, washed with aq. sat. NaHCO3, brine, dried over Na2SO4, filtered, and concentrated. Purification with column chromatography (0-100% EtOAc/Hexane) afforded ((2R,3S,5R)-3-((tert-butyldimethyl-silyl)oxy)-2-ethynyl-5-(2-fluoro-6-tetradecanamido-9H-purin-9-yl)tetrahydrofuran-2-yl)methyl benzoate (209.8 mg, 0.291 mmol, 31.3% yield) as yellow film. ¹HNMR (400 MHz, CHLOROFORM-d) δ ppm 8.33 (s, 1H), 7.96 (s, 1H), 7.92-7.86 (m, 2H), 7.58-7.49 (m, 1H), 7.44-7.35 (m, 2H), 6.28 (dd, J=3.5, 8.0 Hz, 1H), 5.15 (dd, J=6.9, 8.1 Hz, 1H), 4.77 (d, J=12.2 Hz, 1H), 4.43 (d, J=12.2 Hz, 1H), 3.03 (ddd, J=3.3, 7.0, 13.3 Hz, 1H), 2.93 (t, J=7.5 Hz, 2H), 2.78-2.64 (m, 2H), 1.77 (quin, J=7.5 Hz, 2H), 1.50-1.39 (m, 2H), 1.39-1.19 (m, 18H), 0.97 (s, 9H), 0.92-0.84 (m, 3H), 0.29-0.10 (m, 6H); LCMS (m/z) ES+=722.5 (M+1), ES−=720.6 (M−1).

Step 3: ((2R,3S,5R)-2-ethynyl-5-(2-fluoro-6-tetradecanamido-9H-purin-9-yl)-3-hydroxytetrahydrofuran-2-yl) methyl benzoate. An ice cold solution of ((2R,3S,5R)-3-((tert-butyldimethylsilyl)oxy)-2-ethynyl-5-(2-fluoro-6-tetradecanamido-9H-purin-9-yl)tetrahydrofuran-2-yl) methyl benzoate (285 mg, 0.395 mmol) in THF (8 mL) was treated with TBAF (1M in THF) (0.592 mL, 0.592 mmol), and stirred at 0° C. for 2 hours. The mixture was treated with additional 1M TBAF (150 uL) and stirred at 0° C. for 40 min. The reaction was quenched with AcOH (~0.5 mL), diluted with water, and extracted with EtOAc. The combined organics was washed with brine, dried over Na2SO4, filtered, and concentrated. Purification with column chromatography [0-65% (3:1 EtOAc:EtOH)/Hexane] gave ((2R,3S,5R)-2-ethynyl-5-(2-fluoro-6-tetradecanamido-9H-purin-9-yl)-3-hydroxytetrahydrofuran-2-yl)methyl benzoate (194.4 mg, 0.310 mmol, 79% yield) as off-white solid. ¹HNMR (400 MHz, CHLOROFORM-d) δ ppm 8.39 (s, 1H), 8.02-7.93 (m, 3H), 7.62-7.54 (m, 1H), 7.48-7.39 (m, 2H), 6.37 (dd, J=4.5, 7.6 Hz, 1H), 4.95 (q, J=7.0 Hz, 1H), 4.79-4.61 (m, 2H), 3.08 (ddd, J=4.5, 6.8, 13.7 Hz, 1H), 2.94 (t, J=7.4 Hz, 2H), 2.85 (s, 1H), 2.73 (td, J=7.5, 13.6 Hz, 1H), 2.48 (d, J=6.7 Hz, 1H), 1.76 (quin, J=7.5 Hz, 2H), 1.49-1.39 (m, 2H), 1.38-1.20 (m, 18H), 0.96-0.83 (m, 3H); LCMS (m/z) ES+=608.4 (M+1), ES−=606.4 (M−1).

Example 46: ((2R,3S,5R)-5-(6-decanamido-2-fluoro-9H-purin-9-yl)-2-ethynyl-3-hydroxytetrahydrofuran-2-yl)methyl Benzoate

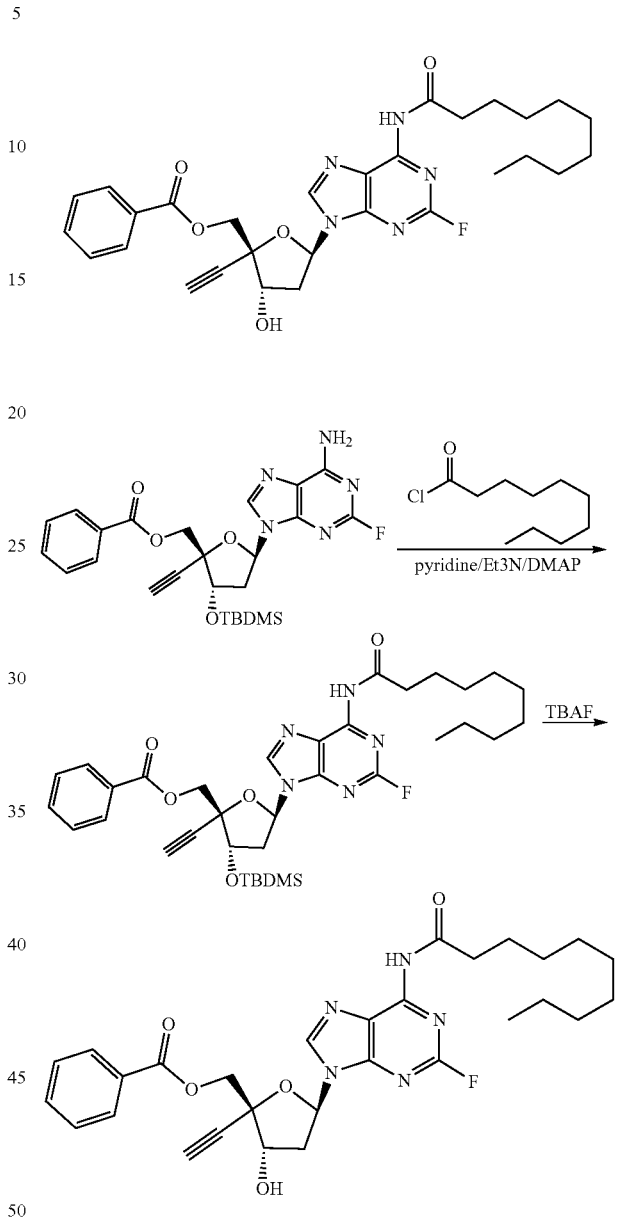

Step 1: ((2R,3S,5R)-3-((tert-butyldimethylsilyl)oxy)-5-(6-decanamido-2-fluoro-9H-purin-9-yl)-2-ethynyltetrahydrofuran-2-yl)methyl benzoate. A solution of ((2R,3S,5R)-5-(6-amino-2-fluoro-9H-purin-9-yl)-3-((tert-butyldimethylsilyl)oxy)-2-ethynyltetrahydrofuran-2-yl) methyl benzoate (470 mg, 0.919 mmol) in DCM (9.2 mL) was treated with Et3N (0.384 mL, 2.76 mmol), pyridine (0.223 mL, 2.76 mmol), decanoyl chloride (0.286 mL, 1.378 mmol), and DMAP (11.22 mg, 0.092 mmol). The reaction was stirred at rt for 18 hours. The reaction was diluted with water, extracted with DCM, washed with aq. sat. NaHCO3, brine, dried over Na2SO4, filtered, and concentrated. Purification with column chromatography (0-100% EtOAc/Hexane) gave ((2R,3S,5R)-3-((tert-butyldimethylsilyl)oxy)-5-(6-decanamido-2-fluoro-9H-purin-9-yl)-2-ethynyltetrahydrofuran-2-yl)methyl benzoate (217.7 mg, 0.327 mmol, 35.6% yield) as yellow film. NMR contained aliphatic impurity. ¹HNMR (400 MHz, CHLOROFORM-d) δ ppm 8.32 (s, 1H), 7.96 (s, 1H), 7.93-7.86 (m, 2H), 7.57-7.49 (m, 1H), 7.44-7.36 (m, 2H), 6.28 (dd, J=3.6, 7.9 Hz, 1H), 5.15 (dd, J=7.0, 8.2 Hz, 1H), 4.77 (d, J=12.2 Hz, 1H), 4.43 (d, J=12.2 Hz, 1H), 3.03 (ddd, J=3.5, 7.0, 13.2 Hz, 1H), 2.97-2.88 (m, 2H), 2.78-2.63 (m, 2H), 1.77 (quin, J=7.5 Hz, 2H), 1.48-1.20 (m, 12H), 0.97 (s, 9H), 0.92-0.84 (m, 3H), 0.21-0.16 (m, 6H); LCMS (m/z) ES⁺=666.5 (M+1), ES⁻=664.6 (M−1).

Step 2: ((2R,3S,5R)-5-(6-decanamido-2-fluoro-9H-purin-9-yl)-2-ethynyl-3-hydroxy-tetrahydrofuran-2-yl)methylbenzoate. An ice cold solution of ((2R,3S,5R)-3-((tert-butyldimethylsilyl)oxy)-5-(6-decanamido-2-fluoro-9H-purin-9-yl)-2-ethynyltetrahydrofuran-2-yl)methyl benzoate (272 mg, 0.408 mmol) in THF (8 mL) was treated with TBAF (1M in THF) (0.613 mL, 0.613 mmol), and stirred at 0° C. for 2 hours. The mixture was treated with additional 1M TBAF (100 uL) and stirred at 0° C. for 40 min. The reaction was quenched with AcOH (~0.5 mL), diluted with water, and extracted with EtOAc. The combined organics was washed with brine, dried over Na2SO4, filtered, and concentrated. Purification with column chromatography [0-65% (3:1 EtOAc:EtOH)/Hexane] gave ((2R,3S,5R)-5-(6-decanamido-2-fluoro-9H-purin-9-yl)-2-ethynyl-3-hydroxytetrahydrofuran-2-yl)methyl benzoate (164.1 mg, 0.292 mmol, 71.4% yield) as light yellow solid. ¹HNMR (400 MHz, CHLOROFORM-d) δ ppm 8.35 (s, 1H), 8.04-7.93 (m, 3H), 7.62-7.54 (m, 1H), 7.47-7.37 (m, 2H), 6.37 (dd, J=4.5, 7.6 Hz, 1H), 4.95 (q, J=7.1 Hz, 1H), 4.78-4.62 (m, 2H), 3.08 (ddd, J=4.5, 6.9, 13.6 Hz, 1H), 2.94 (t, J=7.4 Hz, 2H), 2.85 (s, 1H), 2.73 (td, J=7.4, 13.6 Hz, 1H), 2.45 (d, J=6.9 Hz, 1H), 1.77 (quin, J=7.5 Hz, 2H), 1.47-1.38 (m, 2H), 1.38-1.20 (m, 10H), 0.94-0.85 (m, 3H); LCMS (m/z) ES⁻=550.4 (M−1).

Example 47: ((2R,3S,5R)-2-ethynyl-5-(2-fluoro-6-tetradecanamido-9H-purin-9-yl)-3-hydroxytetrahydrofuran-2-yl)methyl Heptanoate

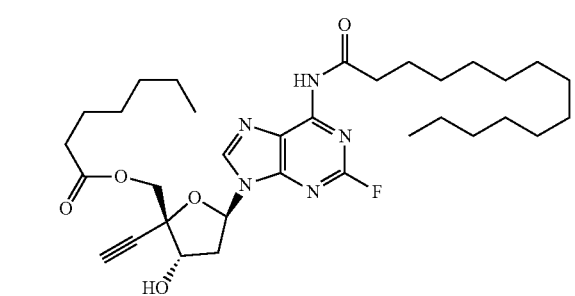 [SMILES: C#C[C@]1(COC(=O)CCCCCC)O[C@@H](n2cnc3c(NC(=O)CCCCCCCCCCCCC)nc(F)nc32)C[C@@H]1O]

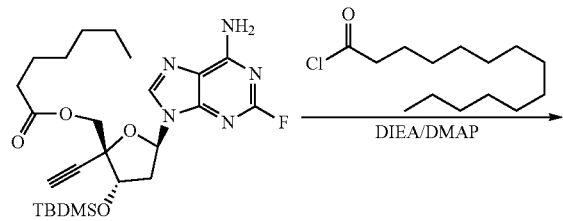

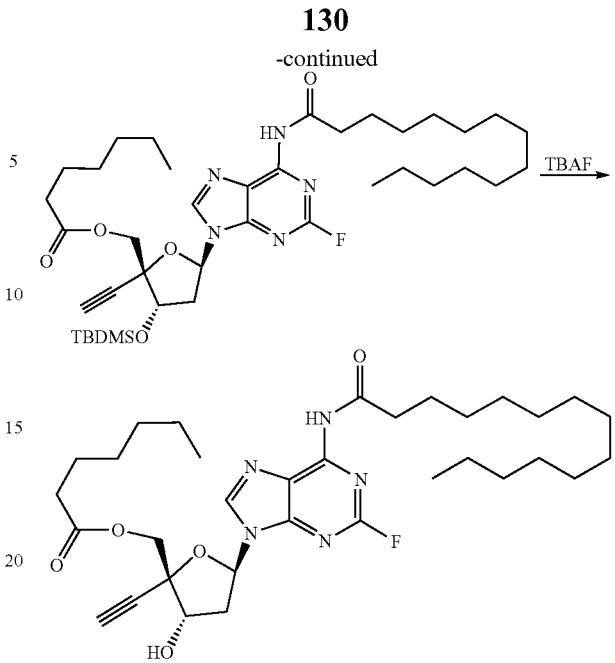

Step 1: ((2R,3S,5R)-3-((tert-butyldimethylsilyl)oxy)-2-ethynyl-5-(2-fluoro-6-tetradecanamido-9H-purin-9-yl)tetrahydrofuran-2-yl)methyl heptanoate. To a solution of ((2R,3S,5R)-5-(6-amino-2-fluoro-9H-purin-9-yl)-3-((tert-butyldimethylsilyl)oxy)-2-ethynyltetrahydrofuran-2-yl) methyl heptanoate (280 mg, 0.539 mmol) and DIEA (0.565 mL, 3.23 mmol) in DCM (7 mL) was added DMAP (32.9 mg, 0.269 mmol) followed by dropwise addition of a solution of tetradecanoyl chloride (266 mg, 1.078 mmol) in dichloromethane (0.5 mL). After 2.5 h more tetradecanoyl chloride (0.09 mL) was added. After 2 h saturated NaHCO₃/water was added and the organic phases were dried (Na2SO4), concentrated, and purified on silica gel (Biotage Isolera 1, 12 g column, 0-100% EtOAc/hexanes 0-100%) to provide ((2R,3S,5R)-3-((tert-butyldimethylsilyl)oxy)-2-ethynyl-5-(2-fluoro-6-tetradecanamido-9H-purin-9-yl)tetrahydrofuran-2-yl)methyl heptanoate (153 mg, 0.207 mmol, 38.5% yield) as a yellowish oil which was in the next step.

Step 2: ((2R,3S,5R)-2-ethynyl-5-(2-fluoro-6-tetradecanamido-9H-purin-9-yl)-3-hydroxytetrahydrofuran-2-yl) methyl heptanoate. To a solution of ((2R,3S,5R)-3-((tert-butyldimethylsilyl)oxy)-2-ethynyl-5-(2-fluoro-6-tetradecanamido-9H-purin-9-yl)tetra-hydrofuran-2-yl) methyl heptanoate (150 mg, 0.205 mmol) in THF (2 mL) at 0° C. was added TBAF (0.226 mL, 0.226 mmol) (1 M/THF) and the mixture was stirred at 0° C. for 3 h (10° C. final bath temperature). acetic acid (0.013 mL, 0.226 mmol) was added and the mixture was concentrated. The residue was purified on silica gel (Biotage Isolera 1, 4 g column, EtOAc/hexanes 0-100%, product eluted at 90-100%) to provide ((2R,3S,5R)-2-ethynyl-5-(2-fluoro-6-tetradecanamido-9H-purin-9-yl)-3-hydroxytetrahydrofuran-2-yl)methyl heptanoate (109.7 mg, 0.176 mmol, 86% yield) as an off-white solid (by dissolving in a small amount of MeOH, adding 2 drops of water and slow evaporation in open container, dried in vacuo). ¹HNMR (400 MHz, CHLOROFORM-d) δ ppm 8.51-8.64 (m, 1H), 8.06 (s, 1H), 6.38 (br dd, J=6.91, 4.77 Hz, 1H), 4.78 (br d, J=6.68 Hz, 1H), 4.47 (s, 2H), 2.91-3.11 (m, 4H), 2.82 (s, 1H), 2.62-2.78 (m, 1H), 2.49 (br d, J=6.44 Hz, 1H), 2.26-2.43 (m, 2H), 1.71-1.92 (m, 3H), 1.14-1.54 (m, 26H), 0.82-1.02 (m, 6H). LCMS (M+1)=617.5.

Example 48: ((2R,3S,5R)-2-ethynyl-5-(2-fluoro-6-tetradecanamido-9H-purin-9-yl)-3-hydroxytetrahydrofuran-2-yl)methyl Decanoate
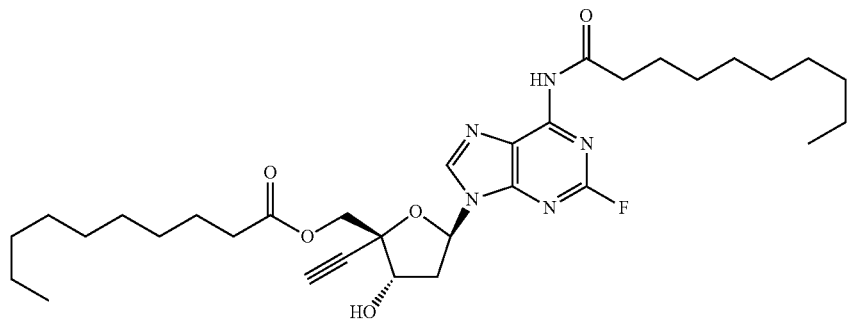 [SMILES: C#C[C@]1(COC(=O)CCCCCCCCC)O[C@@H](n2cnc3c(NC(=O)CCCCCCCCC)nc(F)nc32)C[C@@H]1O]
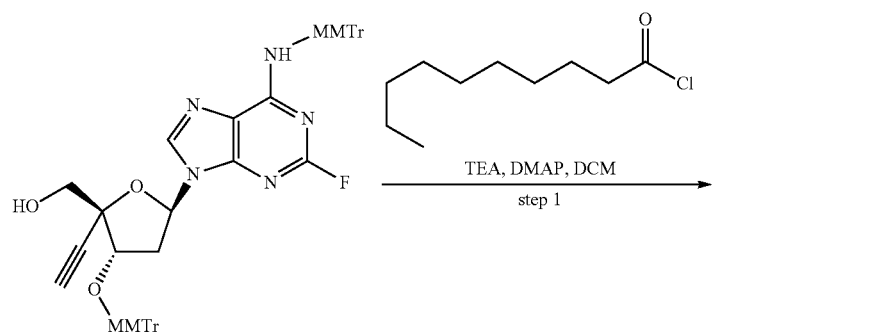
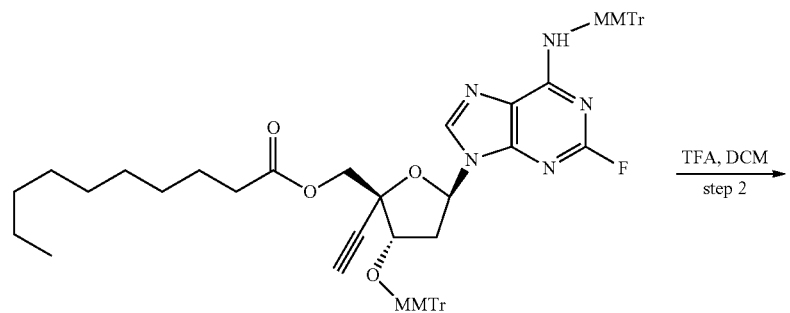
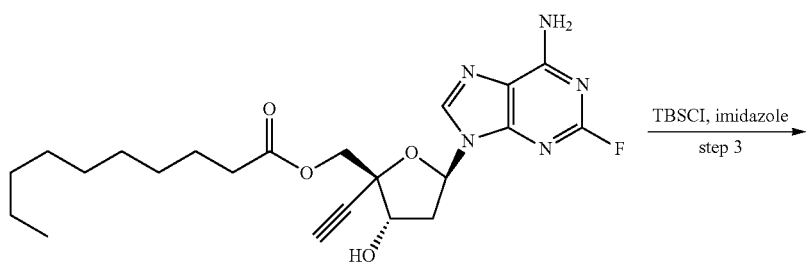

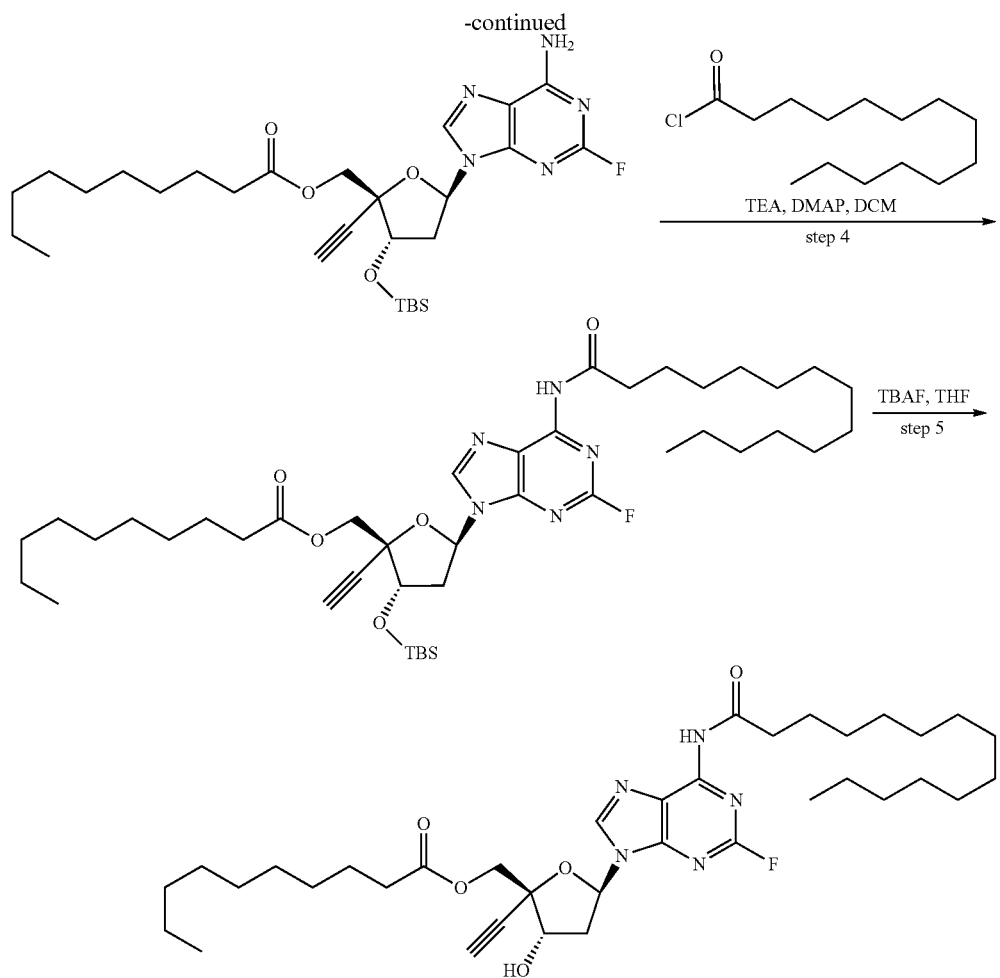

Step 1: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methyl decanoate. To a mixture of ((2R,3S,5R)-2-ethynyl-5-(2-fluoro-6-(((4-methoxyphenyl) diphenylmethyl) amino)-9H-purin-9-yl)-3-((4-methoxyphenyl)diphenyl-methoxy)tetra-hydrofuran-2-yl)methanol (3 g, 3.58 mmol), Et3N (2.495 mL, 17.90 mmol) and DMAP (0.656 g, 5.37 mmol) in DCM (40 mL) was added Et3N (2.495 mL, 17.90 mmol). The reaction mixture was stirred at r.t. for 2 h. LCMS indicated completion of reaction. The reaction mixture was quenched with water (50 mL), extracted with DCM (30 mL*3), the organic phases were combined, washed with brine (30 mL), dried over Na2SO4, concentrated under vacuum. The residue was purified by flash chromatography (silica gel, 120 g, pet. ether:EtOAc=4:1) to give ((2R,3S, 5R)-2-ethynyl-5-(2-fluoro-6-(((4-methoxyphenyl)diphenyl-methyl)amino)-9H-purin-9-yl)-3-((4-methoxyphenyl)diphenyl-methoxy)tetrahydrofuran-2-yl)methyl decanoate (2.7 g, 1.788 mmol, 49.9% yield)) as a yellow solid. LCMS (ESI) m/z calcd for $C_{62}H_{62}FN_5O_6$:991 Found: 992 (M+H)$^+$. $^1$HNMR (400 MHz, CDCl3) δ 8.21 (s, 1H), 7.57-7.50 (m, 4H), 7.40-7.18 (m, 20H), 7.04 (s, 1H), 6.81-6.75 (m, 4H), 6.08 (dd, J=3.2, 8.0 Hz, 1H), 4.31 (d, J=12.0 Hz, 1H), 4.05 (d, J=12.0 Hz, 1H), 3.78-3.72 (m, 6H), 3.00-2.91 (m, 1H), 2.45-2.01 (m, 4H), 1.67-1.59 (m, 2H), 1.33-1.18 (m, 12H), 0.87 (t, J=7.2 Hz, 3H).

Step 2: ((2R,3S,5R)-5-(6-amino-2-fluoro-9H-purin-9-yl)-2-ethynyl-3-hydroxytetrahydro-furan-2-yl)methyl decanoate. To a solution ((2R,3S,5R)-2-ethynyl-5-(2-fluoro-6-(((4-methoxyphenyl)diphenylmethyl)amino)-9H-purin-9-yl)-3-((4-methoxyphenyl)diphenyl-methoxy) tetrahydrofuran-2-yl)methyl decanoate (2.7 g, 2.72 mmol) in DCM (30 mL) stirred at 15° C. was added TFA (5 mL, 64.9 mmol) dropwise. The reaction mixture was stirred at 15° C. for 1 h. LCMS indicated completion of reaction. The reaction mixture was quenched with NaHCO$_3$ (30 ml), and extracted with DCM (30 ml×2), the organic phases were combined, washed with brine (15 ml), dried over Na2SO4, concentrated under vacuum. The residue was purified by flash chromatography (silica gel, 120 g, DCM:MeOH=10:1) to give ((2R,3S,5R)-5-(6-amino-2-fluoro-9H-purin-9-yl)-2-ethynyl-3-hydroxytetrahydro-furan-2-yl)methyl decanoate (1 g, 2.201 mmol, 81% yield) as a white solid. LCMS (ESI) m/z calcd for $C_{22}H_{30}FN_5O_4$: 447 Found: 448 (M+H)$^+$. $^1$HNMR (400 MHz, CDCl3) δ 7.88 (s, 1H), 6.31 (dd, J=4.4, 7.6 Hz, 1H), 6.10 (br, s, 2H), 4.79 (t, J=7.2 Hz, 1H), 4.50-4.40 (m, 2H), 2.99-2.92 (m, 1H), 2.81-2.60 (m, 2H), 2.38-2.30 (m, 2H), 1.65-1.51 (m, 2H), 1.34-1.14 (m, 12H), 0.91-0.75 (m, 3H).

Step 3: ((2R,3S,5R)-5-(6-amino-2-fluoro-9H-purin-9-yl)-3-((tert-butyldimethylsilyl)oxy)-2-ethynyltetrahydrofuran-2-yl)methyl decanoate. To a solution of ((2R,3S,5R)-5-(6-amino-2-fluoro-9H-purin-9-yl)-2-ethynyl-3-hydroxytetrahydrofuran-2-yl)methyl decanoate (1 g, 2.235 mmol) in DCM (60 mL) was added imidazole (1.521 g, 22.35 mmol) and tert-butylchlorodimethylsilane (1.347 g, 8.94 mmol), and the resulting mixture was stirred at 30° C. for overnight. LCMS indicated completion of reaction. The reaction mixture was quenched with water (50 mL), extracted with DCM (20 mL*3), the organic phases were combined, washed with brine (50 mL), dried over Na2SO4, concentrated under vacuum. The residue was purified by gel silica column (120 g, EtOAc:pet. Ether=1:1) to give ((2R,3S,5R)-5-(6-amino-2-fluoro-9H-purin-9-yl)-3-((tert-butyldimethylsilyl)oxy)-2-ethynyltetrahydrofuran-2-yl) methyl decanoate (1.2 g, 98.09%, yield: 94%) as a white solid. LCMS (ESI) m/z calcd for $C_{28}H_{44}FN_5O_4Si$:561. Found: 562 (M+H)+. 1HNMR (400 MHz, CDCl3) δ 7.86 (s, 1H), 6.25 (dd, J=4.0, 8.0 Hz, 1H), 5.94 (br, s, 2H), 4.93 (t, J=7.6 Hz, 1H), 4.45 (d, J=12.0 Hz, 1H), 4.23 (d, J=12.0 Hz, 1H), 2.89-2.82 (m, 1H), 2.68-2.58 (m, 2H), 2.30-2.19 (m, 2H), 1.61-1.50 (m, 2H), 1.33-1.17 (m, 12H), 0.93 (s, 9H), 0.87 (t, J=7.2 Hz, 3H), 0.13 (d, J=4.8 Hz, 6H).

Step 4: ((2R,3S,5R)-3-((tert-butyldimethylsilyl)oxy)-2-ethynyl-5-(2-fluoro-6-tetradecanamido-9H-purin-9-yl)tetrahydrofuran-2-yl)methyl decanoate. To a solution of ((2R,3S,5R)-5-(6-amino-2-fluoro-9H-purin-9-yl)-3-((tert-butyldimethylsilyl)oxy)-2-ethynyltetrahydrofuran-2-yl) methyl decanoate (1.2 g, 2.136 mmol) in DCM (10 mL) was added DMAP (0.391 g, 3.20 mmol), Et3N (1.191 mL, 8.54 mmol) and tetradecanoyl chloride (1.318 g, 5.34 mmol). The reaction mixture was stirred at r.t. for 4 h. LCMS indicated completion of reaction. The reaction mixture was quenched with water (10 mL) and extracted with DCM (10 mL×3), the organic phases were combined, washed with brine (10 mL), dried over Na2SO4, concentrated under vacuum. The residue was purified by gel silica column (80 g, EtOAc:pet. ether=4:1) to give ((2R,3S,5R)-3-((tert-butyldimethylsilyl)oxy)-2-ethynyl-5-(2-fluoro-6-tetradecanamido-9H-purin-9-yl)tetrahydro-furan-2-yl)methyl decanoate (700 mg, 85%, 19.52% yield) as a white semisolid. LCMS (ESI) m/z calcd for $C_{42}H_{70}FN_5O_5Si$:771. Found: 772 (M+H)+. 1HNMR (400 MHz, CDCl3) δ 8.88 (s, 1H), 8.08 (d, J=1.2 Hz, 1H), 6.30 (dd, J=3.6, 7.6 Hz, 1H), 4.89 (t, J=7.2 Hz, 1H), 4.44 (d, J=12.0 Hz, 1H), 4.24 (d, J=12.0 Hz, 1H), 2.96-2.80 (m, 3H), 2.71-2.60 (m, 2H), 2.28-2.22 (m, 2H), 1.80-1.68 (m, 2H), 1.60-1.50 (m, 2H), 1.37-1.17 (m, 32H), 0.93 (s, 9H), 0.90-0.81 (m, 6H), 0.13 (d, J=5.2 Hz, 6H).

Step 5: ((2R,3S,5R)-2-ethynyl-5-(2-fluoro-6-tetradecanamido-9H-purin-9-yl)-3-hydroxytetrahydrofuran-2-yl)methyl decanoate. To a stirred solution of ((2R,3S,5R)-3-((tert-butyldimethylsilyl)oxy)-2-ethynyl-5-(2-fluoro-6-tetradecanamido-9H-purin-9-yl)tetrahydrofuran-2-yl) methyl decanoate (700 mg, 0.907 mmol) in THF (5 mL) was added TBAF (1.08 ml, 1 mol/L in THF). The resulting mixture was stirred for 2 hour at room temperature. LCMS indicated completion of reaction. The majority of solvent was removed under vacuum. The residue was purified by gel silica column (80 g, EtOAc:pet. ether=4:1) to give the desired product (purity:96%) as a white solid. The solid was triturated with ACN (30 ml) for 16 h. The resulting solid was filtered through a Buchner funnel, rinsed with ACN, dried beside sunlight lamp (T=50° C.) for 6 h, and was stored in a cool dry place overnight to give ((2R,3S,5R)-2-ethynyl-5-(2-fluoro-6-tetradecanamido-9H-purin-9-yl)-3-hydroxytetrahydrofuran-2-yl)methyl decanoate (151 mg, 99.05%, yield: 25.08%) as a white solid. LCMS (ESI) m/z calcd for $C_{36}H_{56}FN_5O_5$:657. Found: 658 (M+1)+. 1HNMR (400 MHz, CDCl3) δ 8.66 (s, 1H), 8.06 (s, 1H), 6.36 (dd, J=4.4, 7.6 Hz, 1H), 4.77 (t, J=6.4 Hz, 1H), 4.49-4.41 (m, 2H), 2.98-2.81 (m, 3H), 2.74 (s, 1H), 2.72-2.68 (m, 1H), 2.36-2.32 (m, 2H), 1.79-1.56 (m, 6H), 1.44-1.20 (m, 30H), 0.89-0.85 (m, 6H).

Example 49: ((2R,3S,5R)-2-ethynyl-5-(2-fluoro-6-tetradecanamido-9H-purin-9-yl)-3-hydroxytetrahydrofuran-2-yl)methyl 2-propylpentanoate

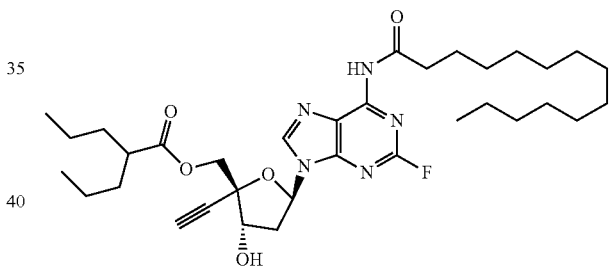

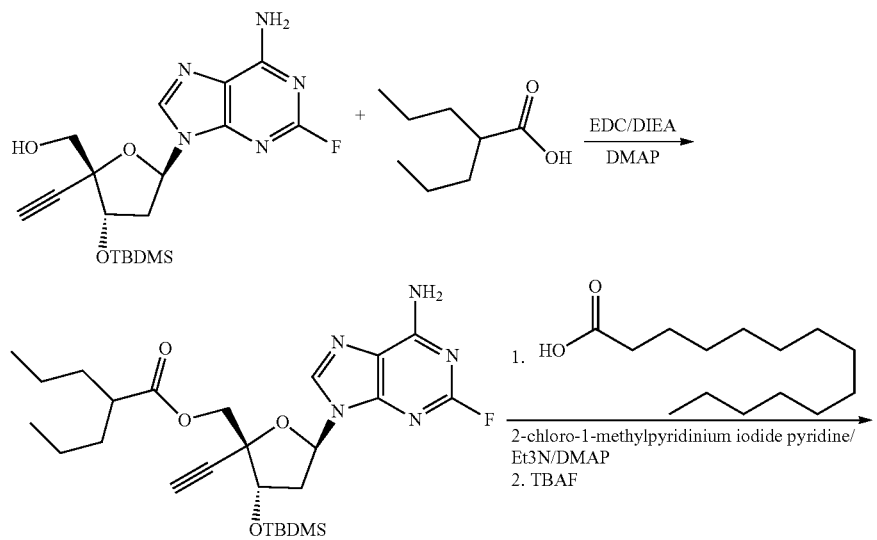

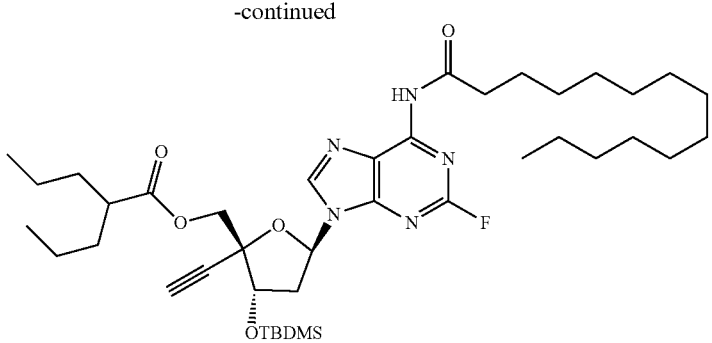

Step 1: ((2R,3S,5R)-5-(6-amino-2-fluoro-9H-purin-9-yl)-3-((tert-butyldimethylsilyl)oxy)-2-ethynyltetrahydrofuran-2-yl)methyl 2-propylpentanoate. To a stirred solution of ((2R,3S,5R)-5-(6-amino-2-fluoro-9H-purin-9-yl)-3-((tert-butyldimethylsilyl)oxy)-2-ethynyltetrahydrofuran-2-yl)methanol (200 mg, 0.491 mmol), EDC (141 mg, 0.736 mmol), and DMAP (60.0 mg, 0.491 mmol)) in DCM (6 mL) was added 2-propylpentanoic acid (0.079 mL, 0.491 mmol) followed by DIEA (0.214 mL, 1.227 mmol) and the mixture was stirred at r.t. for 1 h. The reaction mixture was concentrated and purified by Isco, 40 gram gold column (DCM/MeOH 0-10%) to give the desired product as a white solid (238 mg, 85%). LCMS (M+1)=535.3.

Step 2: ((2R,3S,5R)-2-ethynyl-5-(2-fluoro-6-tetradecanamido-9H-purin-9-yl)-3-hydroxytetrahydrofuran-2-yl)methyl 2-propylpentanoate. To a solution of ((2R,3S,5R)-5-(6-amino-2-fluoro-9H-purin-9-yl)-3-((tert-butyldimethylsilyl)oxy)-2-ethynyltetrahydrofuran-2-yl)methyl 2-propylpentanoate (238 mg, 0.446 mmol), DMAP (5.45 mg, 0.045 mmol) and 2-chloro-1-methylpyridinium iodide (285 mg, 1.115 mmol) in acetonitrile (6.0 mL) and THF (6.0 mL) was added tetradecanoic acid (255 mg, 1.115 mmol) followed by Et3N (0.373 mL, 2.68 mmol) and the mixture was stirred at 60° C. in a sealed tube overnight. The mixture was diluted with DCM and washed with sat. aq. NaHCO₃, the organic layer dried over sodium sulfate and concentrated. Purification by prep. TLC (Hexanes/EtOAc 1:1) afforded the desired product as a solid. ¹HNMR (400 MHz, CHLOROFORM-d) δ ppm 0.16 (s, 3H) 0.17 (s, 3H) 0.80-0.92 (m, 9H) 0.96 (s, 9H) 1.17-1.47 (m, 24H) 1.48-1.56 (m, 2H) 1.62-1.71 (m, 2H) 1.71-1.81 (m, 2H) 2.32 (ddd, J=8.70, 5.36, 3.34 Hz, 1H) 2.35-2.46 (m, 1H) 2.63 (s, 1H) 2.70 (dt, J=13.41, 7.72 Hz, 1H) 2.85-2.95 (m, 2H) 4.26 (d, J=12.16 Hz, 1H) 4.44 (d, J=12.16 Hz, 1H) 4.89 (t, J=7.27 Hz, 1H) 6.34 (dd, J=7.63, 3.81 Hz, 1H) 8.13 (s, 1H) 9.38 (br s, 1H).

To a solution of above solid in THF (5.00 mL) and added TBAF (1M, THF) (0.491 mL, 0.491 mmol) at 0° C. and the mixture was stirred at 0° C. for 1 h and then added acetic acid (0.028 mL, 0.491 mmol) at 0° C., allowed to warm to r.t and concentrated. Purification by Isco, 40 gram gold column (DCM/MeOH 0-5%) afforded the desired product as a solid (98 mg, 34%). ¹HNMR (400 MHz, CHLOROFORM-d) δ ppm 0.82-0.92 (m, 9H) 1.22-1.48 (m, 26H) 1.51-1.66 (m, 2H) 1.74-1.90 (m, 2H) 2.36-2.48 (m, 1H) 2.73 (dt, J=13.71, 6.97 Hz, 1H) 2.82 (s, 1H) 2.92-3.05 (m, 3H) 4.41-4.49 (m, 2H) 4.76 (t, J=6.68 Hz, 1H) 6.41 (dd, J=7.15, 4.77 Hz, 1H) 8.12 (s, 1H) 8.82 (s, 1H). LCMS (M+1)=630.5. LCMS (M−1)=628.5.

Example 50: ((2R,3S,5R)-5-(6-amino-2-fluoro-9H-purin-9-yl)-2-ethynyl-3-hydroxytetrahydrofuran-2-yl)methyl 3-(2-acetoxy-4,6-dimethylphenyl)-3-methylbutanoate

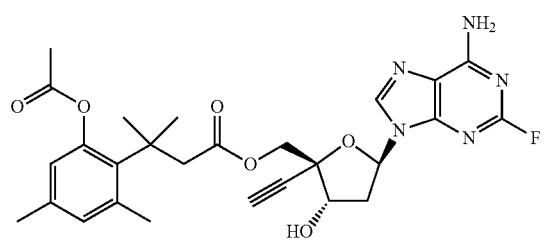 [SMILES: C#C[C@]1(COC(=O)CC(C)(C)c2c(C)cc(C)cc2OC(C)=O)O[C@@H](n2cnc3c(N)nc(F)nc32)C[C@@H]1O]

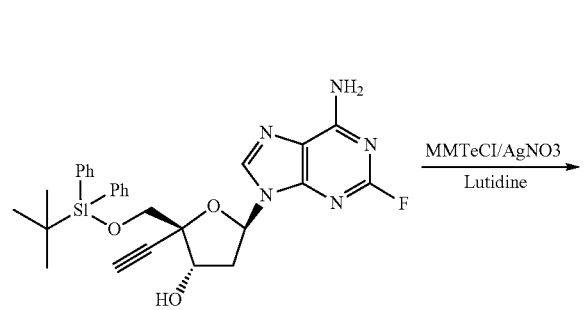

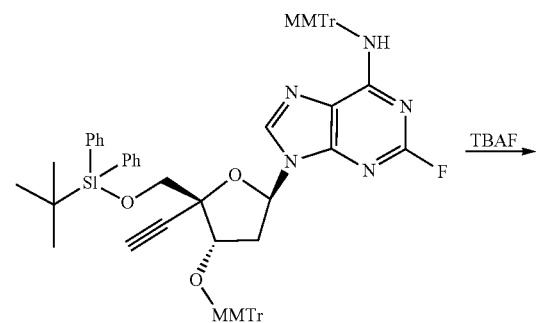

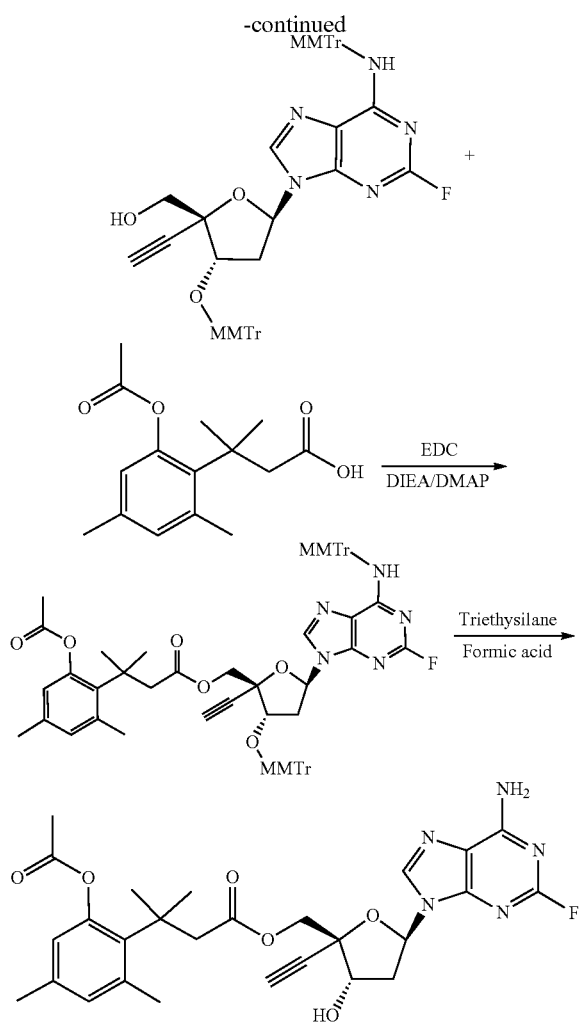

Step 1: 9-((2R,4S,5R)-5-((((tert-butyldiphenylsilyl)oxy)methyl)-5-ethynyl-4-((4-methoxyphen-yl)diphenylmethoxy)tetrahydrofuran-2-yl)-2-fluoro-N-((4-methoxyphenyl)diphenylmethyl)-9H-purin-6-amine. To a stirred suspension of (2R,3S,5R)-5-(6-amino-2-fluoro-9H-purin-9-yl)-2-(((tert-butyldiphenylsilyl)oxy)methyl)-2-ethynyltetrahydrofuran-3-ol (2.66 g, 5.00 mmol) in DCM (60 mL) was added silver nitrate (2.55 g, 15.01 mmol), 2,4,6-trimethylpyridine (4.00 mL, 30.0 mmol) and 4-methoxytriphenylmethyl chloride (4.63 g, 15.01 mmol). The resulting suspension was stirred at ambient temperature for 2 hours. The mixture was diluted with EtOAc and filtered over Celite. The filtrate was washed with 10% citric acid (2×), followed by sat'd NaHCO$_3$ (2×), dried over Na2SO4, filtered and concentrated. The residue was purified on silica gel (120 g column, 0-100% hexanes/EtOAc) to afford title compound as white solid (5.138 g, 95%). LCMS (M+1)=1076.57.

Step 2: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methanol. To stirred solution of 9-((2R,4S,5R)-5-((((tert-butyldiphenylsilyl)oxy)methyl)-5-ethynyl-4-((4-methoxyphen-yl)diphenylmethoxy)tetrahydrofuran-2-yl)-2-fluoro-N-((4-methoxyphenyl) diphenylmethyl)-9H-purin-6-amine (5.138 g, 4.77 mmol) in THF (45 mL) was added 1M TBAF/THF (7.16 mL, 7.16 mmol) and the mixture was allowed to stir at ambient temperature for 90 minutes. The mixture was concentrated and the residue was purified on silica gel (120 g column, 0-100% hexanes/EtOAc) to afford title compound as white solid (3.908 g, 98%). LCMS (M+1)=838.42.

Step 3: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methyl 3-(2-acetoxy-4,6-dimethylphenyl)-3-methylbutanoate. To a mixture of ((2R,3S,5R)-2-ethynyl-5-(2-fluoro-6-(((4-methoxyphenyl)diphenylmethyl)amino)-9H-purin-9-yl)-3-((4-methoxy-phenyl)diphenylmethoxy)tetrahydrofuran-2-yl)methanol (315 mg, 0.376 mmol), 3-(2-acetoxy-4,6-dimethylphenyl)-3-methylbutanoic acid (119 mg, 0.451 mmol), DMAP (45.9 mg, 0.376 mmol) and DIEA (0.328 mL, 1.880 mmol) was added EDC (144 mg, 0.752 mmol) at ambient temperature and the mixture was allowed to stir overnight. The mixture was concentrated and then purified on silica gel (24 g column, 0-70% hexanes/EtOAc) to afford title compound as colorless residue (366 mg, 90%). LCMS (M+1)=1084.61; LCMS (M−1)=1083.79.

Step 4: ((2R,3S,5R)-5-(6-amino-2-fluoro-9H-purin-9-yl)-2-ethynyl-3-hydroxytetrahydro-furan-2-yl)methyl 3-(2-acetoxy-4,6-dimethylphenyl)-3-methylbutanoate. A solution of ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methyl 3-(2-acetoxy-4,6-dimethylphenyl)-3-methylbutanoate (366 mg, 0.338 mmol) in DCM (1.6 mL) was treated with formic Acid (0.4 mL) and triethylsilane (0.108 mL, 0.675 mmol) and then stirred at ambient temperature for 3 hours. The mixture was concentrated and then purified on silica gel (40 g column, 0-10% DCM/MeOH) to afford title compound as white solid (118 mg, 65%). $^1$HNMR (400 MHz, DMSO-d6) δ=8.25 (s, 1H), 7.82 (br s, 2H), 6.77-6.71 (m, 1H), 6.56-6.53 (m, 1H), 6.24 (dd, J=4.3, 7.9 Hz, 1H), 5.71 (d, J=5.5 Hz, 1H), 4.66-4.59 (m, 1H), 4.27 (d, J=11.7 Hz, 1H), 4.00 (d, J=11.9 Hz, 1H), 3.59 (s, 1H), 2.84-2.71 (m, 2H), 2.61 (d, J=16.0 Hz, 1H), 2.53-2.43 (m, 1H, overlapping DMSO peak), 2.41 (s, 3H), 2.18 (s, 3H), 2.14 (s, 3H), 1.40 (s, 3H), 1.35 (s, 3H). LCMS (M+1)=540.31.

Example 51: (2R,3S,5R)-5-(6-amino-2-fluoro-9H-purin-9-yl)-2-ethynyl-2-((heptanoyloxy)methyl)tetrahydrofuran-3-yl Tetradecanoate

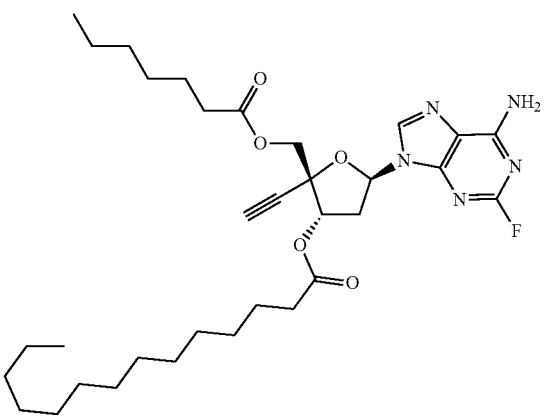 [SMILES: C#C[C@]1(COC(=O)CCCCCC)O[C@@H](n2cnc3c(N)nc(F)nc32)C[C@@H]1OC(=O)CCCCCCCCCCCCC]

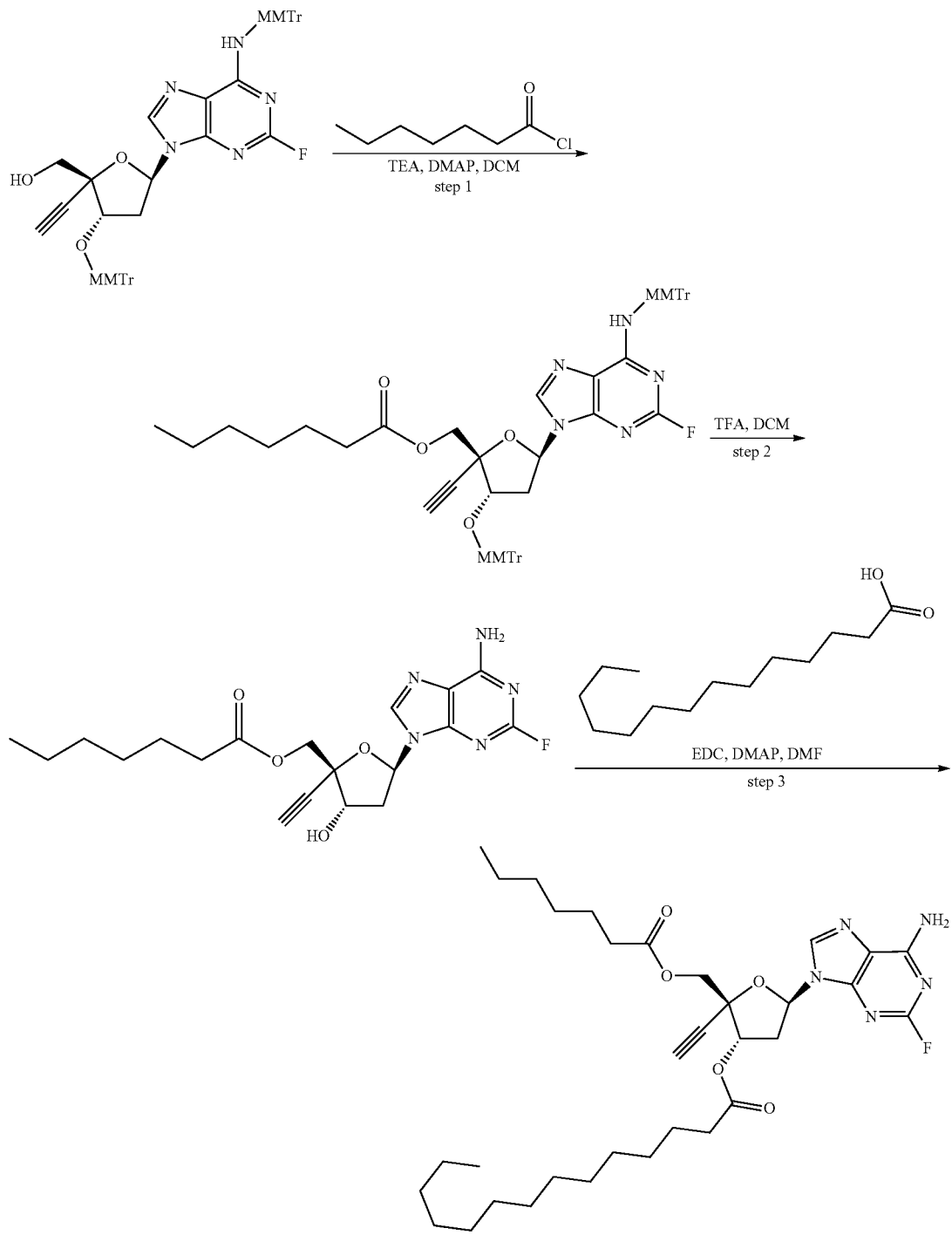

Step 1: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl) methyl heptanoate. To a mixture of ((2R,3S,5R)-2-ethynyl-5-(2-fluoro-6-(((4-methoxyphenyl) diphenylmethyl)amino)-9H-purin-9-yl)-3-((4-methoxyphenyl)diphenylmethoxy) tetrahydro-furan-2-yl)methanol (420 mg, 0.50 mmol) in DCM (10 mL) was added DMAP (61.2 mg, 0.50 mmol), Et3N (0.28 mL, 2.00 mmol) and heptanoyl chloride (149 mg, 1.00 mmol). The reaction mixture was stirred for 16 hours. LCMS indicated completion of reaction. The reaction mixture was diluted with water (10 mL), extracted with DCM (10 mL×3). The combined organic phases were washed with water (20 mL), brine (10 mL) and dried over $Na_2SO_4$. After filtration, the filtrate was concentrated to dryness under vacuum. The residue was purified by silica gel column (120 g, pet. ether:EtOAc=1:1) to afford ((2R,3S,5R)-2-ethynyl-5-(2-fluoro-6-(((4-methoxyphenyl)diphenyl-methyl)amino)-9H-purin-9-yl)-3-((4-methoxyphenyl)diphenylmethoxy)tetrahydrofuran-2-yl)methyl heptanoate (300 mg, 63% yield) as a pale-yellow solid. LCMS (ESI) m/z calcd for $C_{59}H_{56}FN_5O_6$:949. Found: 950 (M+H)$^+$. $^1$HNMR (300 MHz, DMSO-d$_6$) δ 8.06 (s, 1H), 7.96 (s, 1H), 7.53-7.51 (m, 4H), 7.40-7.17 (m, 20H), 6.92-6.78 (m, 4H), 6.13 (dd, J=7.8, 3.9 Hz, 1H), 4.68 (t, J=7.2 Hz, 1H), 4.18 (d, J=12.0 Hz, 1H), 3.97 (s, 1H), 3.79 (d, J=12.0 Hz, 1H), 3.72 (s, 3H), 3.68 (s, 3H), 2.09-2.00 (m, 1H), 1.97-1.79 (m, 3H), 1.37-1.01 (m, 8H), 0.80 (t, J=6.9 Hz, 3H).

Step 2: ((2R,3S,5R)-5-(6-amino-2-fluoro-9H-purin-9-yl)-2-ethynyl-3-hydroxytetrahydrofuran-2-yl)methyl heptanoate. To the mixture of ((2R,3S,5R)-2-ethynyl-5-(2-fluoro-6-(((4-methoxyphenyl)diphenylmethyl) amino)-9H-purin-9-yl)-3-((4-methoxyphenyl)diphenyl-methoxy) tetrahydrofuran-2-yl)methyl heptanoate (300 mg, 0.32 mmol) in DCM (6 mL) was added TFA (1 mL) dropwise at 0° C. The reaction mixture was stirred for 2 h at 0° C. LCMS indicated completion of reaction. The reaction mixture was concentrated to dryness under vacuum. The residue was re-dissolved in DCM (10 mL) and washed with NaHCO$_3$ (aq, 10 mL), brine (10 mL), dried over Na$_2$SO$_4$. After filtration, the filtrate was concentrated to dryness under vacuum to afford ((2R,3S,5R)-5-(6-amino-2-fluoro-9H-purin-9-yl)-2-ethynyl-3-hydroxytetrahydrofuran-2-yl)methyl heptanoate (120 mg, yield: 93%) as a white solid. The crude product was used to next step without further purification. LCMS (ESI) m/z calcd for C19H24FN5O4:405, Found: 406 (M+H)$^+$.

Step 3: (2R,3S,5R)-5-(6-amino-2-fluoro-9H-purin-9-yl)-2-ethynyl-2-((heptanoyloxy)methyl) tetra-hydrofuran-3-yl tetradecanoate. The mixture of tetradecanoic acid (214 mg, 0.94 mmol), EDCI (241 mg, 1.26 mmol) and DMAP (153 mg, 1.25 mmol) in DMF (4 mL) was stirred for 2 h at 25° C. To the above mixture was added ((2R,3S,5R)-5-(6-amino-2-fluoro-9H-purin-9-yl)-2-ethynyl-3-hydroxytetrahydrofuran-2-yl)methyl heptanoate (120 mg, 0.30 mmol). The reaction mixture was stirred at 25° C. for 16 h. LCMS indicated completion of reaction. The reaction mixture was quenched with water (10 mL) and extracted with EtOAc (10 mL×3). The combine organic phases were washed with brine (10 mL) and dried over Na$_2$SO$_4$. After filtration, the solvent was removed under vacuum. The residue was purified by Prep-HPLC:Column: XSelect CSH Prep C18 OBD Column, 5 um, 19×150 mm; Mobile Phase A:water (0.05% TFA), Mobile Phase B:ACN; Flow rate:25 mL/min; Gradient:90 B to 95 B in 8 min; 254 nm; Rt:6.48 min. The collected fraction (RT:6.48 min) was lyophilized to afford (2R,3S,5R)-5-(6-amino-2-fluoro-9H-purin-9-yl)-2-ethynyl-2-((heptanoyloxy)methyl)tetrahydro-furan-3-yl tetradecanoate (93.7 mg, purity:99.66%, yield: 51%) as white solid. LCMS (ESI) m/z calcd for C$_{33}$H$_{50}$FN$_5$O$_5$:615. Found: 616 (M+H)$^+$. $^1$HNMR (300 MHz, DMSO-d$_6$) δ 8.33 (s, 1H), 7.90 (br s, 2H), 6.34 (t, J=6.6 Hz, 1H), 5.70 (t, J=5.4 Hz, 1H), 4.40 (d, J=11.4 Hz, 1H), 4.22 (d, J=11.4 Hz, 1H), 3.79 (s, 1H), 3.17-3.13 (m, 1H), 2.66-2.57 (m, 1H), 2.42-2.37 (m, 2H), 2.32-2.21 (m, 2H), 1.60-1.40 (m, 4H), 1.39-1.22 (m, 26H), 0.89-0.84 (m, 6H).

Example 52: ((2R,3S,5R)-5-(6-amino-2-fluoro-9H-purin-9-yl)-2-ethynyl-3-(((tridecyloxy)carbonyl)oxy) tetrahydrofuran-2-yl)methyl Heptanoate

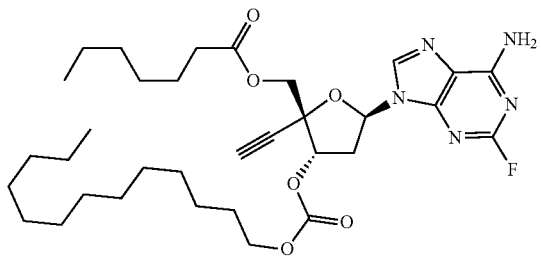 [SMILES: C#C[C@]1(COC(=O)CCCCCC)O[C@@H](n2cnc3c(N)nc(F)nc32)C[C@@H]1OC(=O)OCCCCCCCCCCCCC]

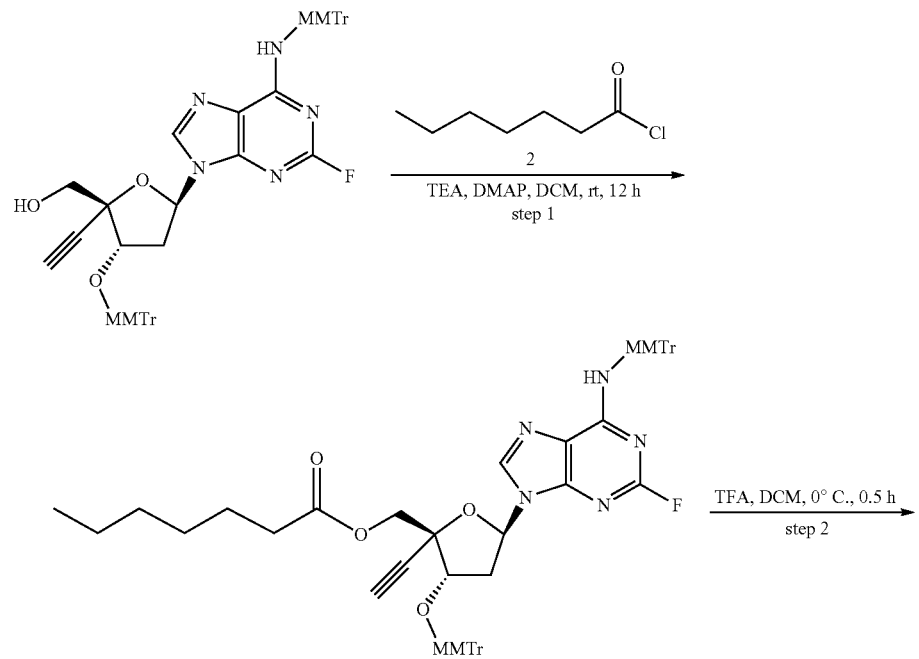

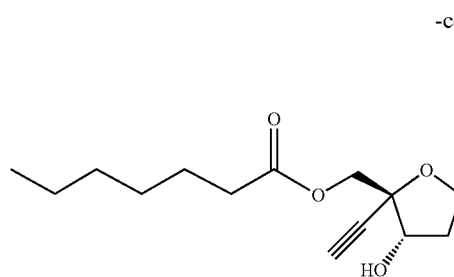

-continued

1) CDI, K₂CO₃, THF
2) 1-tridecanol, CS₂CO₃, THF, rt, 1 h step 3

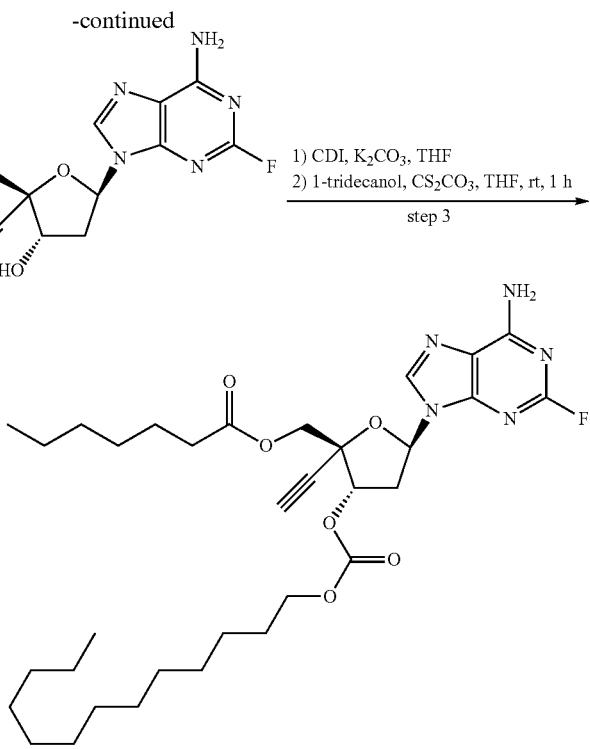

Step 1: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methyl heptanoate. To a mixture of ((2R,3S,5R)-2-ethynyl-5-(2-fluoro-6-(((4-methoxyphenyl) diphenylmethyl)amino)-9H-purin-9-yl)-3-((4-methoxyphenyl)diphenylmethoxy) tetrahydro-furan-2-yl)methanol (1.0 g, 1.19 mmol) in DCM (10 mL) was added DMAP (0.15 g, 1.19 mmol), Et3N (0.67 mL, 4.77 mmol) and heptanoyl chloride (0.355 g, 2.387 mmol). The reaction mixture was stirred for 16 hours. LCMS indicated completion of reaction. The reaction mixture was diluted with water (10 mL), extracted with DCM (10 mL×3). The combined organic phases were washed with water (20 mL), brine (10 mL) and dried over Na₂SO₄. After filtration, the filtrate was concentrated to dryness under vacuum. The residue was purified by silica gel column (120 g, pet. ether:EtOAc=1:1) to afford ((2R,3S,5R)-2-ethynyl-5-(2-fluoro-6-(((4-methoxyphenyl)diphenylmethyl)amino)-9H-purin-9-yl)-3-((4-methoxyphenyl)diphenyl-methoxy) tetrahydrofuran-2-yl)methyl heptanoate (800 mg, yield: 70.6%) as a white solid. LCMS (ESI) m/z calcd for $C_{59}H_{56}FN_5O_6$:949. Found: 950 (M+H)⁺. ¹HNMR (300 MHz, DMSO-d₆) δ 8.06 (s, 1H), 7.94 (s, 1H), 7.52-7.49 (m, 4H), 7.43-7.12 (m, 20H), 6.96-6.76 (m, 4H), 6.13 (dd, J=8.0, 4.0 Hz, 1H), 4.68 (t, J=7.6 Hz, 1H), 4.19 (d, J=12.0 Hz, 1H), 3.96 (s, 1H), 3.80 (d, J=12.0 Hz, 1H), 3.72 (s, 3H), 3.69 (s, 3H), 2.09-2.00 (m, 1H), 1.96-1.80 (m, 3H), 1.41-0.95 (m, 8H), 0.81-0.78 (m, 3H).

Step 2: ((2R,3S,5R)-5-(6-amino-2-fluoro-9H-purin-9-yl)-2-ethynyl-3-hydroxytetrahydro-furan-2-yl)methyl heptanoate. To the mixture of ((2R,3S,5R)-2-ethynyl-5-(2-fluoro-6-(((4-methoxyphenyl)diphenylmethyl)amino)-9H-purin-9-yl)-3-((4-methoxyphenyl)diphenyl methoxy) tetrahydrofuran-2-yl)diphenyl heptanoate (800 mg, 0.84 mmol) in DCM (20 mL) was added TFA (2.0 mL) dropwise at 0° C. The reaction mixture was stirred for 2 h at 0° C. LCMS indicated completion of reaction. The reaction mixture was concentrated to dryness under vacuum. The residue was dissolved in DCM (20 mL) and washed with NaHCO₃ (aq, 10 mL), brine (10 mL), dried over Na₂SO₄. After filtration, the filtrate was concentrated to dryness under vacuum. The crude product was purified by reverse phase Column:C18 (80 g); Mobile Phase A:water (1% FA), Mobile Phase B: ACN; Flow rate: 60 mL/min; Gradient: 0% B to 100% B in 30 min; 254/220 nm. The collected fractions were concentrated to afford ((2R,3S,5R)-5-(6-amino-2-fluoro-9H-purin-9-yl)-2-ethynyl-3-hydroxytetrahydrofuran-2-yl) methyl heptanoate (247 mg, yield: 72.4%) as white solid. LCMS (ESI) m/z calcd for $C_{19}H_{24}FN_5O_4$: 405 Found: 406 (M+H)⁺.

Step 3: ((2R,3S,5R)-5-(6-amino-2-fluoro-9H-purin-9-yl)-2-ethynyl-3-(((tridecyloxy)carbonyl) oxy) tetrahydrofuran-2-yl)methyl heptanoate. To a stirred mixture of ((2R,3S,5R)-5-(6-amino-2-fluoro-9H-purin-9-yl)-2-ethynyl-3-hydroxytetrahydrofuran-2-yl)methyl heptanoate (218 mg, 0.54 mmol) and K₂CO₃ (220 mg, 1.59 mmol) in THF (5 mL) was added di(1H-imidazol-1-yl)methanone (150 mg, 0.93 mmol) at 25° C. The reaction mixture was stirred at 25° C. for 2 h. To the above mixture was added Cs₂CO₃ (380 mg, 1.17 mmol) and tridecan-1-ol (550 mg, 2.74 mmol). The reaction mixture was stirred at 25° C. for 1 h. LCMS indicated completion of reaction. The reaction mixture was quenched with water (10 mL) and extracted with EtOAc (10 mL×3). The organic phases were washed with brine (20 mL), dried over Na₂SO₄, concentrated under reduced pressure. The crude product was purified by PreP-HPLC: Column: XBridge Prep OBD C18 Column, 30×150 mm 5 um; Mobile Phase A:water (0.05% TFA), Mobile Phase B:ACN; Flow rate:254 mL/min; Gradient:55 B to 72 B in 7 min; 254 nm; Rt:6.52 min. The collected fraction (RT:6.52 min) was lyophilized to afford ((2R,3S,5R)-5-(6-amino-2-fluoro-9H-purin-9-yl)-2-ethynyl-3-(((tridecyloxy)carbonyl)oxy)tetrahydrofuran-2-yl)methyl heptanoate (150 mg, purity:98.7%, yield:44%) as white solid. LCMS (ESI) m/z calcd for $C_{33}H_{50}FN_5O_6$: 631. Found: 632 (M+H)$^+$. $^1$HNMR (400 MHz, DMSO-d$_6$) δ 8.33 (s, 1H), 8.07-7.72 (m, 2H), 6.35 (t, J=6.8 Hz, 1H), 5.59 (dd, J=6.8, 5.2 Hz, 1H), 4.42 (d, J=11.6 Hz, 1H), 4.23 (d, J=11.6 Hz, 1H), 4.19-4.07 (m, 2H), 3.81 (s, 1H), 3.25-3.11 (m, 1H), 2.73-2.61 (m, 1H), 2.35-2.16 (m, 2H), 1.68-1.56 (m, 2H), 1.50-1.38 (m, 2H), 1.30-1.15 (m, 26H), 0.90-0.79 (m, 6H).
Example 53: (2R,3S,5R)-5-(6-amino-2-fluoro-9H-purin-9-yl)-2-ethynyl-2-((propionyloxy)methyl)tetrahydrofuran-3-yl Stearate
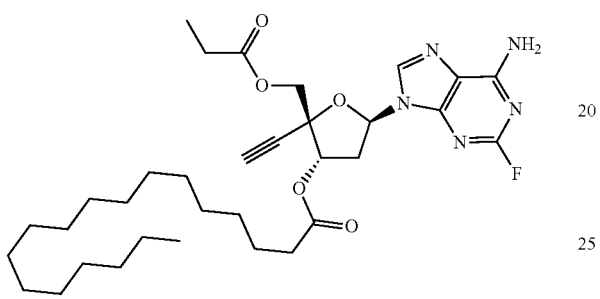
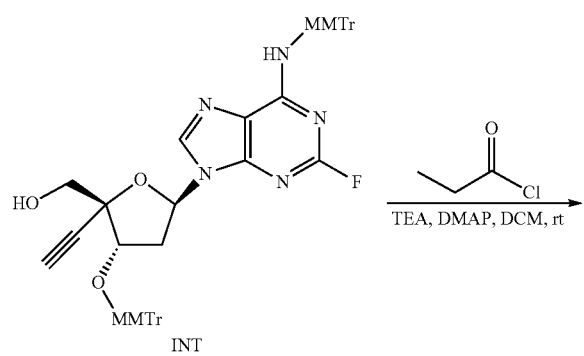
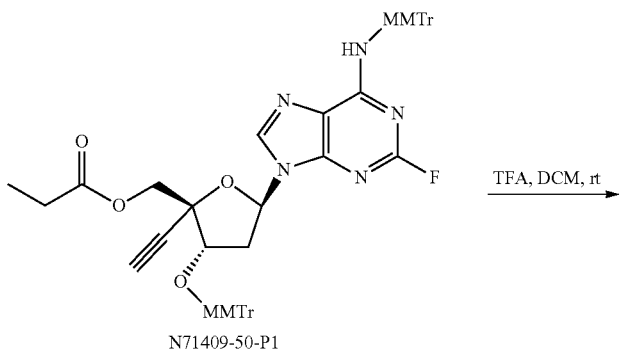

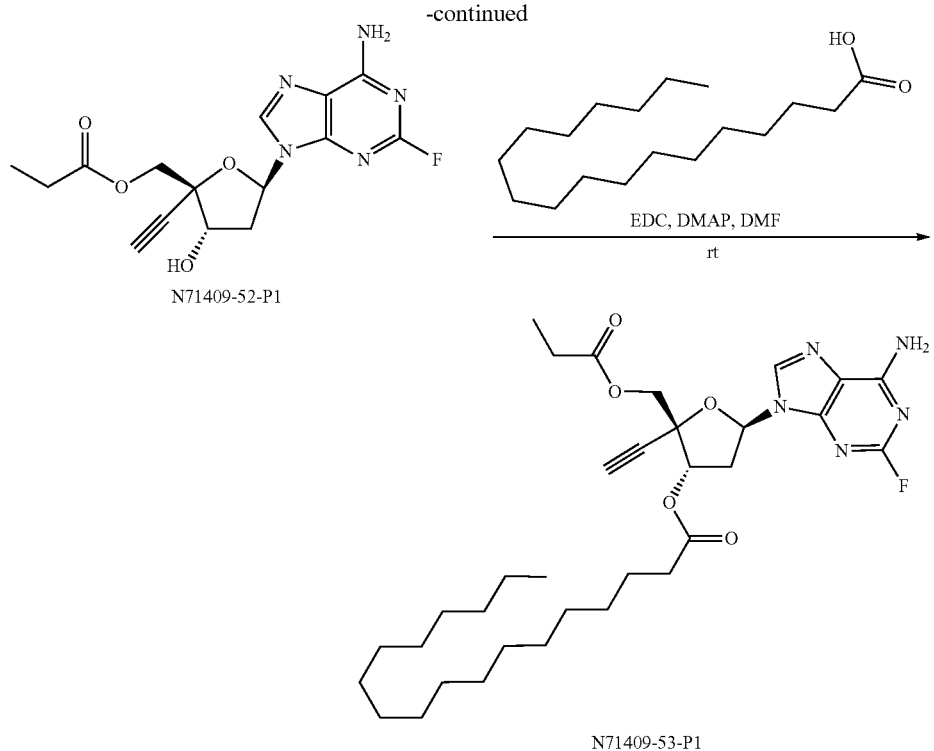

Step 1: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methyl propionate. To a stirred solution of ((2R,3S,5R)-2-ethynyl-5-(2-fluoro-6-(((4-methoxy-phenyl)diphenylmethyl) amino)-9H-purin-9-yl)-3-((4-methoxyphenyl)diphenylmethoxy) tetrahydrofuran-2-yl) methanol (700 mg, 0.84 mmol), Et3N (0.70 mL, 5.01 mmol) and DMAP (51 mg, 0.42 mmol) in DCM (7 mL) was added propionyl chloride (232 mg, 2.506 mmol) dropwise at 0° C. The reaction mixture was stirred at 0° C. for 30 min. LCMS indicated completion of reaction. The reaction was quenched by the addition of water (3 mL), the organic layers were separated and the water phase was extracted with DCM (2 mL*3). The combined organic layers were dried over $Na_2SO_4$ and evaporated to dryness under vacuum to give the crude title compound (800 mg, 94.5%, yield: 89%) as yellow oil. LCMS (ESI) m/z calcd for $C_{55}H_{48}FN_5O_6$: 893. Found: 894 (M+1). ¹HNMR (400 MHz, DMSO-$d_6$) δ 8.07 (s, 1H), 7.99 (s, 1H), 7.60-7.45 (m, 4H), 7.40-7.14 (m, 20H), 6.91-6.77 (m, 4H), 6.15-6.12 (m, 1H), 4.72 (t, J=7.6 Hz, 1H), 4.18 (d, J=12.0 Hz, 1H), 3.96 (s, 1H), 3.75 (d, J=12.0 Hz, 1H), 3.69 (s, 3H), 3.67 (s, 3H), 2.13-2.02 (m, 1H), 1.94-1.90 (m, 3H), 0.75 (t, J=7.6 Hz, 3H).

Step 2: ((2R,3S,5R)-5-(6-amino-2-fluoro-9H-purin-9-yl)-2-ethynyl-3-hydroxytetrahydro-furan-2-yl)methyl propionate. A solution of ((2R,3S,5R)-2-ethynyl-5-(2-fluoro-6-(((4-methoxyphenyl)di-phenylmethyl)amino)-9H-purin-9-yl)-3-((4-methoxyphenyl)diphenyl-methoxy) tetrahydrofuran-2-yl)methyl propionate (630 mg, 0.71 mmol) in DCM (7 mL) was added trifluoroacetic acid (TFA) (0.050 mL). The reaction solution was stirred at 25° C. for 30 min. LCMS indicated completion of reaction. The reaction was diluted with methanol until the yellow solution turn to colorless and concentrated under vacuum. The residue was subjected to HPLC purification (C18, 0-80% ACN/water with 0.1% FA) to give the desired product (200 mg, 98.7%, yield: 80%) as white solid. LCMS (ESI) m/z calcd for $C_{15}H_{16}FN_5O_4$:349. Found: 350 (M+1). ¹HNMR (400 MHz, DMSO-$d_6$) δ 8.28 (s, 1H), 7.86 (br s, 2H), 6.25 (dd, J=8.0, 4.0 Hz, 1H), 5.79 (d, J=5.6 Hz, 1H), 4.74-4.68 (m, 1H), 4.42 (d, J=11.6 Hz, 1H), 4.11 (d, J=11.6 Hz, 1H), 3.64 (s, 1H), 2.90-2.76 (m, 1H), 2.49-2.44 (m, 1H), 2.35-2.15 (m, 2H), 0.95 (t, J=7.6 Hz, 3H).

Step 3: (2R,3S,5R)-5-(6-amino-2-fluoro-9H-purin-9-yl)-2-ethynyl-2-((propionyloxy)methyl) tetrahydrofuran-3-yl stearate. A solution of stearic acid (489 mg, 1.72 mmol) in DMF (8 mL) was added EDC (439 mg, 2.29 mmol) and DMAP (280 mg, 2.29 mmol). The reaction mixture was stirred at 25° C. for 30 min. Then ((2R,3S,5R)-5-(6-amino-2-fluoro-9H-purin-9-yl)-2-ethynyl-3-hydroxytetrahydro-furan-2-yl)methyl propionate (200 mg, 0.57 mmol) was added. The resulting mixture was stirred at 25° C. for 20 hours. LCMS indicated completion of reaction. The reaction was diluted with water (30 ml), and the resulting mixture was extracted with EtOAc (20 ml*3). The combined organic layers were washed with brine (20 mL), dried over anhydrous sodium sulfate and evaporated to dryness under vacuum. The residue was purified by Prep-HPLC (Column: XSelect CSH Prep C18 OBD Column, 5 um, 19*150 mm; Mobile Phase A: Water (0.05% TFA), Mobile Phase B:ACN; Flow rate:25 mL/min; Gradient:95 B to 95 B in 7 min; 254 nm, RT: 6.05 min)) to give the desired product (156.8 g, 99.12%, yield: 44%) as white solid. LCMS (ESI) m/z calcd for $C_{33}H_{50}FN_5O_5$: 615. Found: 616 (M+1)⁺. ¹HNMR (400 MHz, DMSO-$d_6$) δ 8.34 (s, 1H), 7.95 (br s, 2H), 6.34 (t, J=6.8 Hz, 1H), 5.70 (t, J=5.6 Hz, 1H), 4.42 (d, J=11.6 Hz, 1H), 4.21 (d, J=11.6 Hz, 1H), 3.79 (s, 1H), 3.15-3.12 (m, 1H), 2.62-2.58 (m, 1H), 2.41-2.25 (m, 4H), 1.60-1.56 (m, 2H), 1.25-1.23 (m, 28H), 0.98 (t, J=7.6 Hz, 3H), 0.85 (t, J=6.4 Hz, 3H).

Example 54: ((2R,3S,5R)-2-ethynyl-5-(2-fluoro-6-heptanamido-9H-purin-9-yl)-3-hydroxytetrahydrofuran-2-yl)methyl 2-propylpentanoate
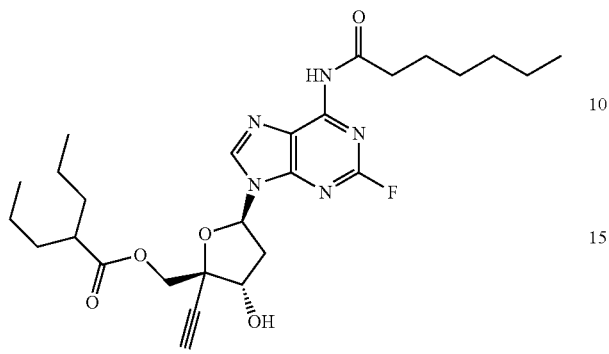
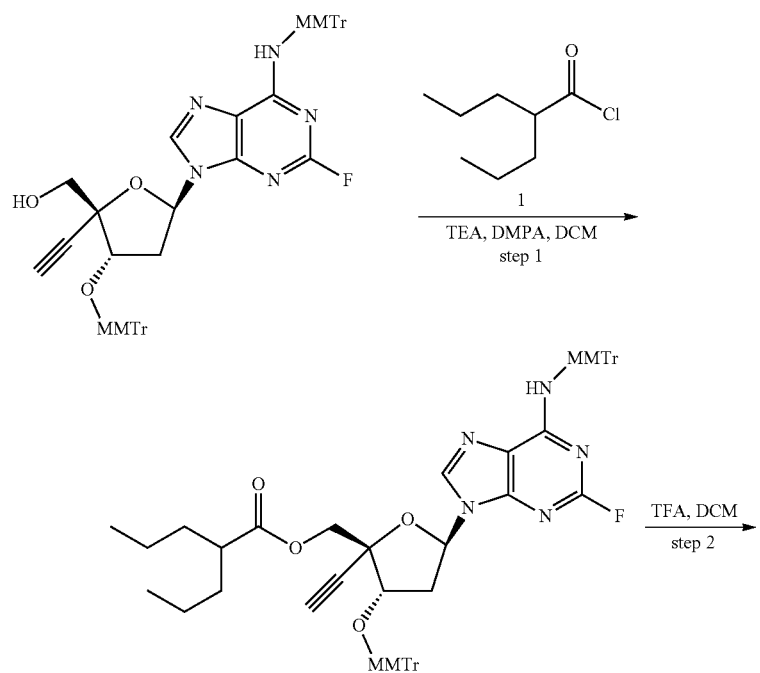
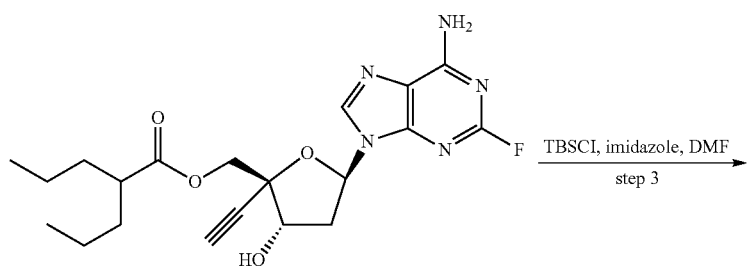

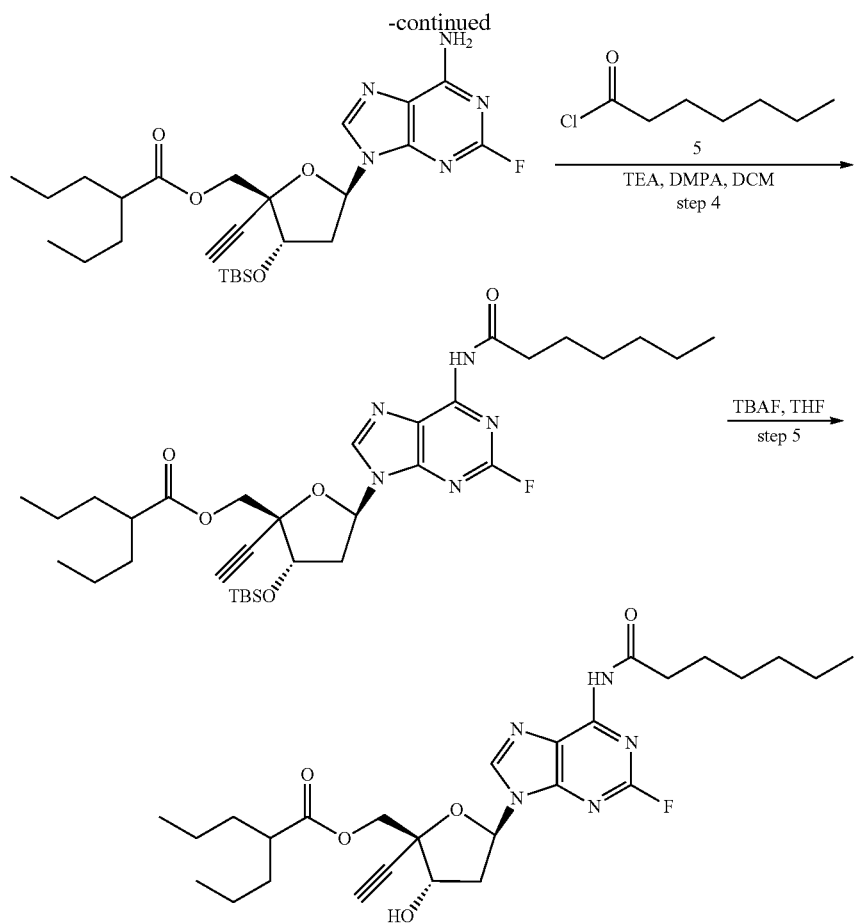

Step 1: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl) methyl 2-propylpentanoate. To a stirred solution of ((2R,3S,5R)-2-ethynyl-5-(2-fluoro-6-(((4-methoxy-phenyl)diphenylmethyl)amino)-9H-purin-9-yl)-3-((4-methoxyphenyl)diphenyl-methoxy)tetrahydro-furan-2-yl)methanol (2.00 g, 2.387 mmol), Et3N (1.0 mL, 7.16 mmol) and DMAP (146 mg, 1.193 mmol) in DCM (20.00 mL) was added a solution of 2-propylpentanoyl chloride (427 mg, 2.63 mmol) in DCM (2 mL) dropwise over 5 min at 0° C. The reaction mixture was stirred at 20° C. for 2 hr. LCMS indicated completion of reaction. The reaction mixture was quenched with water, extracted with EtOAc (3×20 mL). The organic phases were combined, washed with brine, dried over Na$_2$SO$_4$ and concentrated under vacuum. The residue was subjected to Prep-TLC (EtOAc:pet. ether=1:1) to give the desired product (1.7 g, 99%, yield: 73%) as off white solid. LCMS (ESI) m/z calcd for C$_{60}$H$_{58}$FN$_5$O$_6$: 963. Found: 964 (M+1)$^+$. $^1$HNMR (400 MHz, Chloroform-d) δ 7.61 (s, 1H), 7.59-7.54 (m, 4H), 7.44-7.21 (m, 20H), 7.10 (br s, 1H), 6.89-6.78 (m, 4H), 6.14-6.10 (m, 1H), 4.61 (t, J=7.6 Hz, 1H), 4.35 (d, J=12.0 Hz, 1H), 4.19 (d, J=12.0 Hz, 1H), 3.80 (s, 3H), 3.78 (s, 3H), 2.85 (s, 1H), 2.24-2.03 (m, 2H), 1.73-1.60 (m, 2H), 1.46-1.32 (m, 3H), 1.17-1.04 (m, 4H), 0.82-0.78 (m, 6H).

Step 2: ((2R,3S,5R)-5-(6-amino-2-fluoro-9H-purin-9-yl)-2-ethynyl-3-hydroxytetrahydrofuran-2-yl)methyl 2-propyl-pentanoate. To the stirred solution of ((2R,3S,5R)-2-ethy-nyl-5-(2-fluoro-6-(((4-methoxyphenyl)diphenylmethyl)amino)-9H-purin-9-yl)-3-((4-methoxyphenyl) diphenylmethoxy) tetrahydrofuran-2-yl)methyl 2-propylpentanoate (1700 mg, 1.763 mmol) in DCM (20 mL) was added trifluoroacetic acid (TFA) (2 mL). The resulting mixture was stirred for 1 hour at room temperature. LCMS indicated completion of reaction. The reaction was quenched by pouring into sodium carbonate (aq.) and the mixture was extracted with EtOAc (3×20 mL). The organic phases were combined, washed with saturated brine, dried over Na$_2$SO$_4$ and concentrated under vacuum. The residue was purified by flash chromatography (silica gel, 120 g, EtOAc:pet. ether=1:1) to give the desired product as white solid (650 mg, 98%, yield: 86%). LCMS (ESI) m/z calcd for C$_{20}$H$_{26}$FN$_5$O$_4$: 419. Found: 420 (M+1)$^+$. $^1$HNMR (400 MHz, Chloroform-d) δ 7.91 (s, 1H), 6.39-6.34 (m, 1H), 6.12 (br s, 2H), 4.77 (t, J=6.8 Hz, 1H), 4.46 (d, J=1.2 Hz, 2H), 3.04-2.98 (m, 1H), 2.80 (s, 1H), 2.73-2.66 (m, 2H), 2.46-2.39 (m, 1H), 1.66-1.52 (m, 2H), 1.50-1.37 (m, 2H), 1.35-1.18 (m, 4H), 0.89-0.85 (m, 6H).

Step 3: ((2R,3S,5R)-5-(6-amino-2-fluoro-9H-purin-9-yl)-3-((tert-butyldimethylsilyl)oxy)-2-ethynyltetrahydrofuran-2-yl)methyl 2-propylpentanoate. To a solution of ((2R,3S,5R)-5-(6-amino-2-fluoro-9H-purin-9-yl)-2-ethynyl-3-hydroxytetrahydrofuran-2-yl)methyl 2-propylpenta-noate (640 mg, 1.526 mmol) and imidazole (312 mg, 4.58 mmol) in DMF (10.00 mL) was added a solution of TBS-Cl (690 mg, 4.58 mmol) in DMF (1 mL). The reaction mixture was stirred at 40° C. for 16 hr. LCMS indicated completion of reaction. The reaction was quenched by pouring into brine and the mixture was extracted with EtOAc (3×20 mL). The organic phases were combined, washed with saturated brine, dried over Na$_2$SO$_4$ and concentrated under vacuum. The residue was purified by flash chromatography (silica gel, 40 g, EtOAc:pet. ether=1:1) to give the desired product (500 mg, 58%, yield: 95%) as off white solid. LCMS (ESI) m/z calcd for C$_{26}$H$_{40}$FN$_5$O$_4$Si: 533. Found: 534 (M+1)$^+$. $^1$HNMR (400 MHz, Chloroform-d) δ 7.91 (s, 1H), 6.29 (dd, J=7.6, 3.6 Hz, 1H), 5.93 (br s, 2H), 4.94 (t, J=7.2 Hz, 1H), 4.46 (d, J=12.0 Hz, 1H), 4.24 (d, J=12.0 Hz, 1H), 2.96-2.91 (m, 1H), 2.70-2.63 (m, 1H), 2.61 (s, 1H), 2.36-2.29 (m, 1H), 1.61-1.44 (m, 2H), 1.44-1.31 (m, 2H), 1.31-1.18 (m, 4H), 0.96 (s, 9H), 0.87-0.82 (m, 6H), 0.17 (s, 6H).

Step 4: ((2R,3S,5R)-3-((tert-butyldimethylsilyl)oxy)-2-ethynyl-5-(2-fluoro-6-heptanamido-9H-purin-9-yl)tetrahydrofuran-2-yl)methyl 2-propylpentanoate. ((2R,3S,5R)-5-(6-amino-2-fluoro-9H-purin-9-yl)-3-((tert-butyldimethylsilyl)oxy)-2-ethynyltetrahydrofuran-2-yl)methyl 2-propylpenta-noate (750 mg, 1.405 mmol) was dissolved in DCM (20 mL). Et3N (0.979 mL, 7.03 mmol) and DMAP (86 mg, 0.703 mmol) were added, and then heptanoyl chloride (418 mg, 2.81 mmol) was added at 0° C. The reaction mixture was stirred at 0° C. for overnight. LCMS indicated completion of reaction. The solvent was removed under vacuum. The residue was subjected to Prep-TLC (pet. ether:EtOAc=1:1) to give the desired product (400 mg, 92%, yield:42%) as off white oil. LCMS (ESI) m/z calcd for C$_{33}$H$_{52}$FN$_5$O$_5$Si: 645. Found: 646 (M+1)$^+$. $^1$HNMR (400 MHz, Chloroform-d) δ 8.70 (s, 1H), 8.09 (s, 1H), 6.34 (dd, J=7.6, 4.0 Hz, 1H), 4.91 (t, J=7.2 Hz, 1H), 4.45 (d, J=12.0 Hz, 1H), 4.26 (d, J=12.0 Hz, 1H), 3.00-2.87 (m, 3H), 2.73-2.65 (m, 1H), 2.63 (s, 1H), 2.37-2.29 (m, 1H), 1.82-1.74 (m, 2H), 1.61-1.10 (m, 14H), 0.96 (s, 9H), 0.88-0.79 (m, 9H).0.17 (s, 6H).

Step 5: ((2R,3S,5R)-2-ethynyl-5-(2-fluoro-6-heptanamido-9H-purin-9-yl)-3-hydroxytetrahydrofuran-2-yl)methyl 2-propylpentanoate. To the stirred solution of ((2R,3S,5R)-3-((tert-butyldimethylsilyl)oxy)-2-ethynyl-5-(2-fluoro-6-heptanamido-9H-purin-9-yl)tetrahydrofuran-2-yl) methyl 2-propylpentanoate (400 mg, 0.619 mmol) in tetrahydrofuran (THF) (10 mL) was added TBAF (1.2 mL, 1M in THF, 1.2 mmol). The resulting mixture was stirred for 1 hour at room temperature. LCMS indicated completion of reaction. The reaction mixture was concentrated under vacuum. Water was added, the mixture was extracted with EtOAc (3×20 mL). The combined organic phases were washed with brine, dried over Na$_2$SO$_4$ and concentrated under vacuum. The residue was purified by Prep-TLC (MeOH:DCM=1:10) to give crude product. The crude product was re-purified by Prep-HPLC (Column: XSelect CSH Prep C18 OBD Column, 5 um, 19*150 mm; Mobile Phase A:Water (0.05% TFA), Mobile Phase B:ACN; Flow rate:25 mL/min; Gradient:65 B to 86 B in 6 min; 254 nm; RT:4.07) The collected fraction was lyophilized to give the desired product (150 mg, 97%, yield: 44%), LCMS (ESI) m/z calcd for C$_{27}$H$_{38}$FN$_5$O$_5$: 531. Found: 532 (M+1)$^+$. $^1$HNMR (400 MHz, Chloroform-d) δ 8.69 (s, 1H), 8.08 (s, 1H), 6.41 (dd, J=7.6, 5.2 Hz, 1H), 4.75 (t, J=6.8 Hz, 1H), 4.44-4.43 (m, 2H), 3.00-2.92 (m, 3H), 2.80 (s, 1H), 2.74-2.69 (m, 1H), 2.42-2.38 (m, 1H), 2.15 (br s, 1H), 1.78-1.72 (m, 2H), 1.60-1.52 (m, 2H), 1.46-1.22 (m, 12H), 0.91-0.83 (m, 9H).

Example 55: ((2R,3S,5R)-2-ethynyl-5-(2-fluoro-6-tetradecanamido-9H-purin-9-yl)-3-hydroxytetrahydrofuran-2-yl)methyl Propionate

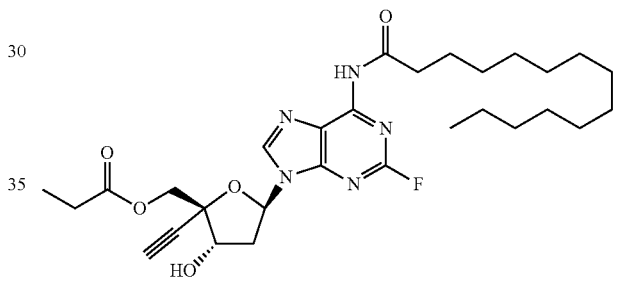

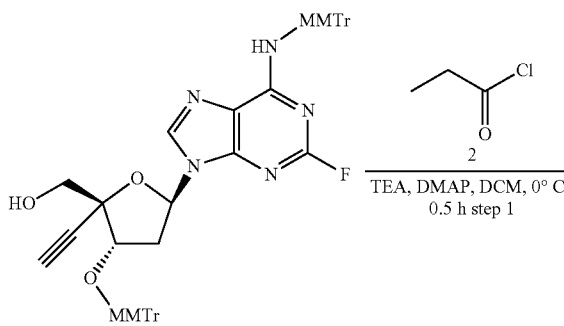

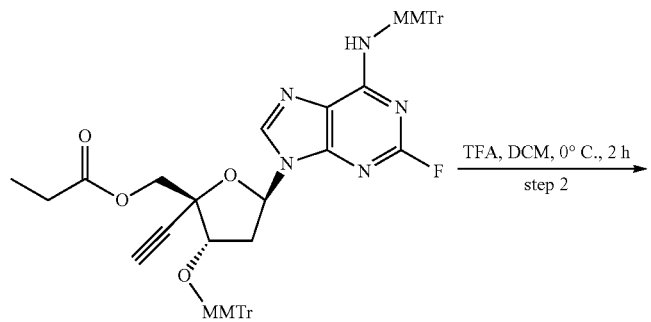

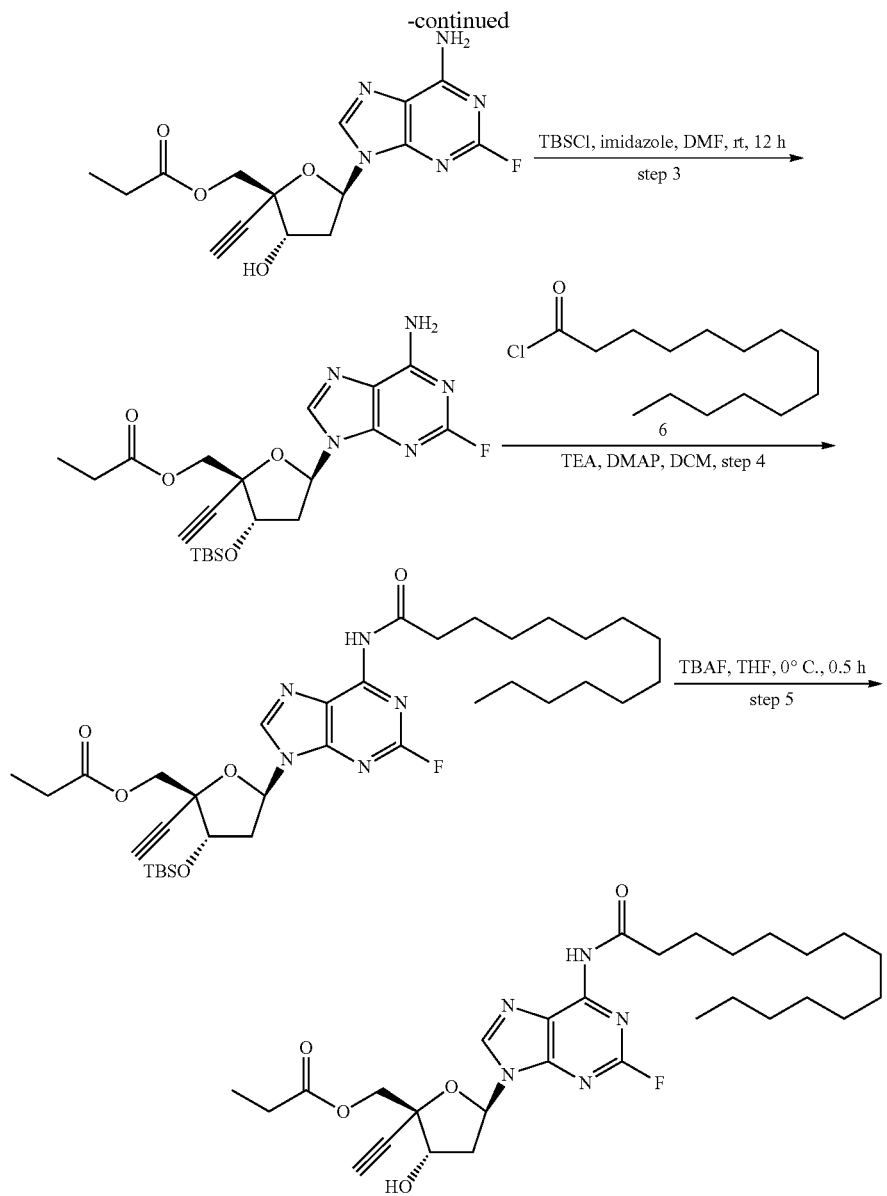

Step 1: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl) methyl propionate. To a stirred mixture of ((2R,3S,5R)-2-ethynyl-5-(2-fluoro-6-(((4-methoxy-phenyl)diphenylmethyl) amino)-9H-purin-9-yl)-3-((4-methoxyphenyl)diphenylmethoxy) tetrahydrofuran-2-yl) methanol (2.5 g, 2.98 mmol), Et3N (1.25 mL, 8.94 mmol) and DMAP (226 mg, 1.85 mmol) in DCM (30 mL) was added propionyl chloride (550 mg, 5.94 mmol) at 0° C. The reaction mixture was stirred at 0° C. for 30 min. LCMS indicated completion of reaction. The reaction mixture was quenched with water (50 mL) and extracted with DCM (30×3 mL). The combined organic layers were washed with brine (30 mL) and dried over Na₂SO₄. After filtration, the filtrate was concentrated to dryness under vacuum. The crude product was purified by silica gel column (120 g, EtOAc:pet. ether=1:1) to afford ((2R,3S,5R)-2-ethynyl-5-(2-fluoro-6-(((4-methoxyphenyl)diphenylmethyl) amino)-9H-purin-9-yl)-3-((4-methoxyphenyl)diphenylmethoxy)tetrahydrofuran-2-yl)methyl propionate (2.18 g, yield:73.6%) as a white solid. LCMS (ESI) m/z calcd for $C_{55}H_{48}FN_5O_6$: 893. Found:894 (M+H)⁺. ¹HNMR (300 MHz, DMSO-$d_6$) δ 8.07 (s, 1H), 7.99 (s, 1H), 7.58-7.43 (m, 4H), 7.40-7.14 (m, 20H), 6.86-6.81 (m, 4H), 6.16-6.12 (m, 1H), 4.74-4.69 (m, 1H), 4.18 (d, J=12.0 Hz, 1H), 3.96 (s, 1H), 3.74 (d, J=12.0 Hz, 1H), 3.72 (s, 3H), 3.69 (s, 3H), 2.13-2.07 (m, 1H), 1.97-1.82 (m, 3H), 0.75 (t, J=7.5 Hz, 3H).

Step 2: ((2R,3S,5R)-5-(6-amino-2-fluoro-9H-purin-9-yl)-2-ethynyl-3-hydroxytetrahydro-furan-2-yl)methyl propionate. To a stirred mixture of ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy) tetrahydrofuran-2-yl)methyl propionate (2.18 g, 2.44 mmol) in DCM (50 mL) was added TFA (5.4 mL) at 0° C. The reaction mixture was stirred at 0° C. for 2 h. LCMS indicated completion of reaction. The reaction mixture was quenched with water (20 mL) and was basified to pH=8 with sat- .NaHCO$_3$.(aq). The precipitated solids were collected by filtration and washed with water to afford ((2R,3S,5R)-5-(6-amino-2-fluoro-9H-purin-9-yl)-2-ethynyl-3-hydroxytetrahydrofuran-2-yl)methyl propionate (660 mg, yield:62%) as white solid. The crude product was used in the next step directly without further purification. LCMS (ESI) m/z calcd for C$_{15}$H$_{16}$FN$_5$O$_4$: 349 Found: 350 (M+H)$^+$.

Step 3: ((2R,3S,5R)-5-(6-amino-2-fluoro-9H-purin-9-yl)-3-((tert-butyldimethylsilyl)oxy)-2-ethynyltetrahydrofuran-2-yl)methyl propionate. To a stirred mixture of ((2R,3S,5R)-5-(6-amino-2-fluoro-9H-purin-9-yl)-2-ethynyl-3-hydroxytetrahydrofuran-2-yl)methyl propionate (640 mg, 1.83 mmol) and imidazole (1.3 g, 19.1 mmol) in DMF (10 mL) was added TBS-Cl (1.1 g, 7.30 mmol) at 25° C. The reaction mixture was stirred at 30° C. for 12 h. LCMS indicated completion of reaction. The reaction mixture was quenched with water (20 mL), extracted with EtOAc (3×20 mL). The combined organic layers were washed with brine (20 mL), dried over with Na$_2$SO$_4$, filtered and concentrated under reduced pressure. The crude product was purified by silica gel (80 g, pet. ether/EtOAc=1:1) to afford ((2R,3S,5R)-5-(6-amino-2-fluoro-9H-purin-9-yl)-3-((tert-butyldimethylsilyl)oxy)-2-ethynyltetrahydrofuran-2-yl)methyl propionate (730 mg, yield:84%) as a white solid. LCMS (ESI) m/z calcd for C$_{21}$H$_{30}$FN$_5$O$_4$Si: 463. Found: 464 (M+H)$^+$. $^1$HNMR (400 MHz, DMSO-d$_6$) δ 8.29 (s, 1H), 7.89 (br s, 2H), 6.30-6.27 (m, 1H), 4.97 (t, J=6.8 Hz, 1H), 4.34 (d, J=12.0 Hz, 1H), 4.12 (d, J=12.0 Hz, 1H), 3.67 (s, 1H), 3.09-2.85 (m, 1H), 2.50-2.37 (m, 1H), 2.31-2.01 (m, 2H), 0.98-0.90 (m, 12H), 0.15 (s, 6H).

Step 4: ((2R,3S,5R)-3-((tert-butyldimethylsilyl)oxy)-2-ethynyl-5-(2-fluoro-6-tetradecanamido-9H-purin-9-yl)tetrahydrofuran-2-yl)methyl propionate. To a stirred mixture of ((2R,3S,5R)-5-(6-amino-2-fluoro-9H-purin-9-yl)-3-((tert-butyldimethylsilyl)oxy)-2-ethynyltetrahydrofuran-2-yl) methyl propionate (580 mg, 1.25 mmol), Et3N (1.38 mL, 9.88 mmol) and DMAP (153 mg, 1.25 mmol) in DCM (10 mL) was added tetradecanoyl chloride (1.23 g, 4.98 mmol) at 0° C. The reaction mixture was stirred at 25° C. for 12 h. LCMS indicated completion of reaction. The reaction mixture was quenched with water (20 mL), extracted with EtOAc (3×20 mL). The combined organic layers were dried over with Na$_2$SO$_4$, filtered and concentrated under reduced pressure. The crude product was purified by silica gel column (80 g, pet. ether/EtOAc=1:1) to afford ((2R,3S,5R)-3-((tert-butyldimethylsilyl)oxy)-2-ethynyl-5-(2-fluoro-6-tetradecanamido-9H-purin-9-yl)tetrahydrofuran-2-yl) methyl propionate (490 mg, yield: 52.3%) as a yellow oil. LCMS (ESI) m/z calcd for C$_{35}$H$_{56}$FN$_5$O$_5$Si: 673. Found: 674 (M+H)$^+$. $^1$HNMR (300 MHz, DMSO-d$_6$) δ 11.02 (s, 1H), 8.60 (s, 1H), 6.41-6.37 (m, 1H), 4.97 (t, J=9.0 Hz, 1H), 4.35 (d, J=12.0 Hz, 1H), 4.15 (d, J=12.0 Hz, 1H), 3.69 (s, 1H), 3.09-2.88 (m, 1H), 2.58 (d, J=7.2 Hz, 2H), 2.26-2.13 (m, 2H), 1.66-1.50 (m, 2H), 1.34-1.17 (m, 24H), 0.96-0.83 (m, 12H), 0.15 (s, 6H).

Step 5: ((2R,3S,5R)-2-ethynyl-5-(2-fluoro-6-tetradecanamido-9H-purin-9-yl)-3-hydroxytetrahydrofuran-2-yl) methyl propionate. To a stirred mixture of ((2R,3S,5R)-3-((tert-butyldimethylsilyl)oxy)-2-ethynyl-5-(2-fluoro-6-tetradecanamido-9H-purin-9-yl)tetrahydrofuran-2-yl) methyl propionate (470 mg, 0.70 mmol) in THF (20 mL) was added TBAF (1.15 mL, 1.15 mmol, 1N in THF) at 0° C. The reaction mixture was stirred at 0° C. for 30 min. LCMS indicated completion of reaction. The reaction mixture was quenched with water (20 mL), extracted with EtOAc (3×20 mL). The combined organic layers were washed with sat.NH$_4$Cl (aq., 3×20 mL), dried over with Na$_2$SO$_4$, filtered and concentrated under reduced pressure. The crude product was purified by Prep-HPLC: Column: XSelect CSH Prep C18 OBD Column, 5 um, 19×150 mm; Mobile Phase A:water (0.1% FA), Mobile Phase B:ACN; Flow rate:25 mL/min; Gradient:67 B to 95 B in 8 min; 254 nm; Rt: 7.23 min. The collected fraction (RT: 7.23 min) was lyophilized to afford ((2R,3S,5R)-2-ethynyl-5-(2-fluoro-6-tetradecanamido-9H-purin-9-yl)-3-hydroxytetra-hydrofuran-2-yl)methyl propionate (252 mg, purity:99.04%, yield:64%) as a white solid. LCMS (ESI) m/z calcd for C$_{29}$H$_{42}$FN$_5$O$_5$: 559. Found: 560 (M+H)$^+$. $^1$HNMR (400 MHz, DMSO-d$_6$) δ 11.0 (s, 1H), 8.59 (s, 1H), 6.36-633 (m, 1H), 5.84 (d, J=5.2 Hz, 1H), 4.73-4.71 (m, 1H), 4.42 (d, J=11.6 Hz, 1H), 4.13 (d, J=11.6 Hz, 1H), 3.66 (s, 1H), 2.90-2.78 (m, 1H), 2.57-2.51 (m, 3H), 2.25-2.19 (m, 2H), 1.60-1.57 (m, 2H), 1.28-1.23 (m, 20H), 0.93 (t, J=7.6 Hz, 3H), 0.85 (t, J=6.4 Hz, 3H).

Example 56: ((2R,3S,5R)-5-(6-amino-2-fluoro-9H-purin-9-yl)-3-((ethoxycarbonyl)oxy)-2-ethynyltetrahydrofuran-2-yl)methyl Tetradecanoate

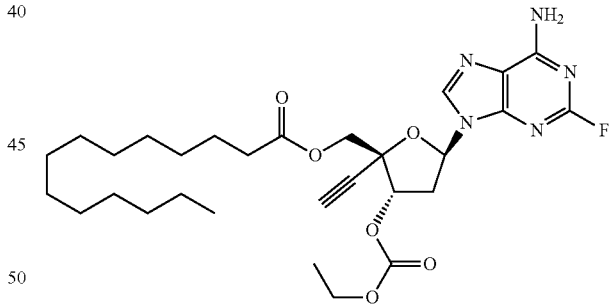

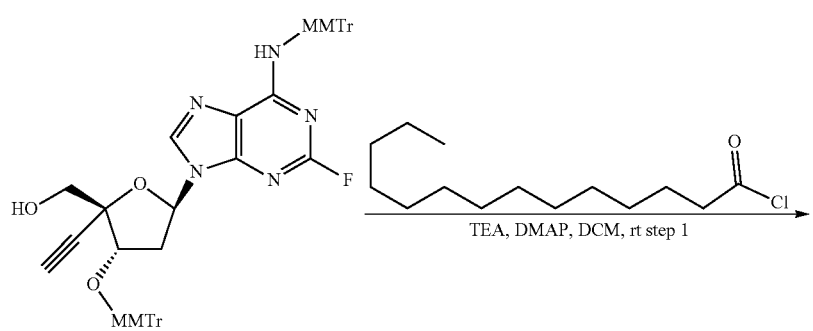

TEA, DMAP, DCM, rt step 1

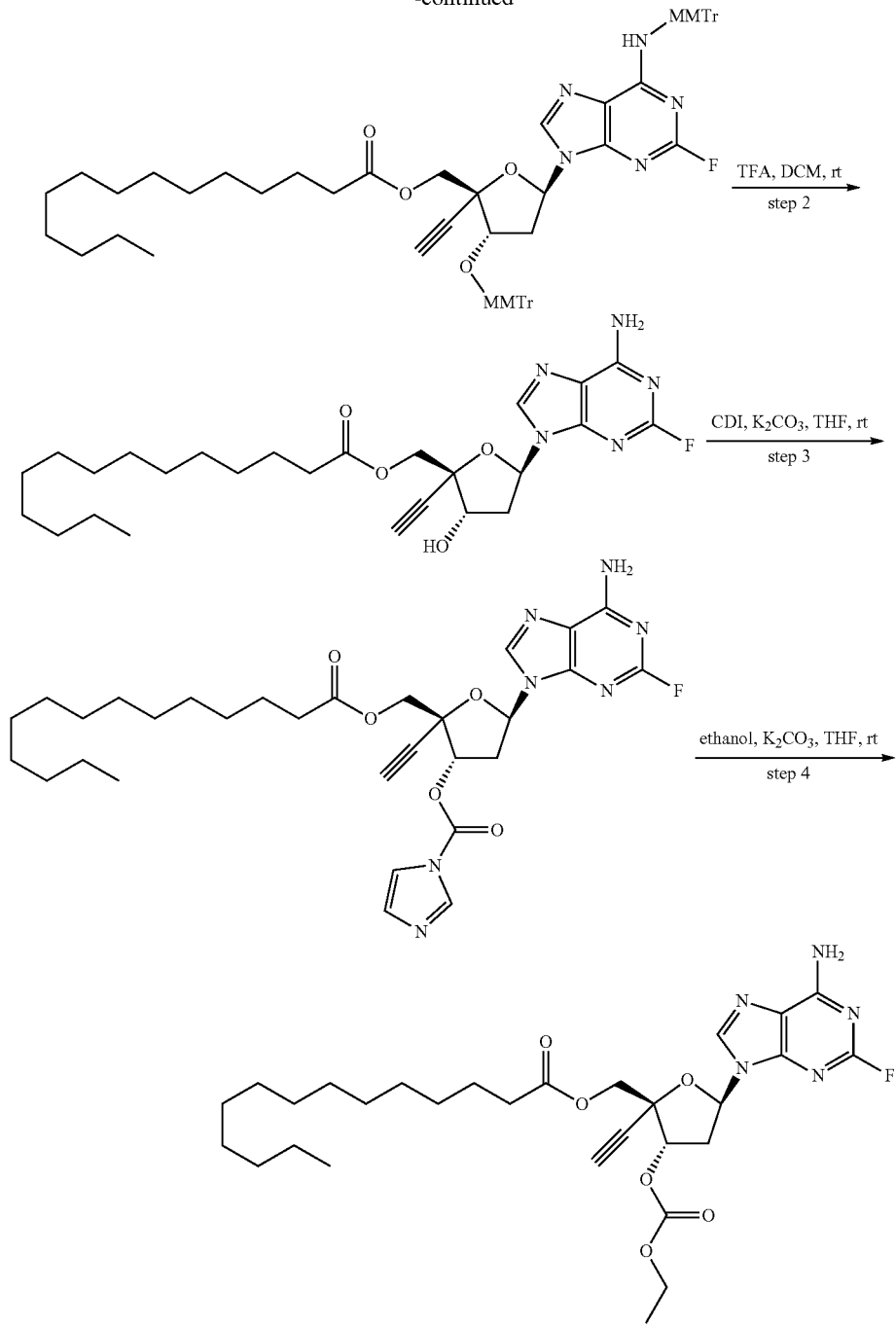

Step 1: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methyl tetradecanoate. To a stirred solution of ((2R,3S,5R)-2-ethynyl-5-(2-fluoro-6-(((4-methoxyphenyl)diphenylmethyl) amino)-9H-purin-9-yl)-3-((4-methoxyphenyl)diphenyl-methoxy)tetrahydrofuran-2-yl) methanol (550 mg, 0.656 mmol), Et3N (0.27 mL, 1.97 mmol) and DMAP (40 mg, 0.328 mmol) in DCM (5 mL) was added tetradecanoyl chloride (486 mg, 1.969 mmol) at 0° C. The reaction mixture was stirred at 0° C. for 30 min. LCMS indicated completion of reaction. The reaction was quenched with water (3 mL). The organic layers were separated out. The water phase was extracted with DCM (2 mL*3). The combined organic layers were dried over anhydrous sodium sulfate and evaporated to dryness concentrated under vacuum. The residue was purified by Prep-TLC (pet. ether:EtOAc=1:1) to give the desired product (638 mg, 92%, yield: 85%) as a yellow solid. LCMS (ESI) m/z calcd for $C_{66}H_{70}FN_5O_6$:1048. Found: 1049 (M+1)$^+$. $^1$HNMR (300 MHz, DMSO-d$_6$) δ 8.06 (s, 1H), 7.92 (s, 1H), 7.56-7.46 (m, 4H), 7.42-7.13 (m, 20H), 6.86-6.83 (m, 4H), 6.15-6.11 (m, 1H), 4.71-4.65 (m, 1H), 4.18 (d, J=12.0 Hz, 1H), 3.96 (s, 1H), 3.79 (d, J=12.0 Hz, 1H), 3.72 (s, 3H), 3.68 (s, 3H), 1.93-1.85 (m, 2H), 1.64 (br s, 2H), 1.24-1.15 (m, 22H), 0.86-0.82 (m, 3H).

Step 2: ((2R,3S,5R)-5-(6-amino-2-fluoro-9H-purin-9-yl)-2-ethynyl-3-hydroxytetrahydrofuran-2-yl)methyl tetradecanoate. A stirred solution of ((2R,3S,5R)-2-ethynyl-5-(2-fluoro-6-(((4-methoxyphenyl)diphenylmethyl)amino)-9H-purin-9-yl)-3-((4-methoxyphenyl)di-phenylmethoxy)tetrahydrofuran-2-yl)methyl tetradecanoate (638 mg, 0.61 mmol) in DCM (6 mL) was added trifluoroacetic acid (TFA) (0.6 mL). The reaction mixture was stirred at 25° C. for 30 minutes in air. LCMS indicated completion of reaction. The reaction mixture was quenched by the addition of methanol until the red solution turn to colorless and concentrated under vacuum. The residue was purified by Prep-HPLC purification (C18, 0-100% ACN/water with 0.1% FA) to give the desired product (270 mg, 100%, yield: 88%). LCMS (ESI) m/z calcd for $C_{26}H_{38}FN_5O_4$:503. Found: 504 (M+1)$^+$. $^1$HNMR (300 MHz, DMSO-$d_6$) δ 8.27 (s, 1H), 7.85 (br s, 2H), 6.26-6.22 (m, 1H), 5.79 (d, J=5.4 Hz, 1H), 4.74-4.67 (m, 1H), 4.42 (d, J=12.0 Hz, 1H), 4.10 (d, J=12.0 Hz, 1H), 3.63 (s, 1H), 2.86-2.70 (m, 1H), 2.47-2.46 (m, 1H), 2.30-2.10 (m, 2H), 1.41 (br s, 2H), 1.41-1.17 (m, 20H), 0.90-0.80 (m, 3H).

Step 3: ((2R,3S,5R)-5-(6-amino-2-fluoro-9H-purin-9-yl)-3-((ethoxycarbonyl)oxy)-2-ethynyltetrahydrofuran-2-yl)methyl tetradecanoate. To a stirred solution of ((2R,3S,5R)-5-(6-amino-2-fluoro-9H-purin-9-yl)-2-ethynyl-3-hydroxytetrahydrofuran-2-yl)methyl tetradecanoate (270 mg, 0.536 mmol) and $K_2CO_3$ (222 mg, 1.608 mmol) in THF (2 mL) was added solid CDI (261 mg, 1.608 mmol) at 25° C. The reaction mixture was stirred at 25° C. for 30 min. LCMS indicated completion of reaction. The reaction was quenched with ice cooled-water (8 mL). The resulting mixture was extracted with EtOAc (10 ml*3). The combined organic layers were washed with brine (10 mL), dried over anhydrous sodium sulfate and evaporated to dryness in vacuum to give the desired product (250 mg, 95%, yield: 74.1%) as white solid. LCMS (ESI) m/z calcd for $C_{30}H_{40}FN_7O_5$: 597. Found: 598 (M+1)$^+$.

Step 4: ((2R,3S,5R)-5-(6-amino-2-fluoro-9H-purin-9-yl)-3-((ethoxycarbonyl)oxy)-2-ethynyltetrahydrofuran-2-yl)methyl tetradecanoate. To a stirred solution of (2R,3S,5R)-5-(6-amino-2-fluoro-9H-purin-9-yl)-2-ethynyl-2-((tetradecanoyloxy)methyl)tetrahydrofuran-3-yl 1H-imidazole-1-carboxylate (250 mg, 0.418 mmol) and $Cs_2CO_3$ (291 mg, 0.894 mmol) in tetrahydrofuran (THF) (4 mL) was added ethanol (193 mg, 4.18 mmol) at 25° C. The reaction mixture was stirred at 25° C. for 2 hours. LCMS indicated completion of reaction. The reaction was quenched with ice cooled-water (8 mL). The resulting mixture was extracted with EtOAc (10 ml*3). The combined organic layers were washed with brine (10 mL), dried over anhydrous sodium sulfate and evaporated to dryness under vacuum. The residue was purified by Prep-HPLC (Column: XBridge Prep C18 OBD Column, 19*150 mm 5 um; Mobile Phase A: Water (0.1% FA), Mobile Phase B: ACN; Flow rate: 25 mL/min; Gradient: 75 B to 95 B in 7 min; 220 nm, 254 nm. RT: 6.06 min) to give the desired product (158 mg, 98.84%, yield: 64.4%) as a white solid. LCMS (ESI) m/z calcd for $C_{29}H_{42}FN_5O_6$: 615. Found: 616 (M+1). $^1$HNMR (400 MHz, DMSO-$d_6$) δ 8.32 (s, 1H), 7.89 (br s, 2H), 6.34 (t, J=6.8 Hz, 1H), 5.58 (t, J=5.2 Hz, 1H), 4.42 (d, J=11.2 Hz, 1H), 4.25-4.17 (m, 3H), 3.82 (s, 1H), 3.23-3.16 (m, 1H), 2.70-2.64 (m, 1H), 2.33-2.18 (m, 2H), 1.43-1.42 (m, 2H), 1.27-1.19 (m, 23H), 0.85 (t, J=6.8 Hz, 3H).

Example 57: ((2R,3S,5R)-5-(6-amino-2-fluoro-9H-purin-9-yl)-2-ethynyl-3-hydroxytetrahydrofuran-2-yl)methyl (1,3-bis(isobutyryloxy)propan-2-yl) Succinate

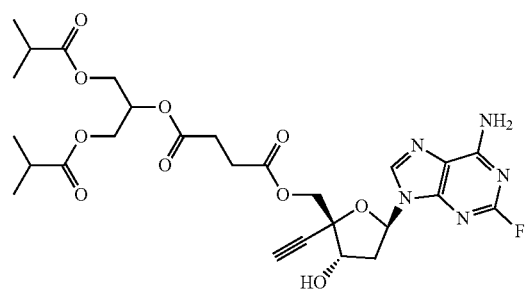 [SMILES: C#C[C@]1(COC(=O)CCC(=O)OC(COC(=O)C(C)C)COC(=O)C(C)C)O[C@@H](n2cnc3c(N)nc(F)nc32)C[C@@H]1O]

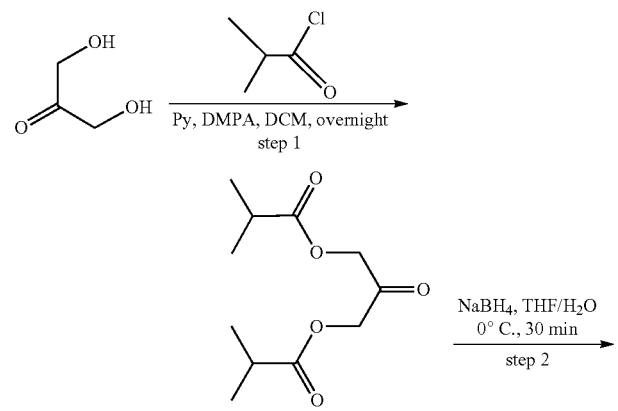

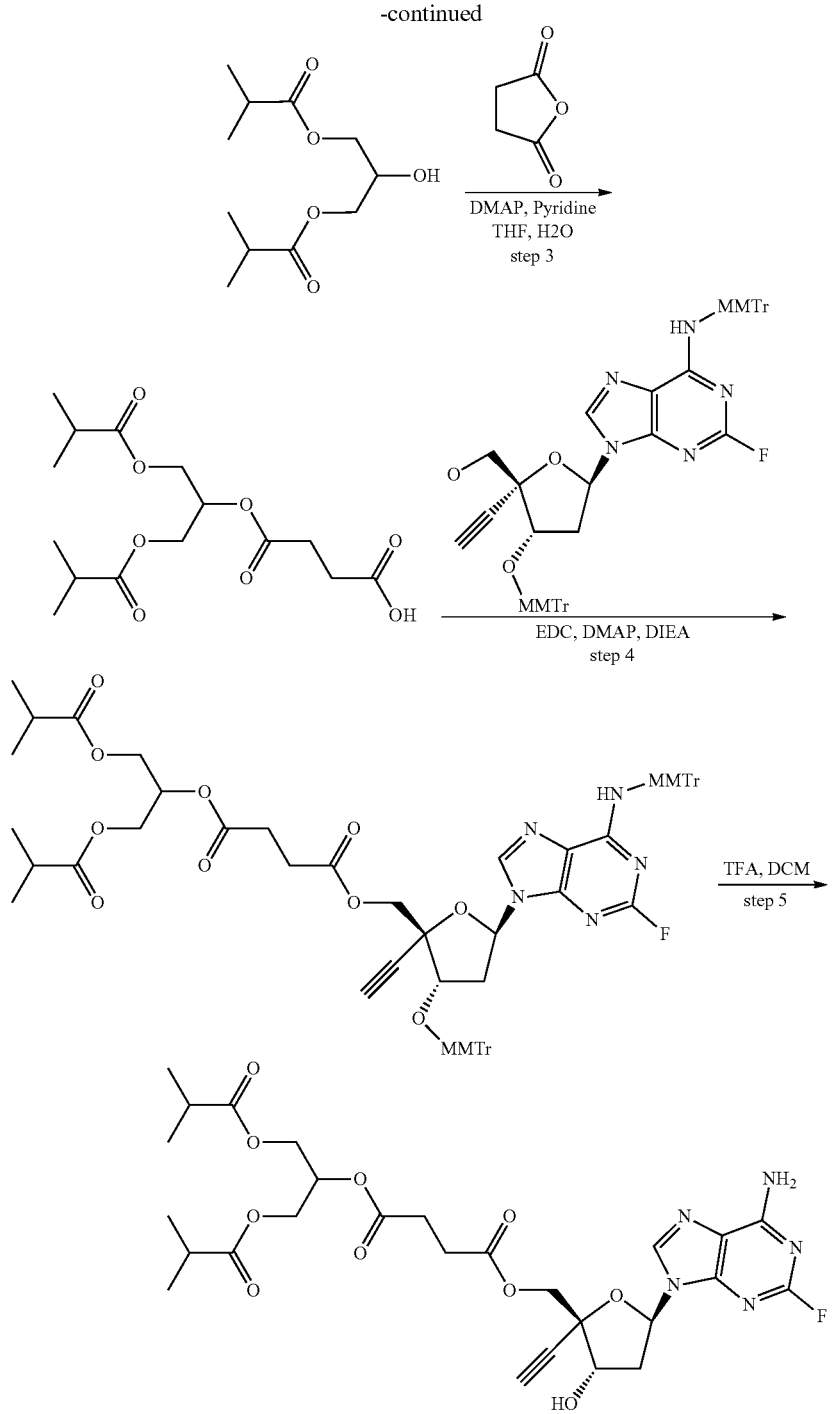

Step 1: 2-oxopropane-1,3-diylbis(2-methylpropanoate). To a solution of 1,3-dihydroxypropan-2-one (30 g, 333 mmol) in DCM (200 mL) stirred under nitrogen at 0° C. was added DMAP (1.22 g, 9.99 mmol), pyridine (81 mL, 999 mmol) and isobutyryl chloride (78 g, 733 mmol) in DCM (100 mL) dropwise during 30 min. The reaction mixture was stirred at 0° C. for overnight. TLC showed the reaction was completed (pet. ether:EtOAc=1:1, colored by KMnO$_4$). The reaction mixture was quenched with saturated NaHCO$_3$ aq. (100 ml) and the organic layers were washed with brine (100 mL*6). The combined organic layers were dried over Na$_2$SO$_4$ and concentrated under vacuum. The residue was purified by flash chromatography (silica gel, 330 g, pet. ether:EtOAc=5:1) to give the desired product (34 g, 90%, yield: 44.3%) as a yellow oil. $^1$HNMR (400 MHz, Chloroform-d) δ 4.77 (s, 4H), 2.60-2.81 (m, 2H), 1.18-1.25 (m, 12H).

Step 2: 2-hydroxypropane-1,3-diyl bis(2-methylpropanoate). To a solution of 2-oxopropane-1,3-diyl bis(2-methylpropanoate) (10 g, 43.4 mmol) in THF (100 mL)/water (10 mL) stirred at 0° C. was added NaBH$_4$ (1.97 g, 52.1 mmol) portionwise. The reaction mixture was stirred at 0° C. for 30 min. TLC traces showed the reaction was completed (pet. ether:EtOAc=1:3, colored by KMnO₄). The reaction mixture was quenched with HCl (1 mmol/L, 100 mL), extracted with EtOAc (80 mL*3). The combined organic layers were dried over Na₂SO₄ and concentrated under vacuum to give the desired product (9 g, 90%, yield: 80%) as a yellow oil. ¹HNMR (400 MHz, Chloroform-d) δ 3.81-4.73 (m, 4H), 2.56-2.71 (m, 2H), 1.18-1.25 (m, 12H).

Step 3: 4-((1,3-bis(isobutyryloxy)propan-2-yl)oxy)-4-oxobutanoic acid. 2-Hydroxypropane-1,3-diyl bis(2-methylpropanoate) (10 g, 43.1 mmol) was dissolved in dichloromethane (DCM) (30 mL)/THF (30 mL)/Pyridine (30 mL), dihydrofuran-2,5-dione (8.62 g, 86 mmol) and DMAP (0.53 g, 4.31 mmol) were added, the resulting mixture was stirred for 6.5 hours at 60° C. LCMS indicated completion of reaction. The reaction mixture was quenched with HCl (1 M, 80 mL), extracted with EtOAc (80 mL*3). The combined organic layers were dried over Na₂SO₄ and concentrated under vacuum. The residue was purified by flash chromatography (silica gel, 330 g, pet. ether:EtOAc=3:2) to give the title compound (13 g, 95%, yield: 86%) as a colorless oil. LCMS (ESI) m/z calcd for C₁₅H₂₄O₈: 332 Found: 355 (M+Na)⁺. ¹HNMR (400 MHz, Chloroform-d) δ5.27-5.36 (m, 1H), 3.96-4.49 (m, 4H), 2.44-2.80 (m, 6H), 1.17-1.21 (m, 12H).

Step 4: 1,3-bis(isobutyryloxy)propan-2-yl (((2R,3S,5R)-2-ethynyl-5-(2-fluoro-6-(((4-methoxyphenyl) diphenylmethyl)amino)-9H-purin-9-yl)-3-((4-methoxyphenyl)diphenyl-methoxy)tetrahydrofuran-2-yl)methyl) succinate. 4-((1,3-bis(isobutyryloxy)propan-2-yl)oxy)-4-oxobutanoic acid (397 mg, 1.19 mmol) was dissolved in DMF (20 mL), DMAP (365 mg, 2.99 mmol) and 3-(((ethylimino)methylene)amino)-N,N-dimethylpropan-1-amine hydrochloride (572 mg, 2.99 mmol) were added, the resulting mixture was stirred for 2 hours at 20° C. Then, ((2R,3S,5R)-2-ethynyl-5-(2-fluoro-6-(((4-methoxyphenyl)diphenyl-methyl)amino)-9H-purin-9-yl)-3-((4-methoxyphenyl)diphenyl-methoxy)tetrahydrofuran-2-yl)methanol (500 mg, 0.60 mmol) was added and the resulting mixture was stirred for overnight at 20° C. LCMS indicated completion of reaction. The reaction was quenched with water (80 mL) and the mixture was extracted with EtOAc (50 mL*3). The combined organic layers were dried over Na₂SO₄ and concentrated under vacuum. The residue was purified by flash chromatography (silica gel, 120 g, pet. ether:EtOAc=1:1) to give the desired product (600 mg, 95%, yield: 83%) as a white solid. LCMS (ESI) m/z calcd for C₆₇H₆₆FN₅O₁₂: 1151. Found: 1152 (M+H)⁺. ¹HNMR (400 MHz, Chloroform-d) δ 7.62 (s, 1H), 7.54-7.57 (m, 4H), 7.38-7.46 (m, 2H), 7.23-7.36 (m, 18H), 7.07 (s, 1H), 6.76-6.88 (m, 4H), 6.11 (dd, J=8.0, 3.6 Hz, 1H), 5.22-5.35 (m, 1H), 4.64 (t, J=8.0 Hz, 1H), 4.26-4.41 (m, 3H), 4.15-4.20 (m, 2H), 3.96-4.06 (m, 1H), 3.79 (d, J=16.4 Hz, 6H), 2.86 (s, 1H), 2.15-2.69 (m, 8H), 1.17-1.25 (m, 12H).

Step 5: ((2R,3S,5R)-5-(6-amino-2-fluoro-9H-purin-9-yl)-2-ethynyl-3-hydroxytetrahydro-furan-2-yl)methyl (1,3-bis(isobutyryloxy)propan-2-yl) succinate. To a solution of 1,3-bis(isobutyryloxy) propan-2-yl (((2R,3S,5R)-2-ethynyl-5-(2-fluoro-6-(((4-methoxy-phenyl)diphenylmethyl)amino)-9H-purin-9-yl)-3-((4-methoxyphenyl)diphenylmethoxy) tetrahydrofuran-2-yl)methyl) succinate (600 mg, 0.52 mmol) in DCM (10 mL) stirred at 15° C. was added TFA (1 ml) dropwise. The reaction mixture was stirred at 15° C. for 1 hour. LCMS indicated completion of reaction. The reaction mixture was quenched with saturated NaHCO₃ aq (30 ml), and extracted with DCM (15 ml*2). The combined organic phases were washed with brine (15 ml) and concentrated under vacuum. The residue was purified by Prep-HPLC purification (Column: XBridge Prep OBDC18 Column, 19*250 mm, 5 um; Mobile Phase A: Water (10 MMOL/L NH₄HCO₃+0.1% NH₃·H₂O), Mobile Phase B: ACN; Flow rate: 25 mL/min; Gradient: 35 B to 57 B in 11 min; 254 nm; RT:9.13 min). The collected fraction (RT: 9.13 min) was lyophilized to give the desired product (103 mg, 98.2%, yield: 32%) as a white solid. LCMS (ESI) m/z calcd for C₂₇H₃₄FN₅O₁₀: 607. Found: 608 (M+H)⁺. ¹HNMR (400 MHz, DMSO-d₆) δ 8.27 (s, 1H), 7.85 (br, s, 2H), 6.25 (dd, J=8.0, 4.4 Hz, 1H), 5.80 (d, J=5.2, 1H), 5.17 (dd, J=6.4, 4.0 Hz, 1H), 4.68 (dd, J=13.2, 7.6 Hz, 1H), 4.39 (d, J=11.6, 1H), 4.26-4.09 (m, 5H), 3.62 (s, 1H), 2.80-2.73 (m, 1H), 2.54-2.47 (m, 7H), 1.05 (d, J=6.4 Hz, 12H).

Example 58: (2R,3S,5R)-5-(6-amino-2-fluoro-9H-purin-9-yl)-2-((dodecanoyloxy)methyl)-2-ethynyltetrahydrofuran-3-yl Dodecanoate

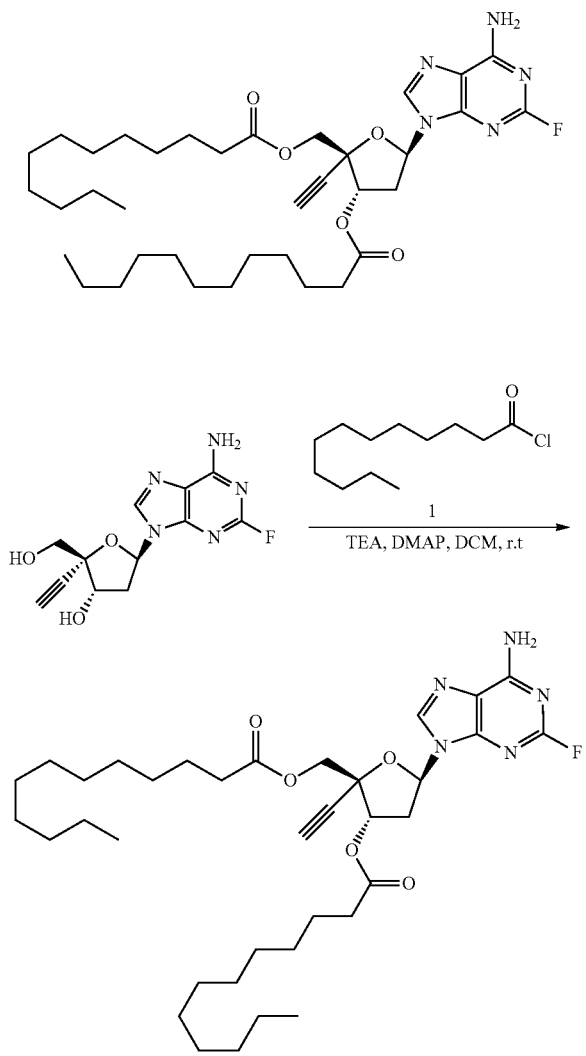

To a stirred mixture of (2R,3S,5R)-5-(6-amino-2-fluoro-9H-purin-9-yl)-2-ethynyl-2-(hydroxymethyl)tetrahydrofuran-3-ol (500 mg, 1.705 mmol), Et3N (0.951 mL, 6.82 mmol) and DMAP (41.7 mg, 0.341 mmol) in DCM (30 mL) was added dodecanoyl chloride (783 mg, 3.58 mmol) dropwise. The reaction mixture was stirred at room temperature for 2 h. LCMS indicated completion of reaction. The reaction was quenched with water (50 ml), and extracted with DCM (3×50 ml). The combined organic phases were dried over sodium sulphate and concentrated under reduced pressure to afford crude product as a yellow solid. The sample was further purified on a silica column (120 g) using 0%-80% EtOAc/pet. ether solvent gradient over 80 mins, Flow rate: 70 mL/min. The appropriate fractions containing desired product were identified by UV absorbance (254 nm), combined and evaporated in vacuo to give white solid. The solid was triturated with ACN (15 ml), stirred at room temperature overnight. The resulting solid was filtered through a Buchner funnel, rinsed with ACN, dried under sun lamp for 1 h, and was put in a cool dry place overnight. Then the solid was collected to give (2R,3S,5R)-5-(6-amino-2-fluoro-9H-purin-9-yl)-2-((dodecanoyloxy)methyl)-2-ethynyltetrahydrofuran-3-yl dodecanoate (520 mg, 0.783 mmol, 45.9% yield) as a white solid. LCMS (ESI) m/z calcd for $C_{36}H_{56}FN_5O_5$:657. Found: 658 (M+H)$^+$. $^1$HNMR (400 MHz, Chloroform-d) δ 7.95 (s, 1H), 6.40 (t, J=6.4 Hz, 1H), 6.09 (br s, 2H), 5.65 (dd, J=7.2, 5.6 Hz, 1H), 4.49 (d, J=12.0 Hz, 1H), 4.39 (d, J=12.0 Hz, 1H), 2.95-3.02 (m, 1H), 2.66-2.75 (m, 2H), 2.30-2.43 (m, 4H), 1.57-1.69 (m, 4H), 1.17-1.40 (m, 32H), 0.85-0.90 (m, 6H).

Example 59: (2R,3S,5R)-5-(6-amino-2-fluoro-9H-purin-9-yl)-2-ethynyl-2-((palmitoyloxy)methyl)tetrahydrofuran-3-yl Palmitate

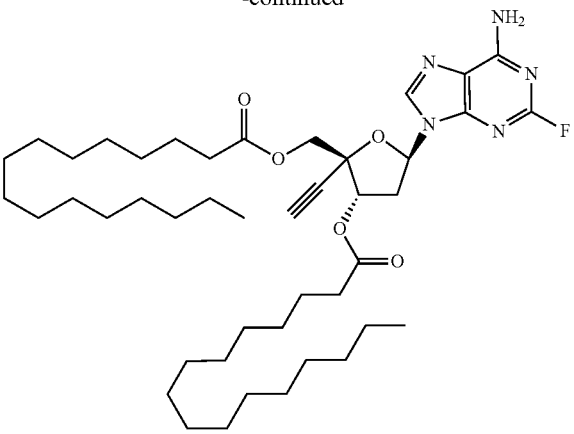

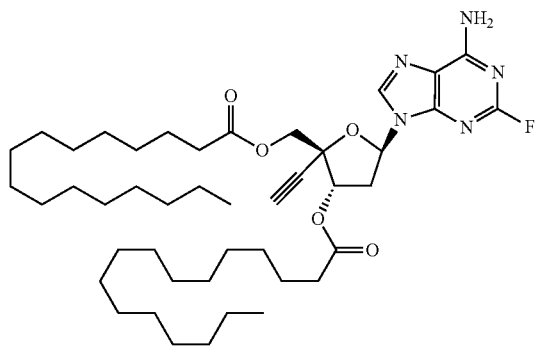 [SMILES: C#C[C@]1(COC(=O)CCCCCCCCCCCCCCC)O[C@@H](n2cnc3c(N)nc(F)nc32)C[C@@H]1OC(=O)CCCCCCCCCCCCCCC]

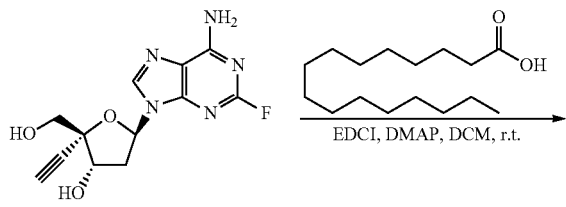

To the stirred mixture of (2R,3S,5R)-5-(6-amino-2-fluoro-9H-purin-9-yl)-2-ethynyl-2-(hydroxymethyl)tetrahydrofuran-3-ol (600 mg, 2.046 mmol) in DCM (60 mL) was added Et3N (1.426 mL, 10.23 mmol), DMAP (50.0 mg, 0.409 mmol) and palmitoyl chloride (1406 mg, 5.11 mmol) at 0° C. The reaction mixture was stirred for 3 h at room temperature. LCMS showed presence 75% of desired product. The reaction mixture was quenched with water (20 mL) and extracted with DCM (20 mL*3). The combined organic layers were washed with water (20 mL), brine (20 mL), dried over Na$_2$SO$_4$. After filtration, the mixture was concentrated to dryness under vacuum. The residue was purified by silica gel column (120 g, pet. ether:EtOAc=1:1) to afford (2R,3S,5R)-5-(6-amino-2-fluoro-9H-purin-9-yl)-2-ethynyl-2-((palmitoyloxy)methyl)tetrahydro-furan-3-yl palmitate (520 mg) as white solid. The solid was crystallized in pentane:EtOAc=10:1 (10 mL) to give a crystal form, which was dried under sun lamp (45° C.) for 2 h to afford (2R,3S,5R)-5-(6-amino-2-fluoro-9H-purin-9-yl)-2-ethynyl-2-((palmitoyloxy)methyl)tetrahydrofuran-3-yl palmitate (428 mg, 0.546 mmol, 26.7% yield) as while crystal solid. LCMS (ESI) m/z calcd for $C_{44}H_{72}FN_5O_5$: 770. Found: 793 (M+23)+, 771 (M+1)$^+$. $^1$HNMR (300 MHz, CDCl$_3$) δ 7.97 (s, 1H), 6.42 (t, J=6.3 HZ, 1H), 5.95 (brs, 2H), 5.69-5.65 (m, 1H), 4.53-4.39 (m, 2H), 3.04-2.99 (m, 1H), 2.75-2.68 (m, 2H), 2.46-2.34 (m, 4H), 1.72-1.61 (m, 4H), 1.42-1.18 (m, 48H), 0.99-0.83 (m, 6H).

Example 60: (2R,3S,5R)-5-(6-amino-2-fluoro-9H-purin-9-yl)-2-ethynyl-2-((icosanoyloxy)methyl)tetrahydrofuran-3-yl Icosanoate

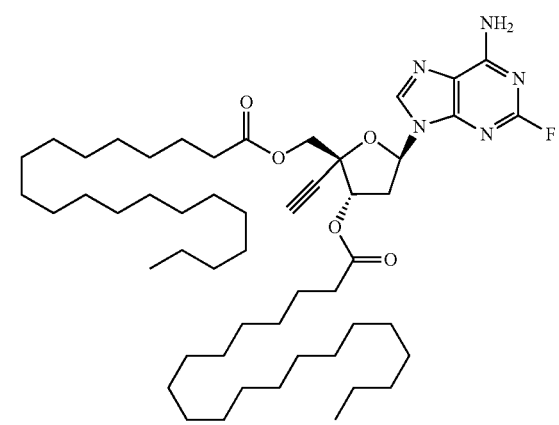 [SMILES: C#C[C@]1(COC(=O)CCCCCCCCCCCCCCCCCCC)O[C@@H](n2cnc3c(N)nc(F)nc32)C[C@@H]1OC(=O)CCCCCCCCCCCCCCCCCCC]

To the mixture of icosanoic acid (2.66 g, 8.52 mmol) in DCM (100 mL) was added EDC (2.61 g, 13.64 mmol). The reaction mixture was stirred for 30 min at 25° C. Then (2R,3S,5R)-5-(6-amino-2-fluoro-9H-purin-9-yl)-2-ethynyl-2-(hydroxymethyl)tetrahydro-furan-3-ol (1.0 g, 3.41 mmol), DMAP (0.833 g, 6.82 mmol)) and DIEA (5.96 mL, 34.1 mmol) were added. The reaction mixture was stirred for overnight at 25° C. LCMS showed no desired mass but a new spot was found by TLC (pet. ether:EtOAc=1:1, rf=0.8). The reaction mixture was quenched with water (100 mL), extracted with DCM (50 mL*3). The combined organic layers were washed with water (100 mL), brine (100 mL), dried over Na2SO4. After filtration, the filtrate was concentrated to dryness under vacuum. The residue was purified by silica gel (330 g, pet. ether:EtOAc=1:1) to afford (2R,3S,5R)-5-(6-amino-2-fluoro-9H-purin-9-yl)-2-ethynyl-2-((icosanoyloxy)methyl)tetra-hydrofuran-3-yl icosanoate (570 mg) as white solid. The solid (500 mg) was dissolved in DCM (250 mL) and MeOH (75 mL), allowed to stand for 3 days at rt and solids collected by filtration to title compound (260 mg) as irregular crystals. The solid was dried under sun lamp (45° C.) for 2 h. LCMS: (ESI) m/z calcd for $C_{52}H_{88}FN_5O_5$: 631. Found: 883 (M+1)+, 905 (M+23)+. $^1$HNMR (300 MHz, CDCl$_3$) δ 7.95 (s, 1H), 6.42 (t, J=6.3 Hz, 1H), 6.05 (br s, 2H), 5.68 (t, J=5.4 Hz, 1H), 4.52 (d, J=12 Hz, 1H), 4.41 (d, J=12 Hz, 1H), 3.07-2.98 (m, 1H), 2.78-2.67 (m, 2H), 2.46-2.34 (m, 4H), 1.69-1.60 (m, 4H), 1.36-1.23 (m, 64H), 0.90 (t, J=6.3 Hz, 3H).

Example 61: (2R,3S,5R)-5-(6-amino-2-fluoro-9H-purin-9-yl)-2-ethynyl-2-((undecanoyloxy)methyl)tetrahydrofuran-3-yl Undecanoate

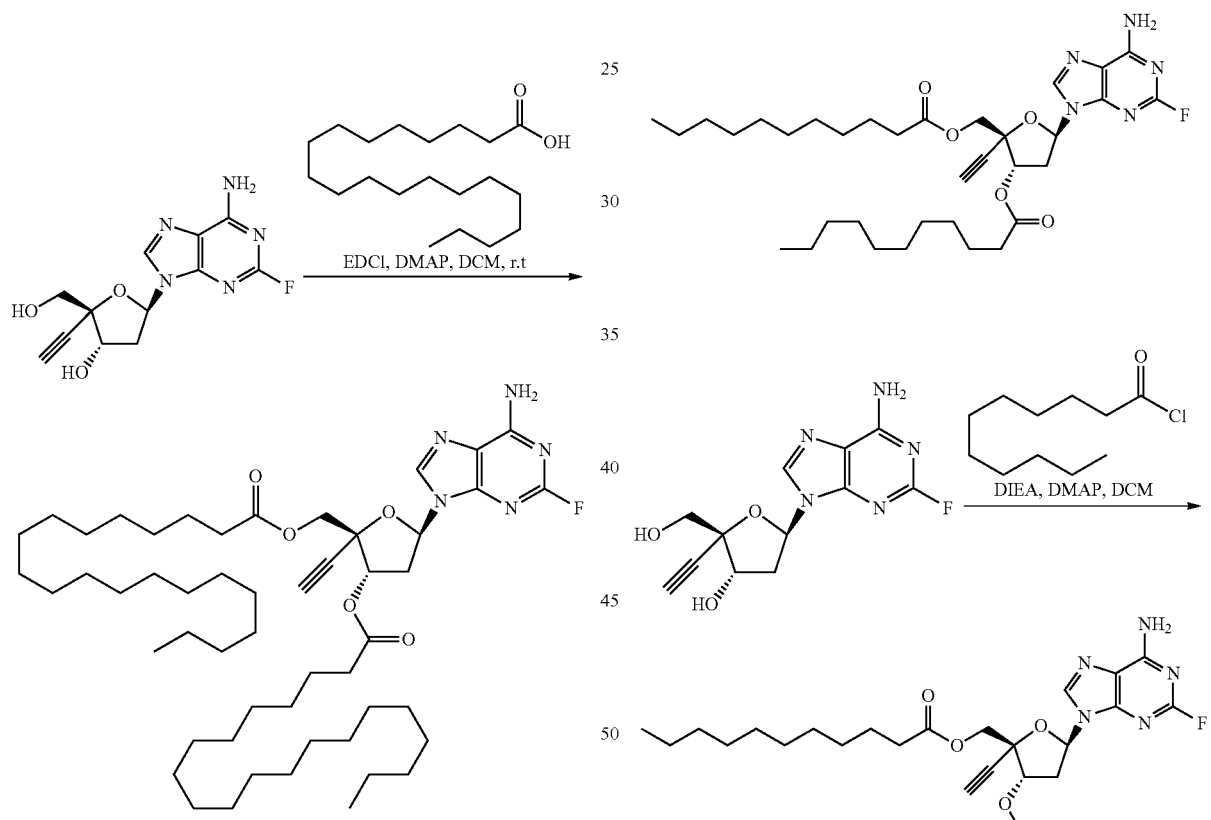

To the mixture of (2R,3S,5R)-5-(6-amino-2-fluoro-9H-purin-9-yl)-2-ethynyl-2-(hydroxymethyl)tetrahydrofuran-3-ol (600 mg, 2.046 mmol), Et3N (1.141 mL, 8.18 mmol) and DMAP (50.0 mg, 0.409 mmol) in DCM (15 mL) was added undecanoyl chloride (1.3 g, 6.35 mmol) dropwise. The reaction mixture was stirred at r.t. for 2 hours. LCMS indicated completion of reaction. The reaction mixture was diluted with water (10 mL), extracted with DCM (10 mL×3). The organic phases were combined, washed with brine (10 mL), dried over Na2SO4, and concentrated under vacuum. The residue was purified by gel silica column (80 g, EtOAc:

pet. ether=1:1) to give the desired product (purity:97%) as a white solid. The solid was triturated with EtOAc (20 ml×3). The resulting solid was filtered through a Buchner funnel, rinsed with EtOAc, dried sun lamp (T=50° C.) for 6 h, and was put in a cool dry place overnight to give (2R,3S,5R)-5-(6-amino-2-fluoro-9H-purin-9-yl)-2-ethynyl-2-((undecanoyloxy)methyl)tetrahydro-furan-3-yl undecanoate (560 mg, 99.59%, 42.7% yield) as a white solid. LCMS (ESI) m/z calcd for $C_{34}H_{52}FN_5O_5$:629. Found: 630 (M+H)$^+$. $^1$HNMR (400 MHz, Chloroform-d) δ 7.95 (s, 1H), 6.40 (t, J=6.0 Hz, 1H), 6.05 (br, s, 2H), 5.65 (dd, J=5.2, 6.8 Hz, 1H), 4.48 (d, J=12.0 Hz, 2H), 4.39 (d, J=12.0 Hz, 1H), 3.03-2.96 (m, 1H), 2.74-2.66 (m, 1H), 2.43-2.30 (m, 4H), 1.70-1.57 (m, 4H), 1.39-1.18 (m, 28H), 0.90-0.85 (m, 6H).

Example 62: (2R,3aS,26aR)-2-(6-amino-2-fluoro-9H-purin-9-yl)-26a-ethynyldocosahydro-2H-furo[3,2-b][1,5]dioxacyclopentacosine-5,24-dione To a solution of 20-(((2R,3S,5R)-5-(6-amino-2-fluoro-9H-purin-9-yl)-2-ethynyl-3-hydroxytetrahydrofuran-2-yl)methoxy)-20-oxoicosanoic acid (1.0 g, 1.456 mmol) in ACN (10 mL) and DCM (10 mL) was added TCFH (1.134 g, 4.05 mmol) and NMI (356 mg, 4.86 mmol). The mixture was stirred at r.t. overnight. The LCMS trace showed the reaction was completed. The mixture was concentrated under vacuum and purified by silica gel (80 g, EtOAc/pet. ether=2/1) to give the crude product (500 mg). The crude product was purified by reversed phase (C18, 120 g, A:water (0.05% TFA), B: ACN: 20% to 100% in 60 min, 254/220 nm), then re-crystallized from (DCM/EtOAc=2/1) to give (2R,3aS,26aR)-2-(6-amino-2-fluoro-9H-purin-9-yl)-26a-ethynyl-docosahydro-2H-furo[3,2-b][1,5]dioxacyclopentacosine-5,24-dione (272.4 mg, 99.5%, yield 27.1%) as a white solid. LCMS (ESI) m/z calcd for $C_{32}H_{46}FN_5O_6$: 599 Found: 600 (M+H)$^+$. $^1$HNMR: (400 MHz, DMSO-d$_6$) δ 8.341 (s, 1H), 7.915-7.894 (brs, 2H), 6.376-6.344 (t, J=6.4 Hz, 1H), 5.737-5.709 (t, J=5.6 Hz, 1H), 4.392 (d, J=11.2 Hz, 1H), 4.267 (d, J=11.2 Hz, 1H), 3.713 (s, 1H), 3.172-3.106 (m, 1H), 2.633-2.584 (m, 1H), 2.443-2.225 (m, 4H), 1.587-1.533 (m, 4H), 1.266-1.243 (m, 28H).

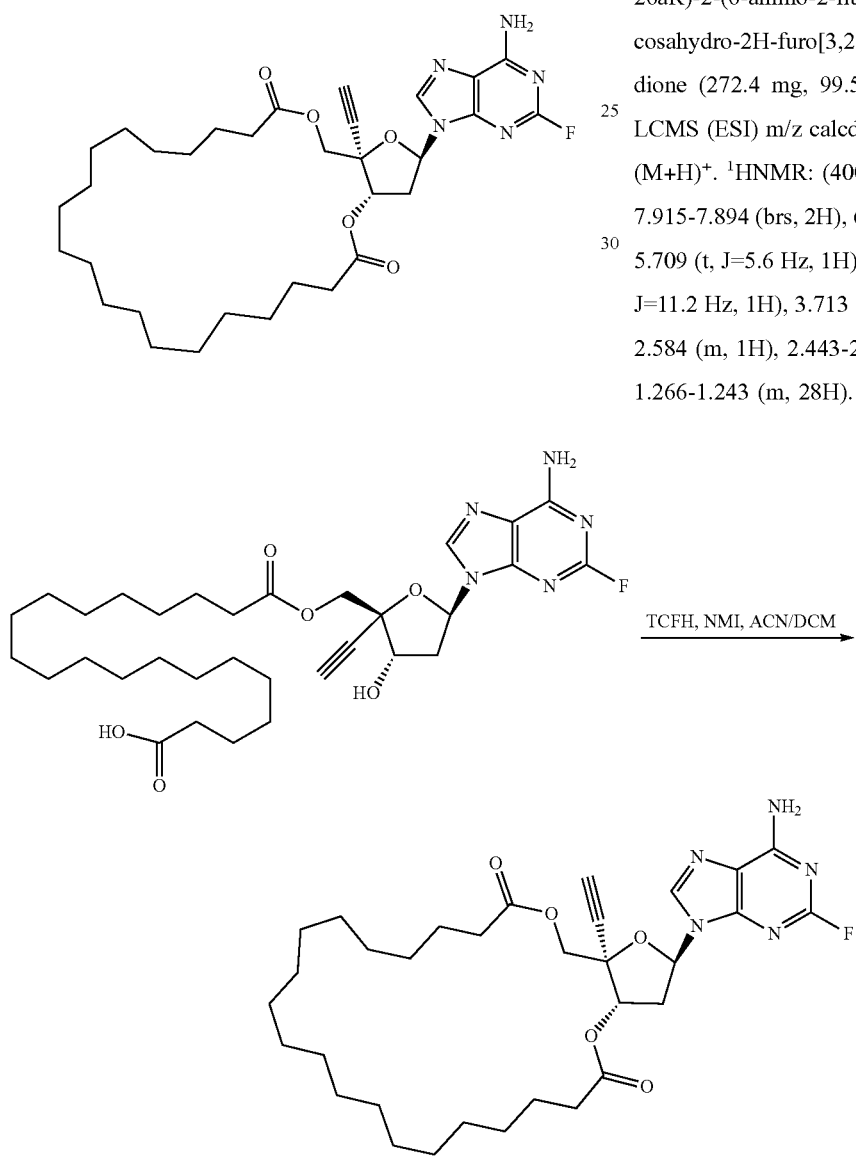

Example 63: (2R,3S,5R)-5-(6-amino-2-fluoro-9H-purin-9-yl)-2-ethynyl-2-((hexanoyloxy)methyl)tetrahydrofuran-3-yl Hexanoate

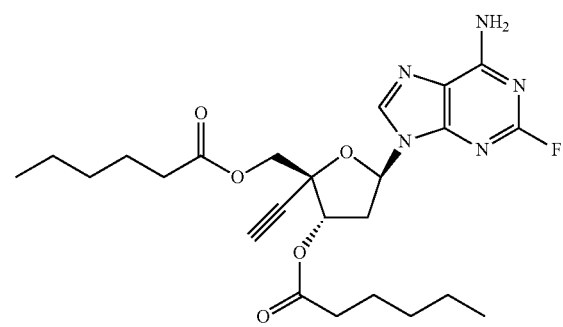 [SMILES: C#C[C@]1(COC(=O)CCCCC)O[C@@H](n2cnc3c(N)nc(F)nc32)C[C@@H]1OC(=O)CCCCC]

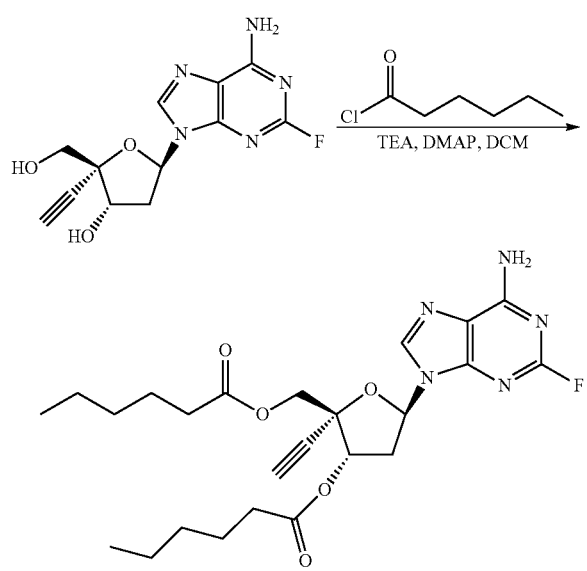

To the mixture of (2R,3S,5R)-5-(6-amino-2-fluoro-9H-purin-9-yl)-2-ethynyl-2-(hydroxymethyl)tetrahydrofuran-3-ol (800 mg, 2.73 mmol), Et3N (1.901 mL, 13.64 mmol) and DMAP (167 mg, 1.364 mmol) in DCM (20 mL) stirred at room temperature was added hexanoyl chloride (1102 mg, 8.18 mmol) dropwise and stirred at for 1 hour. LCMS indicated completion of reaction. The reaction mixture was diluted with water (10 mL), extracted with DCM (10 mL×3). the organic phases were combined, washed with brine (10 mL), dried over Na2SO4, and concentrated under vacuum. The residue was purified by gel silica column (80 g, EtOAc: pet. ether=1:1) to give the desired product as a yellow solid. The solid was triturated with EtOAc (10 ml) and stirred for 16 h, the resulting solid was filtered through a Buchner funnel, rinsed with EtOAc, dried beside sun lamp (T=50° C.) for 6 h, and was put in a cool dry place overnight to give (2R,3S,5R)-5-(6-amino-2-fluoro-9H-purin-9-yl)-2-ethynyl-2-((hexanoyloxy)methyl)tetra-hydrofuran-3-yl hexanoate (215 mg, 98.05% purity, 15.79% yield) as a white solid. LCMS (ESI) m/z calcd for $C_{24}H_{32}FN_5O_5$:489. Found: 490 (M+H)+. 1HNMR (400 MHz, Chloroform-d) δ 8.70 (s, 1H), 6.46 (d, J=5.6 Hz, 1H), 5.51 (d, J=5.2 Hz, 1H), 4.55 (d, J=12.0 Hz, 1H), 4.42 (d, J=12.0 Hz, 1H), 2.92 (s, 2H), 2.74 (s, 1H), 2.46-2.33 (m, 4H), 1.75-1.55 (m, 6H), 1.40-1.25 (m, 8H), 0.97-0.85 (m, 6H).

Example 64: (2R,3S,5R)-5-(6-amino-2-fluoro-9H-purin-9-yl)-2-ethynyl-2-((nonanoyloxy)methyl)tetrahydrofuran-3-yl Nonanoate

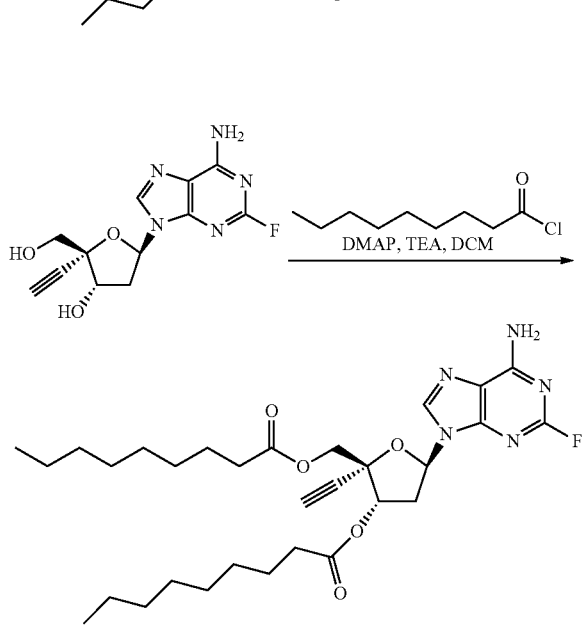

To a stirred mixture of (2R,3S,5R)-5-(6-amino-2-fluoro-9H-purin-9-yl)-2-ethynyl-2-(hydroxy-methyl)tetrahydrofuran-3-ol (500 mg, 1.705 mmol) in DCM (4 mL) was added DMAP (83 mg, 0.682 mmol), triethylamine (863 mg, 8.52 mmol) and nonanoyl chloride (753 mg, 4.26 mmol) at 0° C. The reaction mixture was stirred for 6 h at room temperature. LCMS showed 49% of desired product. The reaction mixture was quenched with water (10 mL), extracted with DCM (3*10 mL). The combined organic layers were washed with brine and dried over $Na_2SO_4$. After filtration, the filtrate was concentrated to dryness in vacuum. The residue was purified by silica gel column (40 g, pet. ether:EtOAc=1:1) to afford (2R,3S,5R)-5-(6-amino-2-fluoro-9H-purin-9-yl)-2-ethynyl-2-((nonanoyloxy)methyl)tetrahydrofuran-3-yl nonanoate as a yellow oil. Then, the product was re-crystallized from EtOAc/Hexane in the ratio of 1:1. The solid was collected by filtration, dried under sun lamp (45° C.) to afford (2R,3S,5R)-5-(6-amino-2-fluoro-9H-purin-9-yl)-2-ethynyl-2-((nonanoyloxy)methyl)tetrahydrofuran-3-yl nonanoate (262 mg, 0.435 mmol, 25.5% yield) as a white solid. LCMS (ESI) m/z calcd for $C_{30}H_{44}FN_5O_5$:573. Found:

574 (M+1)+. 1HNMR (300 MHz, CDCl3) δ 8.00 (s, 1H), 6.47-6.38 (m, 1H), 6.14-5.80 (m, 2H), 5.64 (t, J=6 Hz, 1H), 4.51-4.38 (m, 2H), 3.04-2.97 (m, 1H), 2.77-2.67 (m, 2H), 2.44-2.32 (m, 4H), 1.69-1.50 (m, 4H), 1.48-1.28 (m, 20H), 0.95-0.85 (m, 6H).

Example 65: (2R,3S,5R)-5-(6-amino-2-fluoro-9H-purin-9-yl)-2-ethynyl-2-((octanoyloxy)methyl)tetra-hydrofuran-3-yl Octanoate

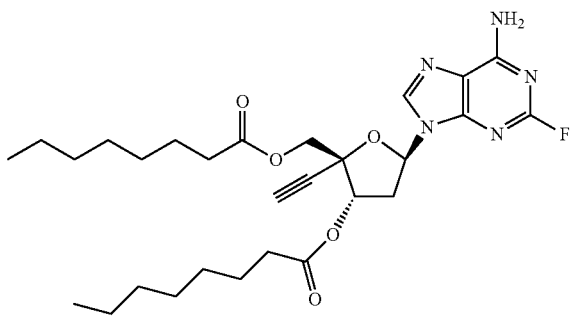 [SMILES: C#C[C@]1(COC(=O)CCCCCCC)O[C@@H](n2cnc3c(N)nc(F)nc32)C[C@@H]1OC(=O)CCCCCCC]

To a solution of (2R,3S,5R)-5-(6-amino-2-fluoro-9H-purin-9-yl)-2-ethynyl-2-(hydroxy-methyl) tetrahydrofuran-3-ol (800 mg, 2.73 mmol), Et3N (1.141 mL, 8.18 mmol) and DMAP (66.7 mg, 0.546 mmol) in DCM (8 mL) stirred under nitrogen at 0° C. was added octanoyl chloride (1331 mg, 8.18 mmol) dropwise. The reaction mixture was stirred at 0° C. for 2 h. LCMS indicated completion of reaction. The reaction mixture was quenched with water and extracted with DCM (20 mL). The organic phases were washed with water 50 mL, dried over sodium sulphate and evaporated in vacuo to give the crude products as a yellow oil. The crude product was added to a gel silica column (120 g, wet method) and was eluted with Hex/EtOAc (0-30%). Collected fractions:evaporated in vacuo to give (2R,3S,5R)-5-(6-amino-2-fluoro-9H-purin-9-yl)-2-ethynyl-2-((octanoyloxy)methyl)tetra-hydrofuran-3-yl octanoate (233.1 mg, purity:99.1%, yield:15.52%) as a white solid. The solid in ACN:water=1:1 (5 mL) was stirred at room temperature for 1 hour to obtain crystalline material. LCMS (ESI) m/z calcd for $C_{26}H_{40}FN_5O_5$:545. Found: 546 (M+1)+. 1HNMR (300 MHz, DMSO-d6) δ 8.32 (s, 1H), 7.89 (s, 2H), 6.34 (t, J=6.6 Hz, 1H), 5.69 (t, J=5.7 Hz, 1H), 4.41 (d, J=11.4 Hz, 1H), 4.23 (d, J=11.7 Hz, 1H), 3.78 (s, 1H), 3.32-3.10 (m, 1H), 2.65-2.56 (m, 1H), 2.41-2.31 (m, 2H), 1.59-1.45 (m, 4H), 1.28-1.20 (m, 16H), 0.92-0.79 (m, 6H).

Example 66: ((2R,3S,5R)-5-(6-amino-2-fluoro-9H-purin-9-yl)-2-ethynyl-3-hydroxytetrahydrofuran-2-yl)methyl 3-(2,4-dimethyl-6-(pivaloyloxy)phenyl)-3-methylbutanoate

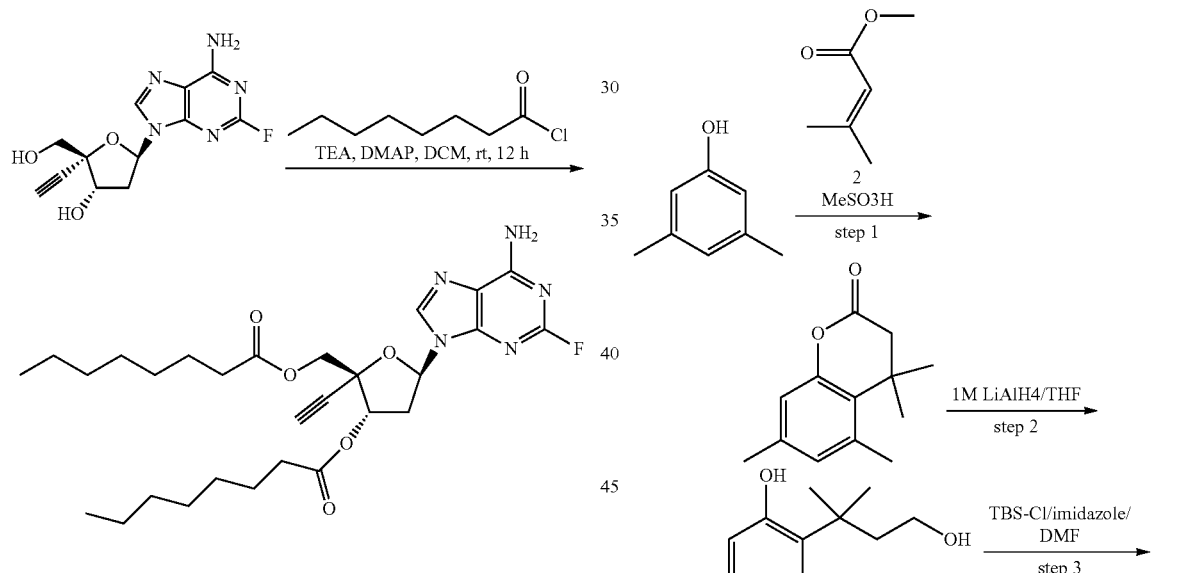

-continued

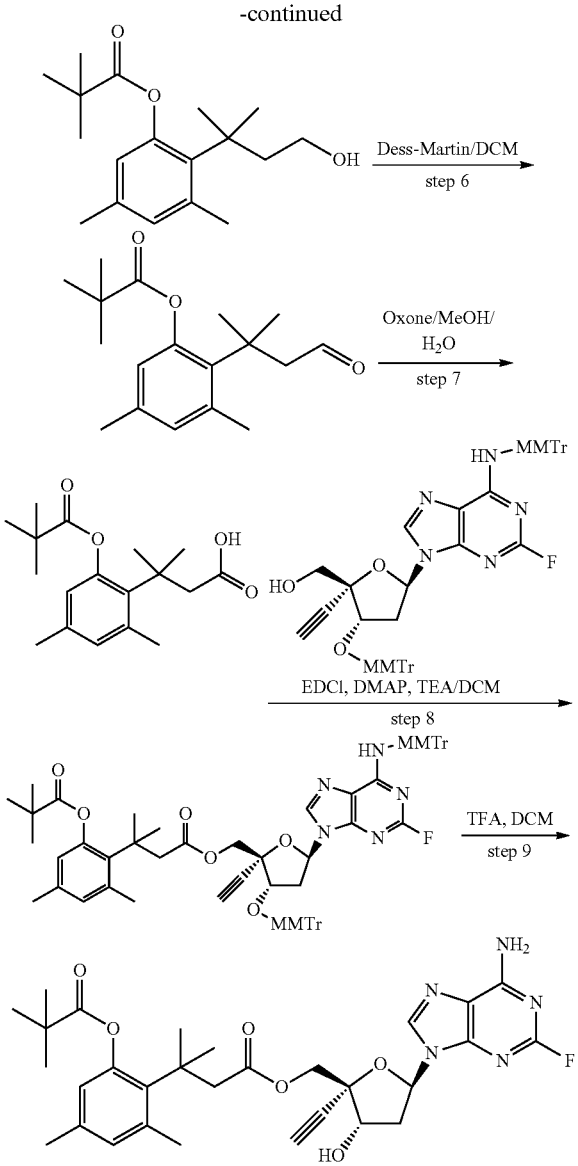

Step 1: 4,4,5,7-tetramethylchroman-2-one. A mixture of 3,5-dimethylphenol (5.0 g, 40.9 mmol) and methyl 3-methylbut-2-enoate (4.67 g, 40.9 mmol) in MeSO$_3$H (25 mL) was stirred at 70° C. for 6 h. Then, the reaction was cooled, diluted with water (30 mL), extracted with ethyl acetate (2*20 mL) and the combined organic extracts were washed with saturated aqueous sodium hydrogencarbonate (2*10 mL) and brine (50 mL). The mixture was concentrated to dryness under vacuum. The residue was purified by silica gel column (80 g, pet. ether:EtOAc=4:1) to afford 4,4,5,7-tetramethylchroman-2-one (8.0 g, 39.2 mmol, 96% yield) as white solid. LCMS (ESI) m/z calcd for $C_{13}H_{16}O_2$: 204. Found: 246 (M+1+ACN)$^+$. $^1$HNMR (300 MHz, CDCl$_3$) δ: 6.76 (s, 2H), 2.61 (s, 2H), 2.48 (s, 3H), 2.29 (s, 3H), 1.46 (s, 6H).

Step 2: 2-(4-hydroxy-2-methylbutan-2-yl)-3,5-dimethylphenol. To a solution of 4,4,5,7-tetramethylchroman-2-one (10 g, 49.0 mmol) in THF (70 mL) was added LiAlH$_4$ (7.43 g, 196 mmol) in portions at 0° C. The reaction mixture was stirred for 12 h at room temperature. LCMS showed the reaction completed. The reaction was quenched with NH$_4$Cl (sat., aq) at 0° C., extracted with EtOAc (200 mL*3). The combine organic layers were washed with brine, dried over Na$_2$SO4. After filtration, the filtrate was concentrated to dryness in vacuum and the resulting crude product was used in the next step without purification. LCMS (ESI) m/z calcd for $C_{13}H_{20}O_2$: 208. Found: 209 (M+1)$^+$.

Step 3: 2-(4-((tert-butyldimethylsilyl)oxy)-2-methylbutan-2-yl)-3,5-dimethylphenol. To a solution of 2-(4-hydroxy-2-methylbutan-2-yl)-3,5-dimethylphenol (10 g, 48.0 mmol) in DMF (100 mL) was added imidazole (8.17 g, 120 mmol) and TBS-Cl (8.68 g, 57.6 mmol) at 25° C. The reaction mixture was stirred for 16 h at room temperature. Then, the reaction mixture was quenched with water (200 mL), extracted with EtOAc (3×100 mL). The combined organic layers were washed with water, brine and dried over Na$_2$SO$_4$. After filtration, the filtrate was concentrated in vacuum. The crude product was purified by silica gel (120 g, pet. ether:EtOAc=20:1) to afford 2-(4-((tert-butyldimethylsilyl)oxy)-2-methylbutan-2-yl)-3,5-dimethylphenol (9 g, 26.5 mmol, 55.2% yield)) as white solid. LCMS (ESI) m/z calcd for $C_{19}H_{34}O_2Si$:322. Found: 323 (M+1)$^+$.

Step 4: 2-(4-((tert-butyldimethylsilyl)oxy)-2-methylbutan-2-yl)-3,5-dimethylphenyl pivalate. To a stirred mixture of 2-(4-((tert-butyldimethylsilyl)oxy)-2-methylbutan-2-yl)-3,5-dimethylphenol (3.0 g, 9.30 mmol) in DCM (30 mL) was added Et3N (1.556 mL, 11.16 mmol), DMAP (0.170 g, 1.395 mmol) and pivaloyl chloride (1.346 g, 11.16 mmol) at 0° C. The reaction mixture was stirred for 6 h at room temperature. Then, the reaction mixture was quenched with water (30 mL), organic layer separated and aqueous layer extracted with DCM (20 mL*3). The combined organic layers were washed with water (20 mL), brine (20 mL) and dried over Na2SO4. After filtration, the filtrate was concentrated to dryness under vacuum. The residue was purified by silica gel column (80 g, pet. ether:EtOAc=4:1) to afford 2-(4-((tert-butyldimethylsilyl)oxy)-2-methylbutan-2-yl)-3,5-dimethylphenyl pivalate (3.4 g, 8.36 mmol, 90% yield) as yellow oil. LCMS (ESI) m/z calcd for $C_{24}H_{42}O_3Si$: 406. Found: 407 (M+1)$^+$.

Step 5: 2-(4-hydroxy-2-methylbutan-2-yl)-3,5-dimethylphenyl pivalate. To a stirred mixture of 2-(4-((tert-butyldimethylsilyl)oxy)-2-methylbutan-2-yl)-3,5-dimethylphenyl pivalate (3.4 g, 8.36 mmol) in THF (35 mL) was added water (35.0 mL) and AcOH (100 mL, 1747 mmol) at room temperature. The reaction mixture was stirred for 6 h at room temperature. Then, the reaction mixture was quenched with water (50 mL) and extracted with DCM (50 mL*3). The combined organic layers were washed with water (20 mL), brine (20 mL) and dried over Na$_2$SO$_4$. After filtration, the filtrate was concentrated to dryness under vacuum. The residue was purified by silica gel column (80 g, pet. ether: EtOAc=3:1) to afford 2-(4-hydroxy-2-methylbutan-2-yl)-3, 5-dimethylphenyl pivalate (2.13 g, 7.28 mmol, 87% yield) as yellow oil. LCMS (ESI) m/z calcd for $C_{18}H_{28}O_3$:292. Found: 293 (M+1)$^+$. $^1$HNMR (300 MHz, CDCl$_3$).δ 6.82 (s, 1H), 6.43 (s, 1H), 3.57 (t, J=6 HZ, 2H), 2.55 (s, 3H), 2.24 (s, 3H), 2.07-2.02 (m, 2H), 1.56 (s, 1H), 1.51 (s, 6H), 1.39 (s, 9H).

Step 6:3,5-dimethyl-2-(2-methyl-4-oxobutan-2-yl)phenyl pivalate. To a stirred mixture of 2-(4-hydroxy-2-methylbutan-2-yl)-3,5-dimethylphenyl pivalate (2.0 g, 6.84 mmol) in DCM (30 mL) was added DMP (5.80 g, 13.68 mmol) at 0° C. The reaction mixture was stirred for 3 h at room temperature. The reaction mixture was quenched with Na$_2$S$_2$O$_3$ (30 ml), NaHCO$_3$ (30 ml) and extracted with DCM (30 mL*3). The combined organic layers were washed with Na$_2$S$_2$O$_3$ (50 mL), NaHCO$_3$ (50 mL), brined (50 mL) and dried over Na₂SO₄. After filtration, the filtrate was concentrated to dryness to afford as yellow oil, which was purified by silica gel column (80 g, pet. ether:EtOAc=5:1) to afford 3,5-dimethyl-2-(2-methyl-4-oxobutan-2-yl)phenyl pivalate (1.6 g, 5.51 mmol, 81% yield) as yellow oil. LCMS (ESI) m/z calcd for $C_{18}H_{26}O_3$: 290. Found: 308 $(M+1+NH_3)^+$.

Step 7: 3-(2,4-dimethyl-6-(pivaloyloxy)phenyl)-3-methylbutanoic acid. To a stirred mixture of 3,5-dimethyl-2-(2-methyl-4-oxobutan-2-yl)phenyl pivalate (1.6 g, 5.51 mmol) in methanol (20 mL) was added water (4.00 mL) and oxone (6.77 g, 11.02 mmol) at 0° C. The reaction mixture was stirred for 6 h at room temperature. The pH was adjusted to 5-6 with saturated aqueous NaHCO₃. Then reaction mixture was concentrated under vacuum. The water was extracted with DCM (30 mL*3). The combined organic layers were washed with water (20 mL), brine (20 mL) and dried over Na₂SO₄. After filtration, the filtrate was concentrated to dryness under vacuum. The residue was purified by silica gel column (80 g, pet. ether:EtOAc=4:1) to afford 3-(2,4-dimethyl-6-(pivaloyloxy)phenyl)-3-methylbutanoic acid (900 mg, 2.94 mmol, 53.3% yield) as white solid. LCMS (ESI) m/z calcd for $C_{18}H_{26}O_4$:306. Found: 324 $(M+1+NH_3)^+$.

Step 8: ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl) methyl 3-(2,4-dimethyl-6-(pivaloyloxy)phenyl)-3-methylbutanoate. To a solution of 3-(2,4-dimethyl-6-(pivaloyloxy)phenyl)-3-methylbutanoic acid (400 mg, 1.305 mmol), 3-(((ethylimino) methylene)amino)-N,N-dimethylpropan-1-amine hydrochloride (501 mg, 2.61 mmol) in DCM (5 mL) stirred at room temperature was added N,N-dimethylpyridin-4-amine (31.9 mg, 0.261 mmol) and Et3N (0.546 mL, 3.92 mmol) at room temperature. The reaction mixture was stirred at room temperature for 1 hr. To the above mixture was added ((2R,3S,5R)-2-ethynyl-5-(2-fluoro-6-(((4-methoxyphenyl)diphenyl-methyl)amino)-9H-purin-9-yl)-3-((4-methoxyphenyl)diphenylmethoxy)tetrahydrofuran-2-yl)methanol (985 mg, 1.175 mmol). The reaction mixture was stirred at room temperature for 16 hr. The reaction mixture was quenched with water (20 mL) and extracted with DCM (3*20 mL). The combined organic layers were washed with brine and dried over Na₂SO₄. After filtration, the filtrate was concentrated to dryness in vacuum. The residue was purified by silica gel column (80 g, DCM:MeOH=1:1) to afford ((2R,3S,5R)-2-ethynyl-5-(2-fluoro-6-(((4-methoxyphenyl)di-phenylmethyl)amino)-9H-purin-9-yl)-3-((4-methoxyphenyl)diphenylmethoxy) tetrahydrofuran-2-yl)methyl 3-(2,4-dimethyl-6-(pivaloyloxy)phenyl)-3-methylbutanoate (1.0 g, 0.888 mmol, 68.0% yield) as yellow oil. LCMS (ESI) m/z calcd for $C_{70}H_{68}FN_5O_8$:1126. Found: 1127 $(M+1)^+$.

Step 9: ((2R,3S,5R)-5-(6-amino-2-fluoro-9H-purin-9-yl)-2-ethynyl-3-hydroxytetrahydro-furan-2-yl)methyl 3-(2,4-dimethyl-6-(pivaloyloxy)phenyl)-3-methylbutanoate. To a stirred mixture of ((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl) methyl 3-(2,4-dimethyl-6-(pivaloyloxy)phenyl)-3-methylbutanoate (1.0 g, 0.888 mmol) in DCM (10 mL) was added TFA (2 mL) at room temperature. The reaction mixture was stirred for 6 h at room temperature. LCMS showed 88% of desired product. The pH of the reaction mixture was adjusted to 6-7 with saturated aqueous NaHCO₃ and extracted with DCM (3*10 mL). The combined organic layers were washed with brine, dried over Na₂SO₄. After filtration, the filtrate was concentrated to dryness in vacuum. The residue was purified by silica gel column (80 g, pet. ether:EtOAc=1:9) to afford ((2R,3S,5R)-5-(6-amino-2-fluoro-9H-purin-9-yl)-2-ethynyl-3-hydroxytetrahydrofuran-2-yl)methyl 3-(2,4-dimethyl-6-(pivaloyloxy)phenyl)-3-methylbutanoate as yellow oil. Then, the product was crystallized from 1:1 EtOAc/Hexane. The solid was collected by filtration and dried under sun lamp (45° C.) to afford ((2R,3S,5R)-5-(6-amino-2-fluoro-9H-purin-9-yl)-2-ethynyl-3-hydroxytetrahydrofuran-2-yl)methyl 3-(2,4-dimethyl-6-(pivaloyloxy)phenyl)-3-methylbutanoate (224 mg, 0.382 mmol, 43.1% yield) as white irregular crystal solid. LCMS (ESI) m/z calcd for $C_{30}H_{36}FN_5O_6$:581. Found: 582 $(M+1)^+$. ¹HNMR (300 MHz, CDCl₃) δ 7.88 (s, 1H), 6.75 (s, 1H), 6.42 (s, 1H), 6.29-6.25 (m, 1H), 6.02 (br s, 2H), 4.27-4.18 (m, 2H), 3.97-3.93 (m, 1H), 3.02 (s, 1H), 2.97 (s, 1H), 2.71-2.56 (m, 7H), 2.19 (s, 3H).1.58 (d, J=6 Hz, 6H), 1.35 (s, 9H).

Example 67: 2-(4-(((2R,3S,5R)-5-(6-amino-2-fluoro-9H-purin-9-yl)-2-ethynyl-3-hydroxytetrahydrofuran-2-yl)methoxy)-2-methyl-4-oxobutan-2-yl)-3,5-dimethylphenyl Decanoate

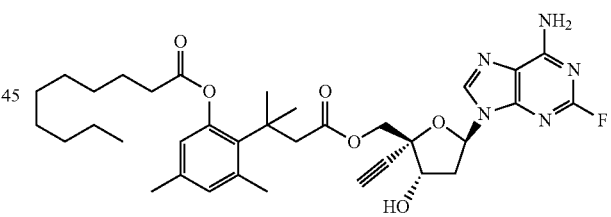

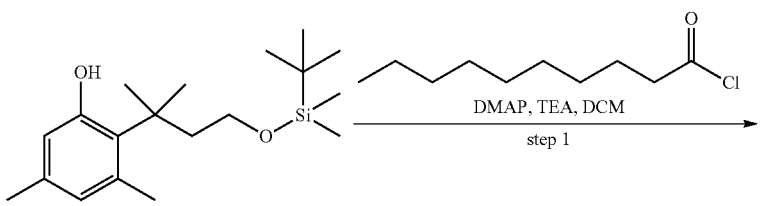
DMAP, TEA, DCM
step 1

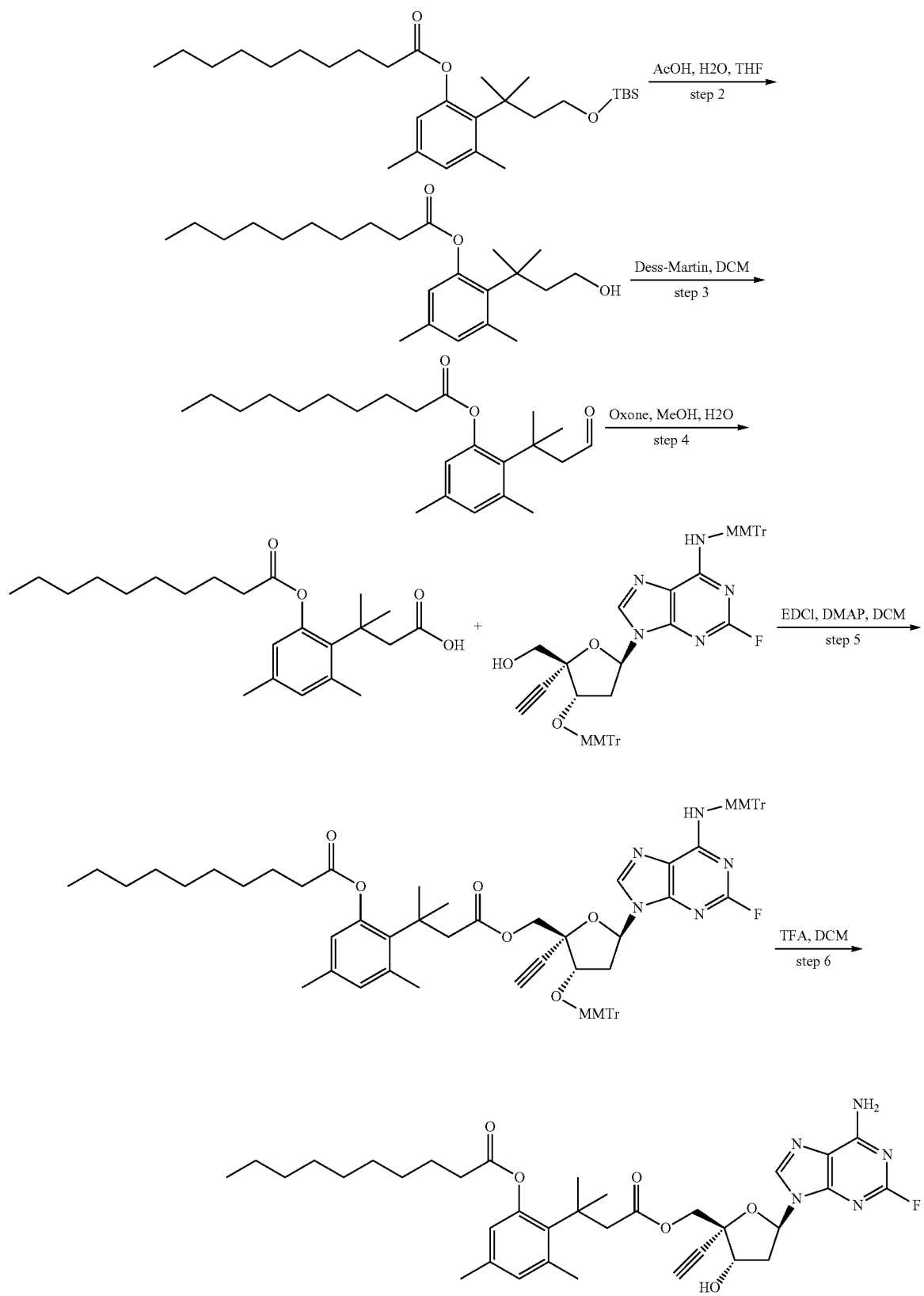

Step 1: 2-(4-((tert-butyldimethylsilyl)oxy)-2-methylbutan-2-yl)-3,5-dimethylphenyl decanoate. To a mixture of 2-(4-((tert-butyldimethylsilyl)oxy)-2-methylbutan-2-yl)-3,5-dimethylphenol (4.5 g, 13.95 mmol), DMAP (0.170 g, 1.395 mmol) and Et3N (2.333 mL, 16.74 mmol) in DCM (45 mL) was added decanoyl chloride (3.19 g, 16.74 mmol) at 0° C. The reaction mixture was stirred for 5 hours at room temperature. LCMS indicated completion of reaction. The reaction mixture was quenched with water (50 mL) and extracted with DCM (3*50 mL). The combined organic layers were washed with brine and dried over $Na_2SO_4$. After filtration, the filtrate was concentrated to dryness in vacuum. The residue was purified by silica gel (120 g, pet. ether:EtOAc=8:1) to afford 2-(4-((tert-butyldimethylsilyl)oxy)-2-methylbutan-2-yl)-3,5-dimethylphenyl decanoate (5.5 g, 11.53 mmol, 83% yield) as colorless oil. LCMS (ESI) m/z calcd for $C_{29}H_{52}O_3Si$: 476. Found: 477 $(M+H)^+$.

Step 2: 2-(4-hydroxy-2-methylbutan-2-yl)-3,5-dimethylphenyl decanoate. To a mixture of 2-(4-((tert-butyldimethylsilyl)oxy)-2-methylbutan-2-yl)-3,5-dimethylphenyl decanoate (3 g, 6.29 mmol) in THF (5 mL) and water (5.00 mL) was added acetic Acid (15.00 mL) at 25° C. The reaction mixture was stirred for 5 hours at 25° C. LCMS indicated completion of reaction. The reaction mixture was quenched with water (30 mL) and extracted with EtOAc (3*30 mL). The combined organic layers were washed with $NaHCO_3$ (aq, 30 mL*2), brine (30 mL) and dried over $Na_2SO_4$. After filtration, the filtrate was concentrated to dryness in vacuum. The residue was purified by gel silica column (80 g, pet. ether:EtOAc=6:1) to give 2-(4-hydroxy-2-methylbutan-2-yl)-3,5-dimethylphenyl decanoate (1.5 g, 3.72 mmol, 59.2% yield) as colorless oil. LCMS (ESI) m/z calcd for $C_{23}H_{33}O_3$: 362. Found: 426 $(M+23+ACN)^+$. $^1$HNMR (400 MHz, Chloroform-d) δ 6.82 (d, J=2.0 Hz, 1H), 6.52 (d, J=2.0 Hz, 1H), 3.54 (t, J=7.2 Hz, 2H), 2.57-2.50 (m, 5H), 2.23 (s, 3H), 2.05 (t, J=7.2 Hz, 2H), 1.81-1.69 (m, 2H), 1.48 (s, 6H), 1.45-1.23 (m, 12H), 0.92-0.84 (m, 3H).

Step 3: 3,5-dimethyl-2-(2-methyl-4-oxobutan-2-yl)phenyl decanoate. To a mixture of 2-(4-hydroxy-2-methylbutan-2-yl)-3,5-dimethylphenyl decanoate (1.5 g, 4.14 mmol) in DCM (30 mL) was added Dess-Martin periodinane (3.51 g, 8.27 mmol) at 25° C. The reaction mixture was stirred for 4 hours at 25° C. LCMS indicated completion of reaction. The reaction mixture was quenched with $Na_2S_2O_3$ (aq, 30 mL), $NaHCO_3$ (aq, 30 mL) and extracted with DCM (3*50 mL). The combined organic layers were concentrated to dryness in vacuum. The residue was purified by silica gel (pet. ether:EtOAc=10:1) to afford 3,5-dimethyl-2-(2-methyl-4-oxobutan-2-yl)phenyl decanoate (910 mg, 2.272 mmol, 54.9% yield) as yellow oil. LCMS (ESI) m/z calcd for $C_{23}H_{36}O_3$: 360. Found: 378 $(M+1+NH_3)^+$.

Step 4: 3-(2-(decanoyloxy)-4,6-dimethylphenyl)-3-methylbutanoic acid. To a mixture of 3,5-dimethyl-2-(2-methyl-4-oxobutan-2-yl)phenyl decanoate (910 mg, 2.52 mmol) in methanol (60 mL) and water (12.00 mL) was added oxone (3103 mg, 5.05 mmol) at 0° C. The reaction mixture was stirred for 12 hours at 25° C. LCMS indicated completion of reaction. The reaction mixture was extracted with ethyl acetate (3*80 mL). The combined organic phases were washed with water and saturated brine, dried over sodium sulphate and evaporated in vacuum to give the crude product as yellow oil. The residue was purified by gel silica column (80 g, pet. ether:EtOAc=1:1) to give 3-(2-(decanoyloxy)-4,6-dimethylphenyl)-3-methylbutanoic acid (450 mg, 1.076 mmol, 42.6% yield) as yellow oil. LCMS (ESI) m/z calcd for $C_{23}H_{36}O_4$: 376. Found: 394 $(M+1+NH_3)^+$. $^1$HNMR (400 MHz, Chloroform-d) δ 6.80 (d, J=2.0 Hz, 1H), 6.56 (d, J=2.0 Hz, 1H), 2.83 (s, 2H), 2.59-2.51 (m, 5H), 2.22 (s, 3H), 1.80-1.70 (m, 2H), 1.56 (s, 6H), 1.44-1.22 (m, 12H), 0.95-0.85 (m, 3H).

Step 5: 2-(4-(((2R,3S,5R)-2-ethynyl-5-(2-fluoro-6-(((4-methoxyphenyl)diphenylmethyl) amino)-9H-purin-9-yl)-3-((4-methoxyphenyl)diphenylmethoxy)tetrahydrofuran-2-yl)methoxy)-2-methyl-4-oxobutan-2-yl)-3,5-dimethylphenyl decanoate. To a solution of 3-(2-(decanoyloxy)-4,6-dimethylphenyl)-3-methylbutanoic acid (400 mg, 1.062 mmol), 3-(((ethylimino)methylene)amino)-N,N-dimethylpropan-1-amine hydrochloride (407 mg, 2.125 mmol) in DCM (5 mL) stirred at room temp was added N,N-dimethylpyridin-4-amine (260 mg, 2.125 mmol). The reaction mixture was stirred at room temperature for 1 hour. To the above mixture was added ((2R,3S,5R)-2-ethynyl-5-(2-fluoro-6-(((4-methoxyphenyl) diphenylmethyl)amino)-9H-purin-9-yl)-3-((4-methoxyphenyl)diphenylmethoxy)tetrahydro-furan-2-yl)methanol (801 mg, 0.956 mmol). The reaction mixture was stirred at room temperature for 24 hours. LCMS indicated completion of reaction. The reaction mixture was quenched with water and extracted with dichloromethane 20 mL. The combined organic phases were washed with saturated brine 10 mL, dried over sodium sulphate and evaporated in vacuum to give the crude product as colorless oil. The residue was purified by gel silica column (40 g, pet. ether:EtOAc=1:1) to give 2-(4-(((2R,3S,5R)-2-ethynyl-5-(2-fluoro-6-(((4-methoxyphenyl)diphenylmethyl) amino)-9H-purin-9-yl)-3-((4-methoxy-phenyl)diphenylmethoxy)tetrahydrofuran-2-yl)methoxy)-2-methyl-4-oxobutan-2-yl)-3,5-dimethylphenyl decanoate (800 mg, 0.595 mmol, 56.0% yield) as colorless oil. LCMS (ESI) m/z calcd for $C_{75}H_{78}FN_5O_8$: 1196. Found: 1197 $(M+H)^+$. $^1$HNMR (400 MHz, Chloroform-d) δ 7.56 (s, 1H), 7.52 (d, J=7.6 Hz, 4H), 7.42-7.34 (m, 2H), 7.34-7.15 (m, 17H), 7.00 (s, 1H), 6.84-6.75 (m, 4H), 6.72 (d, J=2.0 Hz, 1H), 6.51 (d, J=2.0 Hz, 1H), 6.08 (dd, J=7.6, 4.0 Hz, 1H), 4.51 (d, J=7.6 Hz, 1H), 4.21 (d, J=12.4 Hz, 1H), 3.96 (d, J=12.0 Hz, 1H), 3.77 (d, J=18.4 Hz, 6H), 2.78 (s, 1H), 2.71-2.57 (m, 2H), 2.51 (s, 1H), 2.46 (td, J=7.6, 3.6 Hz, 2H), 2.39 (s, 3H), 2.28 (s, 1H), 2.19 (s, 3H), 1.73-1.63 (m, 2H), 1.43 (s, 3H), 1.36 (s, 3H), 1.28 (s, 6H), 1.24 (s, 6H), 0.91-0.83 (m, 3H).

Step 6: 2-(4-(((2R,3S,5R)-5-(6-amino-2-fluoro-9H-purin-9-yl)-2-ethynyl-3-hydroxytetrahydrofuran-2-yl)methoxy)-2-methyl-4-oxobutan-2-yl)-3,5-dimethylphenyl decanoate. To a solution of 2-(4-(((2R,3S,5R)-2-ethynyl-5-(2-fluoro-6-(((4-methoxyphenyl)diphenylmethyl) amino)-9H-purin-9-yl)-3-((4-methoxyphenyl) diphenylmethoxy)tetrahydro-furan-2-yl)methoxy)-2-methyl-4-oxobutan-2-yl)-3,5-dimethylphenyl decanoate (700 mg, 0.585 mmol) in DCM (10 mL) was added TFA (2 ml, 26.0 mmol). The reaction mixture was stirred at room temperature for 1 hr. LCMS indicated completion of reaction. The reaction mixture was quenched with water, extracted with dichloromethane 20 mL. The combined organic phases were washed with saturated brine 10 mL, dried over sodium sulphate and evaporated in vacuum to give the crude product as yellow oil. The residue was purified by reverse phase (C18) column (120 g, FA with water/MeCN=1:10) to 2-(4-(((2R,3S,5R)-5-(6-amino-2-fluoro-9H-purin-9-yl)-2-ethynyl-3-hydroxytetrahydrofuran-2-yl)methoxy)-2-methyl-4-oxobutan-2-yl)-3,5-dimethylphenyl decanoate (104.3 mg, 0.157 mmol, 26.9% yield) as yellow solid. LCMS (ESI) m/z calcd for $C_{35}H_{46}FN_5O_6$: 651. Found: 652 $(M+H)^+$. $^1$HNMR (400 MHz, Chloroform-d) δ 8.03 (s, 1H), 6.73 (d, J=2.0 Hz, 1H), 6.54 (d, J=2.0 Hz, 1H), 6.27 (dd, J=7.2, 4.4 Hz, 1H), 4.21 (q, J=12.2 Hz, 2H), 3.80 (t, J=7.6 Hz, 1H), 3.11-3.00 (m, 2H), 2.71-2.51 (m, 9H), 2.18 (s, 3H), 1.74 (q, J=7.4 Hz, 2H), 1.59 (d, J=18.8 Hz, 6H), 1.43-1.21 (m, 12H), 0.92-0.84 (m, 3H).

Example 68: ((2R,3S,5R)-5-(6-amino-2-fluoro-9H-purin-9-yl)-2-ethynyl-3-hydroxytetrahydrofuran-2-yl)methyl (1,3-bis(heptanoyloxy)propan-2-yl) Succinate
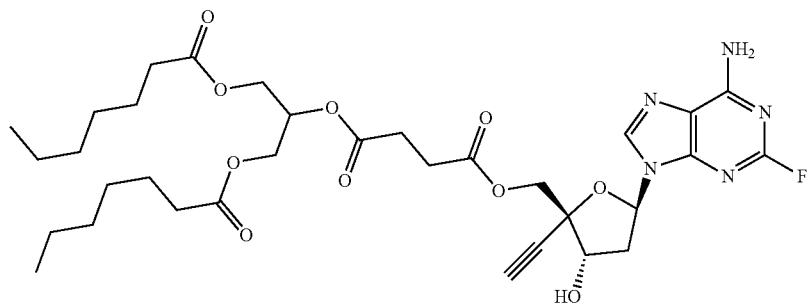 [SMILES: C#C[C@]1(COC(=O)CCC(=O)OC(COC(=O)CCCCCC)COC(=O)CCCCCC)O[C@@H](n2cnc3c(N)nc(F)nc32)C[C@@H]1O]
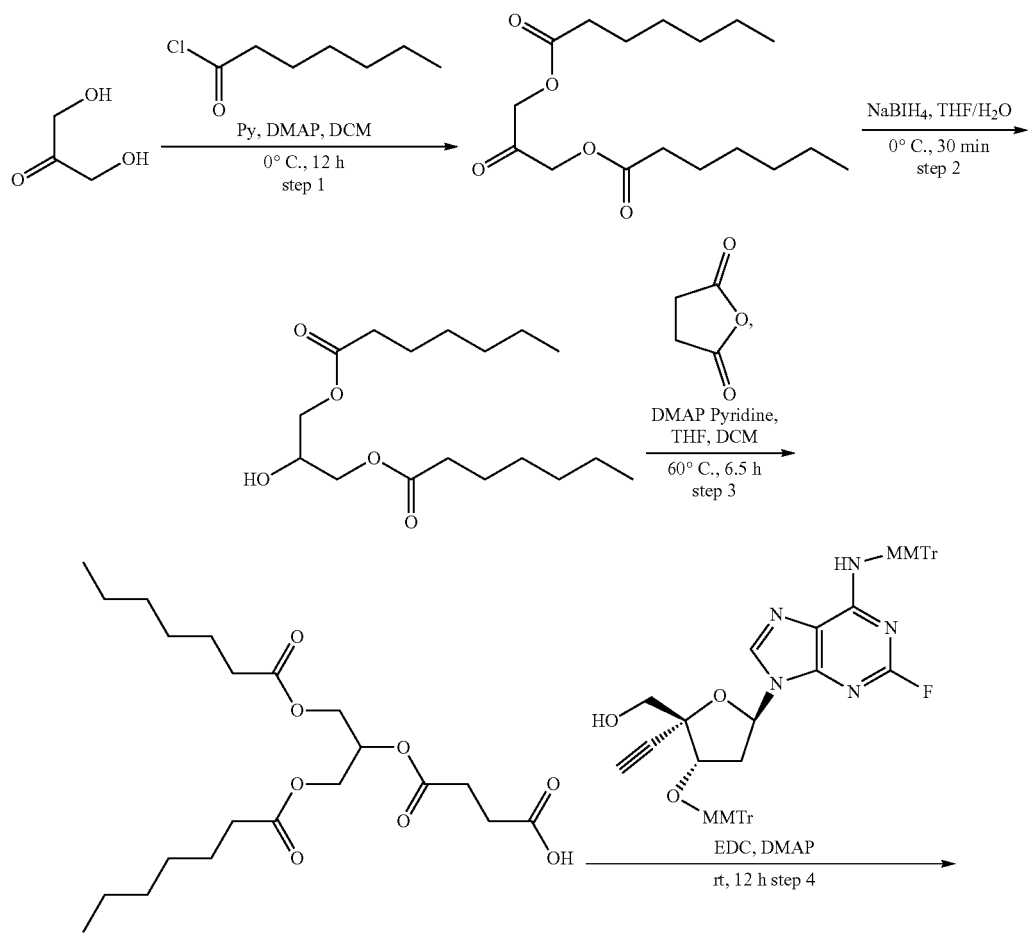

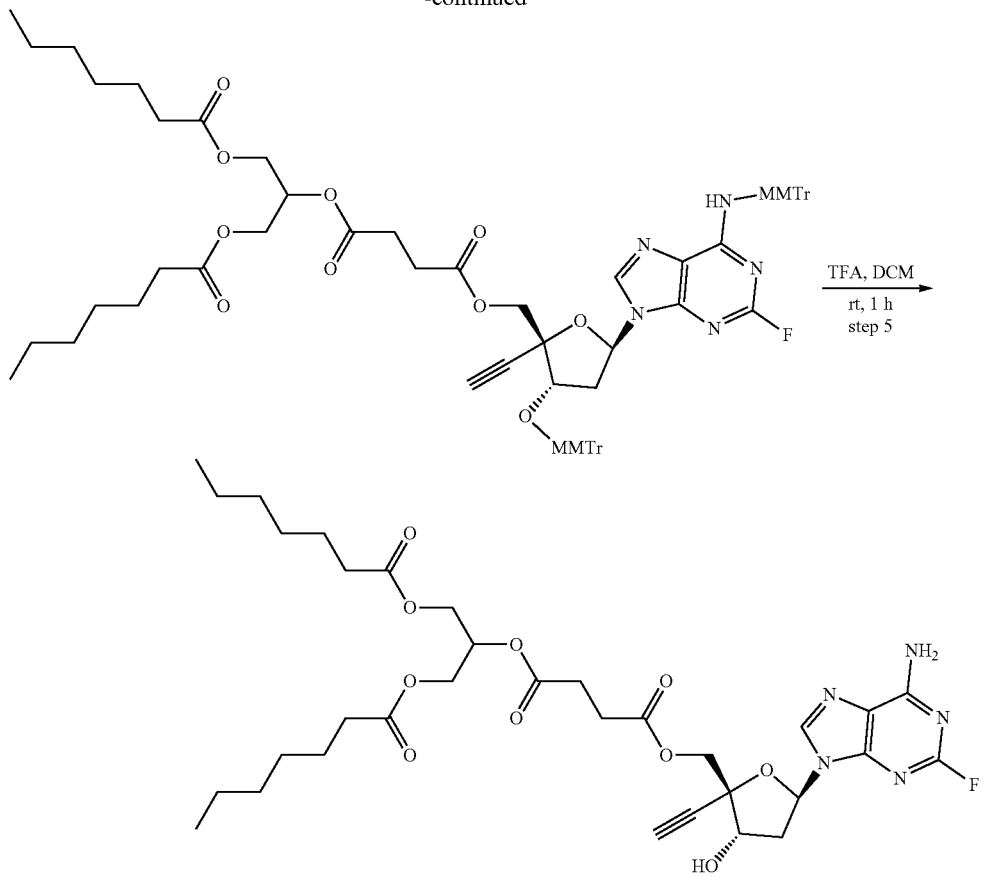

Step 1: 2-oxopropane-1,3-diyl diheptanoate. To a solution of 1,3-dihydroxypropan-2-one (14 g, 155 mmol) in DCM (100 mL) stirred under nitrogen at 0° C. was added pyridine (37.7 mL, 466 mmol), DMAP (0.570 g, 4.66 mmol), and heptanoyl chloride (50.8 g, 342 mmol) in DCM (50 mL) dropwise over 15 min. The reaction mixture was stirred at 0° C. overnight. LCMS indicated completion of reaction. The reaction mixture was quenched with Na2HCO3 (100 ml) and the organic layers were washed with NaCl (100 mL*6), the combined organic layers were dried over Na2SO4 and evaporated to dryness in vacuo. The residue was purified by flash chromatography (silica gel, 120 g, EtOAc:pet. ether=1:1) to give the desired product (18 g, yield: 36.8%) as a yellow solid. LCMS (ESI) m/z calcd for $C_{17}H_{30}O_5$: 314. Found: 315 (M+1)$^+$. $^1$HNMR (400 MHz, Chloroform-d): δ 4.77 (s, 4H), 2.46-2.36 (m, 4H), 1.72-1.59 (m, 4H), 1.41-1.27 (m, 12H), 0.93-0.89 (m, 6H).

Step 2: 2-hydroxypropane-1,3-diyl diheptanoate. To 2-oxopropane-1,3-diyl diheptanoate (18.0 g, 57.2 mmol) in THF (20 mL) and water (2.000 mL) stirred at 0° C. was added sodium borohydride (3.25 g, 86 mmol) portionwise and stirred at 0° C. for 30 min. LCMS indicated completion of reaction. The reaction mixture was added with water (40 mL), extracted with EtOAc (20 mL*3), the organic phases were combined, washed with brine (40 mL), dried over Na2SO4, and concentrated under vacuum to give crude product (14.8 g, yield: 82%) as white solid which was used in the next step without purification. LCMS (ESI) m/z calcd for $C_{17}H_{32}O_5$: 316. Found: 317 (M+1)$^+$. $^1$HNMR (400 MHz, Chloroform-d) δ 4.31-4.06 (m, 4H), 3.73-3.62 (m, 1H), 2.64-2.43 (m, 1H), 2.39-2.30 (m, 4H), 1.66-1.53 (m, 4H), 1.35-1.23 (m, 12H), 0.92-0.86 (m, 6H).

Step 3: 4-((1,3-bis(heptanoyloxy)propan-2-yl)oxy)-4-oxobutanoic acid. To a solution of 2-hydroxypropane-1,3-diyl diheptanoate (6 g, 18.96 mmol) was dissolved in DCM (30 mL)/THF (30.0 mL) was added pyridine (30.0 mL), DMAP (0.232 g, 1.896 mmol) and dihydrofuran-2,5-dione (3.79 g, 37.9 mmol). The resulting mixture was stirred for 6.5 h at 60° C. LCMS indicated completion of reaction. The reaction mixture was diluted with HCl aqueous solution (100 mL), extracted with EtOAc (50 mL*3), the organic phases were combined, dried over Na2SO4, and concentrated under vacuum. The residue was purified by C18 reversed phase column (50-100% ACN/water with 0.1% FA) to give the desired product (7 g, 83.30%, yield: 73.8%) as yellow oil. LCMS (ESI) m/z calcd for $C_{21}H_{36}O$: 416. Found: 417 (M+1)$^+$. $^1$HNMR (300 MHz, DMSO-d$_6$): δ 12.21 (s, 1H), 5.21-5.14 (m, 1H), 4.27-4.09 (m, 4H), 2.46-2.41 (m, 4H), 2.32-2.26 (m, 4H), 1.54-1.45 (m, 4H), 1.29-1.19 (m, 12H), 0.89-0.82 (m, 6H).

Step 4: 1,3-bis(heptanoyloxy)propan-2-yl (((2R,3S,5R)-2-ethynyl-5-(2-fluoro-6-(((4-methoxyphenyl) diphenylmethyl)amino)-9H-purin-9-yl)-3-((4-methoxyphenyl)diphenylmethoxy)tetrahydrofuran-2-yl)methyl) succinate. To a solution of 4-((1,3-bis(heptanoyloxy)propan-2-yl)oxy)-4-oxobutanoic acid (596 mg, 1.432 mmol) in DMF (6 mL) was added DMAP (525 mg, 4.30 mmol) and 3-(((ethylimino) methylene)amino)-N,N-dimethylpropan-1-amine hydrochloride (824 mg, 4.30 mmol). The resulting mixture was stirred for 30 min at room temperature. Then, ((2R,3S,5R)-

2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methanol (600 mg, 0.716 mmol) was added and the resulting mixture was stirred for overnight at room temperature. LCMS indicated completion of reaction. The reaction mixture was quenched with water (10 mL), extracted with EtOAc (5 mL*3), the organic phases were combined, washed with brine (10 mL), dried over Na2SO4, and concentrated under vacuum. The residue was purified by flash chromatography (silica gel, 80 g, EtOAc: pet. ether=1:1) to give the desired product (470 mg, 97.45%, yield: 51.7%) as a white solid. LCMS (ESI) m/z calcd for $C_{73}H_{78}FN_5O_{12}$: 1236. Found: 1237 (M+1)$^+$. $^1$HNMR (400 MHz, Chloroform-d) δ 7.67 (s, 1H), 7.54-7.49 (m, 4H), 7.41-7.36 (m, 2H), 7.33-7.27 (m, 8H), 7.25-7.16 (m, 10H), 6.81-6.77 (m, 4H), 6.10-6.07 (m, 1H), 5.26-5.20 (m, 1H), 4.61-4.54 (m, 1H), 4.34 (d, J=8 Hz, 1H), 4.29-4.24 (m, 2H), 4.16-4.11 (m, 2H), 4.00 (d, J=8 Hz, 1H), 3.76 (d, J=16 Hz, 6H), 2.83 (s, 1H), 2.52-2.43 (m, 1H), 2.47-2.34 (m, 2H), 2.32-2.26 (m, 4H), 1.63-1.58 (m, 8H), 1.31-1.25 (m, 12H), 0.88-0.83 (m, 6H).

Step 5: ((2R,3S,5R)-5-(6-amino-2-fluoro-9H-purin-9-yl)-2-ethynyl-3-hydroxytetrahydrofuran-2-yl)methyl (1,3-bis(heptanoyloxy)propan-2-yl) succinate. To a solution of 1,3-bis(heptanoyloxy)propan-2-yl (((2R,3S,5R)-2-ethynyl-5-(2-fluoro-6-(((4-methoxyphenyl)diphenylmethyl)amino)-9H-purin-9-yl)-3-((4-methoxyphenyl)diphenylmethoxy)tetrahydrofuran-2-yl)methyl) succinate (450 mg, 0.364 mmol) in DCM (5 mL) was added TFA (0.561 mL, 7.28 mmol) and the resulting mixture was stirred for 1 h at room temperature. LCMS indicated completion of reaction. The reaction mixture was added with MeOH (5 mL), then DCM was removed under vacuum. The mixture was subjected to prep-HPLC (Column: XBridge Prep OBD C18 Column, 19*250 mm, 5 um; Mobile Phase A: Water (10 MMOL/L NH4HCO3+0.1% NH3·H2O), Mobile Phase B: ACN; Flow rate: 25 mL/min; Gradient: 65 B to 85 B in 8 min; 254 nm; RT1:6.95) to give the desired product (29.6 mg, 98.89%, yield: 11.63%) as a white solid. LCMS (ESI) m/z calcd for $C_{33}H_{46}FN_5O_{10}$: 691. Found: 692 (M+1)$^+$. $^1$HNMR (400 MHz, DMSO) δ 8.27 (s, 1H), 7.84 (br, 2H), 6.26-6.23 (m, 1H), 5.78 (d, J=4 Hz, 1H), 5.15-5.13 (m, 1H), 5.70-5.64 (m, 1H), 4.39 (d, J=12 Hz, 1H), 4.21-4.09 (m, 5H), 3.62 (s, 1H), 2.79-2.73 (m, 1H), 2.56-2.53 (m, 4H), 2.48-2.42 (m, 1H), 2.29-2.25 (m, 4H), 1.51-1.35 (m, 4H), 1.37-1.18 (m, 12H), 0.84-0.81 (m, 6H).

Anti-HIV Activity

PSV Assay

A pseudotyped virus assay (PSV) was used to assess the potency of the HIV inhibitor. Replication defective virus was produced by co-transfection of a plasmid containing an NL4-3 provirus [containing a mutation in the envelope open reading frame (ORF) and a luciferase reporter gene replacing the nef ORF] and a CMV-promoter expression plasmid containing an ORF for various HIV gp160 envelope clones. The harvested virus was stored at −80 C in small aliquots and the titer of the virus measured to produce a robust signal for antiviral assays.

The PSV assay was performed by using U373 cells stably transformed to express human CD4, the primary receptor for HIV entry and either human CXCR4 or human CCR5 which are the co-receptors required for HIV entry as target cells for infection. Molecules of interest (including, but not limited to small molecule inhibitors of HIV, neutralizing antibodies of HIV, antibody-drug conjugate inhibitors of HIV, peptide inhibitors of HIV, and various controls) are capable of being diluted into tissue culture media and diluted via serial dilution to create a dose range of concentrations, and this was carried out for Example 1. This dose-range was applied to U373 cells and the pre-made pseudotyped virus added. The amount of luciferase signal produced after 3 days of culture was used to reflect the level of pseudotyped virus infection. An $IC_{50}$, or the concentration of inhibitor required to reduce PSV infection by 50% from the infection containing no inhibitor was calculated. Assays to measure cytotoxicity were performed in parallel to ensure the antiviral activity observed for an inhibitor was distinguishable from reduced target cell viability. $IC_{50}$ values were determined from a 10 point dose response curve using 3-4-fold serial dilution for each compound, which spans a concentration range>1000 fold.

These values are plotted against the molar compound concentrations using the standard four parameter logistic equation:

$$y=((Vmax*x\hat{}n)/(K\hat{}n+x\hat{}n))+Y2$$

where:

| | |
|---|---|
| Y2 = minimum y | n = slope factor |
| Vmax = maximum y | x = compound concentration [M] |
| K = $EC_{50}$ | |

The resulting data is shown in Table 3.

TABLE 3

| Example | WT $IC_{50}$ (µM) | M184V $IC_{50}$ (µM) |
|---|---|---|
| 1 | 0.002 | 0.008 |
| 2 | 0.003 | 0.013 |
| 3 | 0.002 | 0.01 |
| 4 | 0.003 | 0.017 |
| 5 | 0.001 | 0.007 |
| 6 | 0.004 | 0.025 |
| 7 | 0.004 | 0.024 |
| 8 | 0.002 | 0.011 |
| 9 | 0.035 | 0.167 |
| 10 | 0.009 | 0.044 |
| 11 | 0.008 | 0.037 |
| 12 | 0.034 | 0.151 |
| 13 | 0.508 | 3.61 |
| 14 | 0.033 | 0.148 |
| 15 | 0.077 | 0.328 |
| 16 | 0.008 | 0.031 |
| 17 | 1.74 | 10.3 |
| 18 | 0.01 | 0.073 |
| 19 | 0.018 | 0.087 |
| 20 | 0.005 | 0.025 |
| 21 | 0.007 | 0.044 |
| 22 | 0.007 | 0.035 |
| 23 | 0.011 | 0.068 |
| 24 | 0.066 | 0.351 |
| 25 | 0.021 | 0.186 |
| 26 | 0.007 | 0.028 |
| 27 | 0.008 | 0.046 |
| 28 | 0.006 | 0.026 |
| 29 | 0.238 | 1.35 |
| 30 | 0.334 | 1.5 |
| 33 | 0.017 | 0.086 |
| 34 | 0.004 | 0.025 |
| 35 | 0.001 | 0.009 |
| 36 | 0.004 | 0.021 |

Antiviral Persistence Assay

The PSV assay was adapted to determine the antiviral persistence of each compound. This assay evaluates the ability of each compound to remain active in cells for two days i.e prevent PSV infection of cells in a dose dependent manner, 48 h after the removal of compound. Duplicate plates of U373 cells were treated with a serial dilution of small molecule inhibitors for 6 h at 37° C. Compounds were removed from cells by washing twice cells with 1×PBS. For baseline group (i.e immediately after washing or 0 h), cells were infected with prepared PSVs and cultured for three days. For experimental group (48 h), the culture medium is added to the washed cells and the plate incubated at 37° C. for 48 h. After two days of culture, the prepared PSVs were added to the cells and the mixture cultured for three days. The amount of luciferase signal produced after culture was used to reflect the level of pseudotyped virus infection in the baseline group (0 h) and experimental group (48 h) for each compound. An $IC_{50}$, or the concentration of inhibitor required to reduce PSV infection by 50% from the infection containing no inhibitor was calculated. The persistence index, which is the ratio of the $IC_{50}$ determined at 48 and 0 h is presented in Table 2 as well as the fold change of the persistence index relative to EFdA [(2R,3S,5R)-5-(6-amino-2-fluoro-9H-purin-9-yl)-2-ethynyl-2-(hydroxymethyl)tetrahydrofuran-3-ol].

Figure 1B:
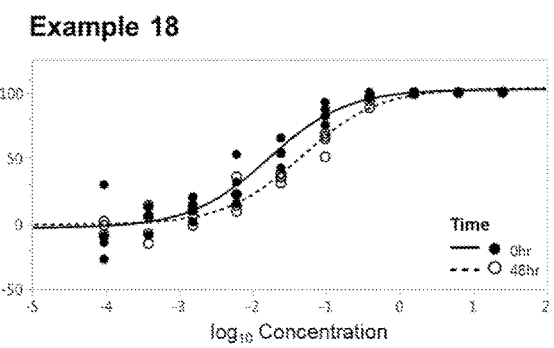
FIG. 1B illustrates an IC$_{50}$ curve shift from t=0 to t=48 h for Example 18 of the present invention.

Statistical analysis and graphing of the data were performed in JMP 13.2.1 (SAS Institute, Cary, NC). A four-parameter logistic Hill Model was fit to % Inhibition and $\log_{10}$ concentration values, separately for each compound, time point and run. A pilot experiment included 2 independent experimental runs and a later follow-up experiment included 4 runs. Quality control criteria based on $R^2$ and 95% confidence interval ranges of all four parameter estimates were used to exclude curves with poor fits. Using inverse prediction, $\log_{10}$ concentrations were obtained that correspond to 50% Inhibition ($\log_{10}IC50^*$) and the $\log_{10}$ persistence index was calculated for each compound and run using the following formula: $\log_{10}$ persistence Index=$\log_{10}IC50^*_{48\ hrs}$−$\log_{10}IC50^*_{0hrs}$. Next, a linear mixed effects model was fit on $\log_{10}$ persistence index values with a fixed effect for compound and a random effect for experimental run, followed by post hoc contrasts to compare the $\log_{10}$ persistence index of the positive control EFdA to the $\log_{10}$ persistence index of other test compounds. The estimated LSMeans and differences were then back-transformed via $10^{Estimate}$ to the original scale and reported as persistence index and fold change respectively. Raw p-values were reported. Antiviral persistence data for examples 15, 16, 18 and EFdA are shown in Table 4. $IC_{50}$ curve shifts from t=0 to t=48 h for EFdA and Example 18 are illustrated in FIGS. 1A and 1B. The curves in FIG. 1 were obtained from a single curve fit across replicate runs instead of separate fits for each run as described above.

TABLE 4

| Example | WT $IC_{50}$ (μM) at t = 0 h | WT $IC_{50}$ (μM) at t = 48 h | Persistence Index | Fold Change vs EFdA | p-Value |
|---|---|---|---|---|---|
| EFdA | 0.0074 | 0.3156 | 42.87 | 1.00 | — |
| 15 | 0.0343 | 0.1203 | 3.51 | 12.23 | 0.0002 |
| 16 | 0.0055 | 0.0359 | 6.49 | 6.61 | 0.0042 |
| 18 | 0.0161 | 0.0442 | 2.75 | 15.59 | <0.0001 |

Pharmacokinetics

Protocol for EFdA Rat PK Studies

A total of seven naïve male Wistar Han rats, 200-250 g, were received from the supplier equipped with a surgically-implanted jugular vein catheter (JVC) for blood sample collection. Following an acclimation period, the animals were assigned to the study based on acceptable health as determined by a staff veterinarian and catheter patency. Animals were placed into two groups of 3 rats per group. Fasting of the animals before or after dosing was not required.

The final study design is presented in the Table 5 below.

TABLE 5

| Group | No. of Males | Test Compound | Dose Level (mg/kg) | Dose Conc. (mg/mL) | Dose Volume (mL/kg) | Dose Vehicle | Dose Route |
|---|---|---|---|---|---|---|---|
| 1 | 3 | EFdA | 20 | 60.46 | 0.33 | 0.5% P407/ 0.5% PEG3350/ 3.5% Mannitol in water | Subcutaneous |
| 2 | 3 |  | 20 | 60.46 | 0.33 |  | Intramuscular |

PEG3350 = Polyethylene glycol 3350.

On Day 1 each animal in Group 1 received a single subcutaneous injection of prepared test article at a target dose level of 20 mg/kg and at a dose volume of 0.33 mL/kg. Each animal in Group 2 received a single intramuscular injection of prepared test article into a thigh muscle at a target dose level of 20 mg/kg and at a dose volume of 0.33 mL/kg. The injection sites were shaved prior to dosing and identified with an indelible marker for daily monitoring during the study. The animals were manually restrained for dosing and were not sedated. The dose suspension was mixed well by inversion before each dose to ensure homogeneity. All dosing was performed as detailed in the study protocol and was completed without incident. Following dosing and at each sample collection time point the animals and injection sites were observed for any clinically relevant abnormalities. In addition, all animals are monitored twice daily by the veterinary staff for clinical abnormalities. No abnormal clinical observations and no injection site reactions were noted during the study period.

Blood samples were collected from the study animals as detailed in the sample collection Table 6 below.

TABLE 6

| Dose Group/ Collection Information | Whole Blood for PK |
|---|---|
| 1 and 2 | 0.5, 1, 4, 7, 24, 48, 72 hours post-dose and Day 6, 8, 11, 15, 22, 25, 29 |

TABLE 6-continued

| Dose Group/ Collection Information | Whole Blood for PK |
|---|---|
| Anticoagulant | NaF/Na$_2$EDTA |
| Volume/Time point | 250 µL |

Each blood sample for PK (250 µL) was collected from the jugular vein catheter or by venipuncture of a jugular vein. The blood was transferred to a tube containing NaF/Na$_2$EDTA anticoagulant and inverted several times to mix. The blood samples were maintained on crushed ice before centrifugation at 2200×g for 10 minutes at 5° C. to isolate plasma. The resulting plasma samples were transferred to individual polypropylene tubes in a 96-well plate format and immediately placed on dry ice until storage at nominally −80° C. prior to analysis.

Figure 2:
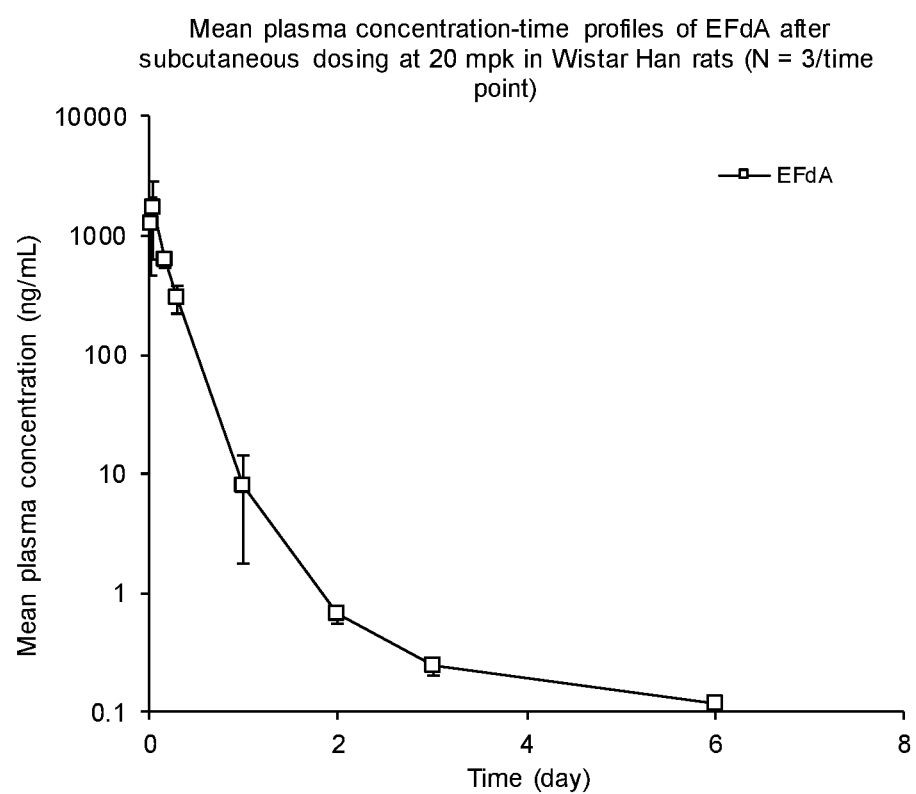
FIG. 2 illustrates the mean plasma concentration-time profiles of EFdA after subcutaneous dosing at 20 mg/kg in Wistar Han rats (N=3/time point)
Figure 3:
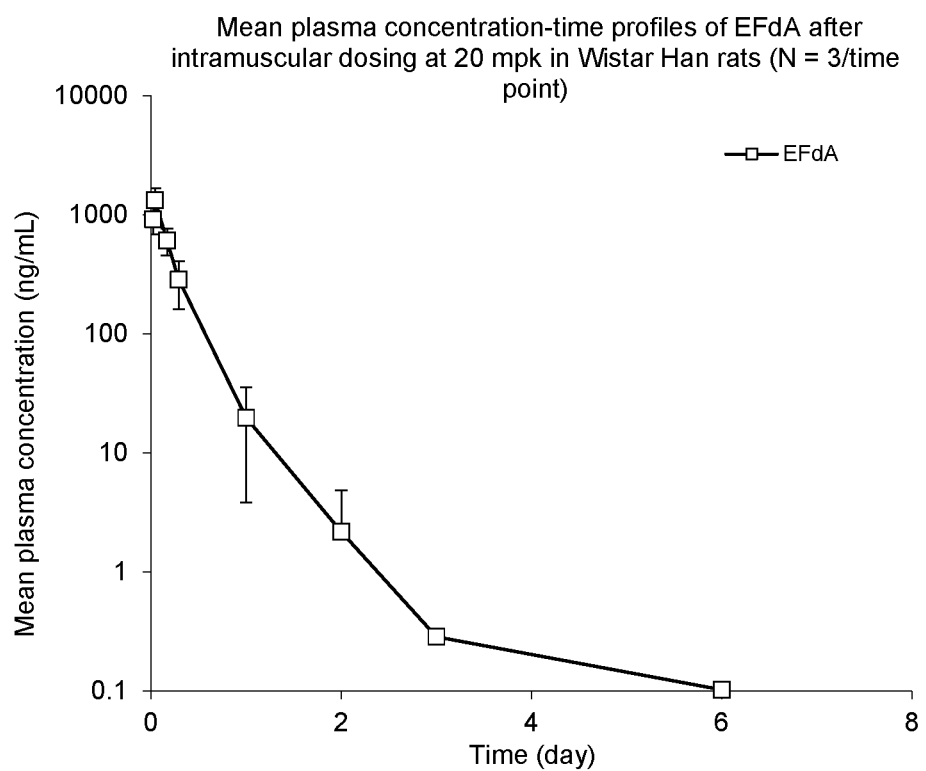
FIG. 3 illustrates the mean plasma concentration-time profiles of EFdA after intramuscular dosing at 20 mg/kg in Wistar Han rats (N=3/time point)
Figure 4:
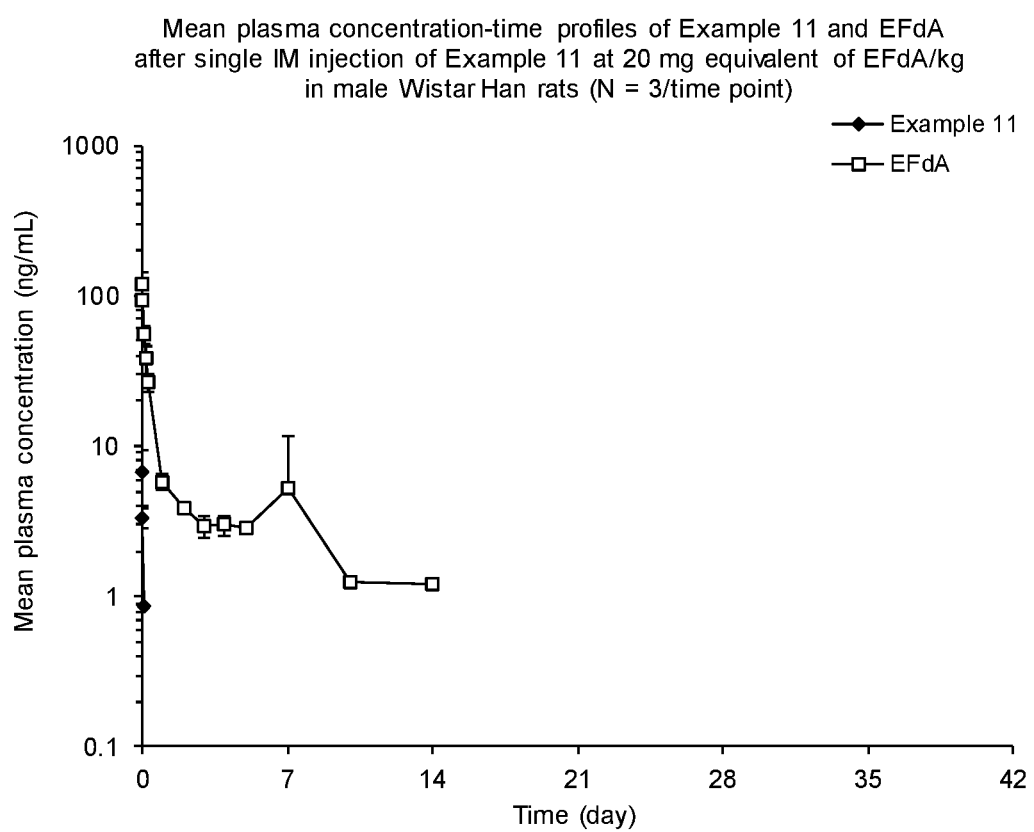
FIG. 4 illustrates the mean plasma concentration-time profiles of Example 11 and EFdA after single IM injection of Example 11 at 20 mg/kg equivalent of EFdA in male Wistar Han rats (N=3/time point)
Figure 5:
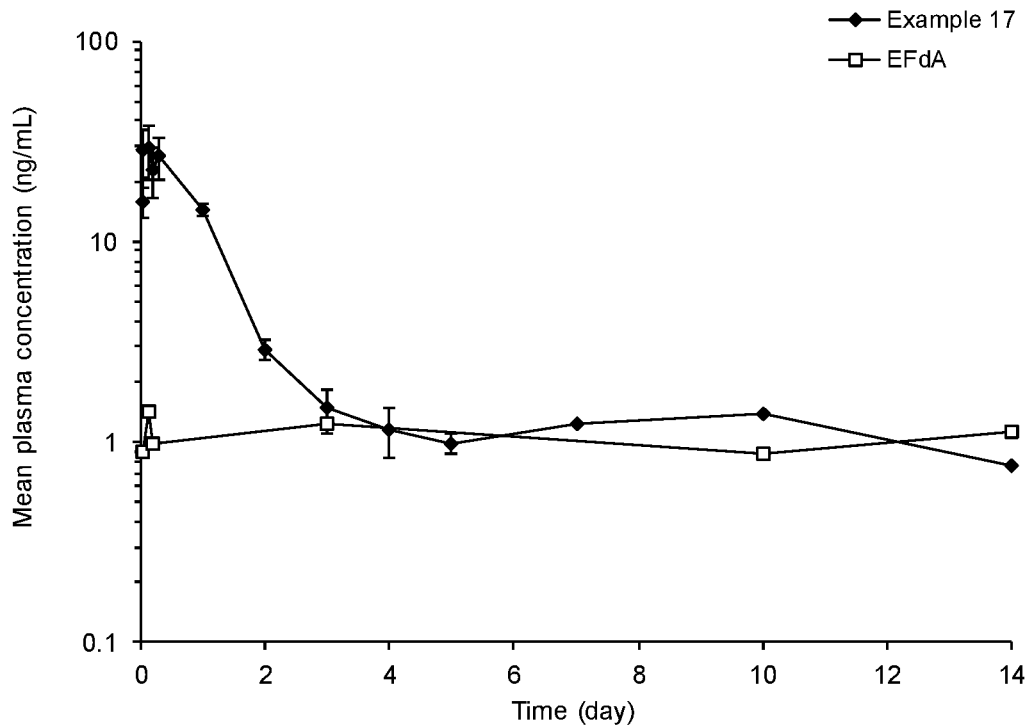
FIG. 5 illustrates the mean plasma concentration-time profiles of Example 17 and EFdA after single IM injection of Example 17 at 20 mg/kg equivalent of EFdA in male Wistar Han rats (N=3/time point)
Figure 6:
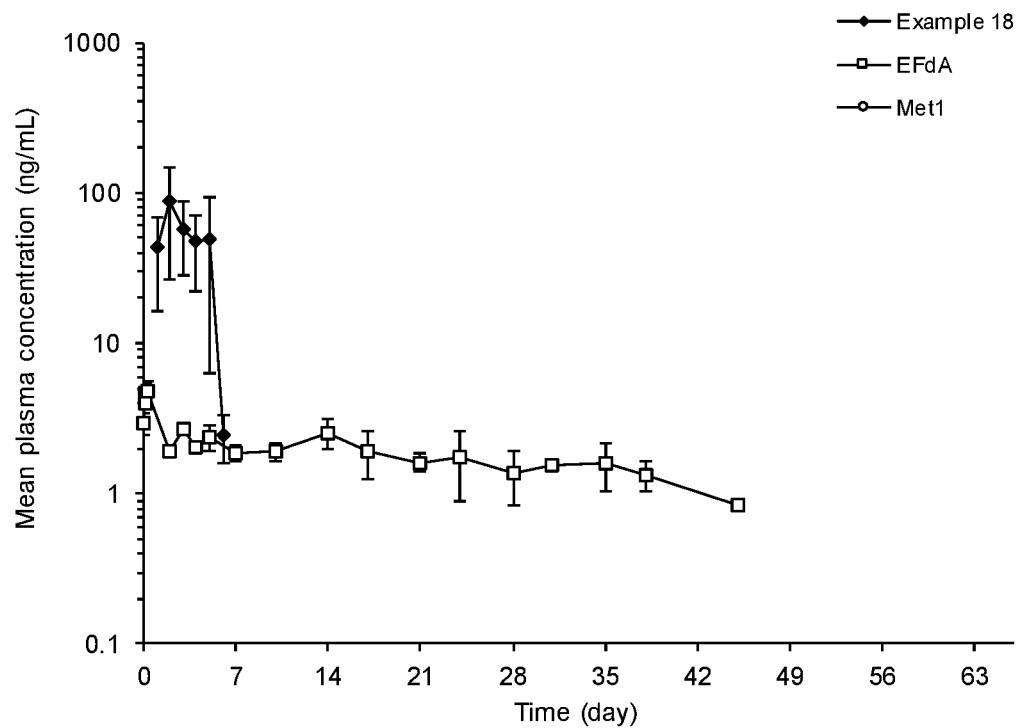
FIG. 6 illustrates the mean plasma concentration-time profiles of Example 18, EFdA and Met1 after single IM injection of Example 18 at 20 mg/kg equivalent of EFdA in male Wistar Han rats (N=3/time point)
Figure 7:
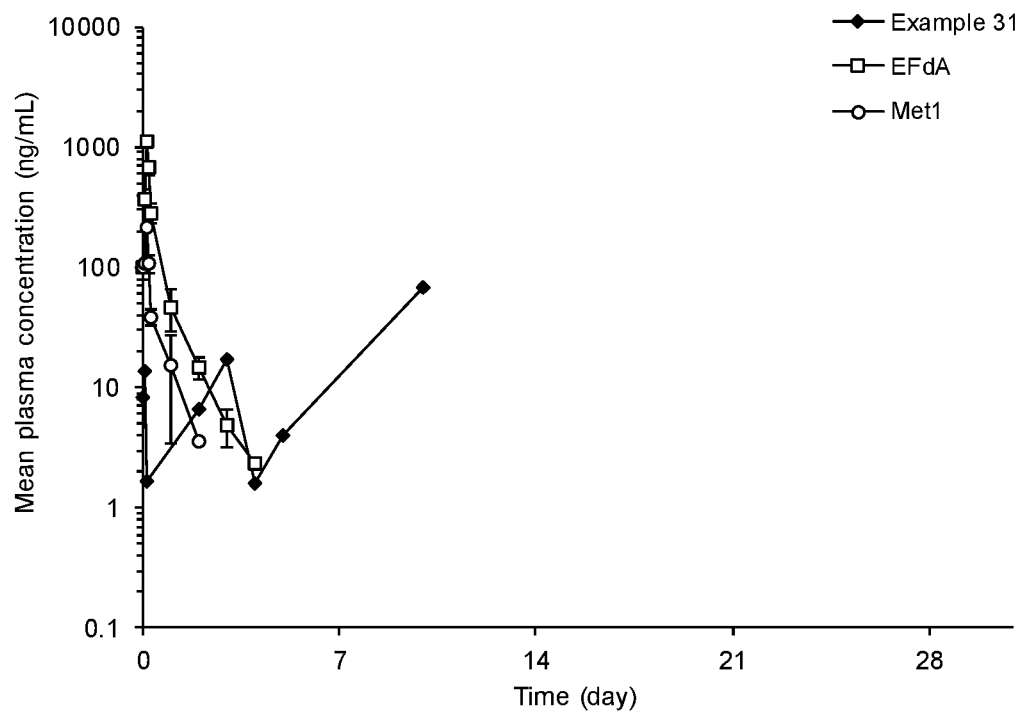
FIG. 7 illustrates the mean plasma concentration-time profiles of Example 31, EFdA and Met1 after single IM injection of Example 31 at 20 mg/kg equivalent of EFdA in male Wistar Han rats (N=3/time point)
Figure 8:
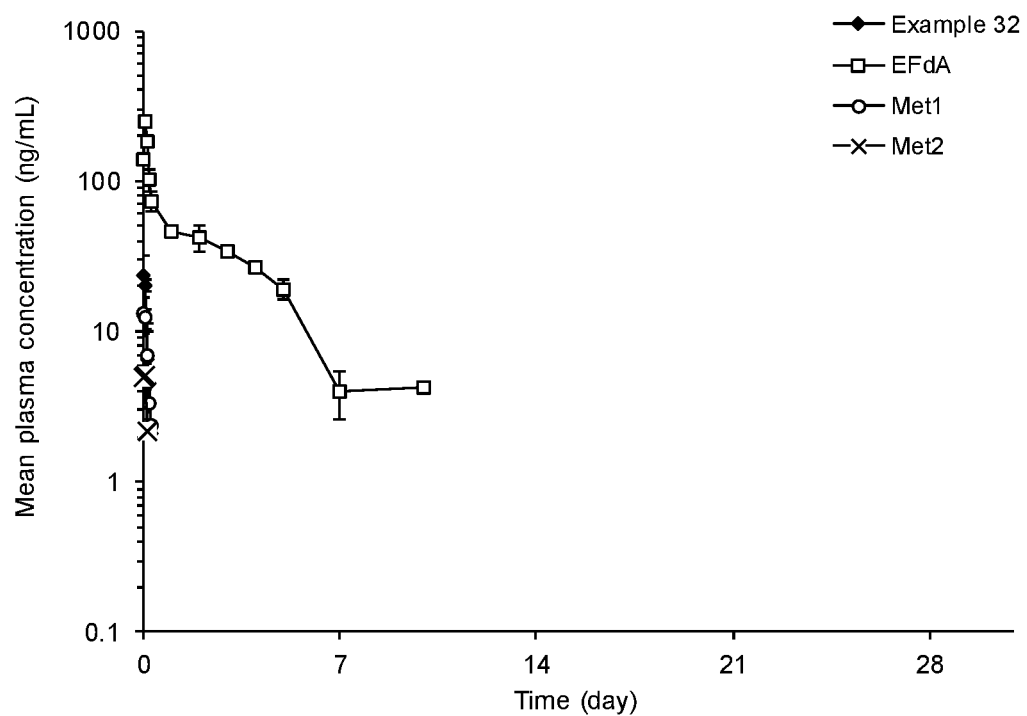
FIG. 8 illustrates the mean plasma concentration-time profiles of Example 32, EFdA, Met1 and Met2 after single IM injection of Example 32 at 20 mg/kg equivalent of EFdA in male Wistar Han rats (N=3/time point)
Figure 9:
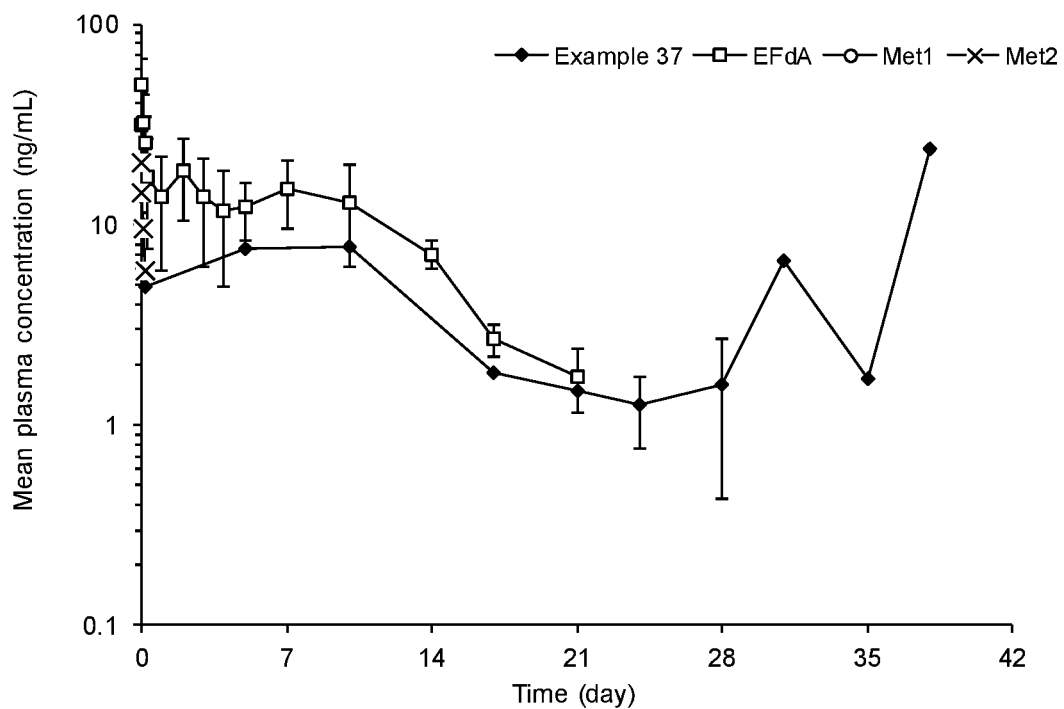
FIG. 9 illustrates the mean plasma concentration-time profiles of Example 37, EFdA, Met1 and Met2 after single IM injection of Example 37 at 20 mg/kg equivalent of EFdA in male Wistar Han rats (N=3/time point)
Figure 10:
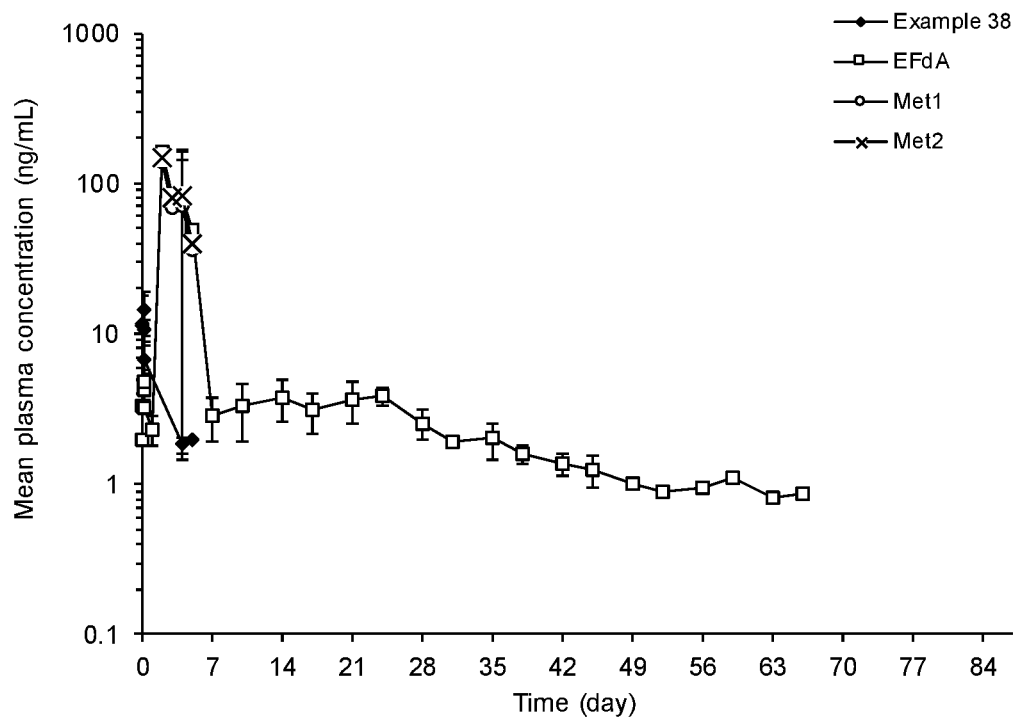
FIG. 10 illustrates the mean plasma concentration-time profiles of Example 38, EFdA, Met1 and Met2 after single IM injection of Example 38 at 20 mg/kg equivalent of EFdA in male Wistar Han rats (N=3/time point)
Figure 11:
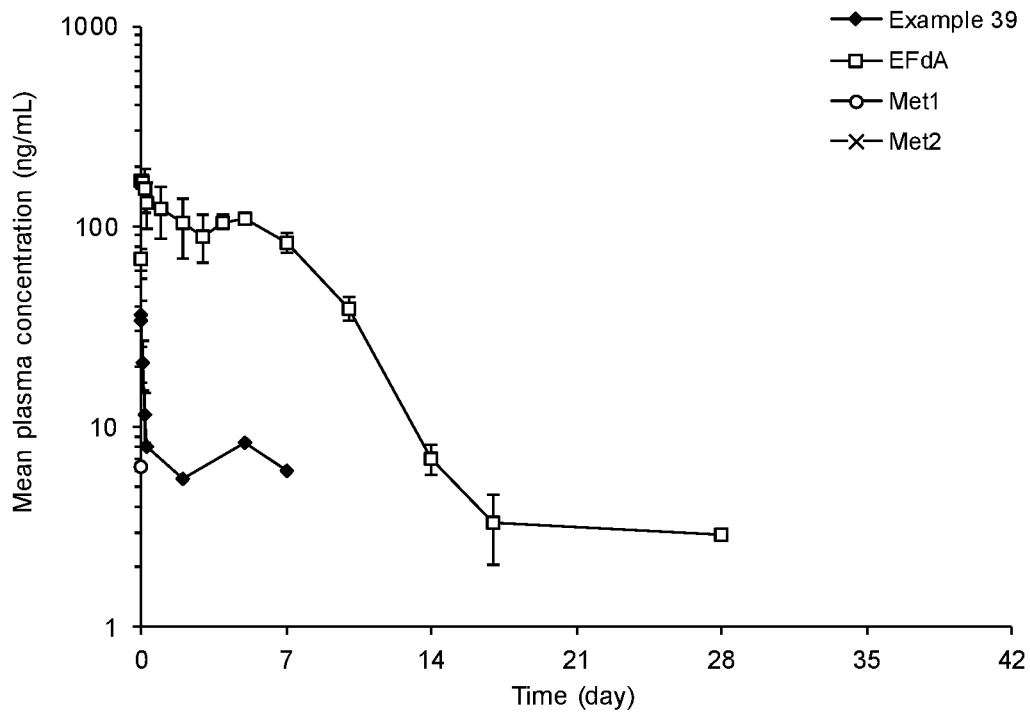
FIG. 11 illustrates the mean plasma concentration-time profiles of Example 39, EFdA, Met1 and Met2 after single IM injection of Met2 at 20 mg/kg equivalent of EFdA in male Wistar Han rats (N=3/time point)
Figure 12:
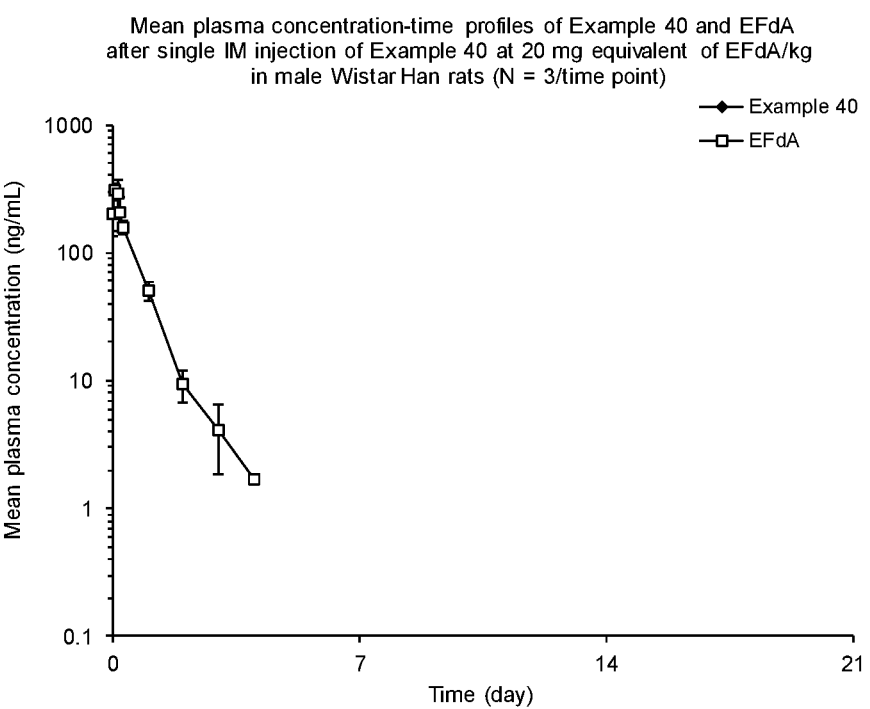
FIG. 12 illustrates the mean plasma concentration-time profiles of Example 40 and EFdA after single IM injection of Example 40 at 20 mg/kg equivalent of EFdA in male Wistar Han rats (N=3/time point)
Figure 13:
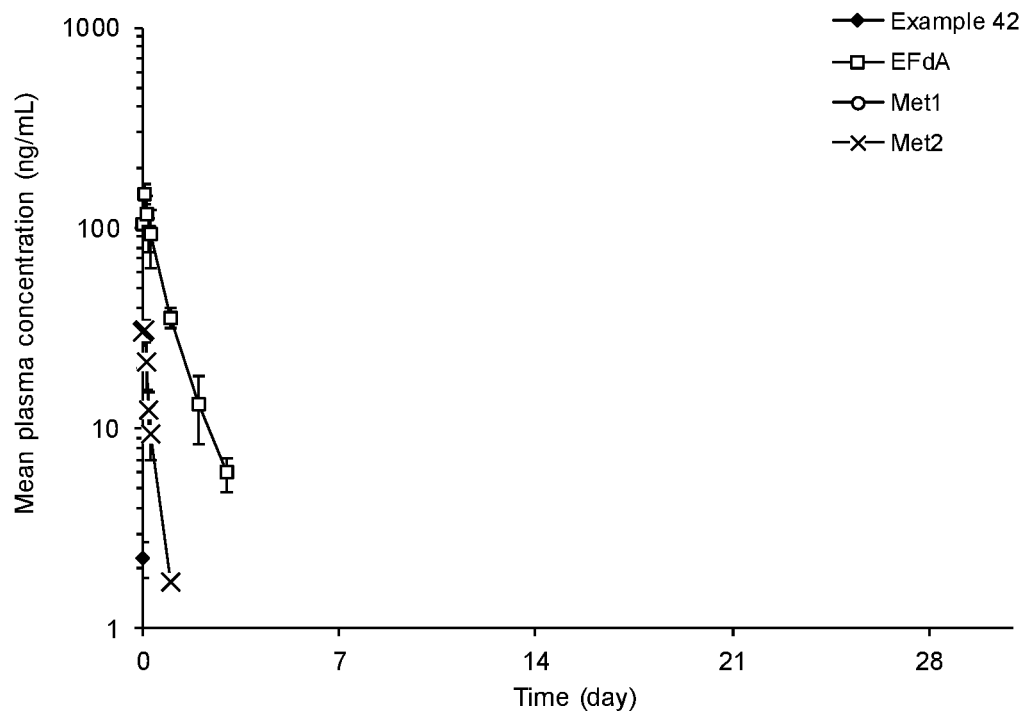
FIG. 13 illustrates the mean plasma concentration-time profiles of Example 42, EFdA, Met1 and Met2 after single IM injection of Example 42 at 20 mg/kg equivalent of EFdA in male Wistar Han rats (N=3/time point)
Figure 14:
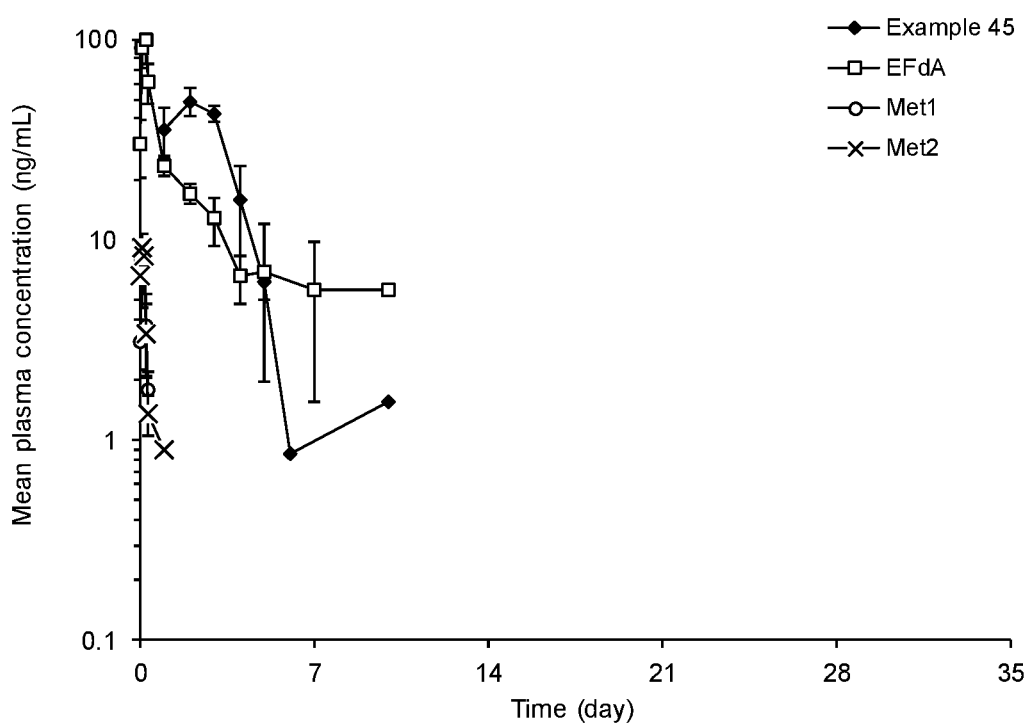
FIG. 14 illustrates the mean plasma concentration-time profiles of Example 45, EFdA, Met1 and Met2 after single IM injection of Example 45 at 20 mg/kg equivalent of EFdA in male Wistar Han rats (N=3/time point)
Figure 15:
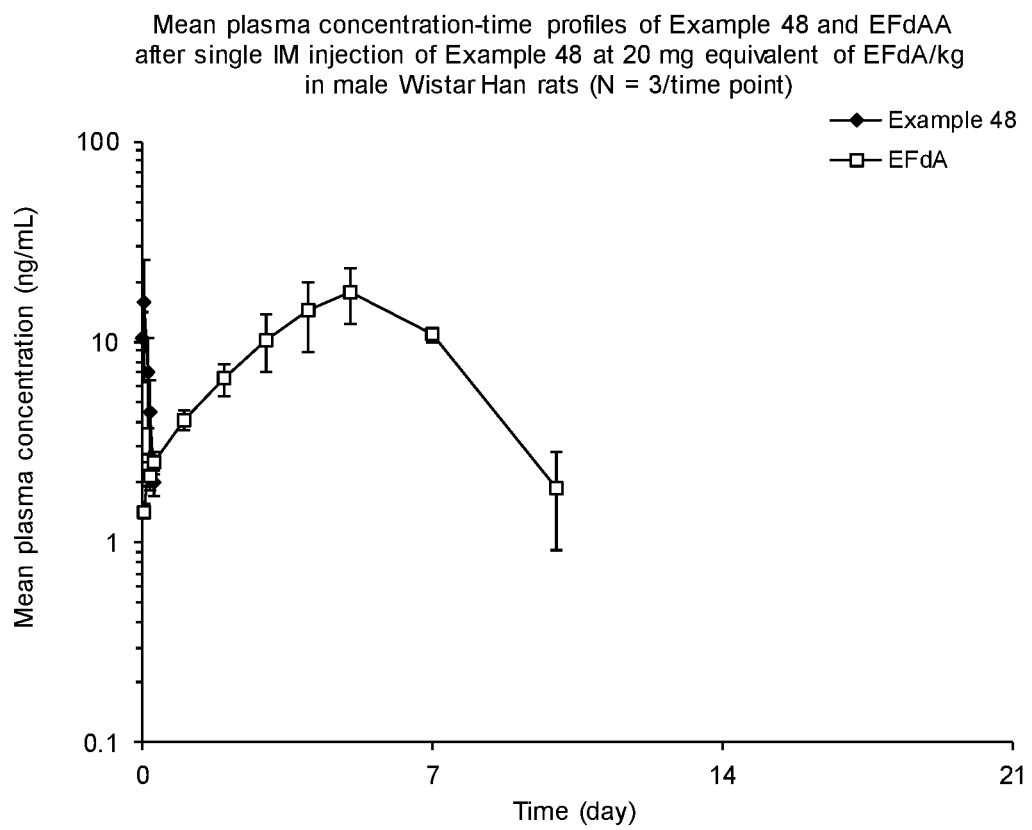
FIG. 15 illustrates the mean plasma concentration-time profiles of Example 48 and EFdA after single IM injection of Example 48 at 20 mg/kg equivalent of EFdA in male Wistar Han rats (N=3/time point)
Figure 16:
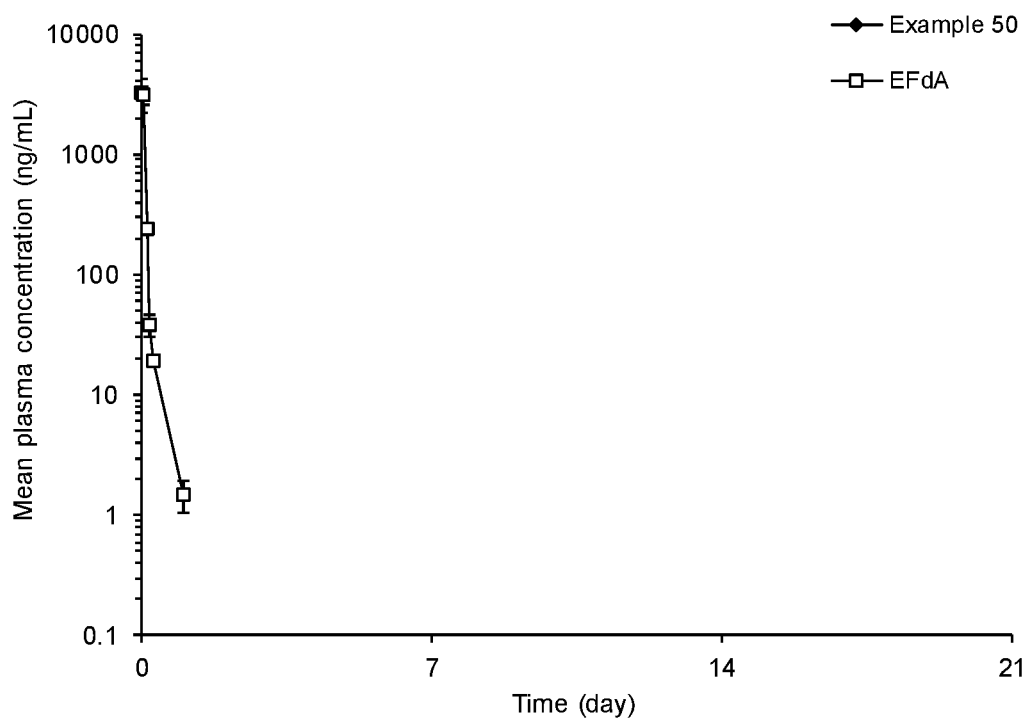
FIG. 16 illustrates the mean plasma concentration-time profiles of Example 50 and EFdA after single IM injection of Example 50 at 20 mg/kg equivalent of EFdA in male Wistar Han rats (N=3/time point)
Figure 17:
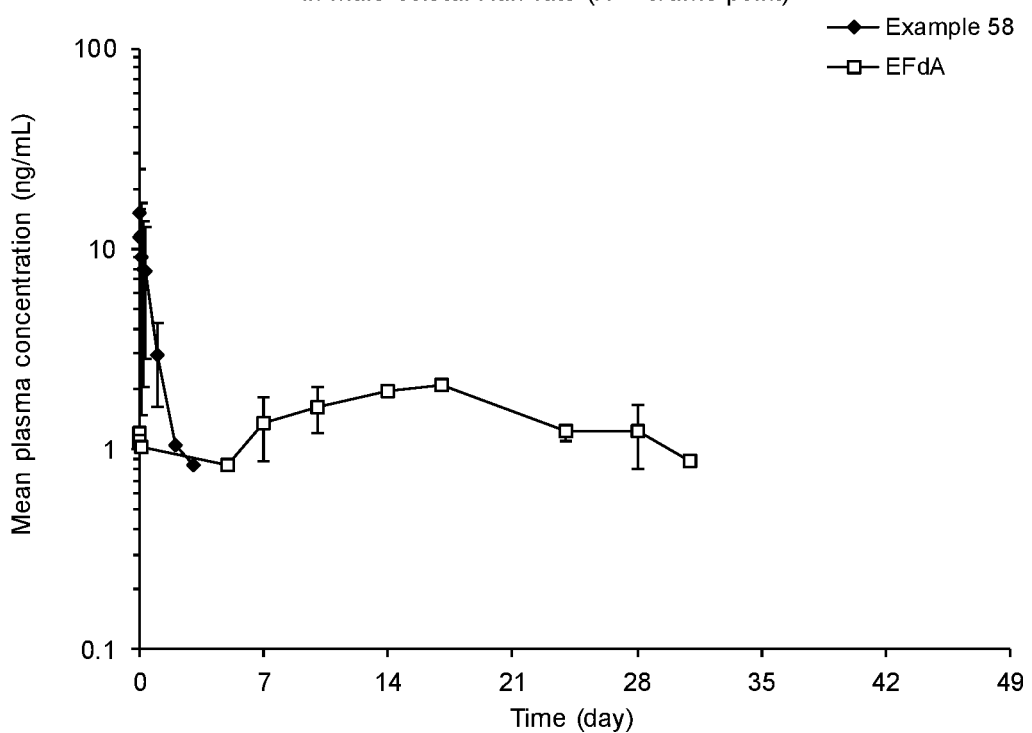
FIG. 17 illustrates the mean plasma concentration-time profiles of Example 58 and EFdA after single IM injection of Example 58 at 20 mg/kg equivalent of EFdA in male Wistar Han rats (N=3/time point)
Figure 18:
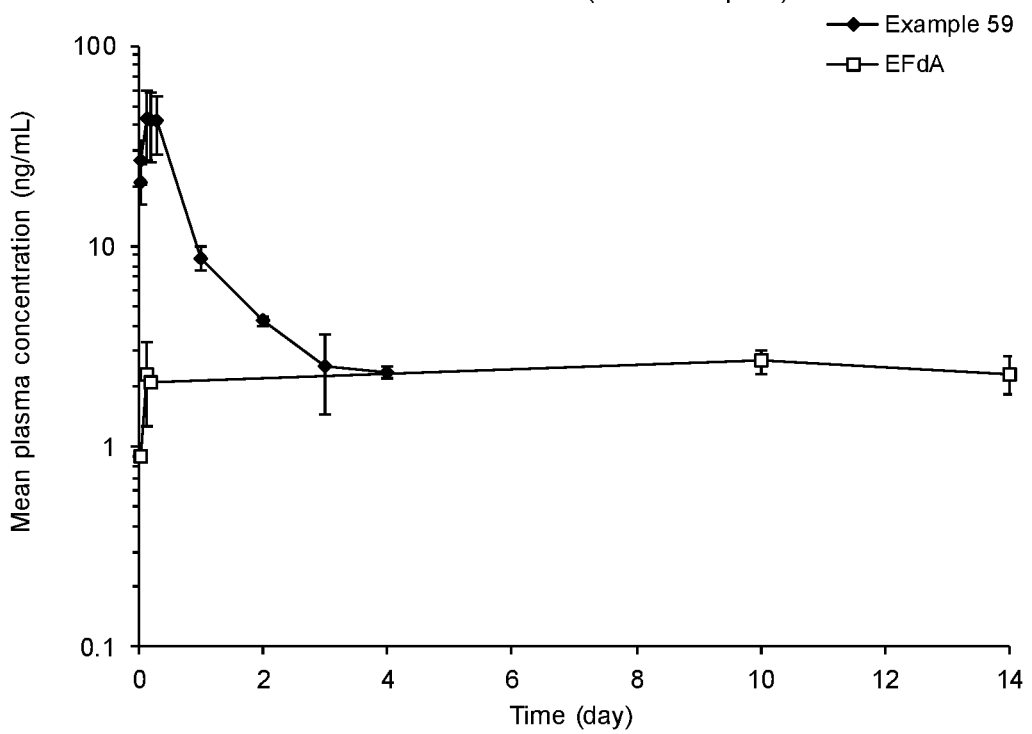
FIG. 18 illustrates the mean plasma concentration-time profiles of Example 59 and EFdA after single IM injection of Example 59 at 20 mg/kg equivalent of EFdA in male Wistar Han rats (N=3/time point)
Figure 19:
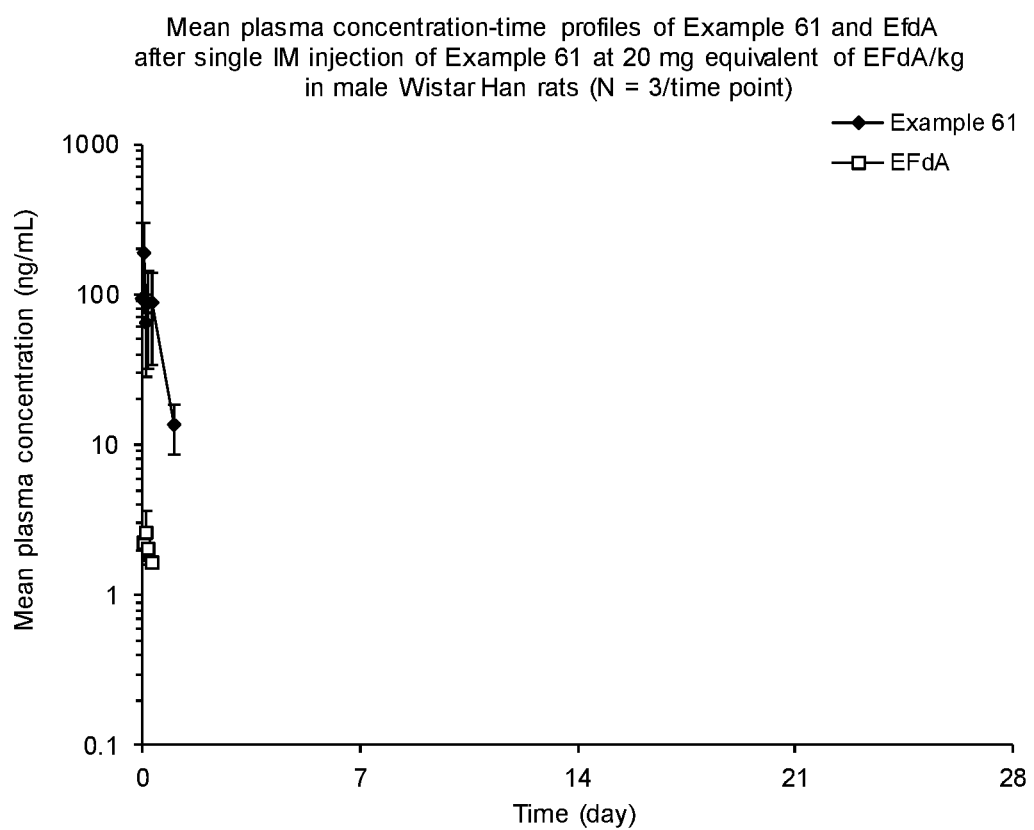
FIG. 19 illustrates the mean plasma concentration-time profiles of Example 61 and EFdA after single IM injection of Example 61 at 20 mg/kg equivalent of EFdA in male Wistar Han rats (N=3/time point)
Figure 20:
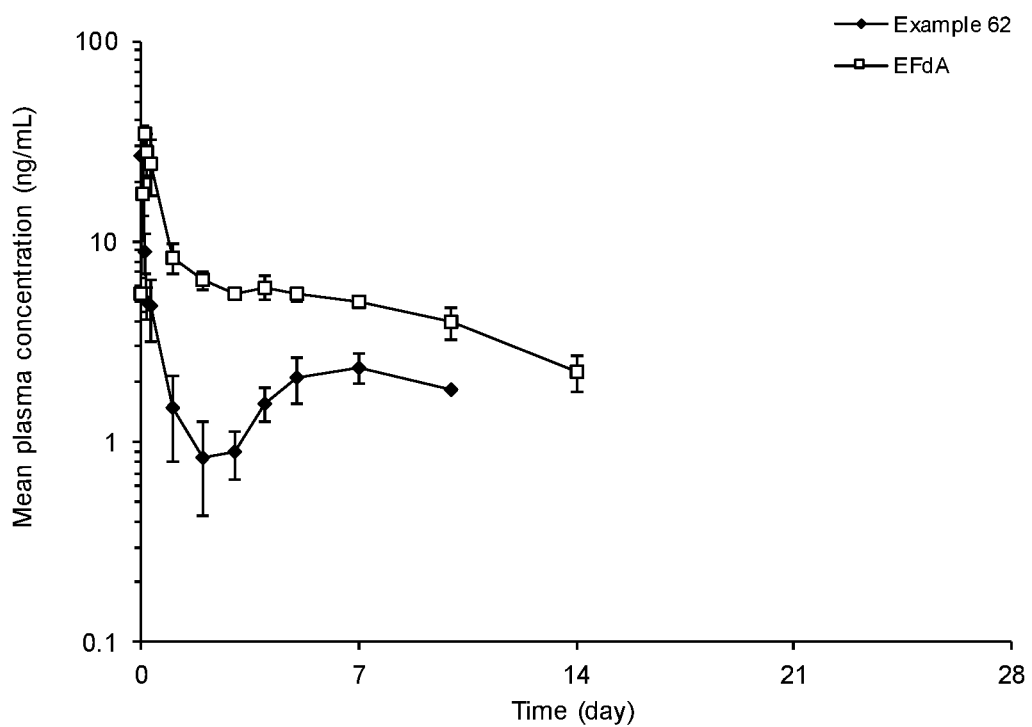
FIG. 20 illustrates the mean plasma concentration-time profiles of Example 62 and EFdA after single IM injection of Example 62 at 20 mg/kg in male Wistar Han rats (N=3/time point)
Figure 21:
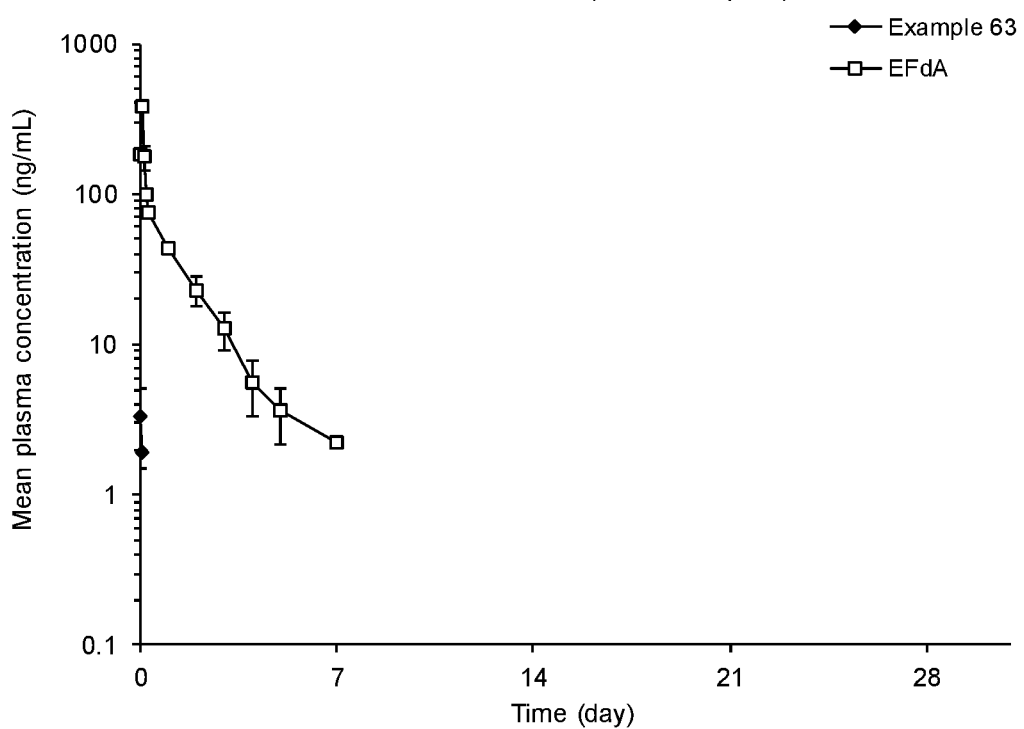
FIG. 21 illustrates the mean plasma concentration-time profiles of Example 63 and EFdA after single IM injection of Example 63 at 20 mg/kg equivalent of EFdA in male Wistar Han rats (N=3/time point)
Figure 22:
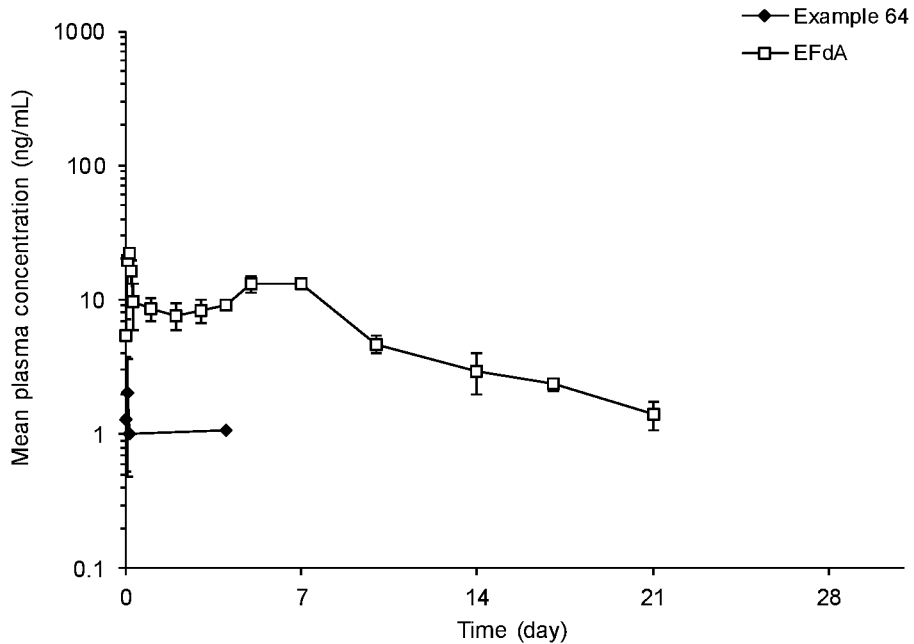
FIG. 22 illustrates the mean plasma concentration-time profiles of Example 64 and EFdA after single IM injection of Example 64 at 20 mg/kg equivalent of EFdA in male Wistar Han rats (N=3/time point)
Figure 23:
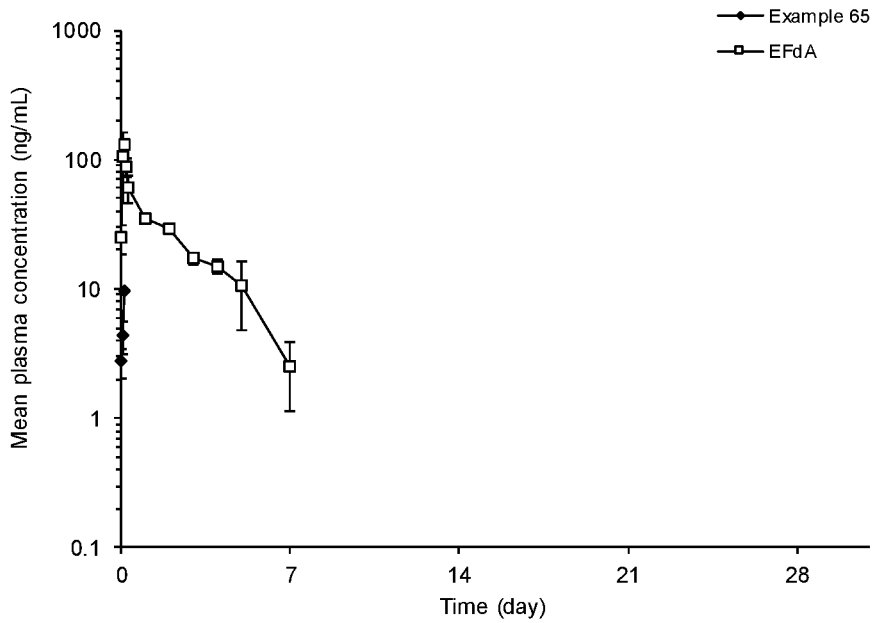
FIG. 23 illustrates the mean plasma concentration-time profiles of Example 65 and EFdA after single IM injection of Example 65 at 20 mg/kg equivalent of EFdA in male Wistar Han rats (N=3/time point)
Figure 24:
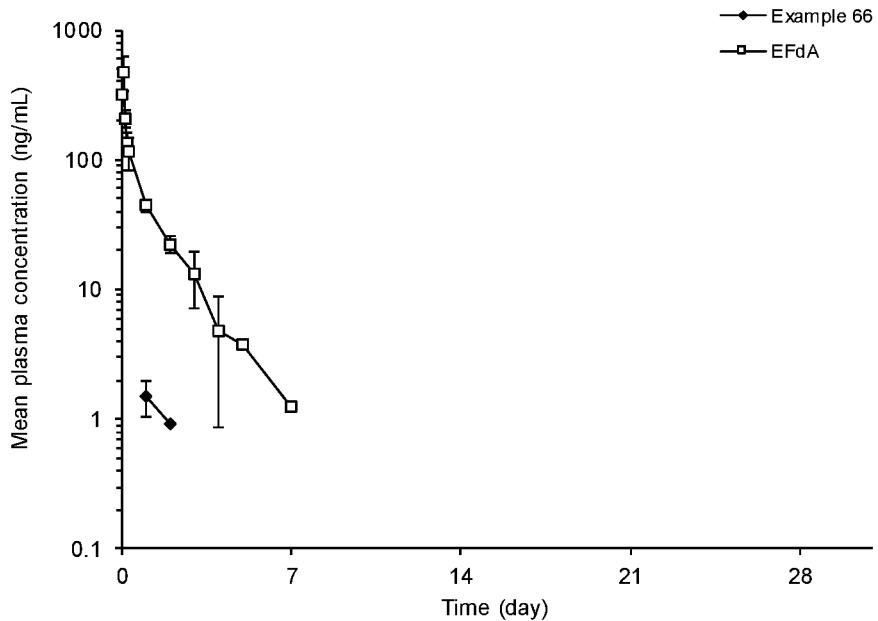
FIG. 24 illustrates the mean plasma concentration-time profiles of example 66 and EFdA after single IM injection of Example 66 at 20 mg/kg equivalent of EFdA in male Wistar Han rats (N=3/time point)

The PK plasma samples were analyzed by the Testing Facility to determine the concentration of EFdA using an LC-MS/MS Research Grade Assay (RGA-1) with sensitivity to 0.1 ng/mL. Following review of sample analysis data through Day 29, further sample analysis was discontinued and the study was terminated. The sample concentration data are presented in Tables 7 and 8 and mean concentration-time profiles are shown in FIGS. 2 and 3.

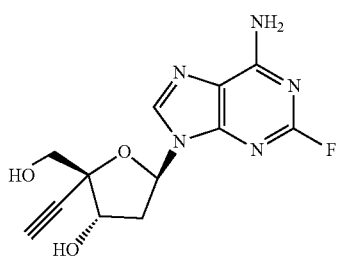 [SMILES: C#C[C@]1(CO)O[C@@H](n2cnc3c(N)nc(F)nc32)C[C@@H]1O]

(2R,3S,5R)-5-(6-amino-2-fluoro-9H-purin-9-yl)-2-ethynyl-2-(hydroxymethyl)tetrahydrofuran-3-ol (EFdA)

TABLE 7

Plasma concentration of EFdA from rat SC PK study
Assayed Concentrations (ng/mL)

| Time | Rat#1 | Rat#2 | Rat#3 | Mean |
|---|---|---|---|---|
| 0.5 hr | 1000 | 640 | 2210 | 1283.33 |
| 1 hr | 1160 | 1040 | 3030 | 1430.0 |
| 4 hr | 534 | 676 | 708 | 639.33 |
| 7 hr | 320 | 372 | 216 | 302.67 |
| 24 hr | 6.70 | 14.7 | 2.53 | 7.98 |
| 48 hr | 0.771 | 0.713 | 0.543 | 0.68 |
| 72 hr | 0.251 | 0.270 | 0.201 | 0.241 |
| Day 6 | BQL | BQL | 0.117 | 0.04 |
| Day 8 | BQL | BQL | BQL | BQL |
| Day 11 | BQL | BQL | BQL | BQL |
| Day 15 | BQL | BQL | BQL | BQL |
| Day 22 | BQL | BQL | BQL | BQL |
| Day 25 | 0.221 | BQL | BQL | 0.221 |
| Day 29 | BQL | BQL | BQL | BQL |

BQL—Below Quantitation Limit, <0.100 ng/mL

TABLE 8

Plasma concentration of EFdA from rat IM PK study
Assayed Concentrations (ng/mL)

| Time | Rat#1 | Rat#2 | Rat#3 | Mean |
|---|---|---|---|---|
| 0.5 hr | 929 | 1150 | 684 | 921.0 |
| 1 hr | 957 | 1640 | 1400 | 1332.33 |
| 4 hr | 662 | 436 | 733 | 610.33 |
| 7 hr | 241 | 191 | 426 | 286.0 |
| 24 hr | 24.7 | 1.96 | 32.6 | 19.75 |
| 48 hr | 5.25 | 0.369 | 0.915 | 2.18 |
| 72 hr | 0.301 | 0.316 | 0.241 | 0.29 |
| Day 6 | 0.102 | BQL | 0.103 | 0.10 |
| Day 8 | BQL | BQL | BQL | BQL |
| Day 11 | BQL | BQL | BQL | BQL |
| Day 15 | BQL | BQL | BQL | BQL |
| Day 22 | BQL | BQL | BQL | BQL |
| Day 25 | BQL | BQL | BQL | BQL |
| Day 29 | BQL | BQL | BQL | BQL |

BQL—Below Quantitation Limit, <0.100 ng/mL

General Protocol for Prodrugs Rat PK Studies

A total of three naïve male Wistar Han rats, 250-300 g, were received and following an acclimation period, the animals were assigned to the study based on acceptable health as determined by a staff veterinarian and catheter patency. Fasting of the animals before or after dosing was not required.

The final study design is presented in the Table 9 below.

TABLE 9

| No. of Males | Dose Level (mg/kg) | Dose Conc. (mg/mL) | Dose Vehicle | Dose Route |
|---|---|---|---|---|
| 3 | 20 (equivalent of EFdA) | 2 | 2% Kolliphor P407 + 2% PEG3350 + 3.5% Mannitol + 92.5% water | Intramuscular |

PEG3350 = Polyethylene glycol 3350.

On Day 1, each animal received a single intramuscular injection of prepared test article at a target dose level of 20 mg/kg equivalent of EFdA and at a dose volume of 2 mL/kg. The injection sites were at gastrocnemius and identified with an indelible marker for daily monitoring during the study. The animals were manually restrained for dosing and were not sedated. The dose suspension was mixed well by inversion before each dose to ensure homogeneity. All dosing was performed as detailed in the study protocol and was completed without incident. Following dosing and at each sample collection time point the animals and injection sites were observed for any clinically relevant abnormalities. In addition, all animals are monitored twice daily by the veterinary staff for clinical abnormalities. No abnormal clinical observations and no injection site reactions were noted during the study period.

Blood samples were collected from the study animals as detailed in the sample collection Table 10 below

TABLE 10

| Collection Information | Whole Blood for PK |
|---|---|
| Collection time | 0.5, 1, 3, 5 and 7 hr, 1, 2, 3, 4, 5 and 7 days post dose then 2×/week (Day10 and Day 14, etc) |
| Anticoagulant | NaF/Na$_2$EDTA |
| Volume/Time point | 200 μL blood |

Each blood sample for PK (200 μL) was collected from tail vein. The blood was transferred to a tube containing NaF/Na$_2$EDTA anticoagulant and inverted several times to mix. Draw 150 μL whole blood from the tube, add 150 uL 100 mM ammonium acetate, pH 4 buffer and mix well. The resulting blood samples were transferred to individual polypropylene tubes and immediately placed on dry ice until storage at nominally −80° C. prior to LC-MS/MS analysis. The mean sample concentration data are presented in Tables 11 to 31 and mean concentration-time profiles are shown in FIGS. 4 to 24.

Reference to Example 11

TABLE 11

Plasma concentration of Example 11 and EFdA from Example 11 rat IM PK study

| Dose (mg/kg)/ Dose route | Sampling time (day) | Mean concentration of Example 11 (ng/mL) | Mean concentration of EFdA (ng/mL) |
|---|---|---|---|
| 20/IM | 0.0208 | 6.71 | 94.0 |
| | 0.0417 | 3.37 | 121 |
| | 0.125 | 0.872 | 55.1 |
| | 0.208 | BQL | 38.1 |
| | 0.292 | BQL | 26.6 |
| | 1 | BQL | 5.77 |
| | 2 | BQL | 3.90 |
| | 3 | BQL | 2.93 |
| | 4 | BQL | 3.00 |
| | 5 | BQL | 2.85 |
| | 7 | BQL | 5.29 |
| | 10 | BQL | 1.26 |
| | 14 | BQL | 1.22 |
| | 17 | | BQL |
| | 21 | | BQL |
| | 24 | | BQL |
| | 28 | | BQL |
| | 31 | | BQL |
| | 35 | | BQL |
| | 38 | | BQL |
| | 42 | | BQL |

Reference to Example 17

TABLE 12

Plasma concentration of Example 17 and EFdA from Example 17 rat IM PK study

| Dose (mg/kg)/ Dose route | Sampling time (day) | Mean concentration of Example 17 (ng/mL) | Mean concentration of EFdA (ng/mL) |
|---|---|---|---|
| 20 (equivalent to EFdA)/IM | 0.0208 | 15.7 | BQL |
| | 0.0417 | 28.4 | 0.900 |
| | 0.125 | 29.1 | 1.43 |
| | 0.208 | 23.0 | 0.981 |
| | 0.292 | 26.7 | BQL |
| | 1 | 14.3 | BQL |
| | 2 | 2.90 | BQL |
| | 3 | 1.47 | 1.23 |
| | 4 | 1.15 | BQL |
| | 5 | 0.99 | BQL |
| | 7 | 1.25 | BQL |
| | 10 | 1.40 | 0.878 |
| | 14 | 0.757 | 1.12 |

Reference to Example 18

TABLE 13

Plasma concentration of Example 18 and EFdA from Example 18 rat IM PK study

| Dose (mg/kg)/ Dose route | Sampling time (day) | Mean concentration of Example 18 (ng/mL) | Mean concentration of EFdA (ng/mL) |
|---|---|---|---|
| 20 (equivalent to EFdA)/IM | 0.0208 | 43.1 | BQL |
| | 0.0417 | 87.0 | 2.97 |
| | 0.125 | 58.0 | 4.62 |
| | 0.208 | 47.1 | 4.02 |
| | 0.292 | 49.2 | 4.74 |
| | 1 | 2.44 | BQL |
| | 2 | BQL | 1.91 |
| | 3 | BQL | 2.69 |
| | 4 | BQL | 2.06 |
| | 5 | BQL | 2.39 |
| | 7 | BQL | 1.88 |
| | 10 | BQL | 1.91 |
| | 14 | BQL | 2.53 |
| | 17 | BQL | 1.90 |
| | 21 | BQL | 1.62 |
| | 24 | BQL | 1.73 |
| | 28 | BQL | 1.38 |
| | 31 | BQL | 1.56 |
| | 35 | BQL | 1.59 |
| | 38 | BQL | 1.35 |
| | 42 | BQL | BQL |
| | 45 | | 0.836 |
| | 49 | | BQL |
| | 52 | | BQL |
| | 56 | | BQL |
| | 59 | | BQL |
| | 63 | | BQL |
| | 66 | | BQL |

Reference to Example 31

TABLE 14

Plasma concentration of Example 31 and EFdA from Example 31 rat IM PK study

| Dose (mg/kg)/ Dose route | Sampling time (day) | Mean concentration of Example 31 (ng/mL) | Mean concentration of EFdA (ng/mL) |
|---|---|---|---|
| 20 (equivalent to EFdA)/IM | 0.0208 | 8.33 | 98.4 |
| | 0.0417 | 13.6 | 370 |
| | 0.125 | 1.65 | 1107 |
| | 0.208 | BQL | 669 |
| | 0.292 | BQL | 284 |
| | 1 | BQL | 46.9 |
| | 2 | 6.51 | 14.7 |
| | 3 | 17.3 | 4.88 |
| | 4 | 1.60 | 2.37 |
| | 5 | 4.05 | BQL |
| | 7 | BQL | BQL |
| | 10 | 68.7 | BQL |
| | 14 | BQL | BQL |
| | 17 | BQL | BQL |
| | 21 | BQL | BQL |
| | 24 | BQL | BQL |
| | 28 | BQL | BQL |
| | 31 | BQL | BQL |

Reference to Example 32

TABLE 15

Plasma concentration of Example 32 and EFdA from Example 32 rat IM PK study

| Dose (mg/kg)/ Dose route | Sampling time (day) | Mean concentration of Example 32 (ng/mL) | Mean concentration of EFdA (ng/mL) |
|---|---|---|---|
| 20 (equivalent to EFdA)/IM | 0.0208 | 23.2 | 138 |
| | 0.0417 | 20.4 | 246 |
| | 0.125 | 6.58 | 185 |
| | 0.208 | 4.58 | 102 |
| | 0.292 | 2.08 | 74.2 |
| | 1 | BQL | 45.9 |
| | 2 | BQL | 41.9 |
| | 3 | BQL | 33.8 |
| | 4 | BQL | 26.8 |
| | 5 | BQL | 19.3 |
| | 7 | BQL | 3.96 |
| | 10 | BQL | 4.28 |
| | 14 | BQL | BQL |
| | 17 | BQL | BQL |
| | 21 | BQL | BQL |
| | 24 | BQL | BQL |
| | 28 | BQL | BQL |
| | 31 | BQL | BQL |

Reference to Example 37

TABLE 16

Plasma concentration of Example 37 and EFdA from Example 37 rat IM PK study

| Dose (mg/kg)/ Dose route | Sampling time (day) | Mean concentration of Example 37 (ng/mL) | Mean concentration of EFdA (ng/mL) |
|---|---|---|---|
| 20 (equivalent to EFdA)/IM | 0.0208 | 13.8 | 31.4 |
| | 0.0417 | 13.7 | 49.3 |
| | 0.125 | 10.0 | 32.3 |
| | 0.208 | 4.84 | 25.4 |
| | 0.292 | BQL | 17.3 |
| | 1 | BQL | 13.7 |
| | 2 | BQL | 18.5 |
| | 3 | BQL | 13.8 |
| | 4 | BQL | 11.7 |
| | 5 | 7.53 | 12.2 |
| | 7 | BQL | 15.2 |
| | 10 | 7.72 | 12.9 |
| | 14 | BQL | 7.13 |
| | 17 | 1.82 | 2.68 |
| | 21 | 1.47 | 1.76 |
| | 24 | 1.25 | BQL |
| | 28 | 1.58 | BQL |
| | 31 | 6.65 | BQL |
| | 35 | 1.70 | BQL |
| | 38 | 24.1 | BQL |
| | 42 | BQL | BQL |

Reference to Example 38

TABLE 17

Plasma concentration of Example 38 and EFdA from Example 38 rat IM PK study

| Dose (mg/kg)/ Dose route | Sampling time (day) | Mean concentration of Example 38 (ng/mL) | Mean concentration of EFdA (ng/mL) |
|---|---|---|---|
| 20 (equivalent to EFdA)/IM | 0.0208 | 11.2 | 1.96 |
| | 0.0417 | 11.5 | 3.34 |
| | 0.125 | 14.3 | 4.30 |
| | 0.208 | 10.5 | 4.78 |
| | 0.292 | 6.80 | 3.25 |
| | 1 | BQL | 2.31 |
| | 2 | BQL | 164 |
| | 3 | BQL | 81.7 |
| | 4 | 1.83 | 80.6 |
| | 5 | 2.00 | 48.9 |
| | 7 | BQL | 2.84 |
| | 10 | BQL | 3.29 |
| | 14 | BQL | 3.75 |
| | 17 | BQL | 3.09 |
| | 21 | BQL | 3.63 |
| | 24 | BQL | 3.86 |
| | 28 | BQL | 2.55 |
| | 31 | BQL | 1.89 |
| | 35 | BQL | 2.02 |
| | 38 | | 1.57 |
| | 42 | | 1.38 |
| | 45 | | 1.25 |
| | 49 | | 0.994 |
| | 52 | | 0.885 |
| | 56 | | 0.949 |
| | 59 | | 1.11 |
| | 63 | | 0.822 |
| | 66 | | 0.868 |
| | 70 | | BQL |
| | 73 | | BQL |

TABLE 17-continued

Plasma concentration of Example 38 and EFdA from Example 38 rat IM PK study

| Dose (mg/kg)/ Dose route | Sampling time (day) | Mean concentration of Example 38 (ng/mL) | Mean concentration of EFdA (ng/mL) |
|---|---|---|---|
| | 77 | | BQL |
| | 80 | | BQL |
| | 84 | | BQL |
| | 87 | | BQL |

Reference to Example 39

TABLE 18

Plasma concentration of Example 39 and EFdA from Example 39 rat IM PK study

| Dose (mg/kg)/ Dose route | Sampling time (day) | Mean concentration of Example 39 (ng/mL) | Mean concentration of EFdA (ng/mL) |
|---|---|---|---|
| 20 (equivalent to EFdA)/IM | 0.0208 | 33.9 | 69.4 |
| | 0.0417 | 36.0 | 168 |
| | 0.125 | 21.0 | 165 |
| | 0.208 | 11.6 | 156 |
| | 0.292 | 7.90 | 131 |
| | 1 | BQL | 121 |
| | 2 | 5.52 | 104 |
| | 3 | BQL | 89.2 |
| | 4 | BQL | 105 |
| | 5 | 8.32 | 109 |
| | 7 | 6.13 | 83.4 |
| | 10 | BQL | 39.3 |
| | 14 | BQL | 6.92 |
| | 17 | BQL | 3.35 |
| | 21 | BQL | BQL |
| | 24 | BQL | BQL |
| | 28 | BQL | 2.88 |
| | 31 | BQL | BQL |
| | 35 | BQL | BQL |
| | 38 | BQL | BQL |
| | 42 | BQL | BQL |

Reference to Example 40

TABLE 19

Plasma concentration of Example 40 and EFdA from Example 40 rat IM PK study

| Dose (mg/kg)/ Dose route | Sampling time (day) | Mean concentration of Example 40 (ng/mL) | Mean concentration of EFdA (ng/mL) |
|---|---|---|---|
| 20 (equivalent to EFdA)/IM | 0.0208 | BQL | 198 |
| | 0.0417 | BQL | 304 |
| | 0.125 | BQL | 288 |
| | 0.208 | BQL | 210 |
| | 0.292 | BQL | 157 |
| | 1 | BQL | 51.0 |
| | 2 | BQL | 9.36 |
| | 3 | BQL | 4.16 |
| | 4 | BQL | 1.67 |
| | 5 | BQL | BQL |
| | 7 | BQL | BQL |
| | 10 | BQL | BQL |
| | 14 | BQL | BQL |

TABLE 19-continued

Plasma concentration of Example 40 and EFdA from Example 40 rat IM PK study

| Dose (mg/kg)/ Dose route | Sampling time (day) | Mean concentration of Example 40 (ng/mL) | Mean concentration of EFdA (ng/mL) |
|---|---|---|---|
| | 17 | BQL | BQL |
| | 21 | BQL | BQL |

Reference to Example 42

TABLE 20

Plasma concentration of Example 42 and EFdA from Example 42 rat IM PK study

| Dose (mg/kg)/ Dose route | Sampling time (day) | Mean concentration of Example 42 (ng/mL) | Mean concentration of EFdA (ng/mL) |
|---|---|---|---|
| 20 (equivalent to EFdA)/IM | 0.0208 | 2.26 | 104 |
| | 0.0417 | BQL | 148 |
| | 0.125 | BQL | 117 |
| | 0.208 | BQL | 94.2 |
| | 0.292 | BQL | 93.2 |
| | 1 | BQL | 35.6 |
| | 2 | BQL | 13.3 |
| | 3 | BQL | 6.00 |
| | 4 | BQL | BQL |
| | 5 | BQL | BQL |
| | 7 | BQL | BQL |
| | 10 | BQL | BQL |
| | 14 | BQL | BQL |
| | 17 | BQL | BQL |
| | 21 | BQL | BQL |
| | 24 | BQL | BQL |
| | 28 | BQL | BQL |
| | 31 | BQL | BQL |

Reference to Example 45

TABLE 21

Plasma concentration of Example 45 and EFdA from Example 45 rat IM PK study

| Dose (mg/kg)/ Dose route | Sampling time (day) | Mean concentration of Example 45 (ng/mL) | Mean concentration of EFdA (ng/mL) |
|---|---|---|---|
| 20 (equivalent to EFdA)/IM | 0.0208 | 35.6 | 30.1 |
| | 0.0417 | 49.1 | 90.3 |
| | 0.125 | 42.8 | 181 |
| | 0.208 | 15.7 | 98.5 |
| | 0.292 | 6.15 | 61.4 |
| | 1 | 0.847 | 23.1 |
| | 2 | BQL | 16.9 |
| | 3 | BQL | 12.7 |
| | 4 | BQL | 6.53 |
| | 5 | 1.56 | 6.96 |
| | 7 | BQL | 5.59 |
| | 10 | BQL | 5.64 |
| | 14 | BQL | BQL |
| | 17 | BQL | BQL |
| | 21 | BQL | BQL |
| | 24 | | BQL |
| | 28 | | BQL |
| | 31 | | BQL |
| | 35 | | BQL |

Reference to Example 48

TABLE 22

Plasma concentration of Example 48 and EFdA from Example 48 rat IM PK study

| Dose (mg/kg)/ Dose route | Sampling time (day) | Mean concentration of Example 48 (ng/mL) | Mean concentration of EFdA (ng/mL) |
|---|---|---|---|
| 20 (equivalent to EFdA)/IM | 0.0208 | 10.4 | BQL |
| | 0.0417 | 15.9 | 1.43 |
| | 0.125 | 7.04 | 2.32 |
| | 0.208 | 4.43 | 2.13 |
| | 0.292 | 2.00 | 2.51 |
| | 1 | BQL | 4.11 |
| | 2 | BQL | 6.57 |
| | 3 | BQL | 10.3 |
| | 4 | BQL | 14.3 |
| | 5 | BQL | 17.7 |
| | 7 | BQL | 10.8 |
| | 10 | BQL | 1.86 |
| | 14 | BQL | BQL |
| | 17 | BQL | BQL |
| | 21 | BQL | BQL |

Reference to Example 50

TABLE 23

Plasma concentration of Example 50 and EFdA from Example 50 rat IM PK study

| Dose (mg/kg)/ Dose route | Sampling time (day) | Mean concentration of Example 50 (ng/mL) | Mean of concentration EFdA (ng/mL) |
|---|---|---|---|
| 20 (equivalent to EFdA)/IM | 0.0208 | BQL | 3223 |
| | 0.0417 | BQL | 3077 |
| | 0.125 | BQL | 239 |
| | 0.208 | BQL | 38.7 |
| | 0.292 | BQL | 19.3 |
| | 1 | BQL | 1.48 |
| | 2 | BQL | BQL |
| | 3 | BQL | BQL |
| | 4 | BQL | BQL |
| | 5 | BQL | BQL |
| | 7 | BQL | BQL |
| | 10 | BQL | BQL |
| | 14 | BQL | BQL |
| | 17 | BQL | BQL |
| | 21 | BQL | BQL |

Reference to Example 58

TABLE 24

Plasma concentration of Example 58 and EFdA from Example 58 rat IM PK study

| Dose (mg/kg)/ Dose route | Sampling time (day) | Mean concentration of Example 58 (ng/mL) | Mean concentration of EFdA (ng/mL) |
|---|---|---|---|
| 20 (equivalent to EFdA)/IM | 0.0208 | 11.4 | 1.20 |
| | 0.0417 | 14.9 | 1.10 |
| | 0.125 | 9.18 | 1.02 |
| | 0.208 | 7.95 | BQL |
| | 0.292 | 7.82 | BQL |
| | 1 | 2.96 | BQL |
| | 2 | 1.05 | BQL |
| | 3 | 0.844 | BQL |

TABLE 24-continued

Plasma concentration of Example 58 and EFdA from Example 58 rat IM PK study

| Dose (mg/kg)/ Dose route | Sampling time (day) | Mean concentration of Example 58 (ng/mL) | Mean concentration of EFdA (ng/mL) |
|---|---|---|---|
| | 4 | BQL | BQL |
| | 5 | BQL | 0.838 |
| | 7 | BQL | 1.34 |
| | 10 | BQL | 1.62 |
| | 14 | | 1.94 |
| | 17 | | 2.10 |
| | 21 | | BQL |
| | 24 | | 1.22 |
| | 28 | | 1.23 |
| | 31 | | 0.879 |
| | 35 | | BQL |
| | 38 | | BQL |
| | 42 | | BQL |
| | 45 | | BQL |
| | 49 | | BQL |

Reference to Example 59

TABLE 25

Plasma concentration of Example 59 and EFdA from Example 59 rat IM PK study

| Dose (mg/kg)/ Dose route | Sampling time (day) | Mean concentration of Example 59 (ng/mL) | Mean concentration of EFdA (ng/mL) |
|---|---|---|---|
| 20 (equivalent to EFdA)/IM | 0.0208 | 20.8 | BQL |
| | 0.0417 | 26.7 | 0.899 |
| | 0.125 | 43.3 | 2.29 |
| | 0.208 | 42.4 | 2.08 |
| | 0.292 | 42.4 | BQL |
| | 1 | 8.72 | BQL |
| | 2 | 4.23 | BQL |
| | 3 | 2.52 | BQL |
| | 4 | 2.36 | BQL |
| | 5 | | BQL |
| | 7 | | BQL |
| | 10 | | 2.66 |
| | 14 | | 2.31 |

Reference to Example 61

TABLE 26

Plasma concentration of Example 61 and EFdA from Example 61 rat IM PK study

| Dose (mg/kg)/ Dose route | Sampling time (day) | Mean concentration of Example 61 (ng/mL) | Mean of concentration EFdA (ng/mL) |
|---|---|---|---|
| 20 (equivalent to EFdA)/IM | 0.0208 | 93.3 | BQL |
| | 0.0417 | 189 | 2.21 |
| | 0.125 | 64.3 | 2.63 |
| | 0.208 | 88.7 | 2.02 |
| | 0.292 | 87.4 | 1.63 |
| | 1 | 13.6 | BQL |
| | 2 | BQL | BQL |
| | 3 | BQL | BQL |
| | 4 | BQL | BQL |
| | 5 | BQL | BQL |
| | 7 | BQL | BQL |
| | 10 | BQL | BQL |
| | 14 | BQL | BQL |

TABLE 26-continued

Plasma concentration of Example 61 and EFdA from Example 61 rat IM PK study

| Dose (mg/kg)/ Dose route | Sampling time (day) | Mean concentration of Example 61 (ng/mL) | Mean of concentration EFdA (ng/mL) |
|---|---|---|---|
| | 17 | BQL | BQL |
| | 21 | BQL | BQL |

Reference to Example 62

TABLE 27

Plasma concentration of Example 62 and EFdA from Example 62 rat IM PK study

| Dose (mg/kg)/ Dose route | Sampling time (day) | Mean concentration of Example 62 (ng/mL) | Mean concentration of EFdA (ng/mL) |
|---|---|---|---|
| 20 (equivalent to EFdA)/IM | 0.0208 | 26.7 | 5.50 |
| | 0.0417 | 27.6 | 17.2 |
| | 0.125 | 8.98 | 34.8 |
| | 0.208 | 4.98 | 27.7 |
| | 0.292 | 4.79 | 24.5 |
| | 1 | 1.47 | 8.31 |
| | 2 | 0.839 | 6.42 |
| | 3 | 0.887 | 5.51 |
| | 4 | 1.57 | 5.93 |
| | 5 | 2.08 | 5.43 |
| | 7 | 2.36 | 5.06 |
| | 10 | 1.82 | 3.94 |
| | 14 | 1.68 | 2.23 |
| | 17 | BQL | BQL |
| | 21 | BQL | BQL |
| | 24 | BQL | BQL |
| | 28 | BQL | BQL |

Reference to Example 63

TABLE 28

Plasma concentration of Example 63 and EFdA from Example 63 rat IM PK study

| Dose (mg/kg)/ Dose route | Sampling time (day) | Mean concentration of Example 63 (ng/mL) | Mean of concentration EFdA (ng/mL) |
|---|---|---|---|
| 20 (equivalent to EFdA)/IM | 0.0208 | 3.28 | 183 |
| | 0.0417 | 1.92 | 386 |
| | 0.125 | BQL | 176 |
| | 0.208 | BQL | 98.0 |
| | 0.292 | BQL | 75.1 |
| | 1 | BQL | 43.6 |
| | 2 | BQL | 23.0 |
| | 3 | BQL | 12.7 |
| | 4 | BQL | 5.64 |
| | 5 | BQL | 3.63 |
| | 7 | BQL | 2.23 |
| | 10 | BQL | BQL |
| | 14 | BQL | BQL |
| | 17 | | BQL |
| | 21 | | BQL |
| | 24 | | BQL |
| | 28 | | BQL |

Reference to Example 64

TABLE 29

Plasma concentration of Example 64 and EFdA from Example 64 rat IM PK study

| Dose (mg/kg)/ Dose route | Sampling time (day) | Mean concentration of Example 64 (ng/mL) | Mean concentration of EFdA (ng/mL) |
|---|---|---|---|
| 20 (equivalent to EFdA)/IM | 0.0208 | 1.30 | 5.48 |
| | 0.0417 | 2.05 | 19.9 |
| | 0.125 | 0.994 | 22.1 |
| | 0.208 | BQL | 16.6 |
| | 0.292 | BQL | 9.58 |
| | 1 | BQL | 8.61 |
| | 2 | BQL | 7.63 |
| | 3 | BQL | 8.31 |
| | 4 | 1.07 | 8.99 |
| | 5 | BQL | 13.2 |
| | 7 | BQL | 13.3 |
| | 10 | BQL | 4.70 |
| | 14 | BQL | 2.98 |
| | 17 | | 2.38 |
| | 21 | | 1.42 |
| | 24 | | BQL |
| | 28 | | BQL |

Reference to Example 65

TABLE 30

Plasma concentration of Example 65 and EFdA from Example 65 rat IM PK study

| Dose (mg/kg)/ Dose route | Sampling time (day) | Mean concentration of Example 65 (ng/mL) | Mean concentration of EFdA (ng/mL) |
|---|---|---|---|
| 20 (equivalent to EFdA)/IM | 0.0208 | 2.75 | 24.7 |
| | 0.0417 | 4.33 | 105 |
| | 0.125 | 9.69 | 130 |
| | 0.208 | BQL | 88.3 |
| | 0.292 | BQL | 61.0 |
| | 1 | BQL | 35.1 |
| | 2 | BQL | 29.5 |
| | 3 | BQL | 17.1 |
| | 4 | BQL | 15.0 |
| | 5 | BQL | 10.5 |
| | 7 | BQL | 2.51 |
| | 10 | | BQL |
| | 14 | | BQL |
| | 17 | | BQL |
| | 21 | | BQL |
| | 24 | | BQL |
| | 28 | | BQL |

Reference to Example 66

TABLE 31

Plasma concentration of Example 66 and EFdA from Example 66 rat IM PK study

| Dose (mg/kg)/ Dose route | Sampling time (day) | Mean concentration of Example 66 (ng/mL) | Mean of concentration EFdA (ng/mL) |
|---|---|---|---|
| 20 (equivalent to EFdA)/IM | 0.0208 | 1.51 | 322 |
| | 0.0417 | 0.928 | 480 |
| | 0.125 | BQL | 209 |
| | 0.208 | BQL | 135 |
| | 0.292 | BQL | 117 |
| | 1 | BQL | 44.7 |
| | 2 | BQL | 22.5 |
| | 3 | BQL | 13.3 |
| | 4 | BQL | 4.83 |
| | 5 | BQL | 3.78 |
| | 7 | BQL | 1.25 |
| | 10 | | BQL |
| | 14 | | BQL |
| | 17 | | BQL |
| | 21 | | BQL |
| | 24 | | BQL |
| | 28 | | BQL |

Protocol for Example 18 Rat PK Studies

Example 18 referenced herein was made in accordance with Synthesis B. A total of seven naïve male Wistar Han rats, 250-275 g, were received from the supplier equipped with a surgically-implanted jugular vein catheter (JVC) to facilitate blood sample collection during the first several days of the study. Following an acclimation period, the animals were assigned to the study based on acceptable health as determined by a staff veterinarian and catheter patency. Six animals were placed into two groups of 3 rats per group. Fasting of the animals before or after dosing was not required. The final study design is presented in the Table 32 below.

TABLE 32

| Group | No. of Males | Test Article | Dose Level (mg/kg) | Dose Conc. (mg/mL) | Dose Volume (mL/kg) | Dose Vehicle | Dose Route |
|---|---|---|---|---|---|---|---|
| 1 | 3 | Example 18 (prodrug) | 20 | 84.53 (prodrug) 41.19 (parent, EFdA) | 0.49 | 1% P407/ 1 % PEG 3350 in PBS | Subcutaneous |
| 2 | 3 | | 20 | 84.53 (prodrug) 41.19 (parent, EFdA) | 0.49 | | Intramuscular |

PEG = polyethylene glycol;
PBS = phosphate-buffered saline

On Day 1 each animal in Group 1 received a single intrascapular subcutaneous injection of prepared test article at a target dose level of 20 mg parent/kg and at a dose volume of 0.49 mL/kg. Each animal in Group 2 received a single intramuscular injection of prepared test article into a thigh muscle at a target dose level of 20 mg parent/kg and at a dose volume of 0.49 mL/kg. The animals were manually restrained for dosing and were not sedated. The dose sites were clipped of hair and wiped with alcohol before dosing. All dosing was performed as detailed in the study protocol and was completed without incident.

Following dosing and at least twice daily until the end of the study, the animals and dose sites were observed for any clinically relevant abnormalities. All animals appeared normal at the time of each observation and no dose site reactions were observed Blood samples were collected from the study animals as detailed in the sample collection Table 33 below.

TABLE 33

| Group/ Collection Information | Whole Blood for PK |
|---|---|
| 1A and 2A (N = 3 per group) | 0.5, 1, 3, 5, 7, 24, 48, 72 hours post-dose and Day 8, 11, 15, 22, 25, 29, 32, 36, 39, 43, 46, 50, 53, 57, 60, 64, 67, 71, 74, 78, 81, 85, 88, 92 |
| Anticoagulant Volume/Time point | NaF tubes containing Na$_2$EDTA 250 µL of whole blood |

Figure 25:
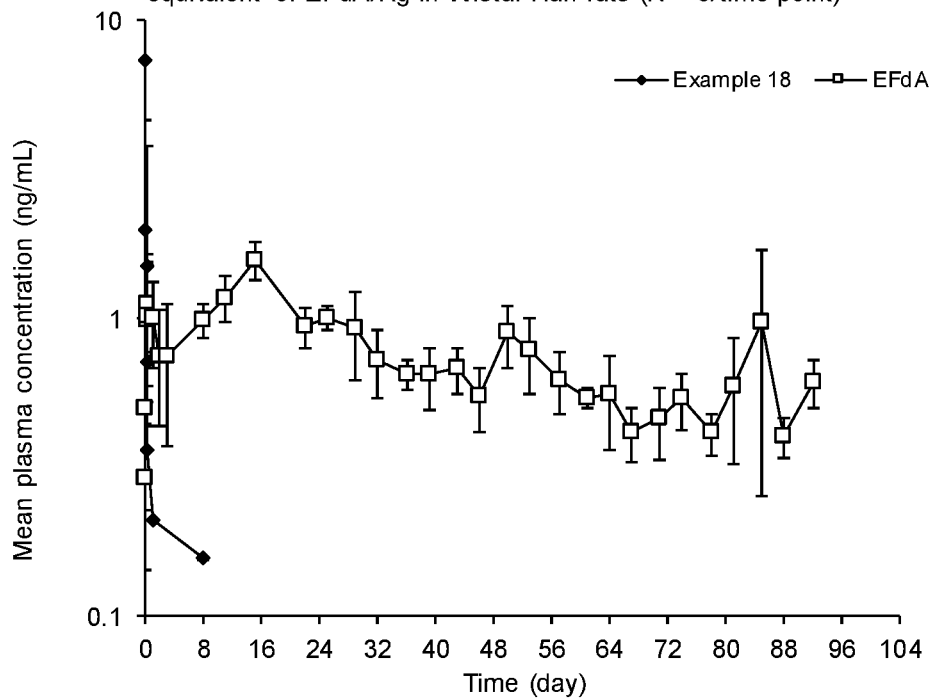
FIG. 25 illustrates the mean plasma concentration-time profiles of Example 18 and EFdA after subcutaneous dosing Example 18 at 20 mg equivalent of EFdA/kg in Wistar Han rats (N=3/time point)
Figure 26:
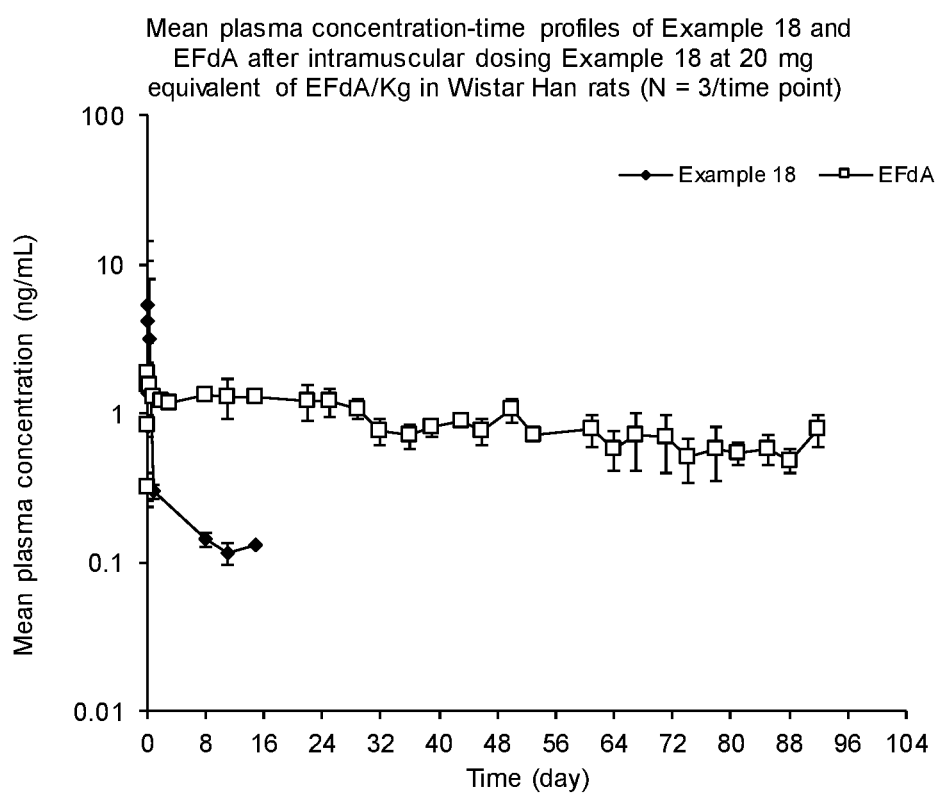
FIG. 26 illustrates the mean plasma concentration-time profiles of Example 18 and EFdA after intramuscular dosing Example 18 at 20 mg equivalent of EFdA/kg in Wistar Han rats (N=3/time point)

Interim blood samples for PK (Groups 1A and 2A) were collected from the jugular vein catheter or by venipuncture of a jugular vein if the catheter was not patent. Blood was transferred to a blood collection tube containing NaF/Na$_2$EDTA anticoagulant, mixed by inversion, and maintained on wet ice until processing. The blood samples were centrifuged at 2200×g for 10 minutes at 5° C. to isolate plasma. The resulting plasma samples were transferred to individual polypropylene tubes in a 96-well plate format and immediately placed on dry ice until storage at nominally −80° C. prior to analysis. The PK plasma samples were analyzed every 1-2 weeks by the Testing Facility to determine the concentration of prodrug and parent using an LC-MS/MS Research Grade Assay (RGA-1) with sensitivity to 0.1 ng/mL. Following interim review of sample analysis data, analysis for prodrug was discontinued after the Day 29 sample collections. The sample concentration data are presented in Tables 34 and 35, and mean concentration-time profiles are shown in FIGS. 25 and 26

TABLE 34

Plasma concentration of Example 18 and EFdA from
Example 18 rat SC PK study
SC Dosing 20 mg/kg equivalent of EFdA

| Time, | Assayed Example 18 Concentrations | | | | Assayed EFdA Concentrations | | | |
|---|---|---|---|---|---|---|---|---|
| Day | Rat#1 | Rat#2 | Rat#23 | Mean | Rat#1 | Rat#2 | Rat#3 | Mean |
| 0.021 | 7.40 | BQL | BQL | 7.40 | 0.464 | 0.194 | 0.220 | 0.29 |
| 0.042 | 3.88 | 0.103 | BQL | 1.99 | 0.819 | 0.337 | 0.349 | 0.50 |
| 0.125 | 4.19 | 0.157 | 0.143 | 1.50 | 1.63 | 0.644 | 0.701 | 0.99 |
| 0.208 | 1.80 | 0.155 | 0.200 | 0.72 | 1.74 | 0.870 | 0.768 | 1.13 |
| 0.292 | 0.804 | 0.127 | 0.150 | 0.36 | 1.61 | 0.770 | 0.704 | 1.03 |
| 1 | 0.211 | BQL | BQL | 0.21 | 1.38 | 0.792 | 0.855 | 1.01 |
| 2 | BQL | BQL | BQL | BQL | 1.11 | 0.631 | 0.515 | 0.75 |
| 3 | BQL | BQL | BQL | BQL | 1.18 | 0.570 | 0.499 | 0.75 |
| 8 | 0.158 | BQL | 0.156 | 0.16 | 1.12 | 0.979 | 0.874 | 0.99 |
| 11 | BQL | BQL | BQL | BQL | 1.32 | 1.28 | 0.949 | 1.18 |
| 15 | 0.101 | BQL | BQL | 0.10 | 1.50 | 1.84 | 1.41 | 1.58 |
| 22 | BQL | BQL | BQL | BQL | 0.787 | 0.971 | 1.07 | 0.94 |
| 25 | BQL | BQL | BQL | BQL | 1.03 | 1.10 | 0.913 | 1.01 |
| 29 | BQL | BQL | BQL | BQL | 0.681 | 1.27 | 0.833 | 0.93 |
| 32 | | | | | 0.533 | 0.905 | 0.742 | 0.73 |
| 36 | | | | | 0.573 | 0.668 | 0.726 | 0.66 |
| 39 | | | | | 0.504 | 0.811 | 0.630 | 0.65 |
| 43 | | | | | 0.546 | 0.728 | 0.768 | 0.68 |
| 46 | | | | | 0.399 | 0.603 | 0.652 | 0.55 |
| 50 | | | | | 0.715 | 0.850 | 1.13 | 0.90 |
| 53 | | | | | 0.696 | 0.614 | 1.04 | 0.78 |
| 57 | | | | | 0.475 | 0.631 | 0.770 | 0.63 |
| 61 | | | | | 0.520 | 0.589 | 0.517 | 0.54 |
| 64 | | | | | 0.359 | 0.567 | 0.742 | 0.56 |
| 67 | | | | | 0.318 | 0.476 | 0.454 | 0.42 |
| 71 | | | | | 0.315 | 0.524 | 0.546 | 0.46 |
| 74 | | | | | 0.673 | 0.476 | 0.473 | 0.54 |
| 78 | | | | | 0.379 | 0.373 | 0.490 | 0.41 |
| 81 | | | | | 0.392 | 0.491 | 0.896 | 0.59 |
| 85 | | | | | 0.719 | 0.423 | 1.80 | 0.98 |
| 88 | | | | | 0.338 | 0.407 | 0.465 | 0.40 |
| 92 | | | | | 0.666 | 0.484 | 0.689 | 0.61 |

TABLE 35

Plasma concentration of Example 18 and EFdA from
Example 18 rat IM PK study
IM Dosing 20 mg/kg equivalent of EFdA

| Time, | Assayed Example 18 Concentrations | | | | Assayed EFdA Concentrations | | | |
|---|---|---|---|---|---|---|---|---|
| Day | Rat#1 | Rat#2 | Rat#23 | Mean | Rat#1 | Rat#2 | Rat#3 | Mean |
| 0.021 | 0.111 | 15.9 | 0.233 | 5.41 | 0.279 | 0.405 | 0.299 | 0.33 |
| 0.042 | 0.620 | 11.5 | 0.408 | 4.18 | 0.734 | 0.779 | 1.01 | 0.84 |
| 0.125 | 0.689 | 1.45 | 0.314 | 0.82 | 1.37 | 1.67 | 1.62 | 1.55 |
| 0.208 | 0.594 | 3.26 | 0.340 | 1.40 | 1.55 | 2.05 | 2.09 | 1.90 |
| 0.292 | 0.377 | 8.80 | 0.239 | 3.14 | 1.41 | 1.75 | 1.46 | 1.54 |
| 1 | 0.325 | 0.276 | BQL | 0.30 | 1.28 | 1.22 | 1.41 | 1.30 |
| 2 | BQL | BQL | BQL | BQL | 1.15 | 1.21 | 1.35 | 1.24 |
| 3 | BQL | BQL | BQL | BQL | 1.33 | 1.12 | 1.12 | 1.19 |
| 8 | 0.133 | 0.156 | BQL | 0.14 | 1.45 | 1.22 | 1.30 | 1.32 |
| 11 | 0.130 | 0.102 | BQL | 0.12 | 1.58 | 0.864 | 1.48 | 1.31 |
| 15 | 0.130 | BQL | BQL | 0.13 | 1.35 | 1.24 | 1.28 | 1.29 |
| 22 | BQL | BQL | BQL | BQL | 1.59 | 0.974 | 1.11 | 1.22 |
| 25 | BQL | BQL | BQL | BQL | 1.23 | 0.934 | 1.45 | 1.20 |
| 29 | BQL | BQL | BQL | BQL | 0.976 | 1.01 | 1.27 | 1.09 |
| 32 | | | | | 0.789 | 0.608 | 0.920 | 0.77 |
| 36 | | | | | 0.688 | 0.588 | 0.857 | 0.71 |
| 39 | | | | | 0.869 | 0.690 | 0.863 | 0.81 |

TABLE 35-continued

Plasma concentration of Example 18 and EFdA from
Example 18 rat IM PK study
IM Dosing 20 mg/kg equivalent of EFdA

| Time, | Assayed Example 18 Concentrations | | | | Assayed EFdA Concentrations | | | |
|---|---|---|---|---|---|---|---|---|
| Day | Rat#1 | Rat#2 | Rat#23 | Mean | Rat#1 | Rat#2 | Rat#3 | Mean |
| 43 | | | | | 0.869 | 0.919 | 0.865 | 0.88 |
| 46 | | | | | 0.875 | 0.595 | 0.825 | 0.77 |
| 50 | | | | | 1.10 | 0.868 | 1.25 | 1.07 |
| 53 | | | | | 0.690 | 0.756 | 0.724 | 0.72 |
| 61 | | | | | 0.571 | 0.903 | 0.923 | 0.80 |
| 64 | | | | | 0.524 | 0.457 | 0.785 | 0.59 |
| 67 | | | | | 0.648 | 0.457 | 1.04 | 0.72 |
| 71 | | | | | 0.468 | 0.597 | 1.03 | 0.70 |
| 74 | | | | | 0.435 | 0.400 | 0.704 | 0.51 |
| 78 | | | | | 0.486 | 0.410 | 0.841 | 0.58 |
| 81 | | | | | 0.563 | 0.444 | 0.622 | 0.54 |
| 85 | | | | | 0.434 | 0.704 | 0.622 | 0.59 |
| 88 | | | | | 0.419 | 0.465 | 0.586 | 0.49 |
| 92 | | | | | 0.734 | 0.628 | 1.02 | 0.79 |

Protocol for Example 18 (Compound) Dog PK Studies

Example 18 referenced herein was made in accordance with Synthesis B. Six male beagle dogs (+1 spare) were selected from the Testing Facility's colony of non-naïve animals. The animals were assigned to the study based on acceptable health as determined by a Testing Facility veterinarian. Six animals were selected and placed into two groups of three animals each. Fasting of the animals before or after dosing was not required.

On Day 1 each animal in Group 1 received a single intrascapular subcutaneous injection of prepared test article at a target dose level of 5 mg parent/kg in 2% P404/2% PEG3350/PBS (dose concentration 97.36 mg/mL prodrug) and at a dose volume of 0.1 mL/kg. Each animal in Group 2 received a single intramuscular injection of prepared test article in a hind quarter (quadriceps) at a target dose level of 5 mg parent/kg in 2% P404/2% PEG3350/PBS (dose concentration 97.36 mg/mL prodrug) and at a dose volume of 0.1 mL/kg. The animals were manually restrained for dosing and were not sedated. The dose sites were clipped of hair and wiped with alcohol before dosing. All dosing was performed as detailed in the study protocol and was completed without incident.

Following dosing and at least twice daily until the end of the study, the animals and dose sites were observed for any clinically relevant abnormalities. All animals appeared normal at the time of each observation and no dose site reactions were observed.

Blood samples were collected from the study animals as detailed in the sample collection Table 26 below.

Blood samples were collected by venipuncture of a cephalic vein. For PK, blood was transferred to a blood collection tube containing NaF/Na2EDTA anticoagulant, mixed by inversion, and maintained on wet ice until processing. The blood samples were centrifuged at 2200×g for 10 minutes at 5° C. to isolate plasma. The resulting plasma samples were transferred to individual polypropylene tubes in a 96-well plate format and immediately placed on dry ice until storage at nominally −20° C. prior to shipment for analysis.

Figure 27:
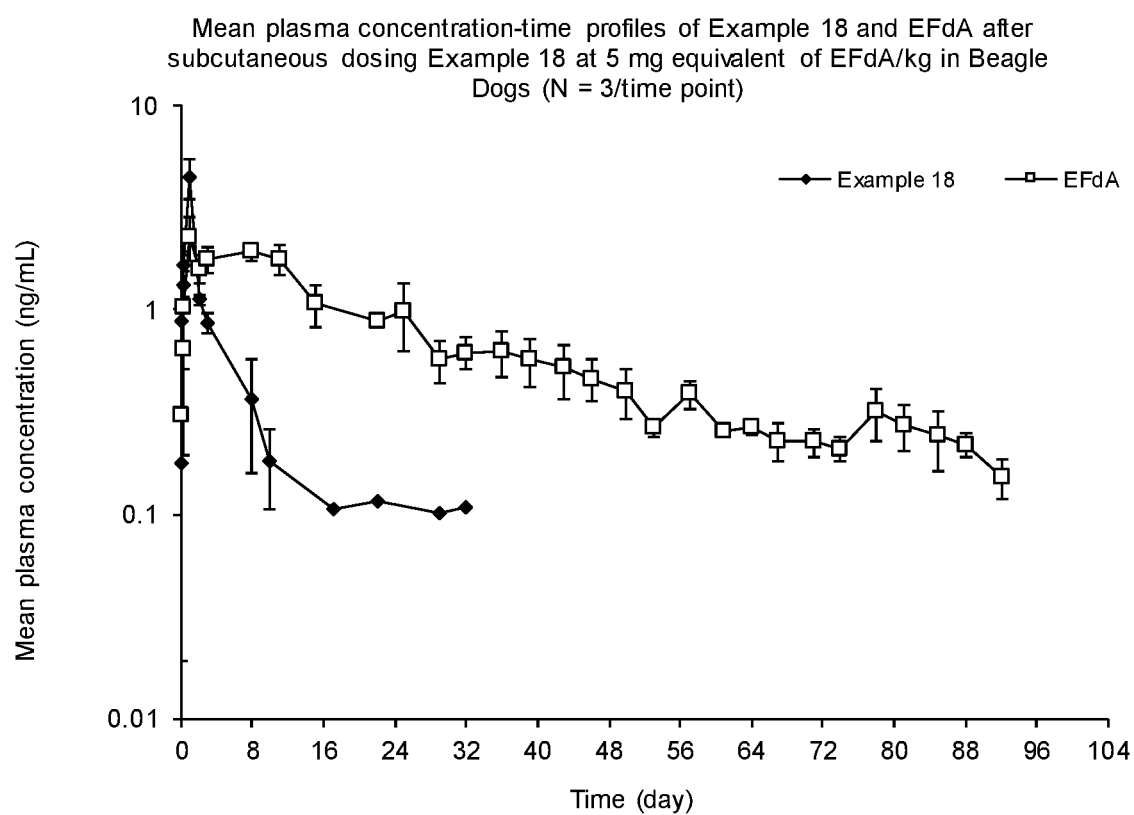
FIG. 27 illustrates the mean plasma concentration-time profiles of Example 18 and EFdA after subcutaneous dosing Example 18 at 5 mg equivalent of EFdA/kg in Beagle Dogs (N=3/time point)
Figure 28:
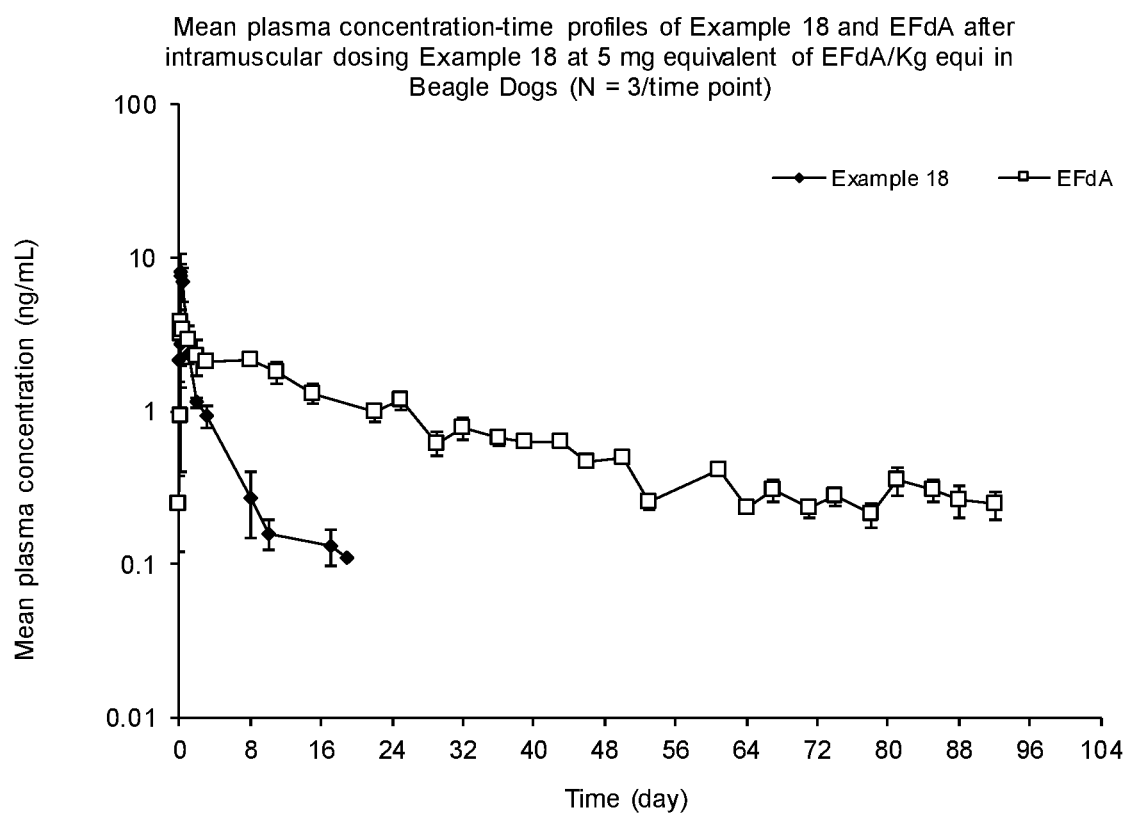
FIG. 28 illustrates the mean plasma concentration-time profiles of Example 18 and EFdA after intramuscular dosing Example 18 at 5 mg equivalent of EFdA/kg in Beagle Dogs (N=3/time point)

The PK plasma samples were analyzed approximately every two weeks by the Testing Facility to determine the concentration of Example 18 (prodrug) and parent using an LC-MS/MS Research Grade Assay (RGA-1) with sensitivity to 0.1 ng/mL. Following interim review of sample analysis data, analysis for Example 18 (prodrug) was discontinued after the Day 57 sample collections. The sample concentration data are presented in Tables 37 and 38, and mean concentration-time profiles are shown in FIGS. 27 and 28

TABLE 36

| Group/Collection Information | Whole Blood for PK |
|---|---|
| 1-2 | 0.5, 1, 3, 5, 7, 24, 48, 72 hours post-dose and Day 8, 10, 17, 19, 22, 25, 29, 32, 36, 39, 43, 46, 50, 53, 57, 60, 64, 67, 71, 74, 78, 81, 85, 88, 92 |
| Anticoagulant | NaF tubes containing Na2EDTA |
| Volume/Time point | 500 µL of whole blood |

TABLE 37

Plasma concentration of Example 18 and EFdA from
Example 18 Dog SC PK study
SC Dosing 20 mg/kg equivalent of EFdA

| Time | Example 18 Assayed Concentrations (ng/mL) | | | | EFdA Assayed Concentrations (ng/mL) | | | |
|---|---|---|---|---|---|---|---|---|
| (days) | Dog1001 | Dog1002 | Dog1003 | Mean | Dog1001 | Dog1002 | Dog1003 | Mean |
| 0.021 | BQL | BQL | BQL | BQL | BQL | BQL | BQL | BQL |
| 0.042 | BQL | 0.176 | BQL | 0.176 | BQL | BQL | BQL | BQL |
| 0125 | 0.205 | 2.00 | 0.461 | 0.889 | 0.110 | 0.638 | 0.174 | 0.307 |
| 0.208 | 0.673 | 1.94 | 1.33 | 1.31 | 0.204 | 1.11 | 0.628 | 0.647 |
| 0.292 | 1.11 | 2.11 | 1.74 | 1.65 | 0.446 | 1.44 | 1.22 | 1.04 |
| 1 | 4.19 | 3.62 | 5.59 | 4.47 | 1.80 | 2.17 | 2.90 | 2.29 |
| 2 | 1.14 | 1.18 | 1.06 | 1.13 | 1.54 | 1.38 | 1.86 | 1.59 |
| 3 | 0.906 | 0.931 | 0.747 | 0.861 | 1.70 | 1.56 | 2.04 | 1.77 |
| 8 | 0.281 | 0.215 | 0.600 | 0.365 | 1.93 | 1.72 | 2.11 | 1.92 |
| 10 | 0.111 | 0.171 | 0.264 | 0.182 | 1.79 | 1.46 | 2.04 | 1.76 |
| 17 | BQL | 0.106 | BQL | 0.106 | 0.916 | 0.942 | 1.37 | 1.08 |
| 19 | BQL | BQL | BQL | BQL | 0.824 | 0.904 | 0.935 | 0.888 |
| 22 | 0.116 | BQL | BQL | 0.116 | 0.869 | 0.699 | 1.40 | 0.989 |
| 25 | BQL | BQL | BQL | BQL | 0.588 | 0.434 | 0.702 | 0.575 |
| 29 | BQL | BQL | 0.101 | 0.101 | 0.555 | 0.556 | 0.747 | 0.619 |
| 32 | BQL | BQL | 0.108 | 0.108 | 0.622 | 0.471 | 0.791 | 0.628 |
| 36 | BQL | BQL | BQL | BQL | 0.533 | 0.440 | 0.738 | 0.570 |
| 39 | BQL | BQL | BQL | BQL | 0.550 | 0.660 | 0.353 | 0.521 |
| 43 | BQL | BQL | BQL | BQL | 0.433 | 0.372 | 0.582 | 0.462 |
| 46 | BQL | BQL | BQL | BQL | 0.364 | 0.319 | 0.526 | 0.403 |
| 50 | BQL | BQL | BQL | BQL | 0.251 | 0.251 | 0.295 | 0.266 |
| 53 | BQL | BQL | BQL | BQL | 0.363 | 0.345 | 0.457 | 0.388 |
| 57 | BQL | BQL | BQL | BQL | 0.265 | 0.244 | 0.249 | 0.253 |
| 60 | | | | | 0.265 | 0.246 | 0.283 | 0.265 |
| 64 | | | | | 0.187 | 0.222 | 0.280 | 0.230 |
| 67 | | | | | 0.189 | 0.229 | 0.260 | 0.226 |
| 71 | | | | | 0.203 | 0.185 | 0.240 | 0.209 |
| 74 | | | | | 0.259 | 0.277 | 0.422 | 0.319 |
| 78 | | | | | 0.229 | 0.235 | 0.350 | 0.271 |
| 81 | | | | | 0.238 | 0.164 | 0.324 | 0.242 |
| 85 | | | | | 0.194 | 0.214 | 0.250 | 0.219 |
| 88 | | | | | 0.146 | 0.123 | 0.190 | 0.153 |
| 92 | | | | | 0.152 | 0.170 | 0.124 | 0.149 |

BQL—Below Quantitation Limit, <0.100 ng/mL

TABLE 38

Plasma concentration of Example 18 and EFdA from
Example 18 dog IM PK study
IM Dosing 20 mg/kg equivalent of EFdA

| Time | Example 18 plasma concentrations (ng/mL) | | | | EFdA plasma concentrations (ng/mL) | | | |
|---|---|---|---|---|---|---|---|---|
| (days) | Dog2001 | Dog2002 | Dog2003 | Mean | Dog2001 | Dog2002 | Dog2003 | Mean |
| 0.021 | 2.43 | 2.67 | 1.47 | 2.19 | 0.158 | 0.344 | BQL | 0.251 |
| 0.042 | 3.38 | 2.85 | 1.90 | 2.71 | 0.682 | 1.51 | 0.566 | 0.919 |
| 0125 | 10.5 | 7.99 | 4.36 | 7.62 | 3.47 | 3.92 | 2.30 | 3.23 |
| 0.208 | 9.34 | 7.61 | 7.51 | 8.15 | 3.79 | 4.17 | 3.61 | 3.86 |
| 0.292 | 8.41 | 7.29 | 4.96 | 6.89 | 3.07 | 3.81 | 3.41 | 3.43 |
| 1 | 2.45 | 2.69 | 2.03 | 2.39 | 2.56 | 3.67 | 2.57 | 2.93 |
| 2 | 1.04 | 1.21 | 1.19 | 1.15 | 1.92 | 2.98 | 2.02 | 2.31 |
| 3 | 1.09 | 0.877 | 0.818 | 0.928 | 1.92 | 2.18 | 2.23 | 2.11 |
| 8 | 0.204 | 0.419 | 0.201 | 0.275 | 2.10 | 2.16 | 2.20 | 2.15 |
| 10 | 0.129 | 0.198 | 0.150 | 0.159 | 1.46 | 1.88 | 2.05 | 1.80 |
| 17 | 0.110 | 0.172 | 0.116 | 0.133 | 1.25 | 1.51 | 1.17 | 1.31 |
| 19 | 0.109 | BQL | BQL | 0.109 | 0.864 | 1.14 | 0.961 | 0.988 |
| 22 | BQL | 0.113 | BQL | BQL | 0.997 | 1.25 | 1.27 | 1.17 |
| 25 | BQL | BQL | BQL | BQL | 0.492 | 0.675 | 0.681 | 0.616 |
| 29 | BQL | BQL | BQL | BQL | 0.734 | 0.679 | 0.927 | 0.780 |

TABLE 38-continued

Plasma concentration of Example 18 and EFdA from
Example 18 dog IM PK study
IM Dosing 20 mg/kg equivalent of EFdA

| Time | Example 18 plasma concentrations (ng/mL) | | | | EFdA plasma concentrations (ng/mL) | | | |
|---|---|---|---|---|---|---|---|---|
| (days) | Dog2001 | Dog2002 | Dog2003 | Mean | Dog2001 | Dog2002 | Dog2003 | Mean |
| 32 | BQL | BQL | BQL | BQL | 0.581 | 0.739 | 0.688 | 0.669 |
| 36 | BQL | BQL | BQL | BQL | 0.643 | 0.575 | 0.702 | 0.640 |
| 39 | BQL | BQL | BQL | BQL | 0.677 | 0.600 | 0.590 | 0.622 |
| 43 | BQL | BQL | BQL | BQL | 0.441 | 0.465 | 0.506 | 0.471 |
| 46 | BQL | BQL | BQL | BQL | 0.519 | 0.464 | 0.527 | 0.503 |
| 50 | BQL | BQL | BQL | BQL | 0.229 | 0.244 | 0.284 | 0.252 |
| 53 | BQL | BQL | BQL | BQL | 0.387 | 0.444 | 0.395 | 0.409 |
| 57 | BQL | BQL | BQL | BQL | 0.218 | 0.244 | 0.244 | 0.235 |
| 60 | | | | | 0.290 | 0.262 | 0.360 | 0.304 |
| 64 | | | | | 0.272 | 0.215 | 0.219 | 0.235 |
| 67 | | | | | 0.308 | 0.244 | 0.277 | 0.276 |
| 71 | | | | | 0.171 | 0.246 | 0.217 | 0.211 |
| 74 | | | | | 0.372 | 0.273 | 0.419 | 0.355 |
| 78 | | | | | 0.364 | 0.285 | 0.269 | 0.306 |
| 81 | | | | | 0.239 | 0.214 | 0.335 | 0.263 |
| 85 | | | | | 0.239 | 0.201 | 0.302 | 0.247 |
| 88 | | | | | 0.182 | 0.165 | 0.210 | 0.186 |
| 92 | | | | | 0.111 | 0.137 | 0.132 | 0.127 |

BQL—Below Quantitation Limit, <0.100 ng/mL

Protocol for Example 18 (Compound) Cynomolgus Monkey PK Study

Example 18 referenced herein was made in accordance with Synthesis B. Six male cynomolgus monkeys (+1 spare) were selected from the Testing Facility's colony of non-naïve animals. The animals were assigned to the study based on acceptable health as determined by a Testing Facility veterinarian. Six animals were selected and placed into two groups of three animals each. Fasting of the animals before or after dosing was not required.

On Day 1 each animal in Group 1 received a single intrascapular subcutaneous injection of prepared test article at a target dose level of 5 mg parent/kg in 2% P404/2% PEG3350/PBS (dose concentration 97.36 mg/mL prodrug) and at a dose volume of 0.1 mL/kg. Each animal in Group 2 received a single intramuscular injection of prepared test article in a hind quarter (quadriceps) at a target dose level of 5 mg parent/kg in 2% P404/2% PEG3350/PBS (dose concentration 97.36 mg/mL prodrug) and at a dose volume of 0.1 mL/kg. The animals were manually restrained for dosing and were not sedated. The dose sites were clipped of hair and wiped with alcohol before dosing. All dosing was performed as detailed in the study protocol and was completed without incident.

Following dosing and at least twice daily until the end of the study, the animals and dose sites were observed for any clinically relevant abnormalities. All animals appeared normal at the time of each observation and no dose site reactions were observed.

Blood samples were collected from the study animals as detailed in the sample collection Table 39 below.

TABLE 39

| Group/Collection Information | Whole Blood for PK |
|---|---|
| 1-2 | 0.5, 1, 3, 5, 7, 24, 48, 72 hours post-dose and Day 8, 10, 17, 19, 22, 25, 29, 32, 36, 39, 43, 46, 50, 53, 57, 60, 64, 67, 71, 74, 78, 81, 85, 88, 92,, 106, |
| Anticoagulant | NaF tubes containing Na2EDTA |
| Volume/Time point | 500 µL of whole blood |

Blood samples were collected by venipuncture of a cephalic vein. For PK, blood was transferred to a blood collection tube containing NaF/Na2EDTA anticoagulant, mixed by inversion, and maintained on wet ice until processing. The blood samples were centrifuged at 2200×g for 10 minutes at 5° C. to isolate plasma. The resulting plasma samples were transferred to individual polypropylene tubes in a 96-well plate format and immediately placed on dry ice until storage at nominally −20° C. prior to shipment for analysis.

Figure 29:
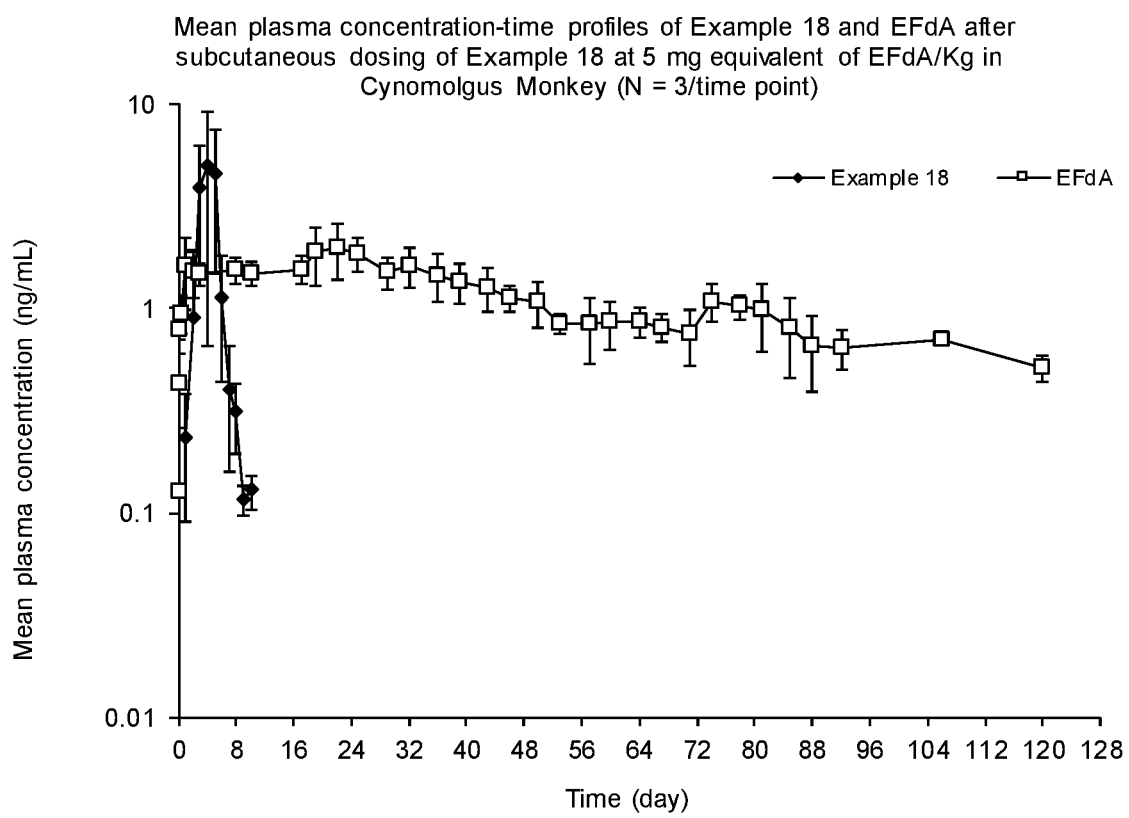
FIG. 29 illustrates the mean plasma concentration-time profiles of Example 18 and EFdA after subcutaneous dosing Example 18 at 5 mg equivalent of EFdA/kg in Cynomolgus Monkey (N=3/time point)
Figure 30:
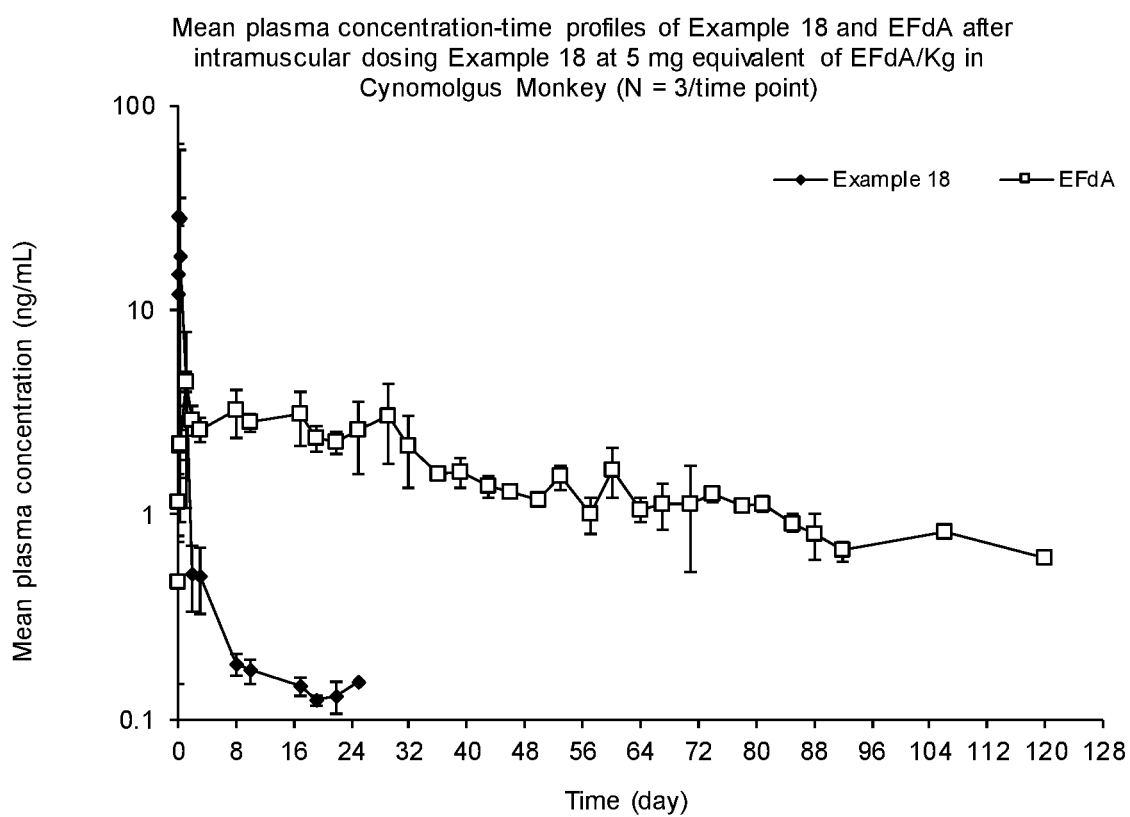
FIG. 30 illustrates the mean plasma concentration-time profiles of Example 18 and EFdA after intramuscular dosing Example 18 at 5 mg equivalent of EFdA/kg in Cynomolgus Monkey (N=3/time point)

The PK plasma samples were analyzed approximately every two weeks by the Testing Facility to determine the concentration of Example 18 (prodrug) and parent using an LC-MS/MS Research Grade Assay (RGA-1) with sensitivity to 0.1 ng/mL. Following interim review of sample analysis data, analysis for Example 18 (prodrug) was discontinued after the Day 57 sample collections. The bioanalytical report and sample concentration data are presented in Tables 40 and 41, and mean concentration-time profiles are shown in FIGS. 29 and 30

TABLE 40

Plasma concentration of Example 18 and EFdA from
Example 18 monkey SC PK study
SC Dosing 20 mg/kg equivalent of EFdA

| | Example 18 plasma concentrations (ng/mL) | | | | EFdA plasma concentrations (ng/mL) | | | |
|---|---|---|---|---|---|---|---|---|
| Time (days) | Monkey 1001 | Monkey 1002 | Monkey 1002 | Mean | Monkey 1001 | Monkey 1002 | Monkey 1003 | Mean |
| 0.021 | 49.4 | 0.337 | 0.133 | 0.235 | BQL | BQL | BQL | BQL |
| 0.042 | 70.3 | 1.63 | 0.179 | 0.905 | 0.126 | BQL | BQL | 0.126 |
| 0.125 | 149 | 5.59 | 2.29 | 3.940 | 0.492 | 0.241 | 0.561 | 0.431 |
| 0.208 | 92.8 | 7.99 | 1.91 | 4.950 | 0.767 | 0.721 | 0.894 | 0.794 |
| 0.292 | 146 | 6.67 | 2.38 | 4.525 | 1.13 | 0.738 | 0.970 | 0.946 |
| 1 | 36.5 | 1.60 | 0.641 | 1.121 | 2.27 | 1.06 | 1.49 | 1.607 |
| 2 | 0.734 | 0.230 | 0.579 | 0.405 | 1.56 | 1.12 | 1.85 | 1.510 |
| 3 | 0.694 | 0.228 | 0.396 | 0.312 | 1.62 | 1.27 | 1.56 | 1.483 |
| 8 | BQL | 0.102 | 0.131 | 0.117 | 1.79 | 1.37 | 1.45 | 1.537 |
| 10 | 0.146 | 0.111 | 0.146 | 129 | 1.64 | 1.28 | 1.57 | 1.497 |
| 17 | BQL | BQL | BQL | BQL | 1.84 | 1.35 | 1.51 | 1.567 |
| 19 | BQL | BQL | BQL | | 2.57 | 1.40 | 1.70 | 1.890 |
| 22 | BQL | BQL | BQL | | 2.71 | 1.59 | 1.68 | 1.993 |
| 25 | BQL | BQL | BQL | | 2.16 | 1.47 | 1.92 | 1.850 |
| 29 | BQL | BQL | BQL | | 1.66 | 1.20 | 1.66 | 1.507 |
| 32 | BQL | BQL | BQL | | 1.94 | 1.23 | 1.67 | 1.613 |
| 36 | BQL | BQL | BQL | | 1.82 | 1.05 | 1.50 | 1.457 |
| 39 | BQL | BQL | BQL | | 1.56 | 1.00 | 1.49 | 1.350 |
| 43 | BQL | BQL | BQL | | 1.36 | 0.929 | 1.52 | 1.270 |
| 46 | BQL | BQL | BQL | | 1.21 | 0.935 | 1.22 | 1.122 |
| 50 | BQL | BQL | BQL | | 1.36 | 0.802 | 1.08 | 1.081 |
| 53 | BQL | BQL | BQL | | 0.895 | 0.741 | 0.908 | 0.848 |
| 57 | BQL | BQL | BQL | | 1.18 | 0.639 | 0.693 | 0.837 |
| 60 | | | | | 1.12 | 0.703 | 0.739 | 0.854 |
| 64 | | | | | 1.02 | 0.721 | 0.847 | 0.863 |
| 67 | | | | | 0.845 | 0.670 | 0.921 | 0.812 |
| 71 | | | | | 1.02 | 0.569 | 0.682 | 0.757 |
| 74 | | | | | 1.32 | 0.876 | 1.08 | 1.092 |
| 78 | | | | | 1.16 | 0.899 | 1.01 | 1.023 |
| 81 | | | | | 1.39 | 0.795 | 0.744 | 0.976 |
| 85 | | | | | 1.16 | 0.490 | 0.744 | 0.798 |
| 88 | | | | | 0.957 | 0.527 | 0.484 | 0.656 |
| 92 | | | | | 0.803 | 0.608 | 0.527 | 0.646 |
| 106 | | | | | 0.713 | 0.692 | 0.696 | 0.700 |
| 120 | | | | | 0.564 | 0.430 | 0.538 | 0.511 |

BQL—Below Quantitation Limit, <0.100 ng/mL

TABLE 41

Plasma concentration of Example 18 and EFdA from
Example 18 monkey IM PK study
IM Dosing 20 mg/kg equivalent of EFdA

| | Example 18 plasma concentrations (ng/mL) | | | | EFdA plasma concentrations (ng/mL) | | | |
|---|---|---|---|---|---|---|---|---|
| Time (days) | Monkey 2001 | Monkey 2002 | Monkey 2003 | Mean | Monkey 2001 | Monkey 2002 | Monkey 2003 | Mean |
| 0.021 | 21.8 | 40.2 | 1.93 | 11.865 | 0.135 | BQL | BQL | 0.135 |
| 0.042 | 29.2 | 82.6 | 0.790 | 14.995 | 0.843 | 0.317 | 0.258 | 0.473 |
| 0.125 | 53.7 | 363 | 3.31 | 28.505 | 1.59 | 1.15 | 0.745 | 1.162 |
| 0.208 | 51.3 | 692 | 5.27 | 28.285 | 3.57 | 1.66 | 1.26 | 2.163 |
| 0.292 | 30.1 | 821 | 6.42 | 18.260 | 2.44 | 2.44 | 1.79 | 2.223 |
| 1 | 6.89 | 110 | 2.08 | 4.485 | 4.24 | 4.15 | 5.01 | 4.467 |
| 2 | 0.652 | 0.674 | 0.387 | 0.520 | 3.35 | 2.93 | 2.42 | 2.900 |
| 3 | 0.379 | 0.533 | 0.630 | 0.505 | 2.86 | 2.77 | 2.24 | 2.623 |
| 8 | 0.203 | 0.248 | 0.171 | 0.187 | 4.03 | 3.34 | 2.31 | 3.227 |
| 10 | 0.156 | 0.251 | 0.190 | 0.173 | 2.99 | 3.02 | 2.50 | 2.837 |
| 17 | 0.135 | 0.160 | 0.154 | 0.145 | 4.10 | 2.28 | 2.90 | 3.093 |
| 19 | 0.119 | 0.149 | 0.129 | 0.124 | 2.72 | 2.04 | 2.30 | 2.353 |
| 22 | 0.146 | 0.114 | 0.113 | 0.130 | 2.21 | 1.99 | 2.53 | 2.243 |
| 25 | BQL | 0.125 | 0.151 | 0.151 | 2.18 | 1.85 | 3.70 | 2.577 |
| 29 | 0.155 | 0.135 | BQL | | 4.39 | 2.90 | 1.87 | 3.053 |
| 32 | BQL | BQL | BQL | | 3.13 | 1.61 | 1.80 | 2.180 |
| 36 | BQL | BQL | BQL | | 1.56 | 1.55 | 1.65 | 1.587 |
| 39 | BQL | BQL | BQL | | 1.92 | 1.51 | 1.41 | 1.613 |
| 43 | BQL | BQL | BQL | | 1.27 | 1.29 | 1.57 | 1.377 |

TABLE 41-continued

Plasma concentration of Example 18 and EFdA from
Example 18 monkey IM PK study
IM Dosing 20 mg/kg equivalent of EFdA

| | Example 18 plasma concentrations (ng/mL) | | | | EFdA plasma concentrations (ng/mL) | | | |
|---|---|---|---|---|---|---|---|---|
| Time (days) | Monkey 2001 | Monkey 2002 | Monkey 2003 | Mean | Monkey 2001 | Monkey 2002 | Monkey 2003 | Mean |
| 46 | BQL | BQL | 0.105 | | 1.29 | 1.19 | 1.36 | 1.280 |
| 50 | BQL | BQL | BQL | | 1.16 | 1.16 | 1.24 | 1.187 |
| 53 | BQL | BQL | BQL | | 1.42 | 1.77 | 1.40 | 1.530 |
| 57 | BQL | BQL | BQL | | 1.20 | 0.791 | 1.05 | 1.014 |
| 60 | | | | | 1.91 | 1.95 | 1.14 | 1.667 |
| 64 | | | | | 1.24 | 0.974 | 0.984 | 1.066 |
| 67 | | | | | 1.23 | 1.36 | 0.817 | 1.136 |
| 71 | | | | | 1.84 | 0.712 | 0.861 | 1.138 |
| 74 | | | | | 1.32 | 1.15 | 1.28 | 1.250 |
| 78 | | | | | 1.12 | 1.09 | 1.10 | 1.103 |
| 81 | | | | | 1.21 | 1.18 | 1.02 | 1.137 |
| 85 | | | | | 0.835 | 1.01 | 0.890 | 0.912 |
| 88 | | | | | 1.02 | 0.750 | 0.626 | 0.799 |
| 92 | | | | | 0.699 | 0.582 | 0.724 | 0.668 |
| 106 | | | | | 0.855 | 0.828 | 0.816 | 0.833 |
| 120 | | | | | 0.643 | 0.595 | 0.589 | 0.609 |

BQL—Below Quantitation Limit, <0.100 ng/mL

As shown above pharmacokinetic results, in rat IM and SC administration of 20 mg/kg EFdA showed a detectable duration of exposure of EFdA for less than 8-days, likely reflecting rapid absorption of the compound as a consequence of its high solubility and high permeability. Therefore, an approach involving design of novel lipophilic prodrugs of EFdA as a means to modulate the physicochemical properties of the EFdA as a strategy to improve its suitability for use as a long-acting injectable antiviral agent was pursued. The rat, dog and monkey IM and SC PK data demonstrate that sustained exposure of EFdA for extended period was achieved with several lipophilic prodrugs suggests potential utility of lipophilic prodrugs in HIV therapy as a long-acting IM or SC administrative prodrugs of EFdA.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present disclosure.

What is claimed is:

1. A compound having the structure:

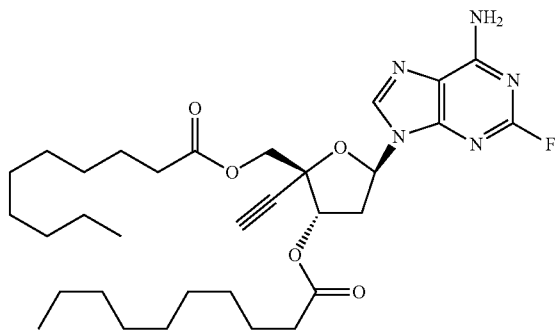 [SMILES: C#C[C@]1(COC(=O)CCCCCCCCC)O[C@@H](n2cnc3c(N)nc(F)nc32)C[C@@H]1OC(=O)CCCCCCCCC]

or a pharmaceutically acceptable salt thereof.

2. A compound having the structure:

3. A pharmaceutical composition comprising a compound according to claim 1, or a pharmaceutically acceptable salt thereof, and a pharmaceutically acceptable excipient.

4. The composition of claim 3, wherein the composition is present in parenteral form.

5. The composition of claim 3, wherein the composition is in a tablet form.

6. The composition of claim 3, wherein the composition is formulated as a long acting parenteral injection.

7. The composition of claim 3, wherein the composition is a nano-particle composition.

8. A pharmaceutical composition comprising a compound according to claim 2, or a pharmaceutically acceptable salt thereof, and a pharmaceutically acceptable excipient.

9. The composition of claim 8, wherein the composition is present in parenteral form.

10. The composition of claim 8, wherein the composition is in a tablet form.

11. The composition of claim 8, wherein the composition is formulated as a long acting parenteral injection.

12. The composition of claim 8, wherein the composition is a nano-particle composition.

13. A kit comprising the compound or a pharmaceutically acceptable salt thereof according to claim 1.

14. A kit comprising the compound according to claim 2.

15. A method of treating an HIV infection in a subject comprising administering to the subject a compound of claim 1, or a pharmaceutically acceptable salt thereof.

16. A method of treating an HIV infection in a subject comprising administering to the subject a compound of claim 2, or a pharmaceutically acceptable salt thereof.

* * * * *